US012679826B2

(12) United States Patent
Saito et al.

(10) Patent No.: US 12,679,826 B2
(45) Date of Patent: Jul. 14, 2026

(54) COMPOUND, MATERIAL FOR ORGANIC ELECTROLUMINESCENCE DEVICE, ORGANIC ELECTROLUMINESCENCE DEVICE, AND ELECTRONIC APPARATUS

(71) Applicant: IDEMITSU KOSAN CO., LTD., Tokyo (JP)

(72) Inventors: Masatoshi Saito, Sodegaura (JP); Kei Yoshida, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 926 days.

(21) Appl. No.: 17/922,706

(22) PCT Filed: May 7, 2021

(86) PCT No.: PCT/JP2021/017434

§ 371 (c)(1),
(2) Date: Nov. 1, 2022

(87) PCT Pub. No.: WO2021/230141

PCT Pub. Date: Nov. 18, 2021

(65) Prior Publication Data

US 2023/0200226 A1 Jun. 22, 2023

(30) Foreign Application Priority Data

May 12, 2020 (JP) ................................ 2020-084093

(51) Int. Cl.

| | |
|---|---|
| ***H10K 85/60*** | (2023.01) |
| ***C07D 403/10*** | (2006.01) |
| ***H10K 59/00*** | (2023.01) |
| *H10K 50/16* | (2023.01) |

(52) U.S. Cl.

CPC ........... *C07D 403/10* (2013.01); *H10K 59/00* (2023.02); *H10K 85/654* (2023.02); *H10K 85/6572* (2023.02); *H10K 50/166* (2023.02)

(58) Field of Classification Search

None

See application file for complete search history.

(56) References Cited

U.S. PATENT DOCUMENTS

| | | | | |
|---|---|---|---|---|
| 2004/0086745 A1 | 5/2004 | Iwakuma et al. | | |
| 2005/0249976 A1 | 11/2005 | Iwakuma et al. | | |
| 2012/0298975 A1 | 11/2012 | Iwakuma et al. | | |
| 2012/0319099 A1 | 12/2012 | Iwakuma et al. | | |
| 2021/0135127 A1 | 5/2021 | Jung et al. | | |
| 2021/0202849 A1* | 7/2021 | Jung | .................... | C07D 263/52 |
| 2022/0173334 A1* | 6/2022 | Itoi | ...................... | H10K 85/623 |

FOREIGN PATENT DOCUMENTS

| | | | | |
|---|---|---|---|---|
| JP | 2019-119723 A | 7/2019 | | |
| KR | 10-2015-0002072 A | 2/2016 | | |
| KR | 10-1926771 B1 | 12/2018 | | |
| KR | 10-2019-0045653 A | 5/2019 | | |
| WO | WO-03/080760 A1 | 10/2003 | | |
| WO | WO-2019/101594 A1 | 5/2019 | | |
| WO | WO-2020/197240 A1 | 10/2020 | | |
| WO | WO-2020/209299 A1 | 10/2020 | | |
| WO | WO-2020209309 A1 * | 10/2020 | ......... | H10K 85/6574 |

OTHER PUBLICATIONS

International Preliminary Report on Patentability and Written Opinion issued in connection with PCT Appl. Ser. No. PCT/JP2021/017434, English translation dated Nov. 15, 2022 (7 pages).

International Search Report issued in connection with PCT Appl. Ser. No. PCT/JP2021/017434 dated Jul. 6, 2021 (3 pages).

* cited by examiner

*Primary Examiner* — Robert S Loewe

(74) *Attorney, Agent, or Firm* — Foley & Lardner LLP

(57) ABSTRACT

A compound represented by the following formula (1), wherein $L_1$ is a single bond or an arylene group, and $Ar_1$ and $Ar_2$ are an unsubstituted aryl group.

(1)

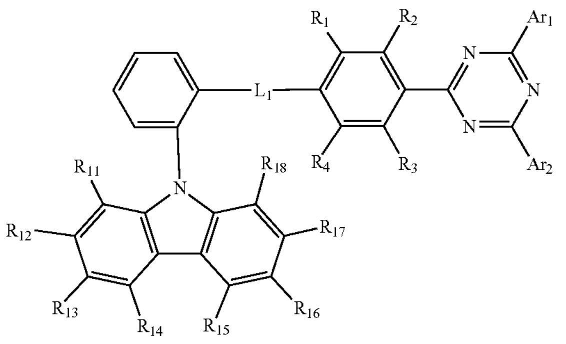

19 Claims, 1 Drawing Sheet

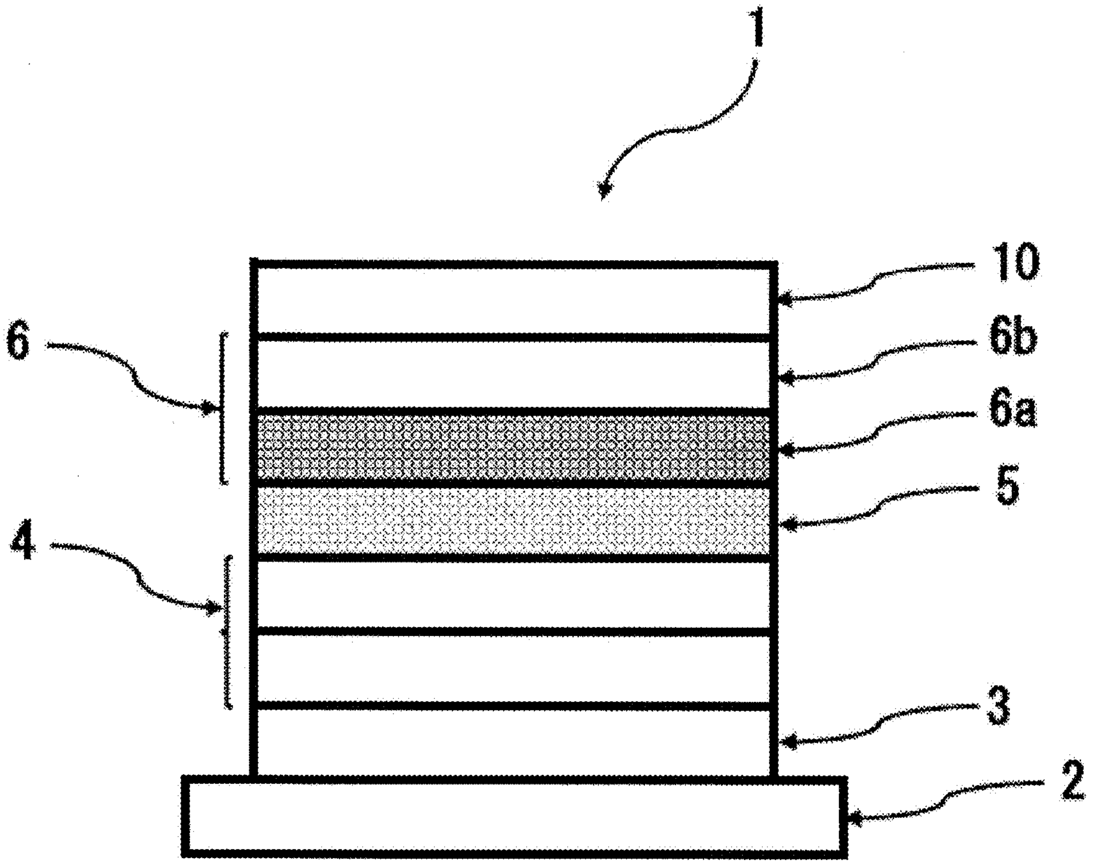
1
10
6b
6a
5
3
2
6
4

COMPOUND, MATERIAL FOR ORGANIC ELECTROLUMINESCENCE DEVICE, ORGANIC ELECTROLUMINESCENCE DEVICE, AND ELECTRONIC APPARATUS

CROSS-REFERENCE TO RELATED APPLICATIONS

The present application claims priority under 37 U.S.C. § 371 to International Patent Application No. PCT/JP2021/017434, filed May 7, 2021, which claims priority to and the benefit of Japanese Patent Application No. 2020-084093, filed on May 12, 2020. The contents of these applications are hereby incorporated by reference in their entireties.

TECHNICAL FIELD

The present invention relates to a novel compound, a material for an organic electroluminescence device, an organic electroluminescence device and an electronic apparatus.

BACKGROUND ART

When voltage is applied to an organic electroluminescence device (hereinafter, frequently referred to as an organic EL device), holes and electrons are injected into an emitting layer from an anode and a cathode, respectively. Then, thus injected holes and electrons are recombined in the emitting layer, and excitons are formed therein.

Patent Document 1 discloses, as a material for an organic EL device, a compound in which an azine ring and a carbazole ring are bonded to each other via a linking group, and an organic EL device using the compound.

Patent Document 2 discloses a compound in which an o-phenylene group bonded with an azine ring and an o-phenylene group bonded with a carbazole ring are bonded to each other via a linker, and an organic EL device using the compound.

Patent Document 3 discloses a compound in which a m-phenylene group bonded with an azine ring and an o-phenylene group bonded with a carbazole ring are bonded to each other via a linker, and an organic EL device using the compound.

RELATED ART DOCUMENTS

Patent Documents

[Patent Document 1] WO2003/080760 A1
[Patent Document 2] KR2019-0045653
[Patent Document 3] KR2015-0002072

SUMMARY OF THE INVENTION

It is an object of the present invention to provide a novel compound useful as a material of an organic electroluminescence device, a material for an organic electroluminescence device including the same, an organic electroluminescence device, and an electronic apparatus.

According to the present invention, the following compound, material for an organic electroluminescence device, organic electroluminescence device, and electronic apparatus are provided.

1. A compound represented by the following formula (1):

(1)

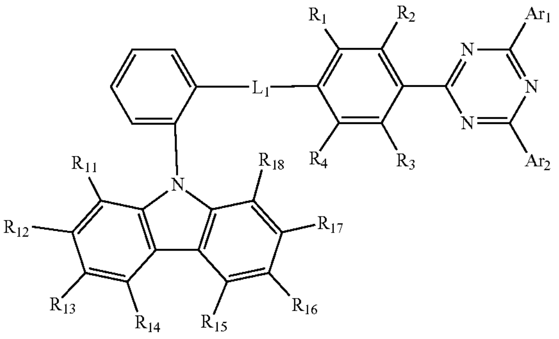

wherein in the formula (1), $Ar_1$ and $Ar_2$ are independently an unsubstituted aryl group having 6 to 50 ring carbon atoms;

$R_1$ and $R_2$ form an unsubstituted, saturated or unsaturated hydrocarbon ring having 6 to 50 ring carbon atoms by bonding with each other, or do not form the ring;

$R_3$ and $R_4$, and $R_1$ and $R_2$ which do not form the ring are independently a hydrogen atom, or a substituent $R_a$;

one or more sets of the adjacent two or more of $R_{11}$ to $R_{18}$ form an unsubstituted, saturated or unsaturated hydrocarbon ring having 6 to 50 ring carbon atoms, or an unsubstituted, saturated or unsaturated heterocyclic ring having 5 to 50 ring atoms, by bonding with each other, or do not form the rings;

$R_{11}$ to $R_{18}$ which do not form the rings are independently a hydrogen atom, or a substituent $R_a$;

$L_1$ is a single bond, or a divalent group represented by any one of the following formulas (a1) to (a9):

(a1)

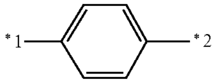

(a2)

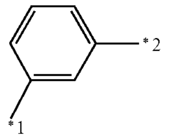

(a3)

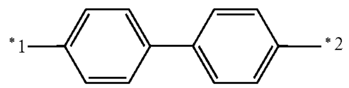

(a4)

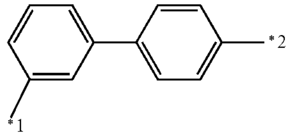

(a5)

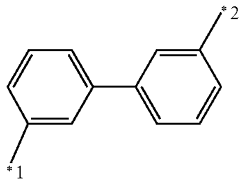

-continued (a6)

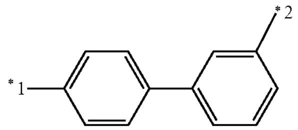

(a7)

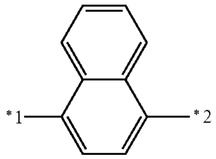

(a8)

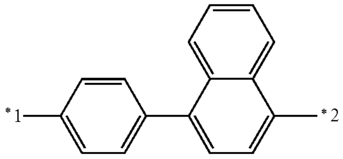

(a9)

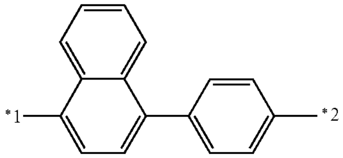

wherein in the formulas (a1) to (a9), *1 is bonded with a benzene ring on a carbazolyl group side, and *2 is bonded with a benzene ring on a triazine ring side.

2. An electron-transporting material for an organic electroluminescence device, comprising the compound according to 1.

3. An organic electroluminescence device comprising a cathode;

an anode; and one or two or more organic layers arranged between the cathode and the anode, wherein at least one layer of the organic layers comprises the compound according to 1.

4. An electronic apparatus comprising the organic electroluminescence device according to 3.

According to the present invention, there can be provided a novel compound useful as a material of an organic electroluminescence device, a material for an organic electroluminescence device including the same, an organic electroluminescence device, and an electronic apparatus.

The FIGURE is a schematic diagram of an organic EL device according to an aspect of the present invention.

MODE FOR CARRYING OUT THE INVENTION

Definition

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms which do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group" is a "ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent" .). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1 B is further substituted by a substituent, and a group in which a hydrogen atom of a substituent in the "substituted aryl group" of the following specific group G1 B is further substituted by a substituent.

Unsubstituted Aryl Group (Specific Example Group G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived by removing one hydrogen atom from the ring structures represented by any of the following general formulas (TEMP-1) to (TEMP-15).

(TEMP-1)
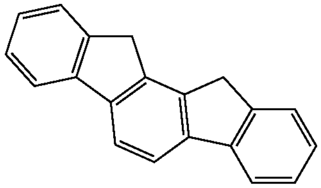
(TEMP-2)
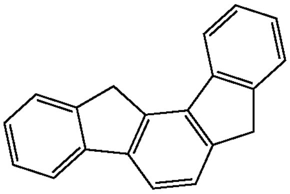
(TEMP-3)
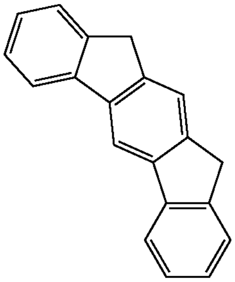
(TEMP-4)
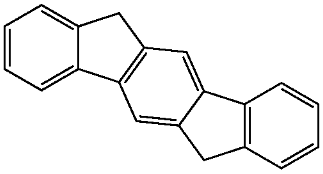
(TEMP-5)
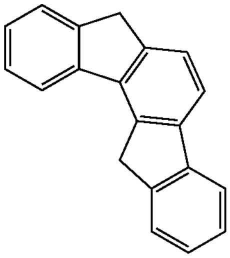
(TEMP-6)
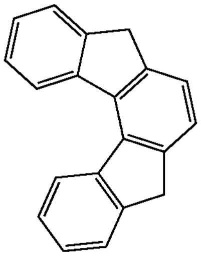
(TEMP-7)
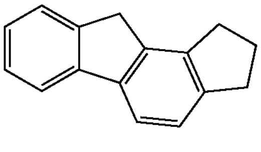
-continued
(TEMP-8)
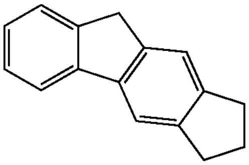
(TEMP-9)
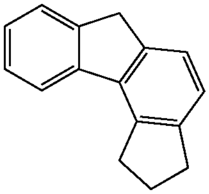
(TEMP-10)
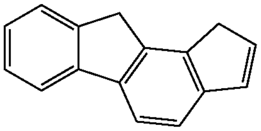
(TEMP-11)
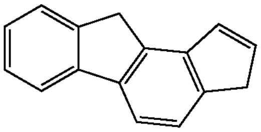
(TEMP-12)
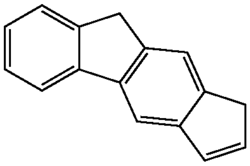
(TEMP-13)
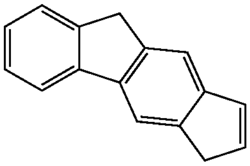
(TEMP-14)
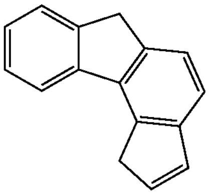
(TEMP-15)
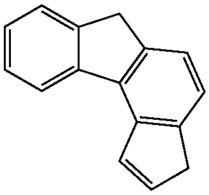
Substituted Aryl Group (Specific Example Group G1 B):
- an o-tolyl group,
- a m-tolyl group,
- a p-tolyl group,
- a p-xylyl group,
- a m-xylyl group,
- an o-xylyl group,
- a p-isopropylphenyl group, a m-isopropylphenyl group,
an o-isopropylphenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
a group in which one or more hydrogen atoms of a monovalent group derived from the ring structures represented by any of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group" is a "heterocyclic group substituted by a substituent".). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by any of the following general formulas (TEMP-16) to (TEMP-33)(specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by any of the following general formulas (TEMP-16) to (TEMP-33) are substituted by a substituent (specific example group G2B4).

Unsubstituted Heterocyclic Group Containing a Nitrogen Atom (Specific Example Group G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
a benzimidazolyl group,
an idazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing an Oxygen Atom (Specific Example Group G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing a Sulfur Atom (Specific Example Group G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent heterocyclic group derived by removing one hydrogen atom from the ring structures represented by any of the following general formulas (TEMP-16) to (TEMP-33)(specific example group G2A4):

(TEMP-16)

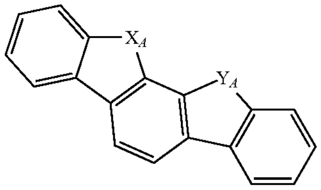

(TEMP-17)

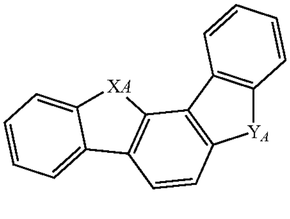

-continued (TEMP-18)

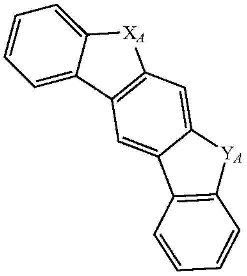

(TEMP-19)

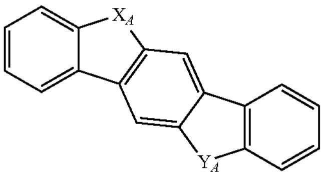

(TEMP-20)

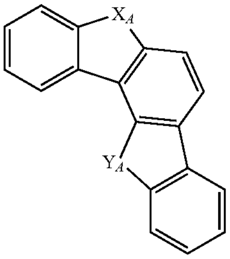

(TEMP-21)

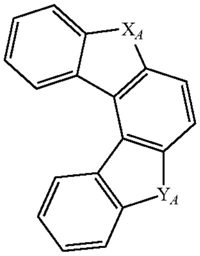

(TEMP-22)

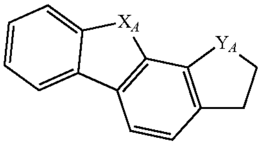

(TEMP-23)

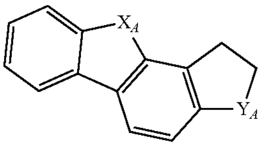

(TEMP-24)

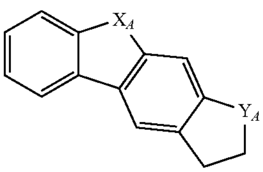

-continued (TEMP-25)

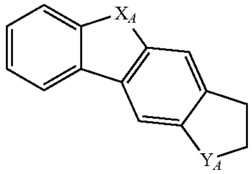

(TEMP-26)

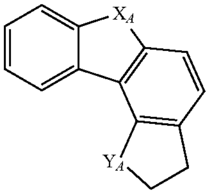

(TEMP-27)

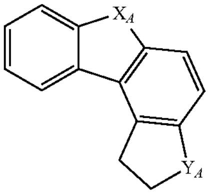

(TEMP-28)

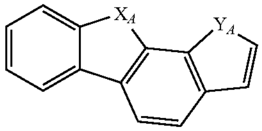

(TEMP-29)

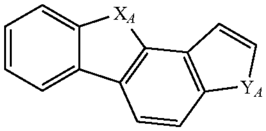

(TEMP-30)

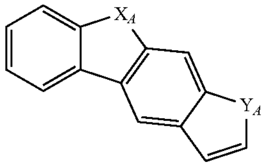

(TEMP-31)

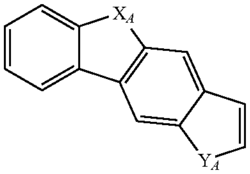

(TEMP-32)

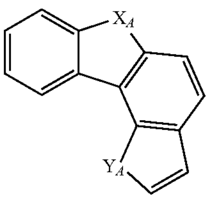

-continued (TEMP-33)

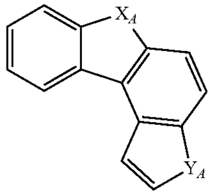

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic group derived from the ring structures represented by any of the general formulas (TEMP-16) to (TEMP-33) includes a monovalent group derived by removing one hydrogen atom from these NH or $CH_2$.

Substituted heterocyclic group containing a nitrogen atom (specific example group G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Substituted heterocyclic group containing an oxygen atom (specific example group G2B2):

a phenyldibenzofuranyl group,
a methyldibenzofuranyl group,
a t-butyldibenzofuranyl group, and
a monovalent residue of spiro[9H-xanthene-9,9'-[9H]fluorene].

Substituted heterocyclic group containing a sulfur atom (specific example group G2B3):

a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Group in which one or more hydrogen atoms of the monovalent heterocyclic group derived from the ring structures represented by any of the following general formulas (TEMP-16) to (TEMP-33) are substituted by a substituent (specific example group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent".). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted alkyl group (specific example group G3A):

a methyl group,
an ethyl group,
a n-propyl group,
an isopropyl group,
a n-butyl group,
an isobutyl group,
a s-butyl group, and
a t-butyl group.

Substituted alkyl group (specific example group G3B):

a heptafluoropropyl group (including isomers),
a pentafluoroethyl group,
a 2,2,2-trifluoroethyl group, and
a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group" is a "alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted Alkenyl Group (Specific Example Group G4A):

a vinyl group,
an allyl group,
a 1-butenyl group,
a 2-butenyl group, and
a 3-butenyl group.

Substituted Alkenyl Group (Specific Example Group G4B):

a 1,3-butanedienyl group,
a 1-methylvinyl group,
a 1-methylallyl group,
a 1,1-dimethylallyl group,
a 2-methylally group, and
a 1,2-dimethylallylgroup.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent".). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted Alkynyl Group (Specific Example Group G5A):

an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group" is a "cycloalkyl group substituted by a substituent".). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted Cycloalkyl Group (Specific Example Group G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted cycloalkyl group (specific example group G6B):

a 4-methylcyclohexyl group.

"Group represented by —Si($R_{901}$)($R_{902}$)($R_{903}$)"

Specific examples of the group represented by —Si($R_{901}$)($R_{902}$)($R_{903}$) described in this specification (specific example group G7) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —Si(G1)(G1)(G1) are the same or different.

Plural G2's in —Si(G1)(G2)(G2) are the same or different.

Plural G1's in —Si(G1)(G1)(G2) are the same or different.

Plural G2's in —Si(G2)(G2)(G2) are be the same or different.

Plural G3's in —Si(G3)(G3)(G3) are the same or different.

Plural G6's in —Si(G6)(G6)(G6) are be the same or different.

"Group Represented by —O—($R_{904}$)"

Specific examples of the group represented by —O—($R_{904}$) in this specification (specific example group G8) include:

—O(G1),
—O(G2),
—O(G3), and
—O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{905}$) in this specification (specific example group G9) include:

—S(G1),
—S(G2),
—S(G3), and
—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by -N($R_{906}$)($R_{907}$)"

Specific examples of the group represented by -N($R_{906}$)($R_{907}$) in this specification (specific example group G10) include:

—N(G1)(G1),
—N(G2)(G2),
—N(G1)(G2),
—N(G3)(G3), and
—N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —N(G1)(G1) are the same or different.

Plural G2's in —N(G2)(G2) are the same or different.

Plural G3's in —N(G3)(G3) are the same or different.

Plural G6's in —N(G6)(G6) are the same or different.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. Plural G3's in —Si(G3)(G3)(G3) are the same or different. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-α-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

(TEMP-Cz1)

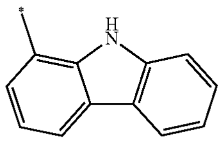

(TEMP-Cz2)

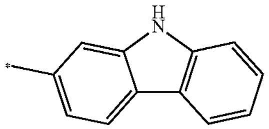

(TEMP-Cz3)

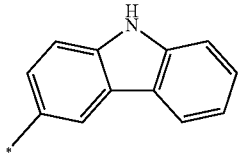

(TEMP-Cz4)

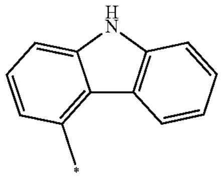

(TEMP-Cz5)

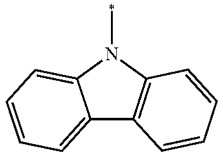

In this specification, the (9-phenyl)carbazolyl group is specifically any of the following groups, unless otherwise specified in this specification.

(TEMP-Cz6)

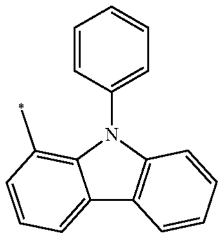

-continued (TEMP-Cz7)

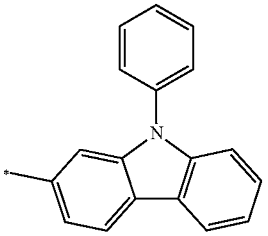

(TEMP-Cz8)

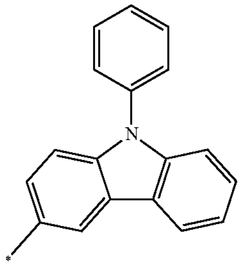

(TEMP-Cz9)

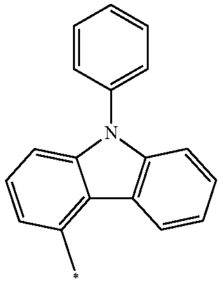

In the general formulas (TEMP-Cz1) to (TEMP-Cz9), * represents a bonding site.

In this specification, the dibenzofuranyl group and the dibenzothiophenyl group are specifically any of the following groups, unless otherwise specified in this specification.

(TEMP-34)

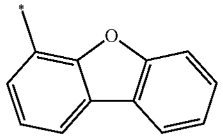

(TEMP-35)

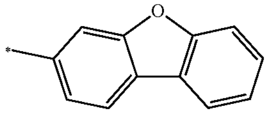

(TEMP-36)

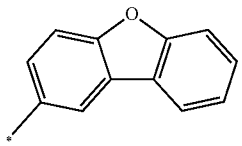

-continued (TEMP-37)

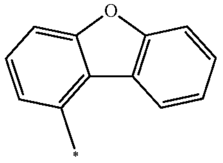

(TEMP-38)

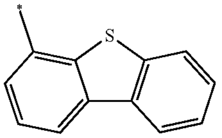

(TEMP-39)

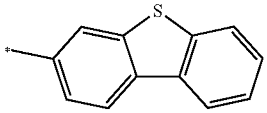

(TEMP-40)

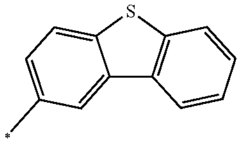

(TEMP-41)

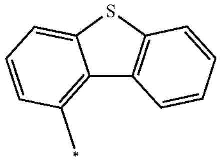

In the general formulas (TEMP-34) to (TEMP-41), * represents a bonding site.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocycle of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocycle of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

(TEMP-42)

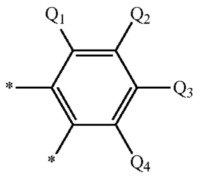

(TEMP-43)

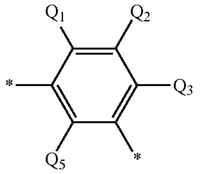

(TEMP-44)

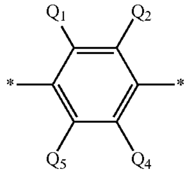

(TEMP-45)

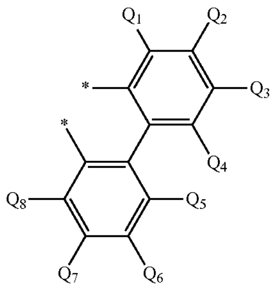

(TEMP-46)

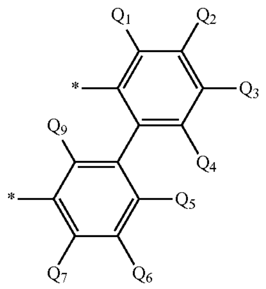

-continued
(TEMP-47)
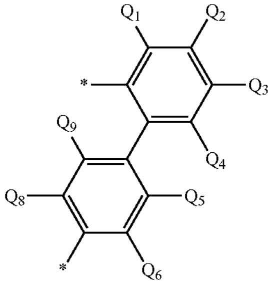
(TEMP-48)
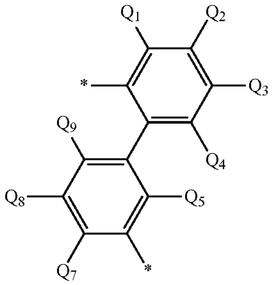
(TEMP-49)
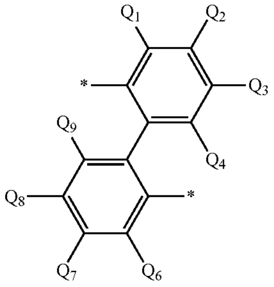
(TEMP-50)
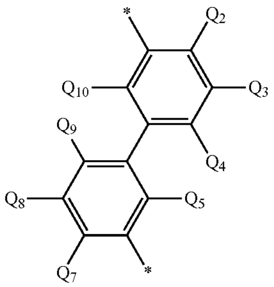
(TEMP-51)
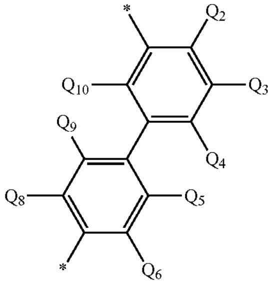
-continued
(TEMP-52)
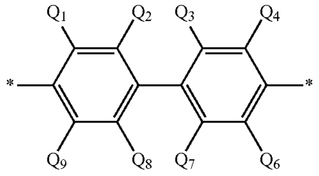
In the general formulas (TEMP-42) to (TEMP-52), $Q_1$ to $Q_{10}$ are independently a hydrogen atom or a substituent.
In the general formulas (TEMP-42) to (TEMP-52), * represents a bonding site.
(TEMP-53)
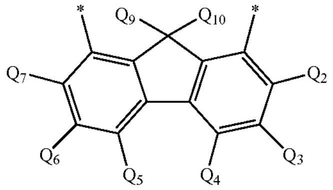
(TEMP-54)
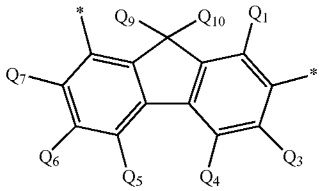
(TEMP-55)
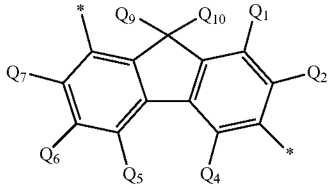
(TEMP-56)
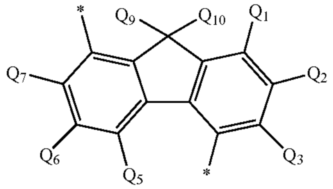
(TEMP-57)
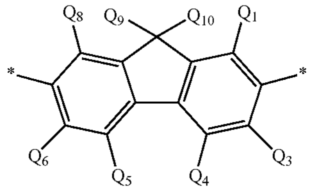
(TEMP-58)
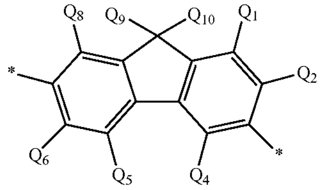

-continued (TEMP-59)

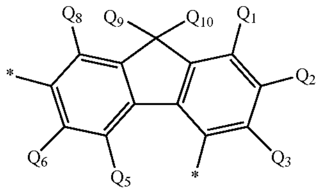

(TEMP-60)

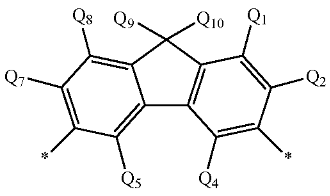

(TEMP-61)

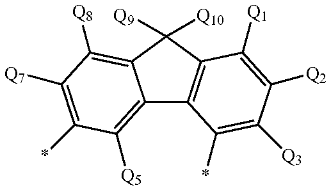

(TEMP-62)

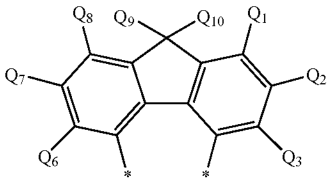

In the general formulas (TEMP-53) to (TEMP-62), $Q_1$ to $Q_{10}$ are independently a hydrogen atom or a substituent.

$Q_9$ and $Q_{10}$ may be bonded with each other via a single bond to form a ring.

In the general formulas (TEMP-53) to (TEMP-62), * represents a bonding site.

(TEMP-63)

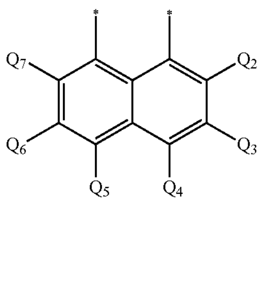

(TEMP-64)

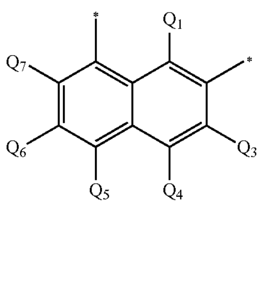

-continued (TEMP-65)

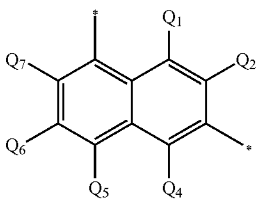

(TEMP-66)

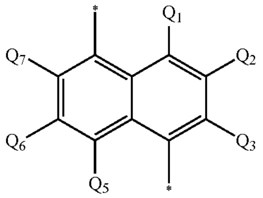

(TEMP-67)

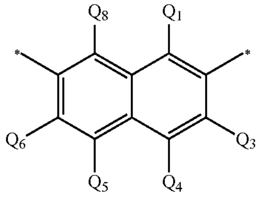

(TEMP-68)

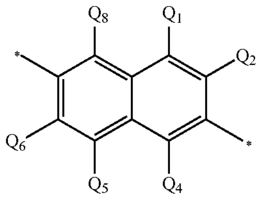

In the general formulas (TEMP-63) to (TEMP-68), $Q_1$ to $Q_8$ are independently a hydrogen atom or a substituent.

In the general formulas (TEMP-63) to (TEMP-68), * represents a bonding site.

The substituted or unsubstituted divalent heterocyclic group described in this specification is preferably any group of the following general formulas (TEMP-69) to (TEMP-102), unless otherwise specified in this specification.

(TEMP-69)

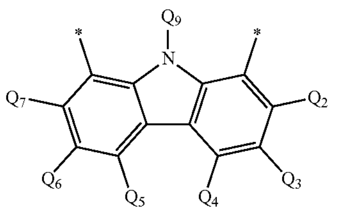

(TEMP-70)

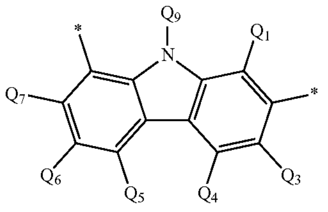

-continued
(TEMP-71)
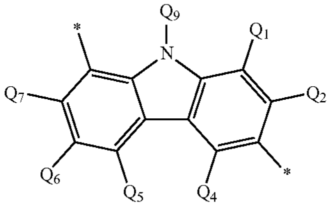
(TEMP-72)
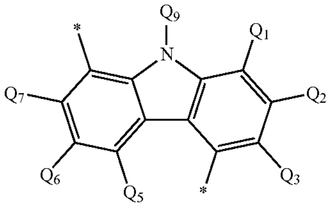
(TEMP-73)
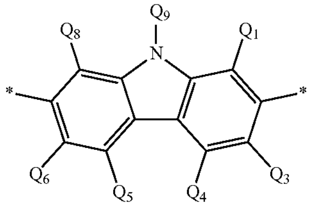
(TEMP-74)
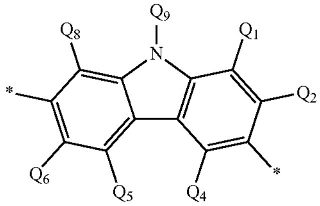
(TEMP-75)
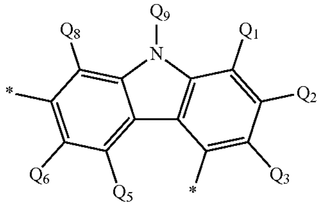
(TEMP-76)
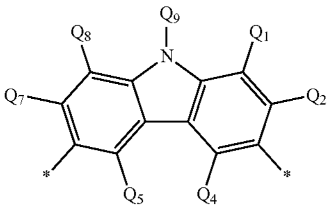
(TEMP-77)
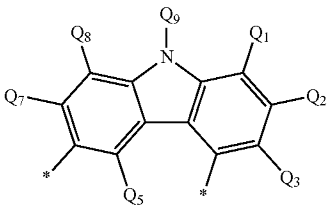
-continued
(TEMP-78)
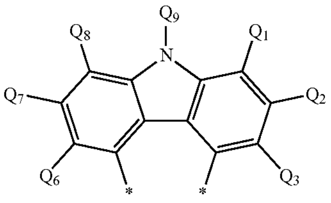
(TEMP-79)
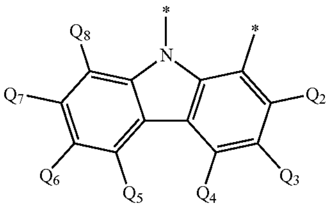
(TEMP-80)
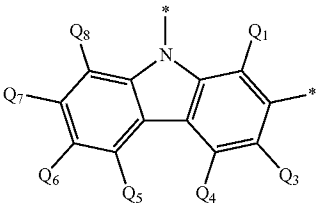
(TEMP-81)
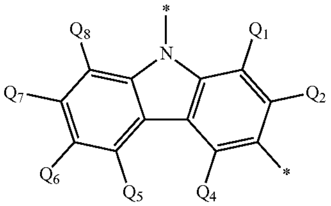
(TEMP-82)
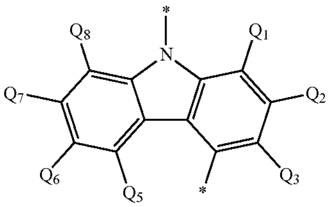
In the general formulas (TEMP-69) to (TEMP-82), $Q_1$ to $Q_9$ are independently a hydrogen atom or a substituent.
(TEMP-83)
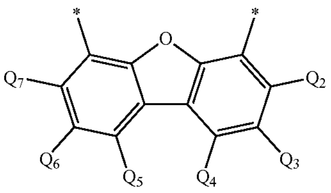
(TEMP-84)
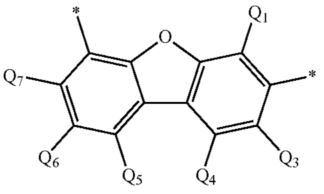

-continued
(TEMP-85)
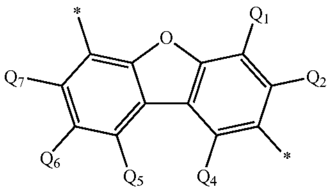
(TEMP-86)
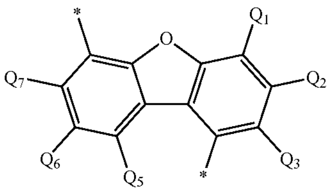
(TEMP-87)
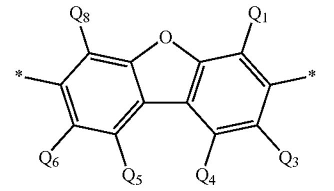
(TEMP-88)
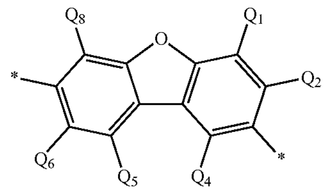
(TEMP-89)
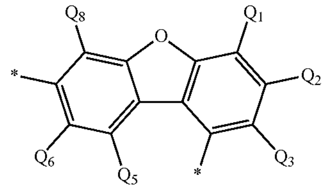
(TEMP-90)
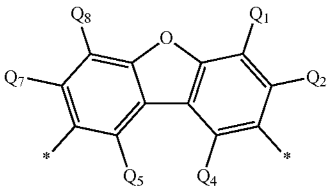
(TEMP-91)
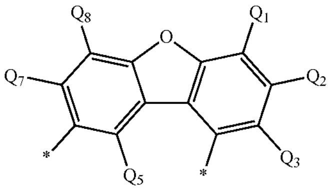
(TEMP-92)
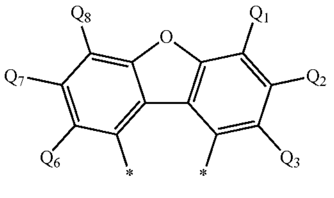
-continued
(TEMP-93)
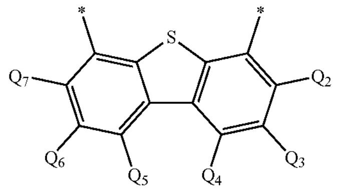
(TEMP-94)
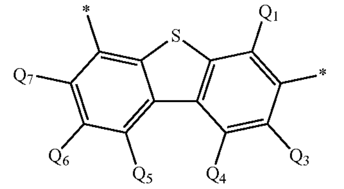
(TEMP-95)
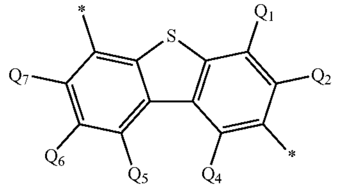
(TEMP-96)
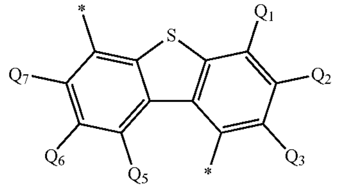
(TEMP-97)
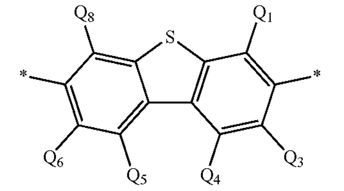
(TEMP-98)
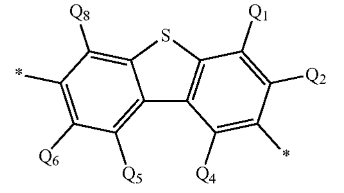
(TEMP-99)
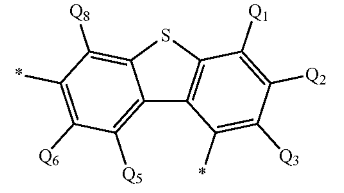
(TEMP-100)
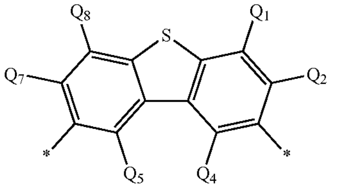

-continued (TEMP-101)

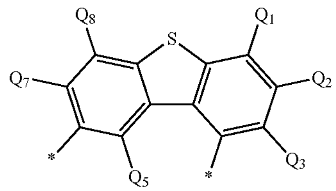

(TEMP-102)

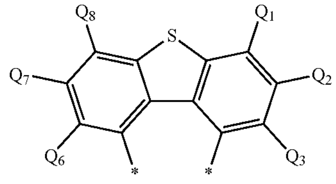

In the general formulas (TEMP-83) to (TEMP-102), $Q_1$ to $Q_8$ are independently a hydrogen atom or a substituent.

The above is the explanation of the "Substituent described in this specification."

"the Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

(TEMP-103)

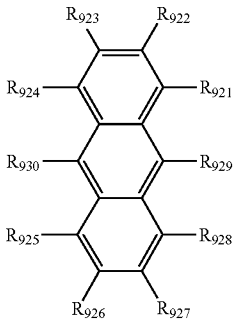

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{p23}$, a pair of $R_{923}$ and $R_{924}$, a pair of $R_{924}$ and $R_{930}$, a pair of $R_{930}$ and $R_{925}$, a pair of $R_{925}$ and 926, a pair of $R_{926}$ and $R_{927}$, a pair of $R_{927}$ and 928, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

(TEMP-104)

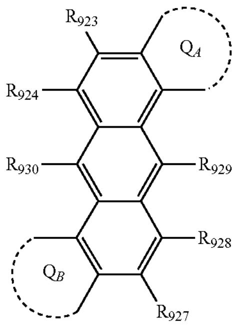

The case where the "set of adjacent two or more" form a ring includes not only the case where the set (pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and 8923 form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

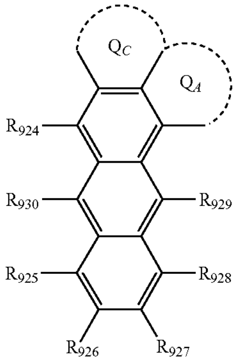

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may form a saturated ring or an unsaturated ring. For example, the ring $Q_A$ and the ring $Q_B$ formed in the general formula (TEMP-104) are independently a "monocycle" or a "fused ring." The ring $Q_A$ and the ring $Q_C$ formed in the general formula (TEMP-105) are "fused ring." The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" includes, in addition to an aromatic hydrocarbon ring and an aromatic heterocycle, an aliphatic hydrocarbon ring with an unsaturated bond, i.e., double and/or triple bonds in the ring structure (e.g., cyclohexene, cyclohexadiene, etc.), and a non-aromatic heterocycle with an unsaturated bond (e.g., dihydropyran, imidazoline, pyrazoline, quinolizine, indoline, isoindoline, etc.). The "saturated ring" includes an aliphatic hydrocarbon ring without an unsaturated bond and a non-aromatic heterocycle without ab unsaturated bond.

Specific examples of the aromatic hydrocarbon ring include a structure in which the group listed as a specific example in the specific example group G1 is terminated by a hydrogen atom.

Specific examples of the aromatic heterocycle include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with plural atoms of the mother skeleton, or with plural atoms of the mother skeleton and one or more arbitrary atoms in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary atoms. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary atom" is preferably at least one atom selected from the group consisting of a carbon atom, a nitrogen atom, an oxygen atom, and a sulfur atom, unless otherwise specified in this specification. In the arbitrary atom (for example, a carbon atom or a nitrogen atom), a bond which does not form a ring may be terminated with a hydrogen atom or the like, or may be substituted with "arbitrary substituent" described below. When an arbitrary atom other than a carbon atom is contained, the ring formed is a heterocycle.

The number of "one or more arbitrary atom(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from plural atoms of the mother skeleton and one or more and 15 or less atoms which is at least one kind selected from a carbon atom, a nitrogen atom, an oxygen atom, and a sulfur atom.

The substituent in the case where the above-mentioned "monocycle" or "fused ring" has a substituent is, for example, an "arbitrary substituent" described below. Specific examples of the substituent which the above-mentioned "monocycle" or "fused ring" has include the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has include the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the Case of "Substituted or Unsubstituted"

In one embodiment in this specification, the substituent (in this specification, sometimes referred to as an "arbitrary substituent") in the case of "substituted or unsubstituted" is, for example, a group selected from the group consisting of:

an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
$—Si(R_{901})(R_{902})(R_{903})$,
$—O—(R_{904})$,
$—S—(R_{905})$,
$—N(R_{906})(R_{907})$,
a halogen atom, a cyano group, a nitro group,
an unsubstituted aryl group including 6 to 50 ring carbon atoms, and
an unsubstituted heterocyclic group including 5 to 50 ring atoms, wherein, $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted heterocyclic group including 5 to 50 ring atoms.

When two or more $R_{901}$'s are present, the two or more $R_{901}$'s may be the same or different.

When two or more $R_{902}$'s are present, the two or more $R_{902}$'s may be the same or different.

When two or more $R_{903}$'s are present, the two or more $R_{903}$'s may be the same or different.

When two or more $R_{904}$'s are present, the two or more $R_{904}$'s may be the same or different.

When two or more $R_{905}$'s are present, the two or more $R_{905}$'s may be the same or different.

When two or more $R_{906}$'s are present, the two or more $R_{906}$'s may be the same or different.

When two or more $R_{907}$'s are present, the two or more $R_{907}$'s may be the same or different.

In one embodiment, the substituent in the case of "substituted or unsubstituted" is a group selected from the group consisting of:

an alkyl group including 1 to 50 carbon atoms, an aryl group including 6 to 50 ring carbon atoms, and a heterocyclic group including 5 to 50 ring atoms.

In one embodiment, the substituent in the case of "substituted or unsubstituted" is a group selected from the group consisting of:

an alkyl group including 1 to 18 carbon atoms, an aryl group including 6 to 18 ring carbon atoms, and a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Compound]

A compound according to an aspect of the present invention is represented by the following formula (1).

(1)

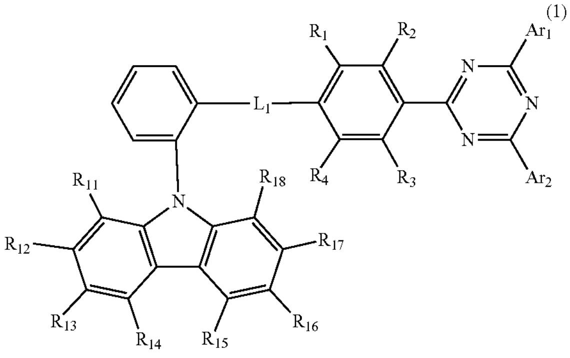

In the formula (1), $Ar_1$ and $Ar_2$ are independently an unsubstituted aryl group having 6 to 50 ring carbon atoms;

$R_1$ and $R_2$ form an unsubstituted, saturated or unsaturated hydrocarbon ring having 6 to 50 ring carbon atoms by bonding with each other, or do not form the ring;

$R_3$ and $R_a$, and $R_1$ and $R_2$ which do not form the ring are independently a hydrogen atom, or a substituent $R_a$;

one or more sets of the adjacent two or more of $R_{11}$ to $R_{18}$ form an unsubstituted, saturated or unsaturated hydrocarbon ring having 6 to 50 ring carbon atoms, or an unsubstituted, saturated or unsaturated heterocyclic ring having 5 to 50 ring atoms, by bonding with each other, or do not form the rings;

$R_{11}$ to $R_{18}$ which do not form the rings are independently a hydrogen atom, or a substituent $R_a$;

$L_1$ is a single bond, or a divalent group represented by any one of the following formulas (a1) to (a9):

(a1)

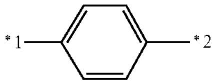

(a2)

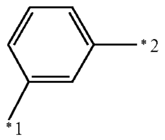

(a3)

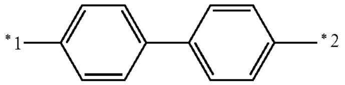

(a4)

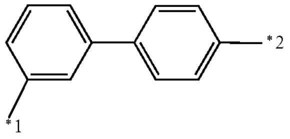

(a5)

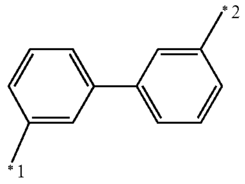

(a6)

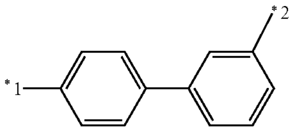

(a7)

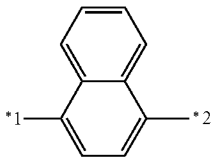

(a8)

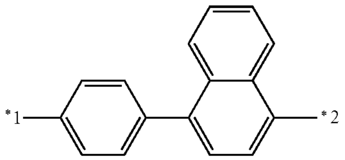

-continued (a9)

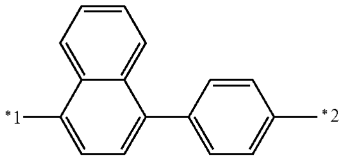

wherein in the formulas (a1) to (a9), *1 is bonded with a benzene ring on a carbazolyl group side, and *2 is bonded with a benzene ring on a triazine ring side.

When two or more substituents $R_a$ are present, the two or more substituents $R_a$ may be the same as or different from each other.

The compound represented by the formula (1) is useful as a material for an organic electroluminescence device.

The compound represented by the formula (1)(hereinafter, frequently referred to as compound (1)) is particularly useful as an electron-transporting material for an organic EL device.

The compound (1) has an effect of prolonging the lifetime of the organic EL device fabricated using the same. When the compound (1) is used, a blue emitting organic EL device with long lifetime can be obtained.

The compound (1) is described below.

In the compound (1), the N-carbazolyl group is bonded to the linker $L_1$ via the o-phenylene group, and the triazine ring is bonded to the same linker $L_1$ via the substituted or unsubstituted p-phenylene group.

When the compound (1) has the structure that the N-carbazolyl group is bonded to the linker $L_1$ via the o-phenylene group, luminous efficiency can be expected to improve.

When the compound (1) has the structure that the triazine ring is bonded to the same linker $L_1$ via the p-phenylene group, an effect of prolonging the lifetime of the organic EL device can be obtained.

In one embodiment, the compound represented by the formula (1) is a compound represented by any one of the following formulas (2-1) to (2-8).

(2-1)

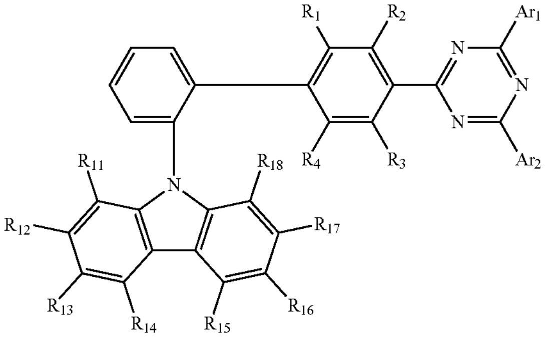

-continued (2-2)

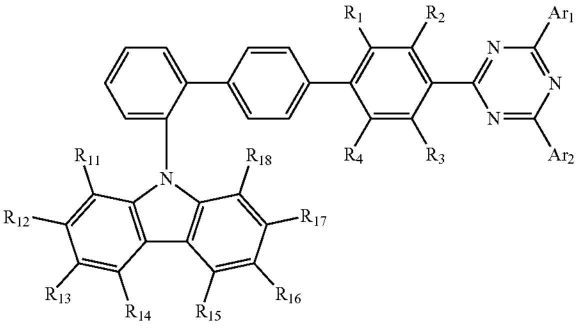

(2-3)

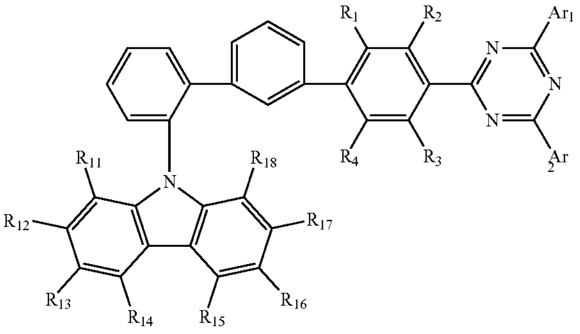

(2-4)

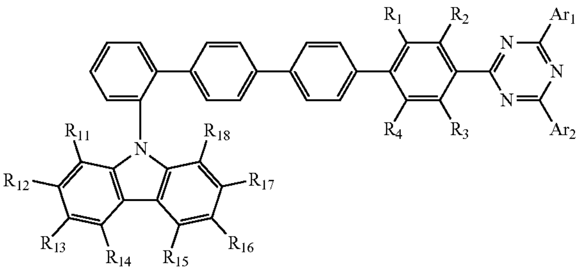

(2-5)

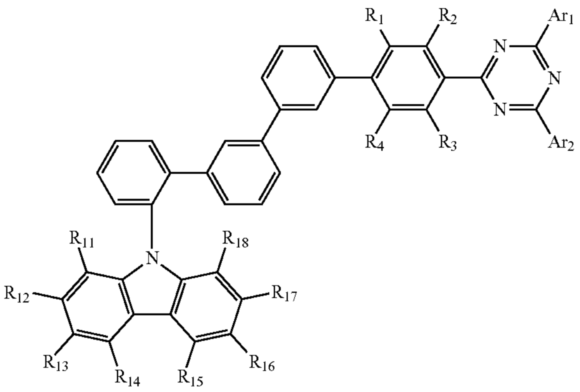

-continued (2-6)

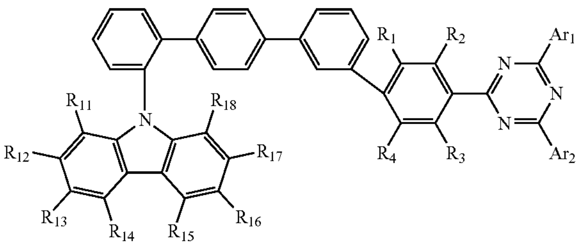

(2-7)

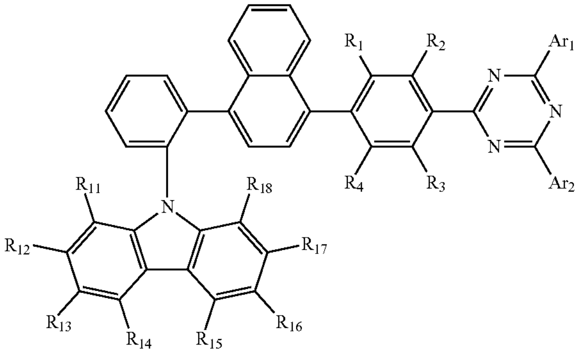

(2-8)

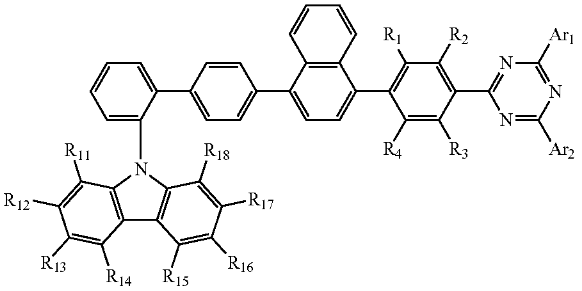

In the formulas (2-1) to (2-8), $Ar_1$, $Ar_2$, $R_1$ to $R_4$, and $R_{11}$ to $R_{18}$ are the same as defined in the formula (1).

In one embodiment, $L_1$ in the formula (1) is a single bond, or a group represented by the formula (a1). The group represented by the formula (a1) means that $L_1$ is a p-phenylene group.

In one embodiment, $Ar_1$ and $Ar_2$ in the formula (1) are independently an unsubstituted phenyl group, an unsubstituted biphenyl group, an unsubstituted terphenyl group, an unsubstituted naphthyl group, or an unsubstituted phenanthryl group.

In one embodiment, $Ar_1$ and $Ar_2$ in the formula (1) are independently a group represented by any one of the following formulas (b1) to (b4).

(b1)

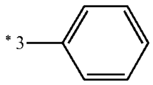

(b2)

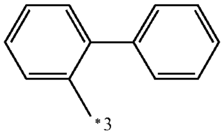

(b3)

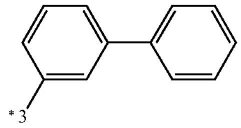

(b4)

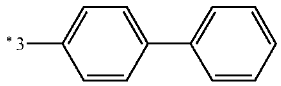

In the formulas (b1) to (b4), *3 represents a binding site with a triazine ring.

In one embodiment, the compound represented by the formula (1) is a compound represented by any one of the following formulas (4-1) to (4-6).

(4-1)

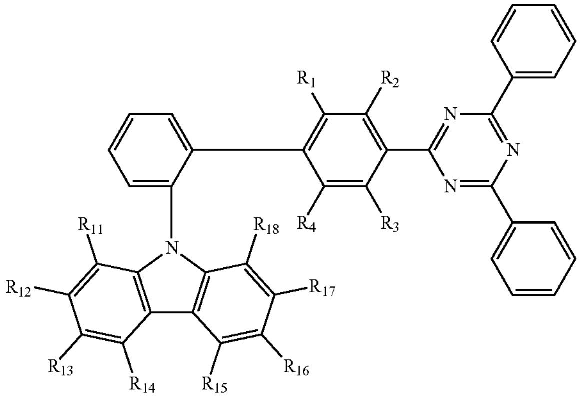

(4-2)

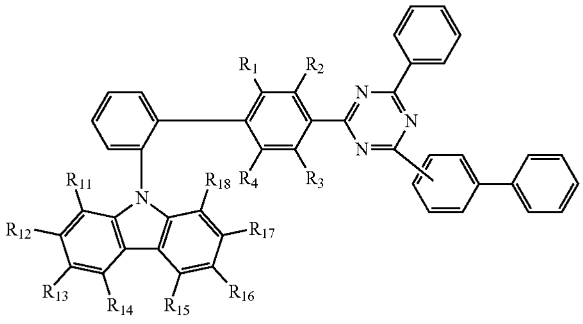

-continued
(4-3)
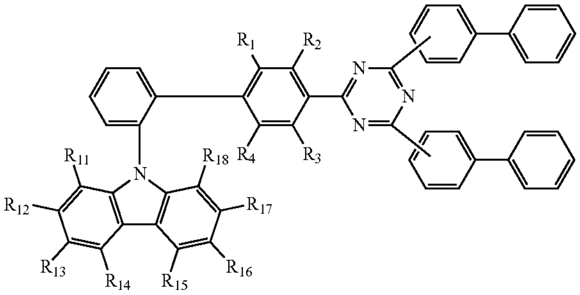
(4-4)
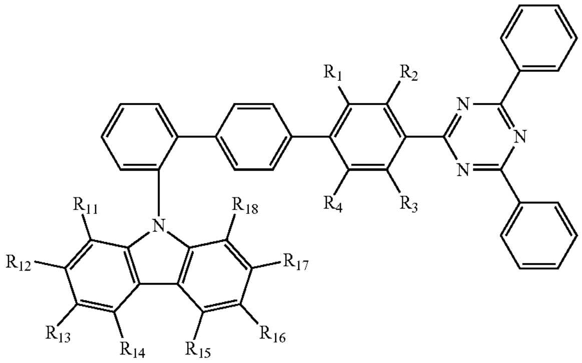
(4-5)
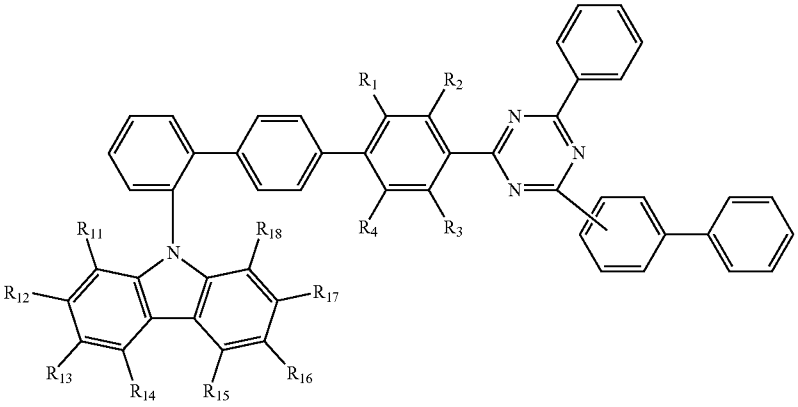
(4-6)
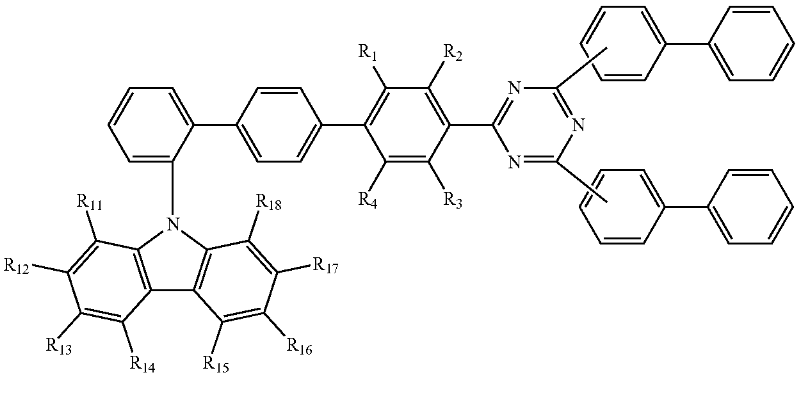

In the formulas (4-1) to (4-6), $R_1$ to $R_4$, and $R_{11}$ to $R_{18}$ are the same as defined in the formula (1).

In one embodiment, $R_1$ and $R_2$ in the formula (1) are a hydrogen atom. That is, the compound represented by the formula (1) is a compound represented by the following formula (3-1).

(3-1)

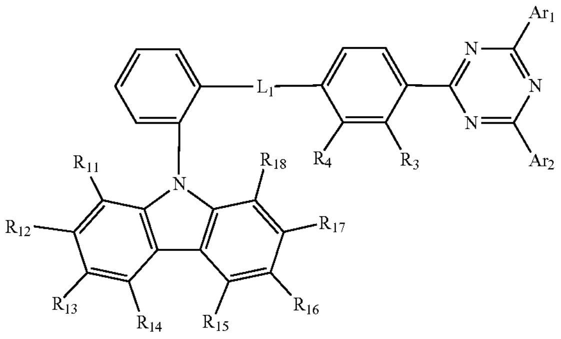

In the formula (3-1), $Ar_1$, $Ar_2$, $R_3$, $R_4$, and $R_{11}$ to $R_{18}$ are the same as defined in the formula (1).

In one embodiment, the compound represented by the formula (1) is a compound represented by the following formula (5).

(5)

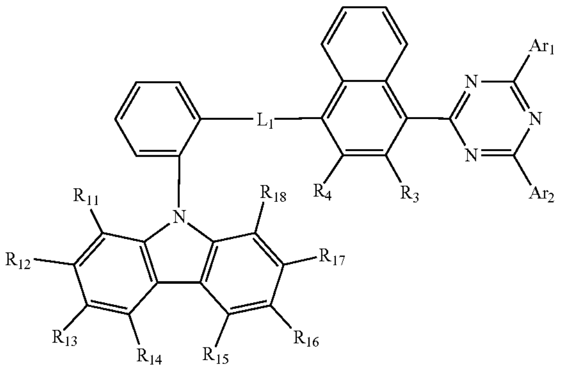

In the formula (5), $L_1$, $Ar_1$, $Ar_2$, $R_3$, $R_4$, and $R_{11}$ to $R_{18}$ are the same as defined in the formula (1).

In one embodiment, $R_3$ and $R_4$ in the formula (1) are a hydrogen atom.

In one embodiment, $R_{11}$ to $R_{18}$ in the formula (1) are a hydrogen atom.

In one embodiment, the substituent $R_a$ is selected from the group consisting of a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, and a substituted or unsubstituted aryl group having 6 to 50 ring carbon atoms (wherein, $R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, or a substituted or unsubstituted aryl group having 6 to 50 ring carbon atoms; when two or more of each of $R_{901}$ to $R_{907}$ are present, the two or more of each of $R_{901}$ to $R_{907}$ may be the same as or different from each other).

In one embodiment, the substituent $R_a$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms.

The atoms and groups are the same as described detailedly in [Definition] of the present specification.

As defined in the Definition, the "hydrogen atom" used in the present specification includes a protium atom, a deuterium atom, and a tritium atom. Accordingly, the inventive compounds may contain naturally derived deuterium atoms.

In addition, deuterium atoms may be intentionally introduced into the inventive compound by using a deuterated compound as a part or all of raw material compounds. Accordingly, in one embodiment of the present invention, the compound represented by the formula (1) includes at least one deuterium atom. That is, the compound of the present embodiment may be the compound represented by the formula (1), wherein at least one of hydrogen atoms contained in the compound is a deuterium atom.

In the compound represented by the formula (1), at least one hydrogen atom selected from hydrogen atoms possessed by the unsubstituted aryl group represented by $Ar_1$ and $Ar_2$;

hydrogen atoms represented by $R_1$ to $R_4$, and $R_{11}$ to $R_{18}$; hydrogen atoms possessed by the substituent $R_a$ represented by $R_1$ to $R_4$, and $R_{11}$ to $R_{18}$, hydrogen atoms possessed by the hydrocarbon ring, when $R_1$ and $R_2$ form an unsubstituted, saturated or unsaturated hydrocarbon ring by bonding with each other;

hydrogen atoms possessed by the hydrocarbon ring and the heterocyclic ring, when one or more sets of the adjacent two or more of $R_{11}$ to $R_{18}$ form the unsubstituted, saturated or unsaturated hydrocarbon ring, or the unsubstituted, saturated or unsaturated heterocyclic ring, by bonding with each other;

hydrogen atoms possessed by the divalent group represented by any one of the formulas (a1) to (a9) represented by $L_1$;

may be a deuterium atom.

The deuteration rate of the compound depends on the deuteration rate of the raw material compounds used. Even if a raw material having a predetermined deuteration rate is used, a protium atom isotope may be included at a certain proportion derived naturally. Accordingly, an aspect of the deuteration rate includes a proportion in which a trace amount of naturally derived isotopes is considered, based on a proportion obtained by simply counting the number of deuterium atoms represented by the chemical formula.

In one embodiment, the deuteration rate of the compound is preferably 1% or more, more preferably 3% or more, still more preferably 5% or more, still more preferably 10% or more, and still more preferably 50% or more.

Specific examples of the compound represented by the formula (1) will be described below, but these are merely examples, and the compound represented by the formula (1) is not limited to the following specific examples. In the following specific examples, "D" represents a deuterium atom.

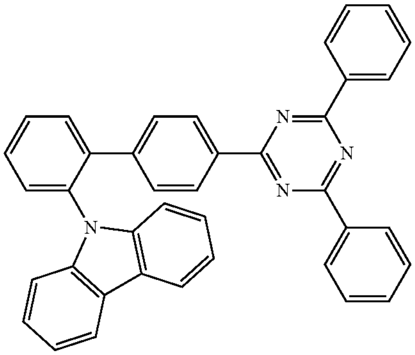

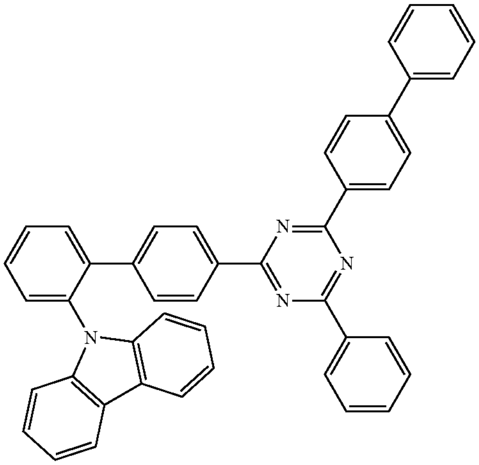

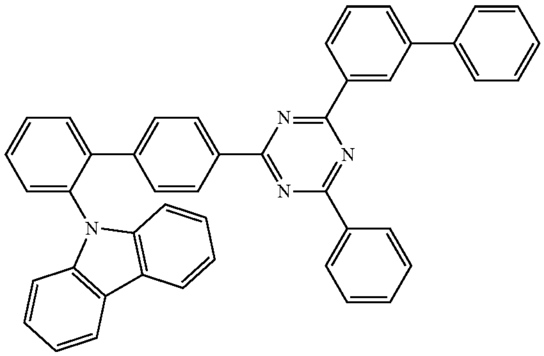

-continued

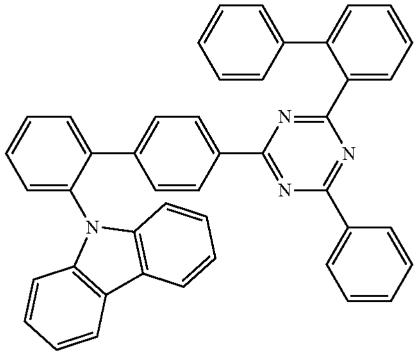

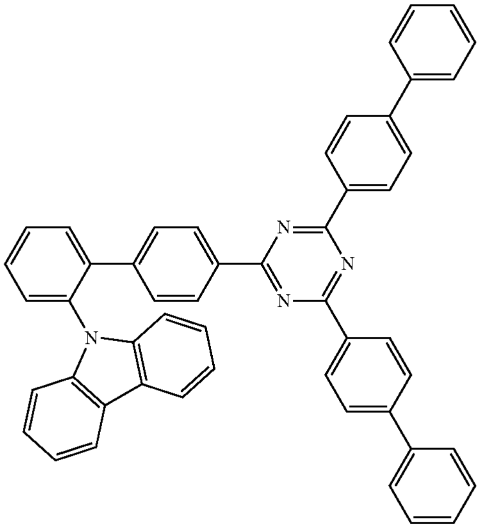

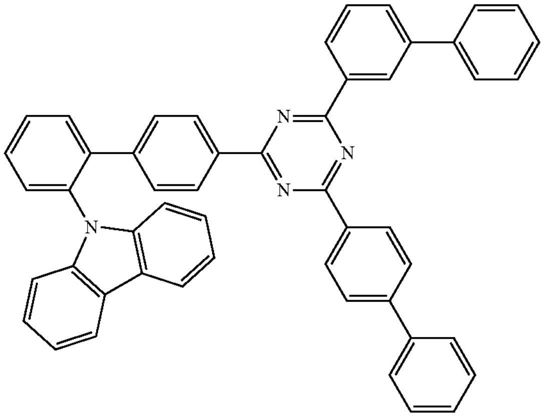

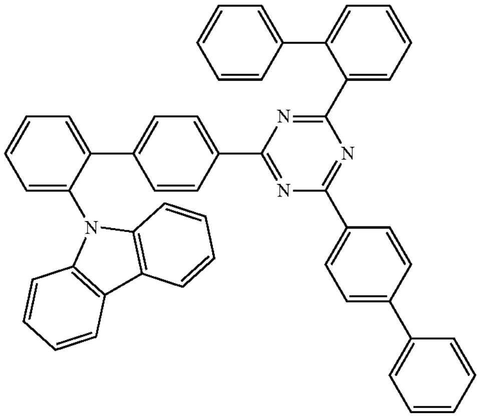

-continued
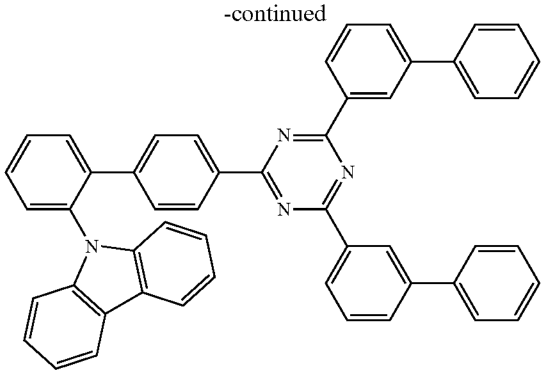
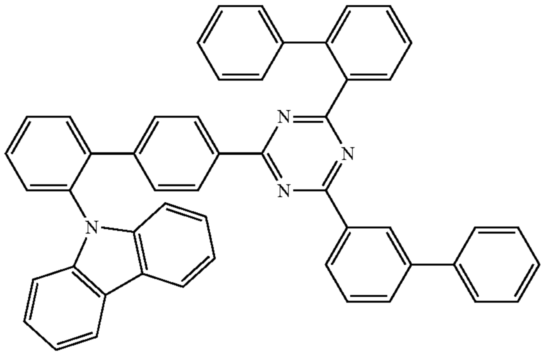
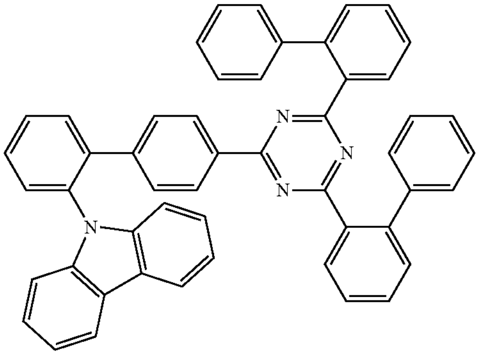
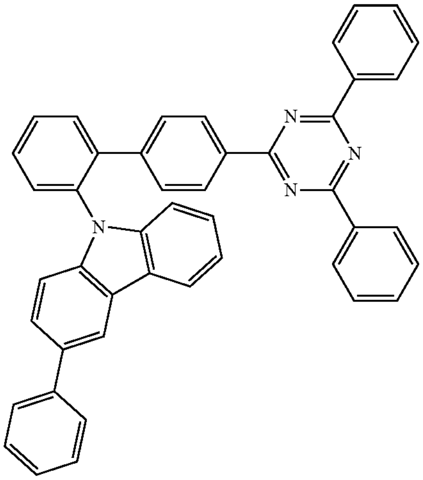
-continued
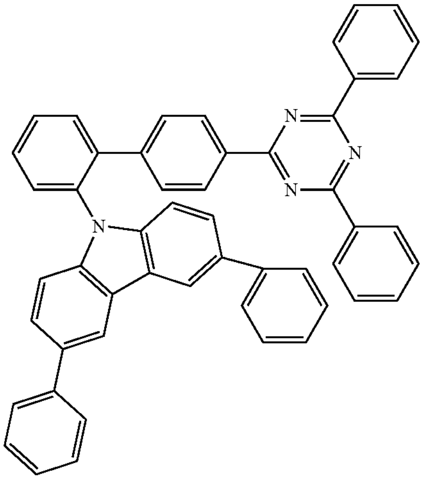
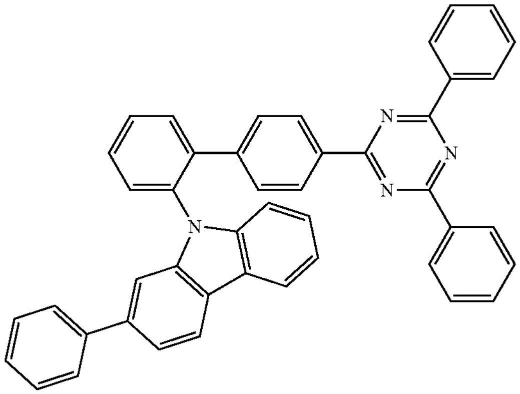
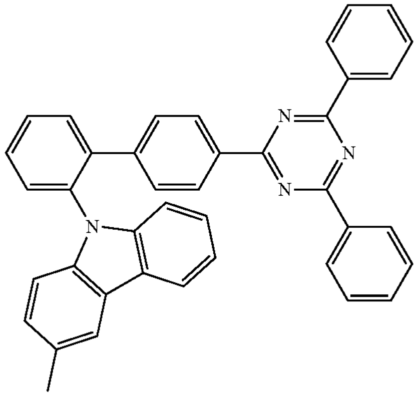
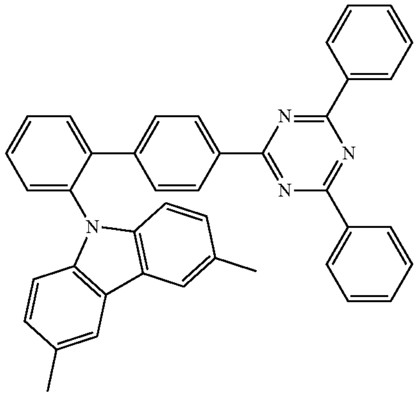

-continued
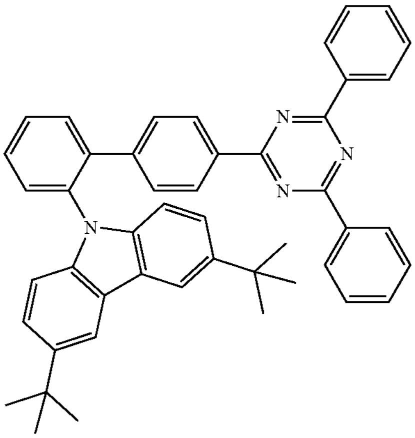
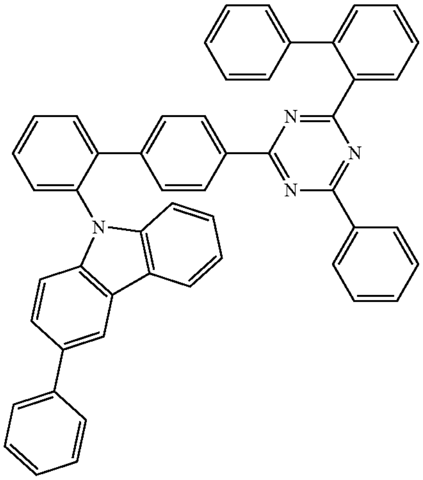
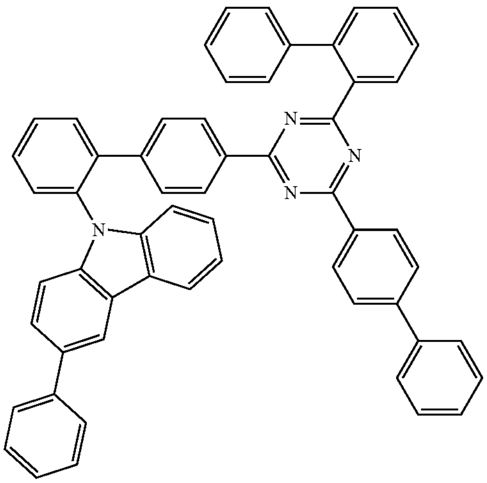
-continued
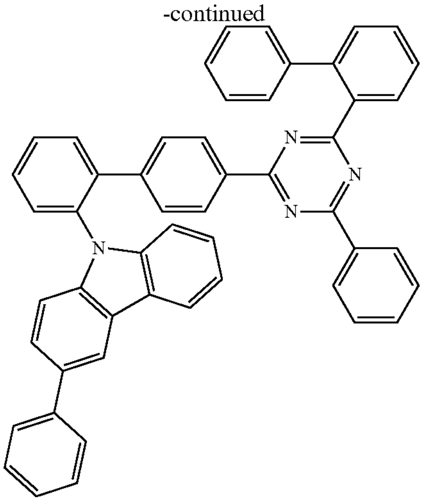
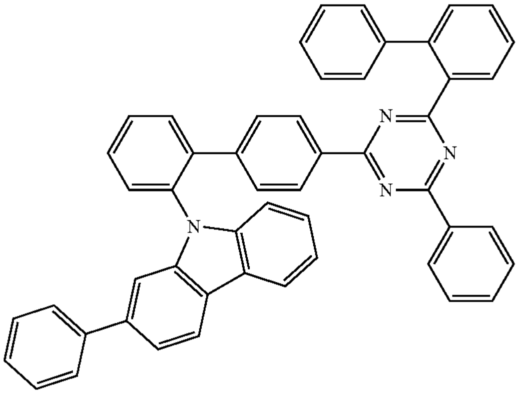
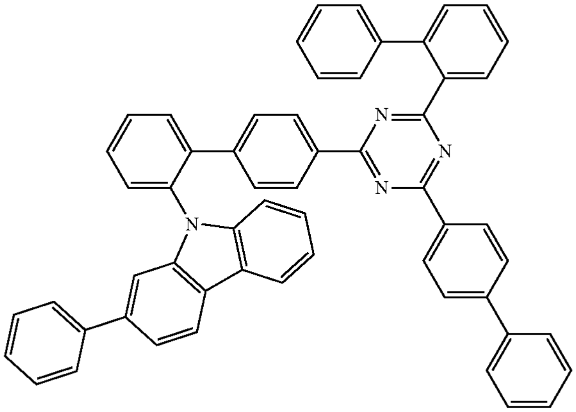
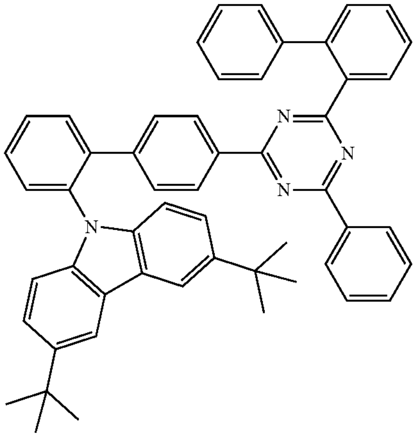

-continued
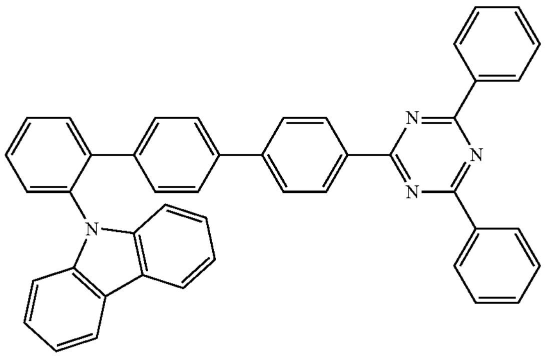
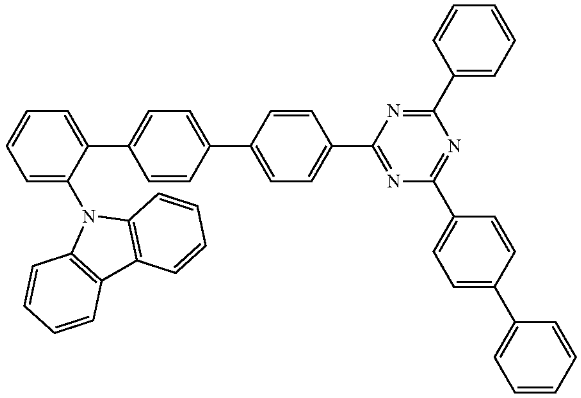
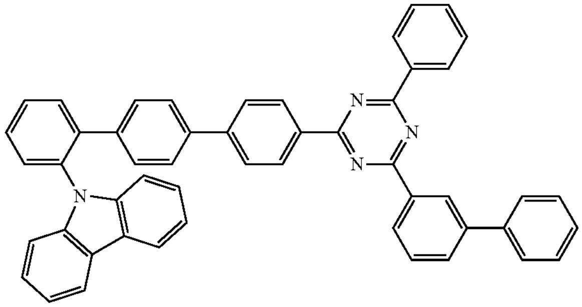
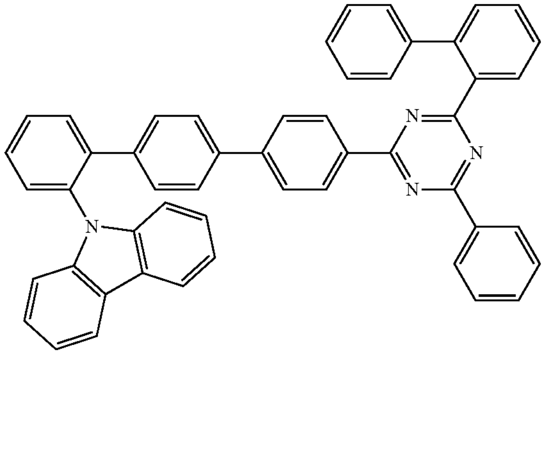
-continued
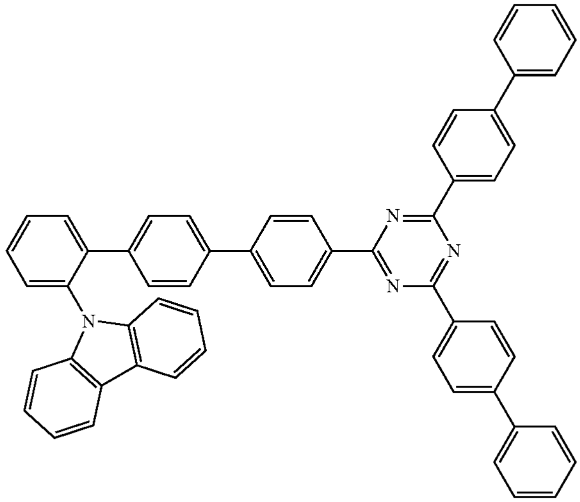
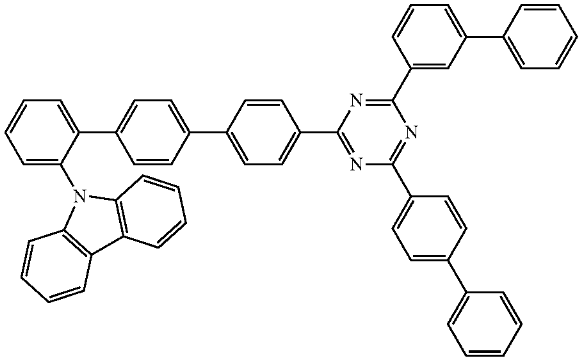
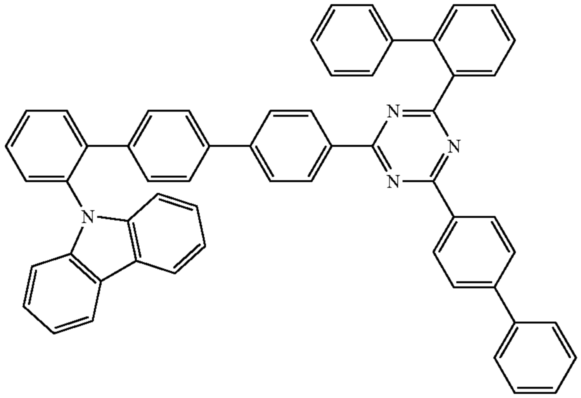
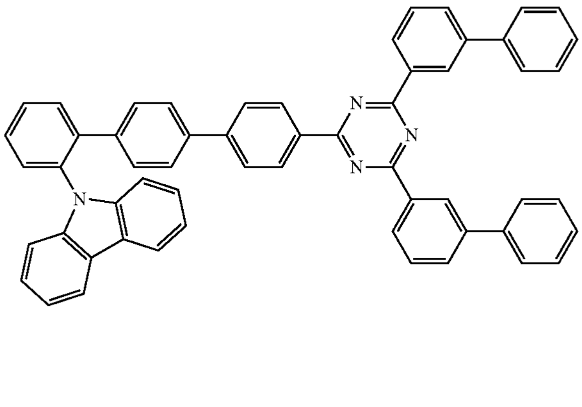

-continued
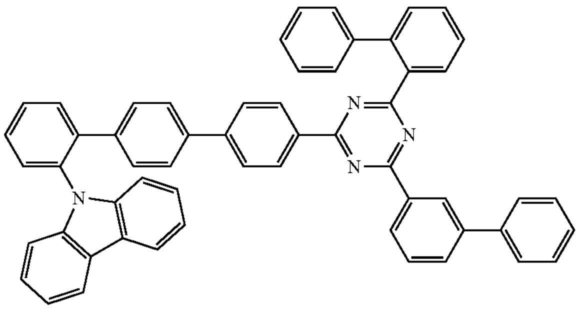
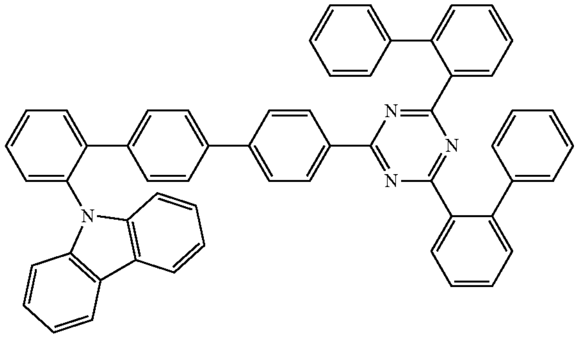
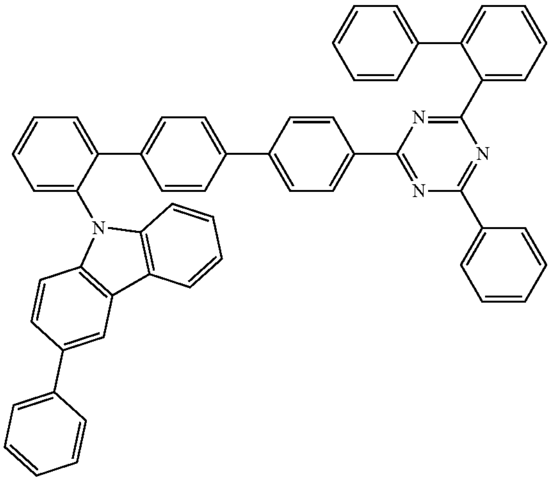
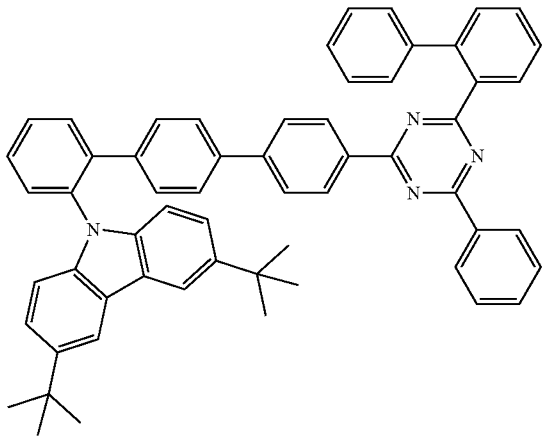
-continued
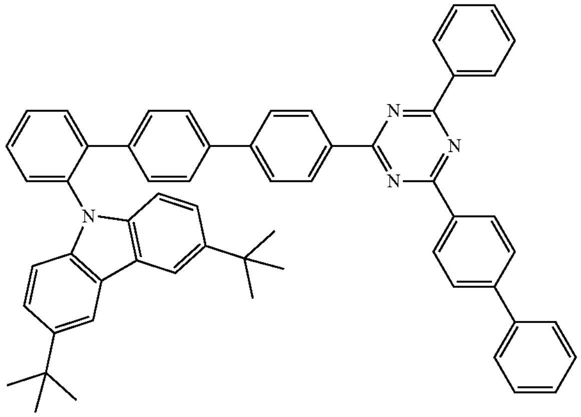
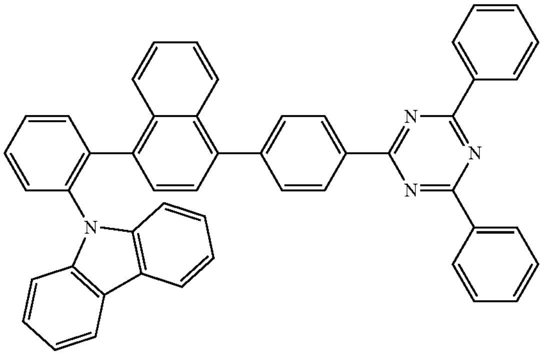
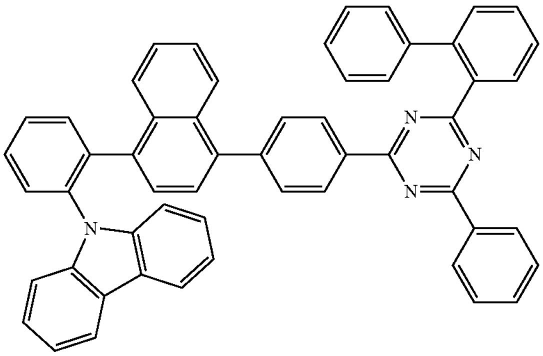
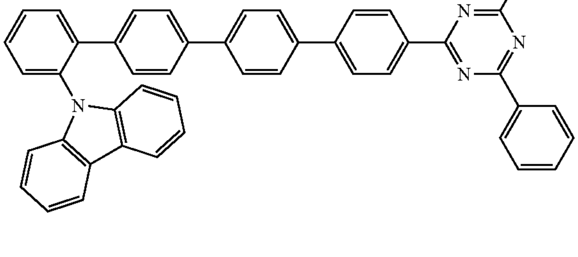

-continued
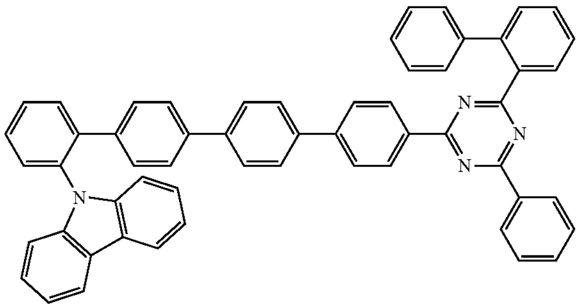
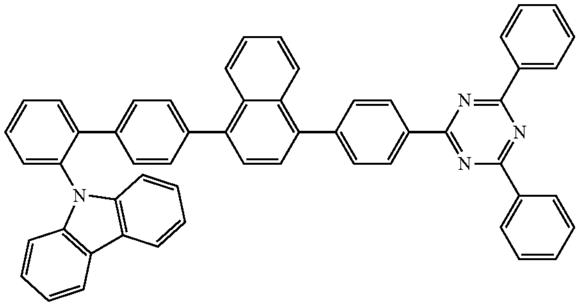
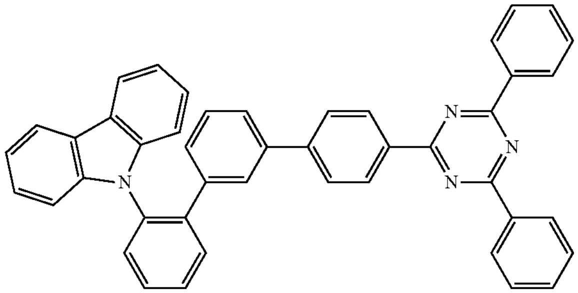
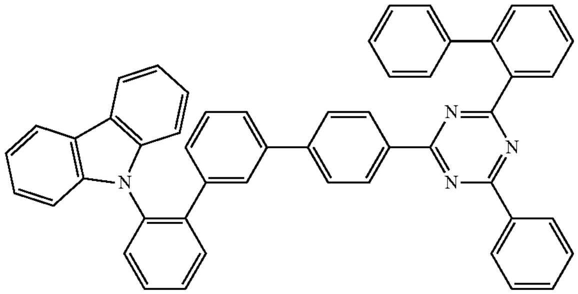
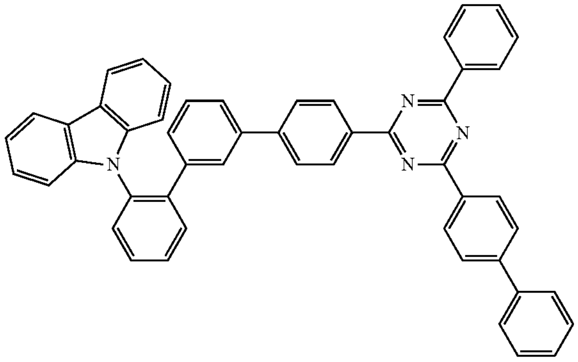
-continued
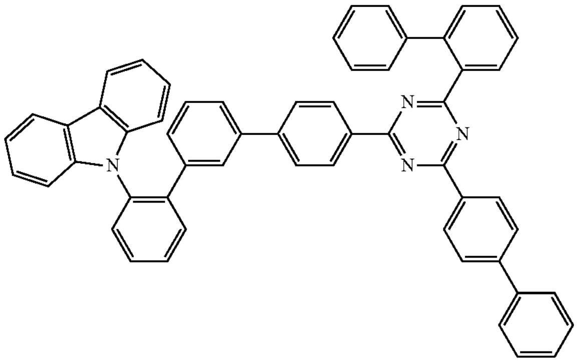
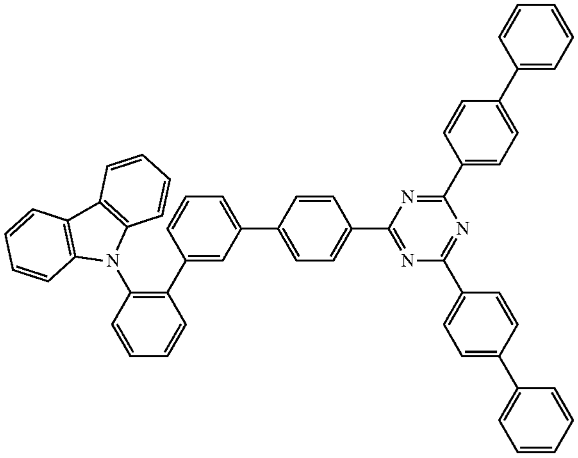
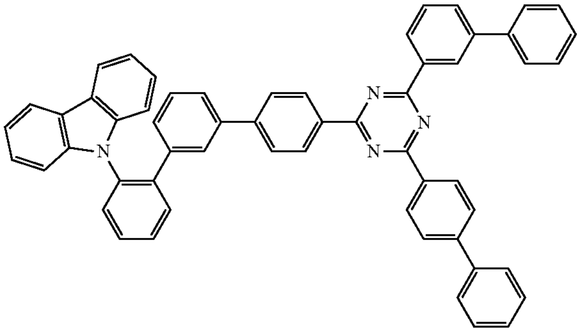
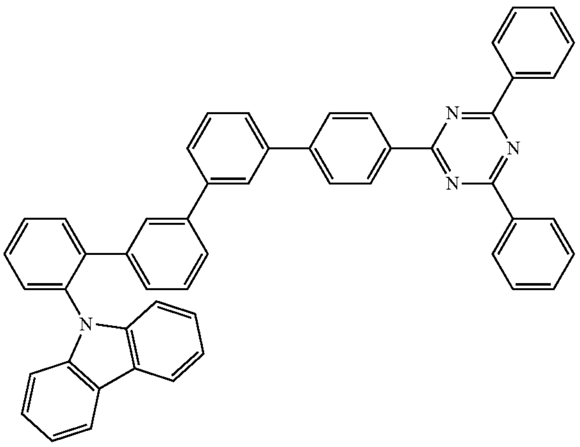

-continued
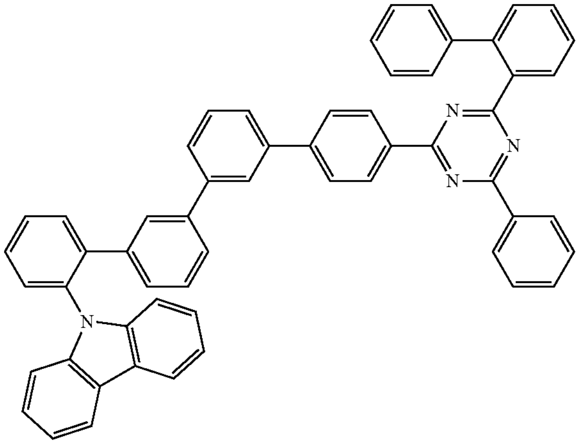
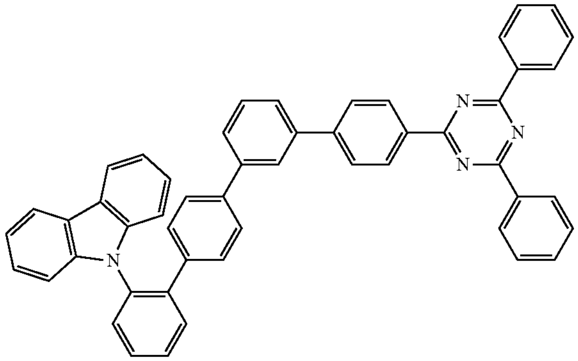
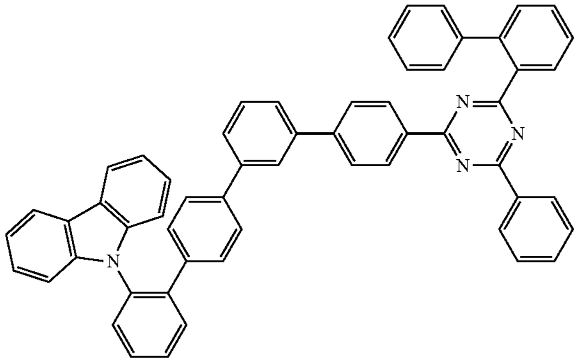
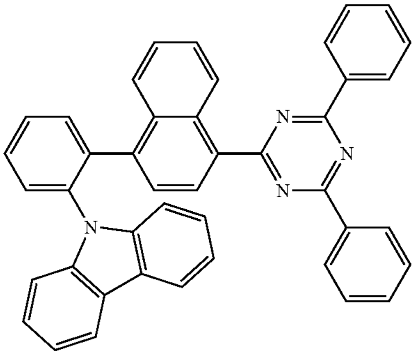
-continued
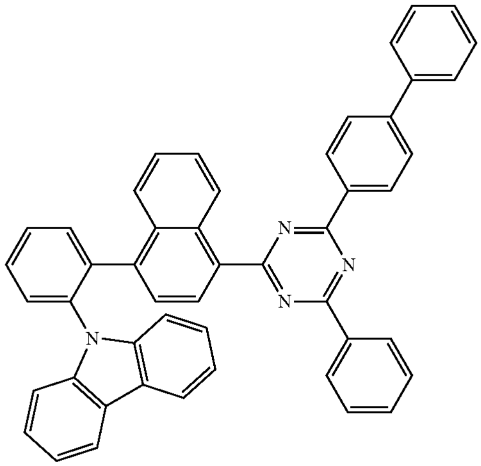
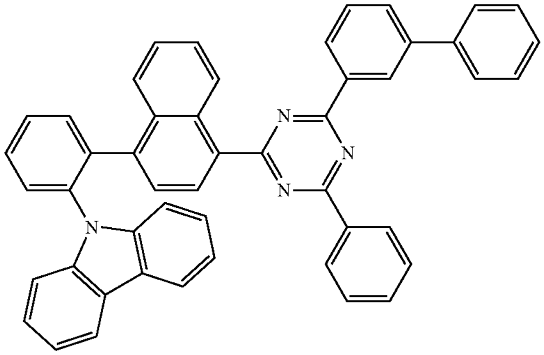
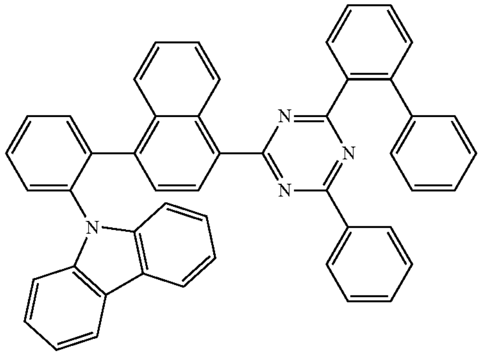
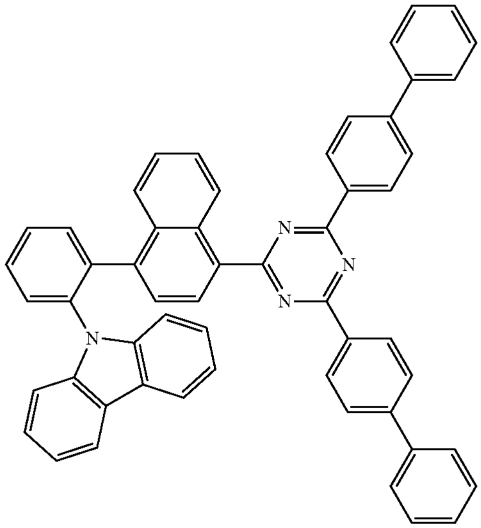

-continued
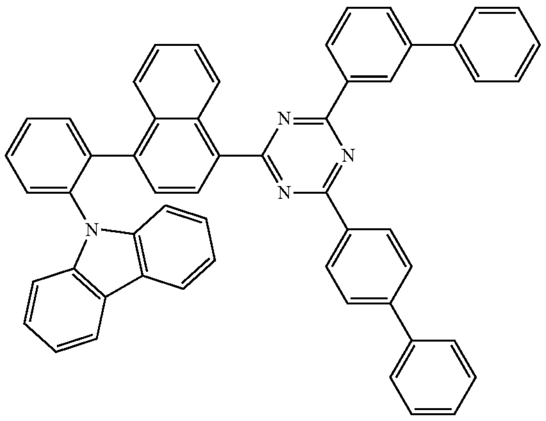
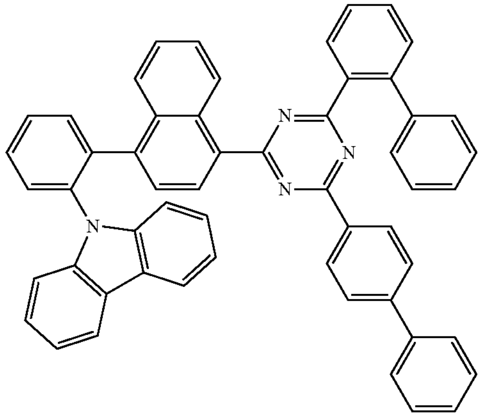
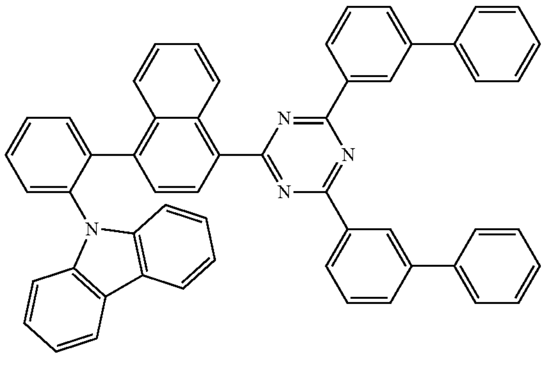
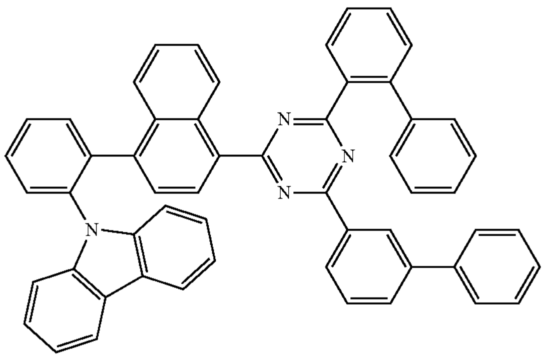
-continued
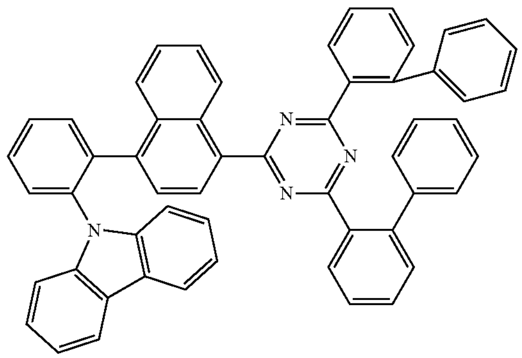
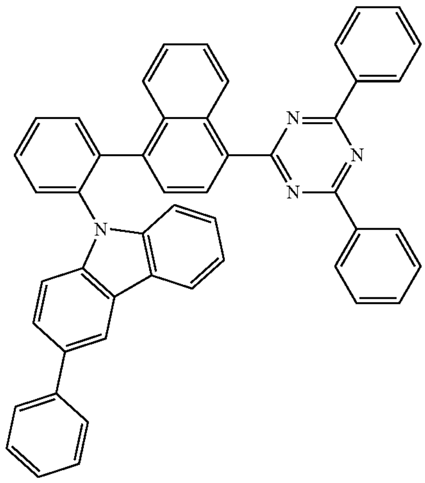
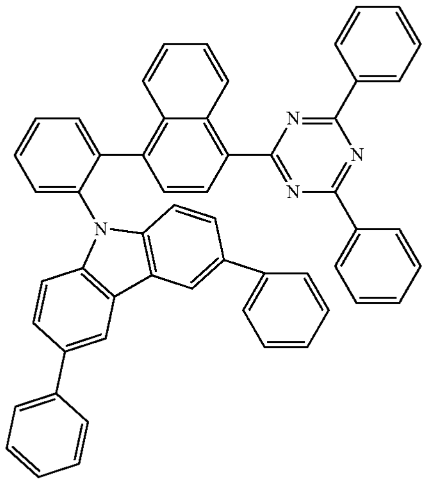
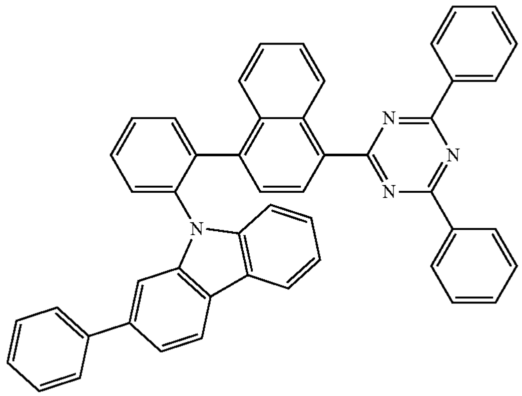

-continued
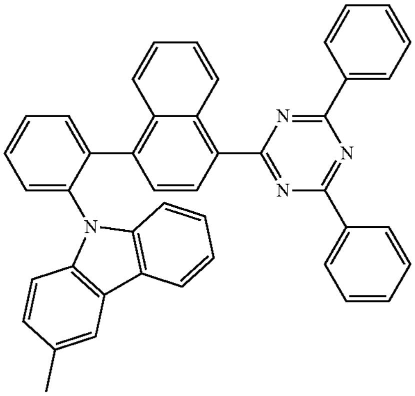
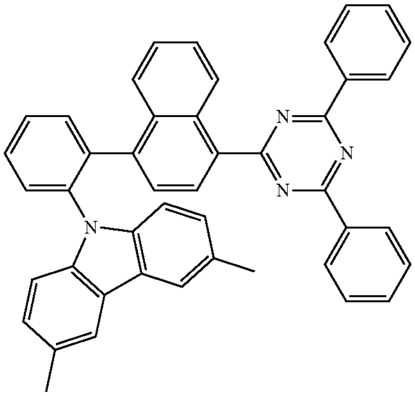
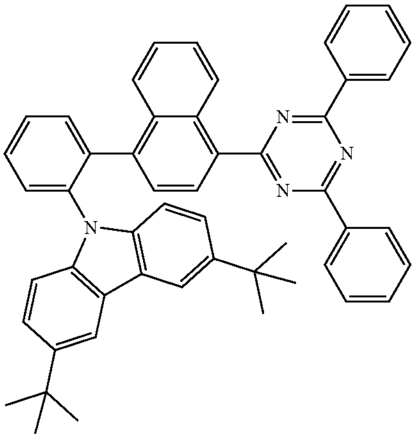
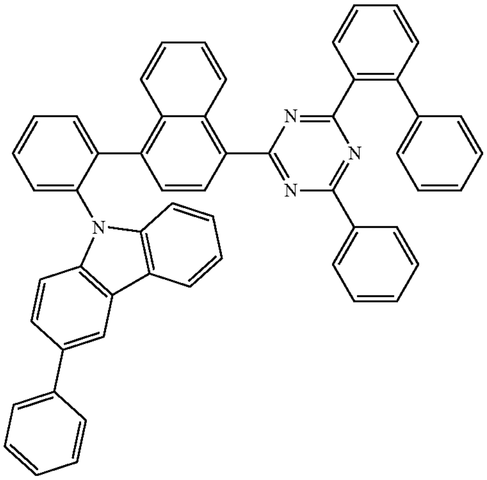
-continued
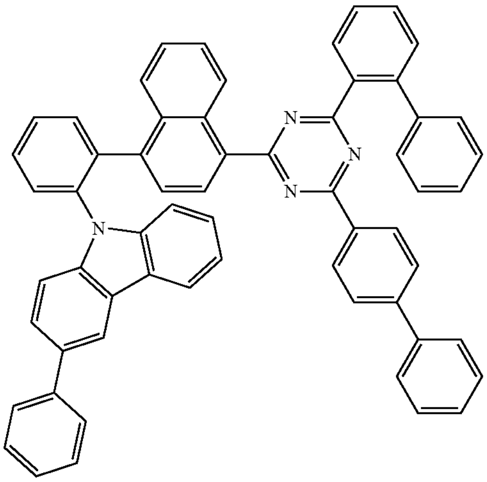
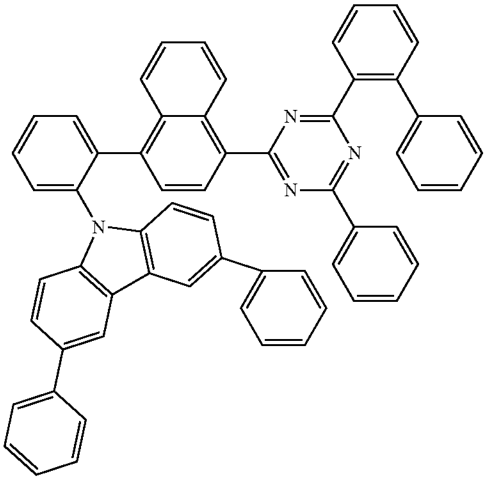
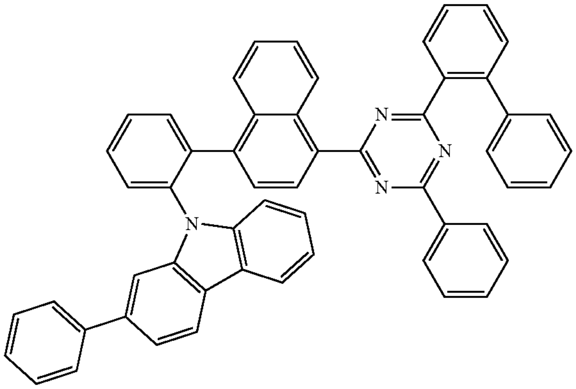

-continued
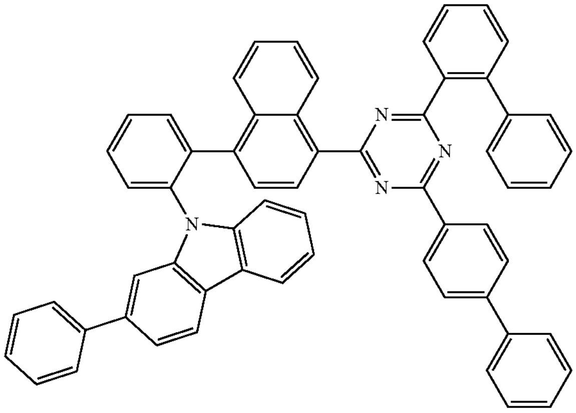
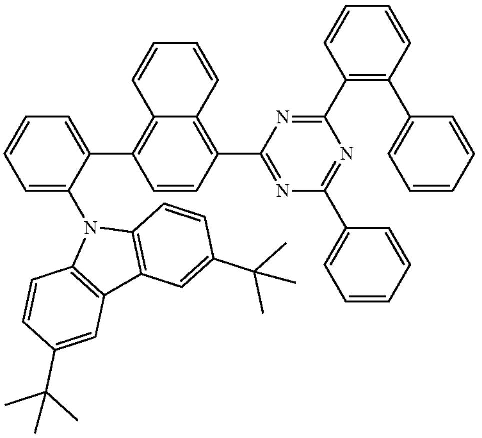
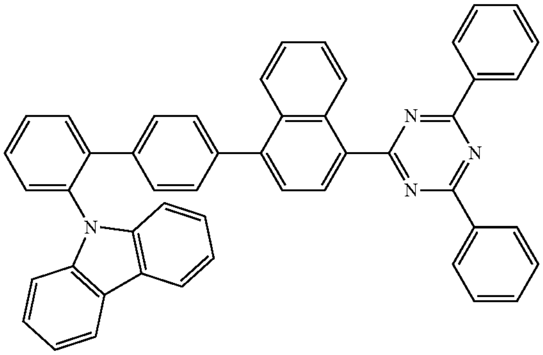
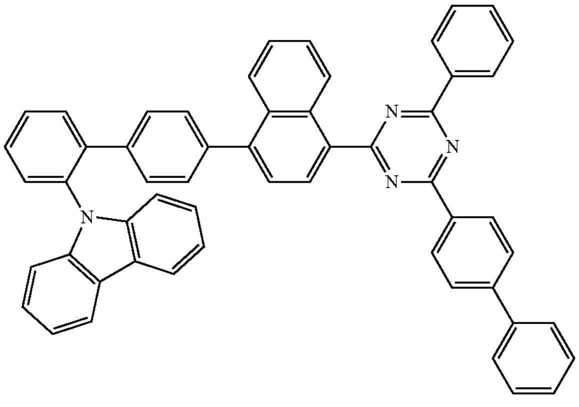
-continued
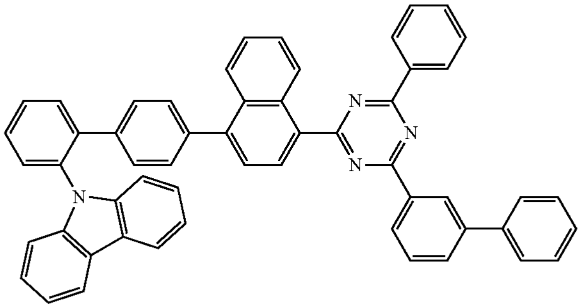
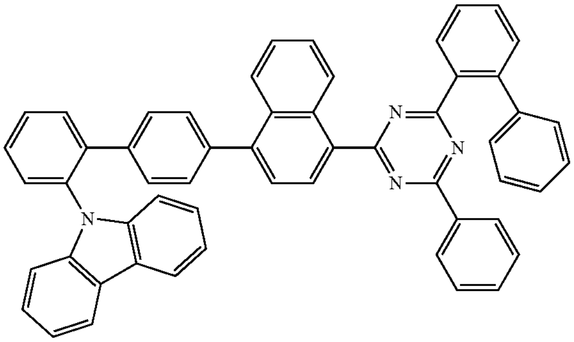
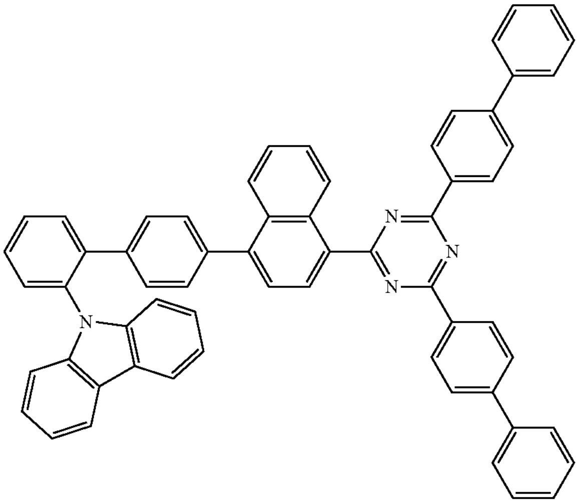
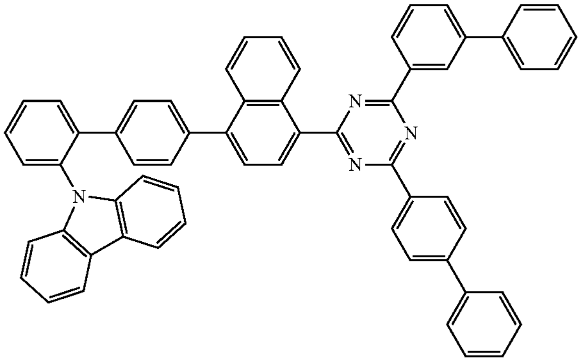

-continued
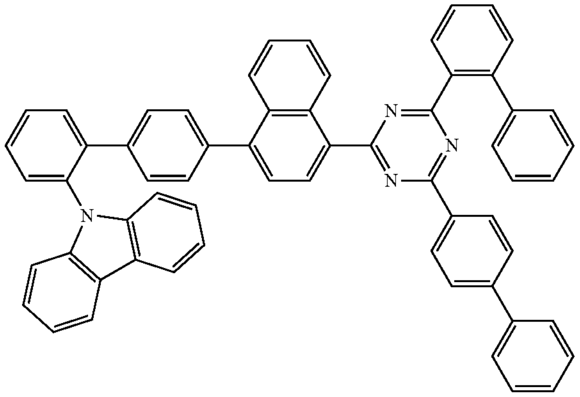
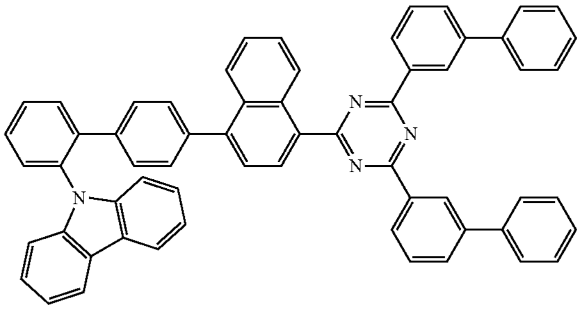
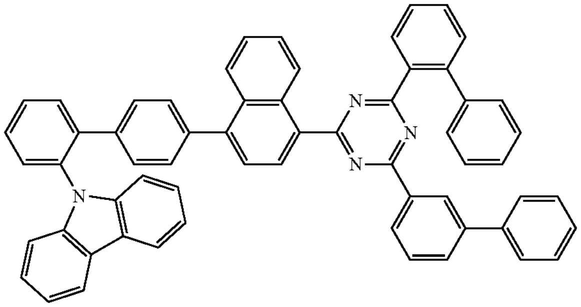
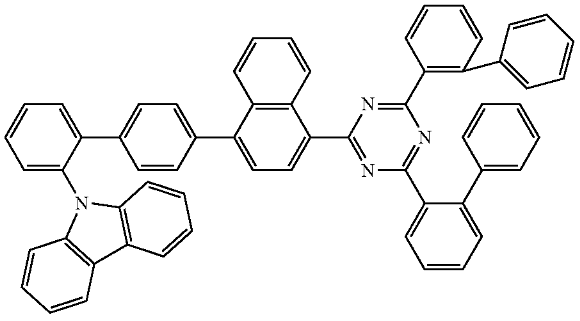
-continued
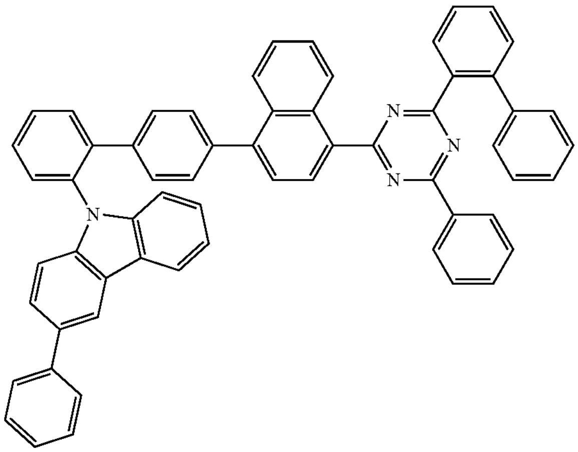
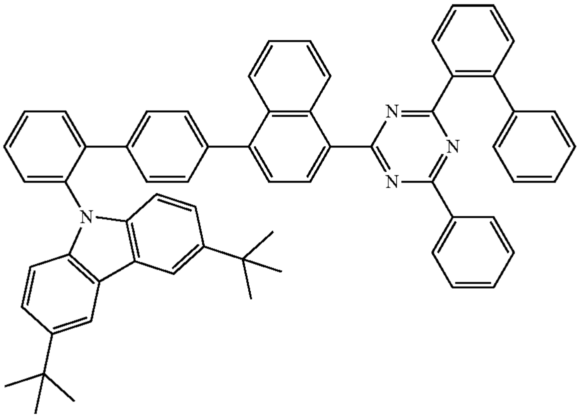
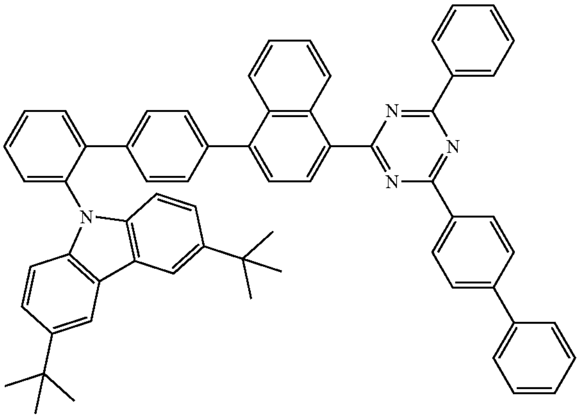
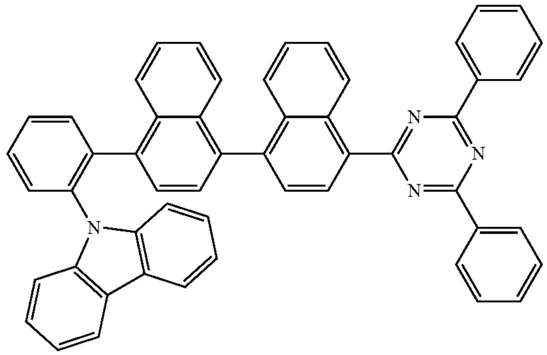

-continued
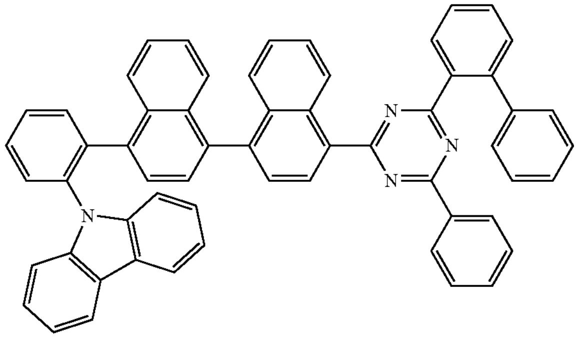
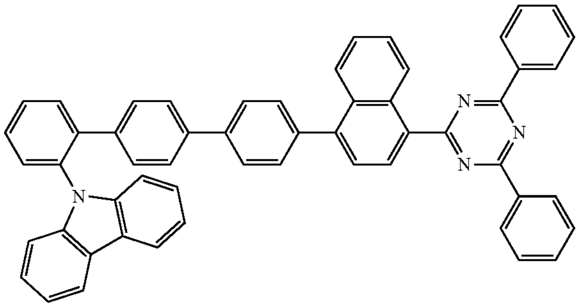
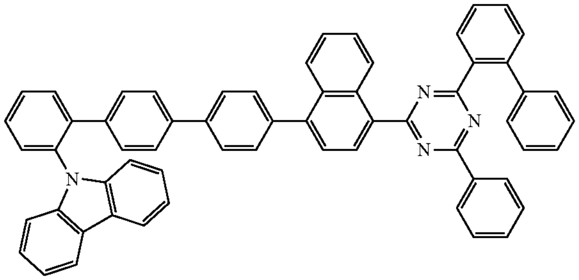
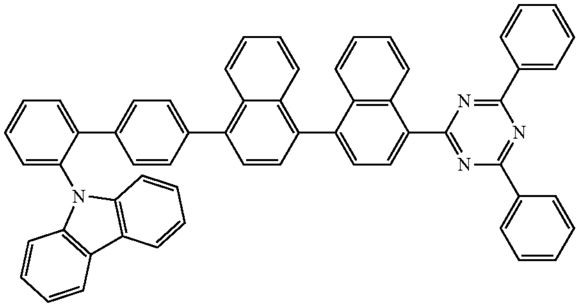
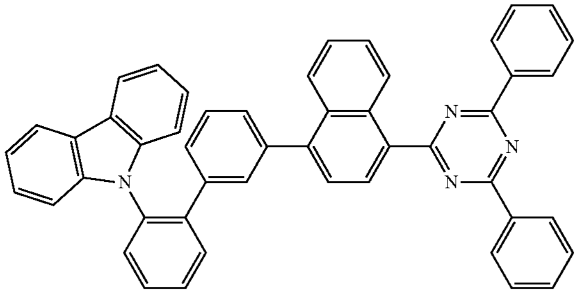
-continued
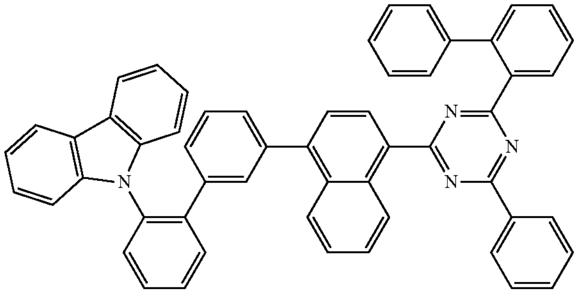
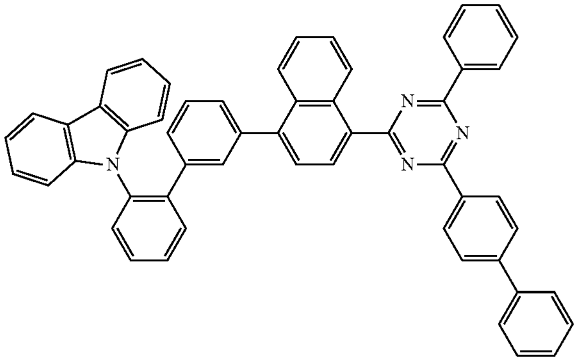
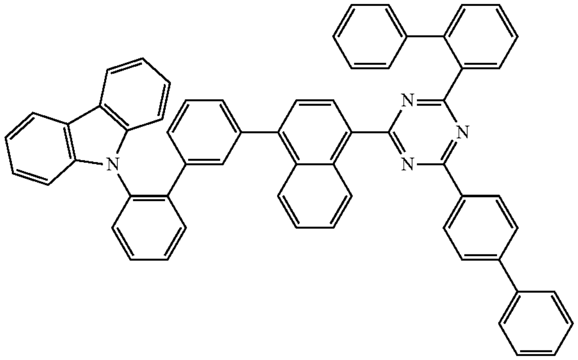
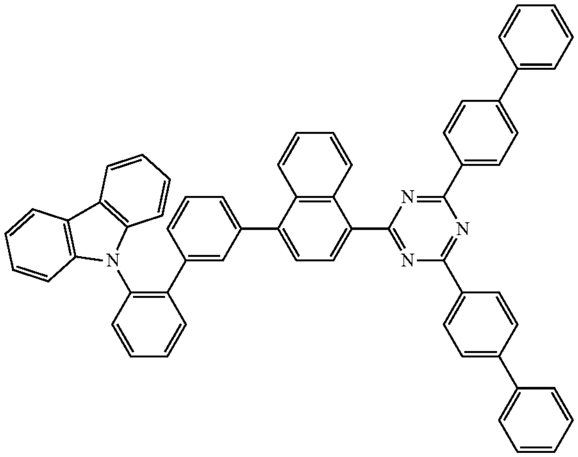

-continued
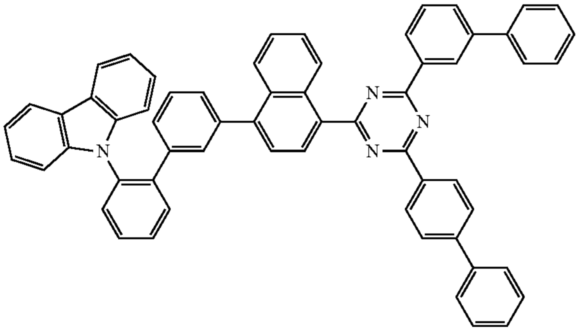
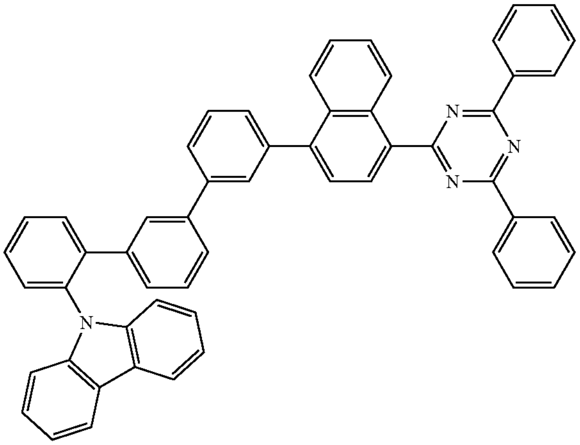
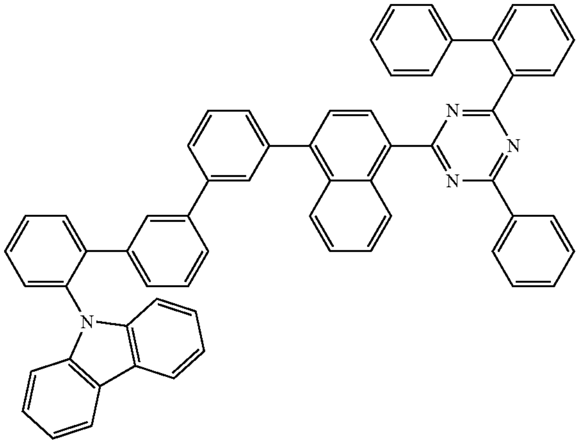
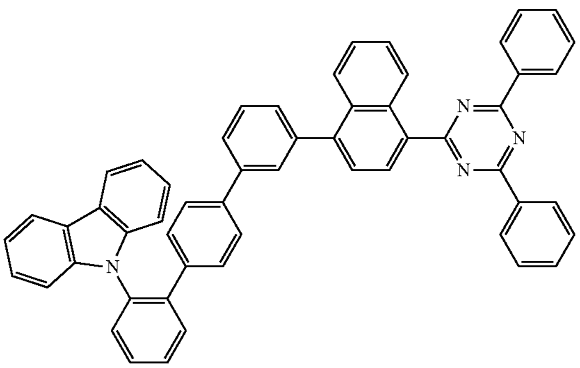
-continued
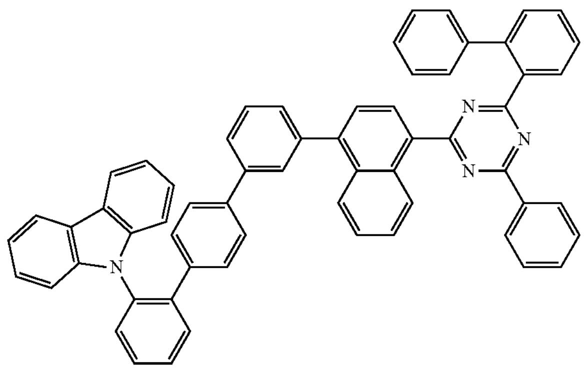
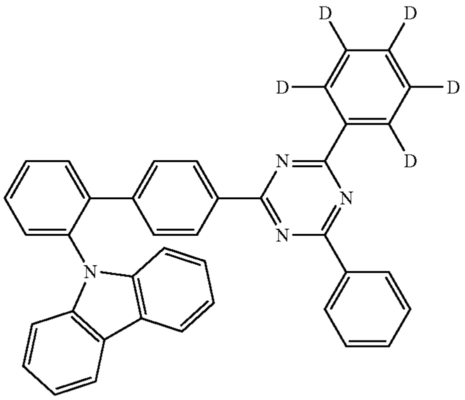
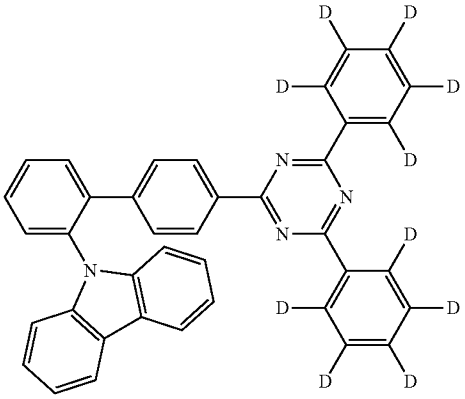
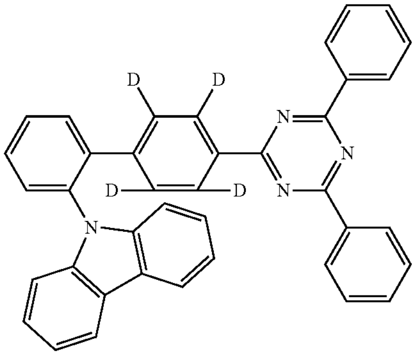

-continued
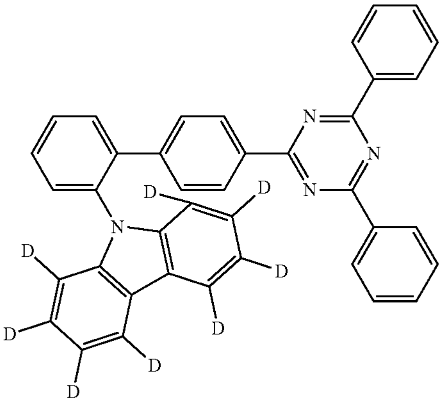
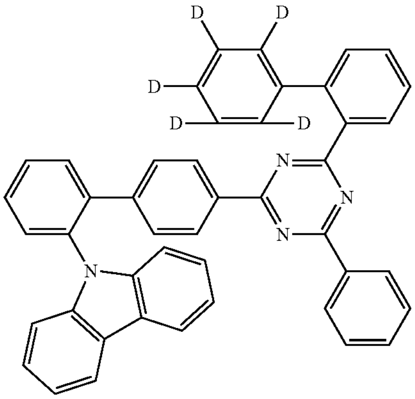
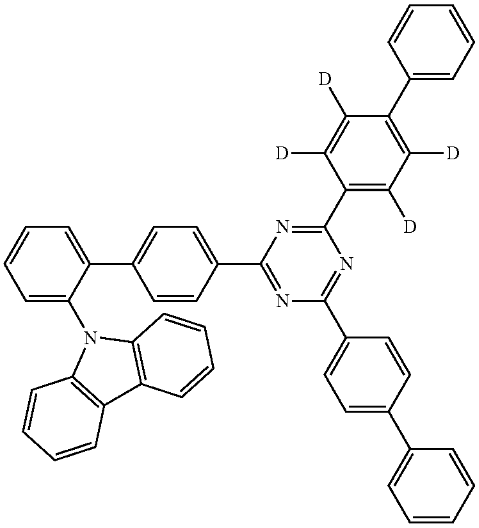
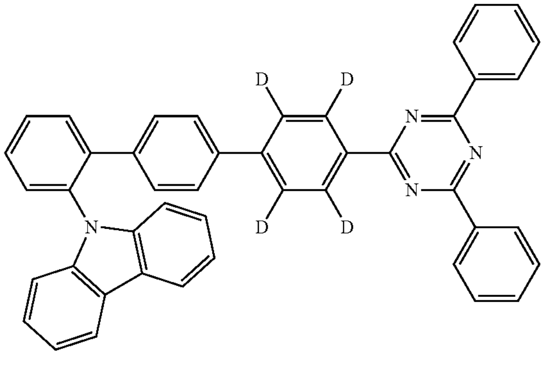
-continued
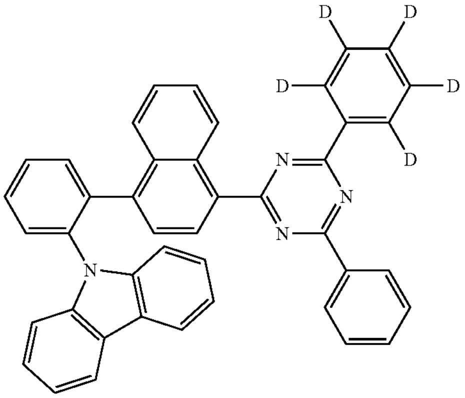
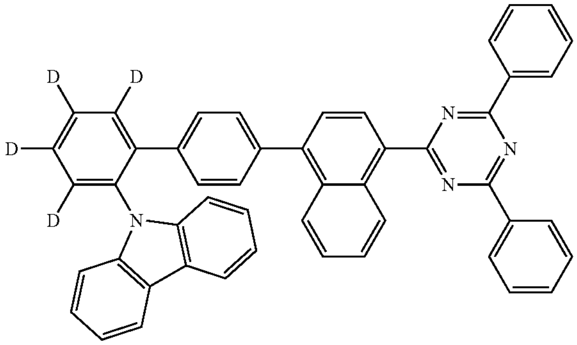
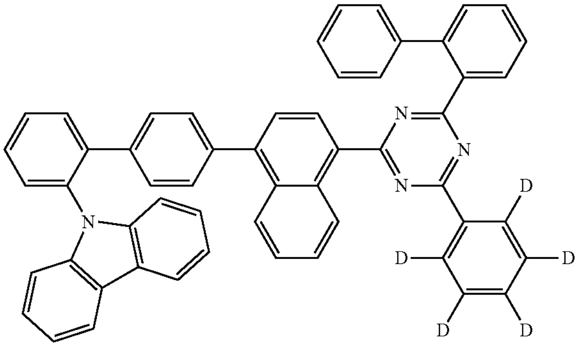
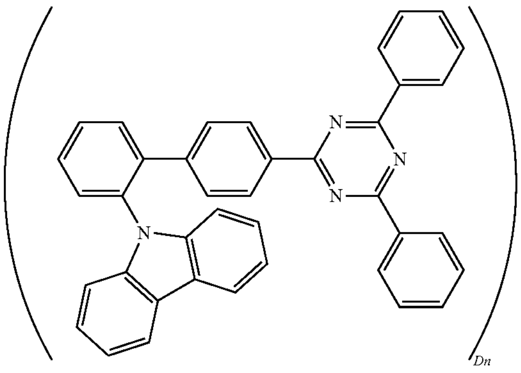
n=1~26

-continued

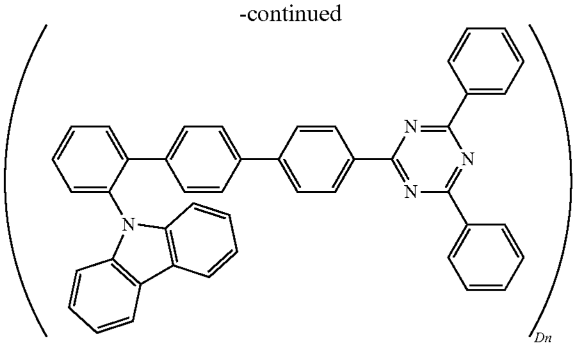

n=1~30

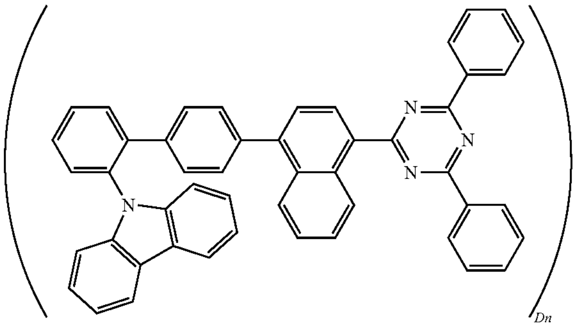

n=1~32

The compound represented by the formula (1) can be synthesized in accordance with the method in Examples described later by using known alternative reactions or raw materials adapted to the target compound.

[Electron-Transporting Material for Organic EL Device]

The compound (1) is useful as a material for an organic EL device, and is particularly useful as an electron-transporting material.

An electron-transporting material for an organic electroluminescence device according to an aspect of the present invention includes the compound represented by the formula (1).

[Organic Electroluminescence Device]

An organic EL device according to an aspect of the present invention includes a cathode;

an anode; and one or two or more organic layers arranged between the cathode and the anode, wherein at least one layer of the organic layers includes the compound represented by the above-mentioned formula (1).

When the organic EL device includes a plurality of organic layers, the compound (1) may be included in any of the organic layers. The types of organic layers will be described later.

A schematic configuration of organic EL device according to an aspect of the present invention will be explained with reference to The FIGURE.

The organic EL device 1 according to an aspect of the present invention includes a substrate 2, an anode 3, an organic thin film layer 4, an emitting layer 5, an organic thin film layer 6, and a cathode 10 in this order. The organic thin film layer 4 arranged between the anode 3 and the emitting layer 5 functions as a hole-transporting region, and the organic thin film layer 6 arranged between the emitting layer 5 and the cathode 10 functions as an electron-transporting region.

The organic thin film layer 6 includes a first electron-transporting layer 6*a* (frequently referred to as a hole-blocking layer) arranged on the emitting layer 5 side and a second electron-transporting layer 6*b* (frequently referred to as an electron-injecting layer) arranged on the cathode 10 side.

Either one or both of the first electron-transporting layer 6*a* and the second electron-transporting layer 6*b* contain the compound (1). When the first electron-transporting layer 6*a* or the second electron-transporting layer 6*b* contains the compound (1), an organic EL device with improved luminous efficiency can be obtained.

The organic electroluminescence device according to an aspect of the present invention includes an anode, an emitting layer, an electron-transporting region, and a cathode in this order, wherein the electron-transporting region includes the compound represented by the formula (1).

The electron-transporting region includes a first electron-transporting layer and a second electron-transporting layer, the organic electroluminescence device includes the emitting layer, the first electron-transporting layer, and the second electron-transporting layer in this order, and at least one layer of the first electron-transporting layer and the second electron-transporting layer includes the compound (1).

When either one or both of the first electron-transporting layer and the second electron-transporting layer include the compound represented by the formula (1), the lifetime of the organic EL device is improved.

In one embodiment, the second electron-transporting layer includes compound (1).

In one embodiment, the organic EL device includes a hole-transporting region between the anode and the emitting layer.

In one embodiment, the emitting layer includes the compound represented by the following formula (10).

(10)

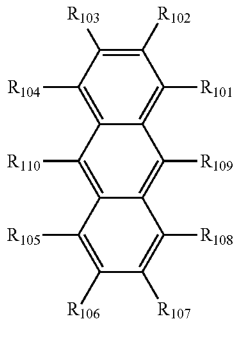

In the formula (10), one or more sets of the adjacent two or more of $R_{101}$ to $R_{110}$ form a substituted or unsubstituted, saturated or unsaturated ring or do not form the substituted or unsubstituted, saturated or unsaturated ring;

$R_{101}$ to $R_{110}$ which do not form the substituted or unsubstituted, saturated or unsaturated ring are independently a hydrogen atom, a substituent R, or a group represented by the following formula (11):

$L_{101}$-$Ar_{101}$ (11).

In the formula (11), $L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted monovalent heterocyclic group having 5 to 50 ring atoms;

the substituent R is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

when two or more substituents R are present, the two or more substituents R may be the same as or different from each other;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

when two or more of each of $R_{901}$ to $R_{907}$ are present, the two or more of each of $R_{901}$ to $R_{907}$ may be the same as or different from each other;

here, at least one of $R_{101}$ to $R_{110}$ which does not form the substituted or unsubstituted, saturated or unsaturated ring is the group represented by the formula (11); when two or more groups represented by the formula (11) are present, each of the two or more groups represented by the formula (11) may be the same as or different from each other.

The compound represented by the formula (10) may have a deuterium atom as a hydrogen atom.

In one embodiment, at least one of $Ar_{101}$ in the formula (10) is a substituted or unsubstituted aryl group having 6 to 50 ring carbon atoms.

In one embodiment, at least one of $Ar_{101}$ in the formula (10) is a substituted or unsubstituted monovalent heterocyclic group having 5 to 50 ring atoms.

In one embodiment, all of $Ar_{101}$'s in the formula (10) are substituted or unsubstituted aryl groups having 6 to 50 ring carbon atoms. The plurality of $Ar_{101}$'s may be the same as or different from each other.

In one embodiment, one of $Ar_{101}$ in the formula (10) is a substituted or unsubstituted monovalent heterocyclic group having 5 to 50 ring atoms, and the remaining $Ar_{101}$ is a substituted or unsubstituted aryl group having 6 to 50 ring carbon atoms. The plurality of $Ar_{101}$'s may be the same as or different from each other.

In one embodiment, at least one of $L_{101}$ in the formula (10) is a single bond.

In one embodiment, all of $L_{101}$ in the formula (10) are single bonds.

In one embodiment, at least one of $L_{101}$ in the formula (10) is a substituted or unsubstituted arylene group having 6 to 50 ring carbon atoms.

In one embodiment, at least one of $L_{101}$ in the formula (10) is a substituted or unsubstituted phenylene group, or a substituted or unsubstituted naphthyl group.

In one embodiment, the group represented by $-L_{101}-Ar_{101}$ in the formula (10) is selected from the group consisting of:

a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In one embodiment, the substituent R in the formula (10) are independently a substituted or unsubstituted alkyl group having 1 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, or a substituted or unsubstituted aryl group having 6 to 50 ring carbon atoms.

$R_{901}$ to $R_{907}$ are the same as defined in the formula (10).

In one embodiment, the substituent of "substituted or unsubstituted" in the formula (10) is independently (a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms.

$R_{901}$ to 8907 are the same as defined in the formula (10).

In one embodiment, the substituent of "substituted or unsubstituted" in the formula (10) is independently a substituted or unsubstituted alkyl group having 1 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, or a substituted or unsubstituted aryl group having 6 to 50 ring carbon atoms.

$R_{901}$ to $R_{907}$ are the same as defined in the formula (10).

In one embodiment, the substituent in the case of "substituted or unsubstituted" in the formula (10) is selected from the group consisting of an alkyl group having 1 to 18 carbon atoms, an aryl group having 6 to 18 ring carbon atoms, and a monovalent heterocyclic group having 5 to 18 ring atoms.

In one embodiment, the substituent in the case of "substituted or unsubstituted" in the formula (10) is an alkyl group having 1 to 5 carbon atoms.

In one embodiment, the compound represented by the formula (10) is a compound represented by the following formula (20).

(20)

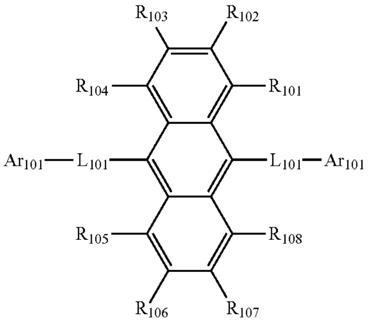

In the formula (20), $R_{101}$ to $R_{108}$, $L_{101}$'s and $Ar_{101}$'s are the same as defined in the formula (10).

The compound represented by the formula (20) may have a deuterium atom as a hydrogen atom.

That is, in one embodiment, the compound represented by the formula (10) or the formula (20) has at least two groups represented by the formula (11).

In one embodiment, the compound represented by the formula (10) or the formula (20) has two or three groups represented by the formula (11).

In one embodiment, $R_{101}$ to $R_{110}$ in the formulas (10) and (20) do not form the substituted or unsubstituted, saturated or unsaturated ring.

In one embodiment, $R_{101}$ to $R_{110}$ in the formulas (10) and (20) are a hydrogen atom.

In one embodiment, the compound represented by the formula (20) is a compound represented by the following formula (30).

(30)

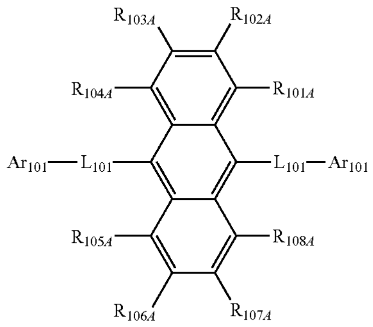

In the formula (30), $L_{101}$'s and $Ar_{101}$'s are the same as defined in the formula (10).

The adjacent two of $R_{101A}$ to $R_{108A}$ do not form any substituted or unsubstituted, saturated or unsaturated ring.

$R_{101A}$ to $R_{108A}$ are independently a hydrogen atom, or a substituent R.

The substituent R is the same as defined in the formula (10).

That is, the compound represented by the formula (30) is a compound having two groups represented by the formula (11).

The compound represented by the formula (30) has substantially only protium atoms as hydrogen atoms.

The expression "having substantially only protium atoms" means the case where the proportion of protium compound based on the total amount of a compound having only protium atoms as hydrogen atoms (protium compound) and a compound having a deuterium atom (deuterium compound), which have the same structure, is 90 mol % or more, 95 mol % or more, or 99 mol % or more.

In one embodiment, the compound represented by the formula (30) is a compound represented by the following formula (31).

(31)

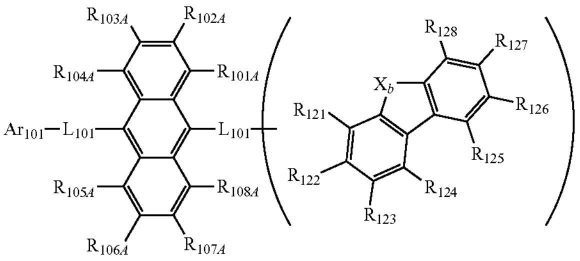

In the formula (31), $L_{101}$'s and $Ar_{101}$ are the same as defined in the formula (10).

$R_{101A}$ to $R_{108A}$ are the same as defined in the formula (30).

$X_b$ is O, S, N($R_{131}$), or C($R_{132}$)($R_{133}$).

One of $R_{121}$ to $R_{128}$ , and $R_{131}$ to $R_{133}$ is a single bond bonding with $L_{101}$.

One or more sets of the adjacent two or more of $R_{121}$ to $R_{128}$ which are not single bonds bonding with $L_{101}$ form a substituted or unsubstituted, saturated or unsaturated ring, or do not form the substituted or unsubstituted, saturated or unsaturated ring.

$R_{121}$ to $R_{128}$ which are not single bonds bonding with $L_{101}$ and which do not form the substituted or unsubstituted, saturated or unsaturated ring are independently a hydrogen atom, or a substituent R.

The substituent R is the same as defined in the formula (10).

$R_{131}$ to $R_{133}$ which are not single bonds bonding with $L_{101}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

When two or more $R_{131}$ to $R_{133}$ are present, each of the two or more $R_{131}$ to $R_{133}$ may be the same as or different from each other.

In one embodiment, the compound represented by the formula (31) is a compound represented by the following formula (32).

(32)

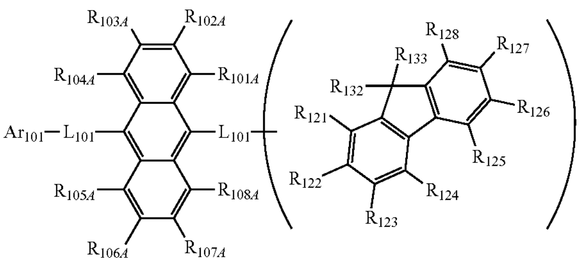

In the formula (32), $R_{101A}$ to $R_{108A}$, $L_{101}$'s, $Ar_{101}$, $R_{121}$ to $R_{128}$, $R_{132}$ and $R_{133}$ are the same as defined in the formula (31).

In one embodiment, the compound represented by the formula (31) is a compound represented by the following formula (33).

(33)

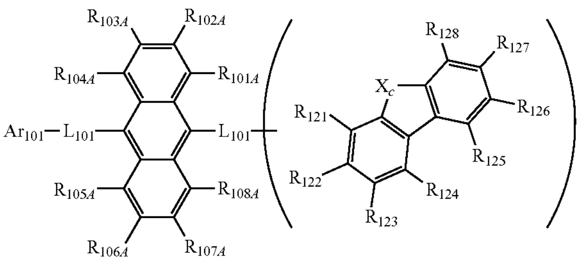

In the formula (33), $R_{101A}$ to $R_{108A}$, $L_{101}$'s, $Ar_{101}$, and $R_{121}$ to $R_{128}$ are the same as defined in the formula (31).

$X_c$ is O, S, or $NR_{131}$.

$R_{131}$ is the same as defined in the formula (31).

In one embodiment, the compound represented by the formula (31) is a compound represented by the following formula (34).

(34)

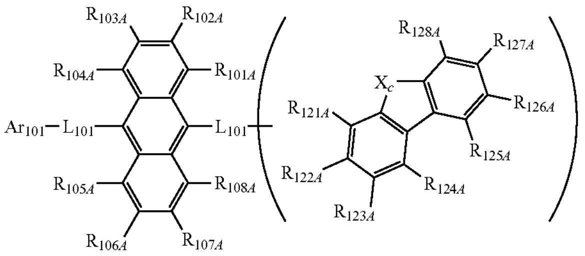

In the formula (34), $R_{101A}$ to $R_{108A}$, $L_{101}$'s and $Ar_{101}$ are the same as defined in the formula (31).

$X_c$ is O, S or $NR_{131}$.

$R_{131}$ is the same as defined in the formula (31).

One of $R_{121}$A to $R_{128A}$ is a single bond bonding with $L_{101}$.

One or more sets of the adjacent two or more of $R_{121A}$ to $R_{128A}$ which are not single bonds bonding with $L_{101}$ do not form the substituted or unsubstituted, saturated or unsaturated ring.

$R_{121}$A to $R_{128A}$ which are not single bonds bonding with $L_{101}$ are independently a hydrogen atom, or a substituent R.

The substituent R is the same as defined in the formula (10).

In one embodiment, the compound represented by the formula (31) is a compound represented by the following formula (35).

(35)

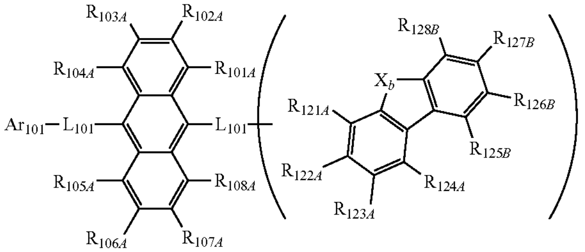

In the formula (35), $R_{101A}$ to $R_{108A}$, $L_{101}$'s, $Ar_{101}$ and $X_b$ are the same as defined in the formula (31).

One or more sets of the adjacent two or more of $R_{121A}$ to $R_{124A}$ do not form a substituted or unsubstituted, saturated or unsaturated ring by bonding with each other.

Any one set of $R_{125B}$ and $R_{126B}$, $R_{1261B}$ and $R_{127B}$, and $R_{127B}$ and $R_{128B}$ forms a ring represented by the following formula (35a) or (35b) by bonding with each other.

(35a)

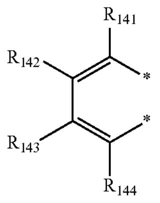

-continued (35b)

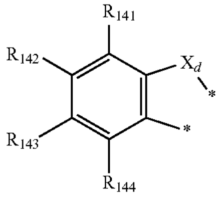

In the formulas (35a) and (35b), each of two *'s is bonded with each of any one set of $R_{125B}$ and $RR_{126B}$, $R_{126B}$ and $R_{127B}$, and $R_{127B}$ and $R_{128B}$.

$R_{141}$ to $R_{144}$ are independently a hydrogen atom, or a substituent R.

The substituent R is the same as defined in the formula (10).

$X_d$ is O or S.

One of $R_{121}A$ to $R_{124}A$, $R_{125B}$ to $R_{128B}$ which do not form the ring represented by the formula (35a) or (35b), and $R_{141}$ to $R_{144}$ is a single bond bonding with $L_{101}$.

$R_{121A}$ to $R_{124A}$ which are not single bonds bonding with $L_{101}$, and $R_{125}B$ to $R_{128}B$ which are not single bonds bonding with $L_{101}$ and which do not form the ring represented by the formula (35a) or (35b) are independently a hydrogen atom, or a substituent R.

The substituent R is the same as defined in the formula (10).

In one embodiment, the compound represented by the formula (35) is a compound represented by the following formula (36).

(36)

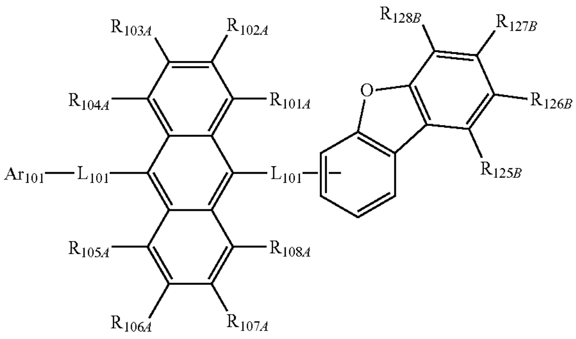

In the formula (36), $R_{101A}$ to $R_{108A}$, $L_{101}$'s, $Ar_{101}$, and $R_{125}B$ to $R_{128}B$ are the same as defined in the formula (35).

In one embodiment, the compound represented by the formula (34) is a compound represented by the following formula (37).

(37)

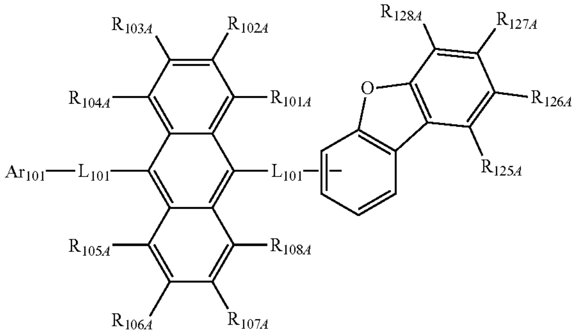

In the formula (37), $R_{101A}$ to $R_{108A}$, $R_{125}A$ to $R_{128}A$, $L_{101}$'s and $Ar_{101}$ are the same as defined in the formula (34).

In one embodiment, $R_{101A}$ to $R_{108A}$ in the formulas (30) to (37) is a hydrogen atom.

In one embodiment, the compound represented by the formula (10) is a compound represented by the following formula (40).

(40)

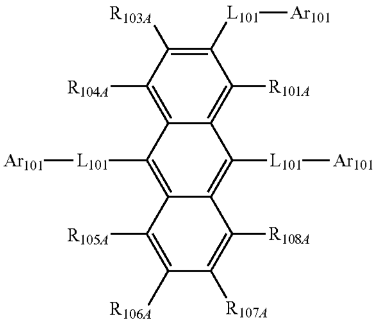

In the formula (40), $L_{101}$'s and $Ar_{101}$'s are the same as defined in the formula (10). One or more sets of the adjacent two or more of $R_{101A}$, and $R_{103A}$ to $R_{108A}$ form a substituted or unsubstituted, saturated or unsaturated ring, or do not form the substituted or unsubstituted, saturated or unsaturated ring.

$R_{101A}$, and $R_{103A}$ to $R_{108A}$ which do not form the substituted or unsubstituted, saturated or unsaturated ring are independently a hydrogen atom, or a substituent R.

The substituent R is the same as defined in the formula (10).

That is, the compound represented by the formula (40) is a compound having three groups represented by the formula (11). Furthermore, the compound represented by the formula (40) has substantially only protium atoms as hydrogen atoms.

In one embodiment, the compound represented by the formula (40) is represented by the following formula (41).

(41)

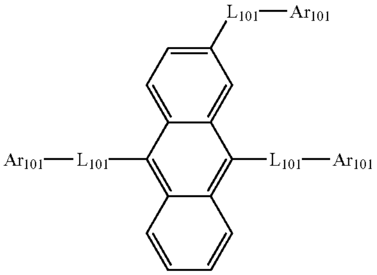

In the formula (41), $L_{101}$'s and $Ar_{101}$'s are the same as defined in the formula (40).

In one embodiment, the compound represented by the formula (40) is a compound represented by any one of the following formulas (42-1) to (42-3).

(42-1)

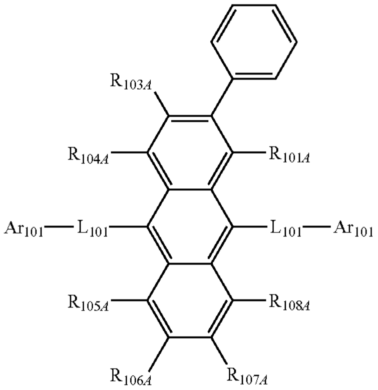

(42-2)

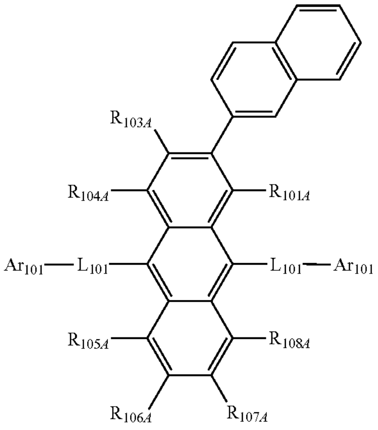

-continued (42-3)

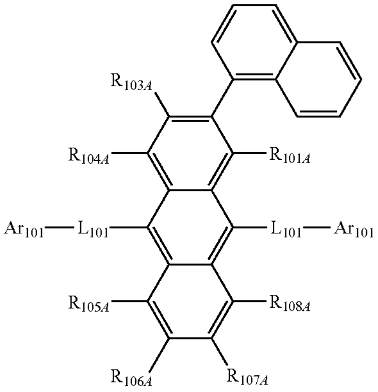

In the formulas (42-1) to (42-3), $R_{101A}$ to $R_{108A}$, $L_{101}$'s and $Ar_{101}$'s are the same as defined in the formula (40).

In one embodiment, the compounds represented by the formulas (42-1) to (42-3) are a compound represented by any one of the following formulas (43-1) to (43-3).

(43-1)

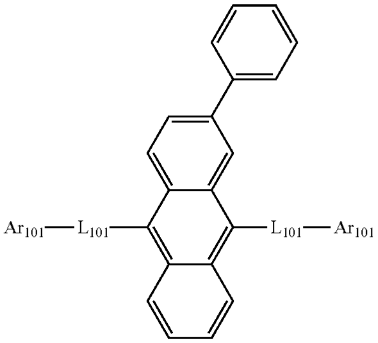

(43-2)

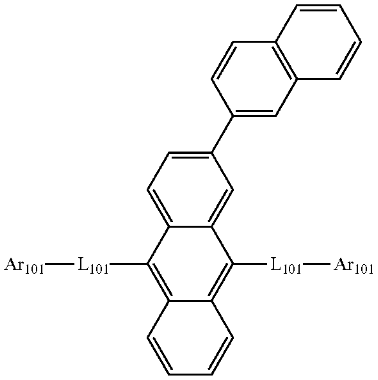

-continued (43-3)

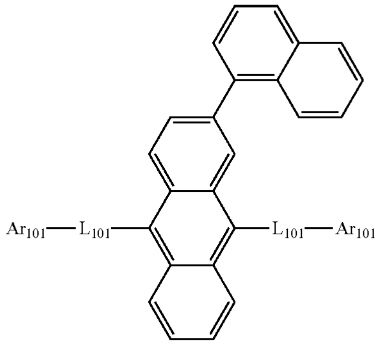

In the formulas (43-1) to (43-3), $L_{101}$'s and $Ar_{101}$'s are the same as defined in the formula (40).

In one embodiment, the group represented by $-L_{101}-Ar_{101}$ in the formulas (40), (41), (42-1) to (42-3), and (43-1) to (43-3) is selected from the group consisting of a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In one embodiment, the compound represented by the formula (10) or the formula (20) includes a compound in which at least one of the hydrogen atoms possessed by these compounds is a deuterium atom.

In one embodiment, in the formula (20), at least one of, $R_{101}$ to $R_{108}$ which are hydrogen atoms, hydrogen atoms possessed by $R_{101}$ to $R_{108}$ which are the substituents R, hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ is a deuterium atom.

The compounds represented by the formulas (30) to (37) include compounds in which at least one of the hydrogen atoms possessed by these compounds is a deuterium atom.

In one embodiment, at least one of the hydrogen atoms bonding to the carbon atoms constituting the anthracene skeletons in the compounds represented by the formulas (30) to (37) is a deuterium atom.

In one embodiment, the compound represented by the formula (30) is a compound represented by the following formula (30D).

(30D)

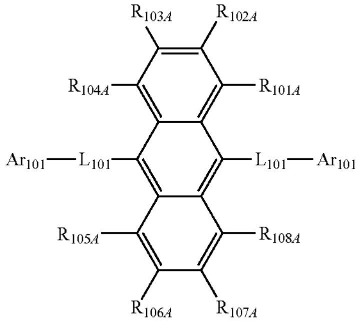

In the formula (30D), $R_{101A}$ to $R_{108A}$, $L_{101}$'s and $Ar_{101}$'s are the same as defined in the formula (30).

Here, at least one of, $R_{101A}$ to $R_{110A}$ which are hydrogen atoms, hydrogen atoms possessed by $R_{101A}$ to R110A which are the substituents R, hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ is a deuterium atom.

That is, the compound represented by the formula (30D) is a compound in which at least one of the hydrogen atoms possessed by the compound represented by the formula (30) is a deuterium atom.

In one embodiment, at least one of $R_{101A}$ to $R_{108A}$ which is a hydrogen atom in the formula (30D) is a deuterium atom.

In one embodiment, the compound represented by the formula (30D) is a compound represented by the following formula (31 D).

(31D)

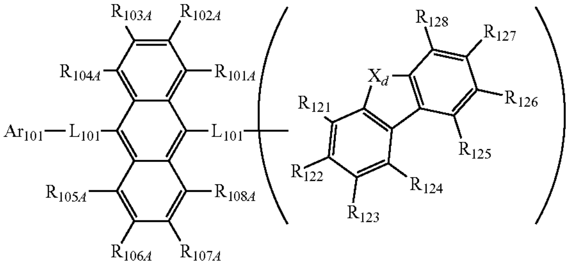

In the formula (31 D), $R_{101A}$ to $R_{108A}$, $L_{101}$'s and $Ar_{101}$ are the same as defined in the formula (30D).

$X_d$ is O or S.

One of $R_{121}$ to $R_{128}$ is a single bond bonding with $L_{101}$.

One or more sets of the adjacent two or more of $R_{121}$ to $R_{128}$ which are not single bonds bonding with $L_{101}$ form a substituted or unsubstituted, saturated or unsaturated ring, or do not form the substituted or unsubstituted, saturated or unsaturated ring.

$R_{121}$ to $R_{128}$ which are not a single bond bonding with $L_{101}$ and which do not form the substituted or unsubstituted, saturated or unsaturated ring are independently a hydrogen atom, or a substituent R.

The substituent R is the same as defined in the formula (10).

Here, at least one of, $R_{101A}$ to $R_{110A}$ which are hydrogen atoms, hydrogen atoms possessed by $R_{101A}$ to $R_{110A}$ which are the substituents R, hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, $R_{121}$ to $R_{128}$ which are hydrogen atoms, and hydrogen atoms possessed by $R_{121}$ to $R_{128}$ which are the substituents R is a deuterium atom.

In one embodiment, the compound represented by the formula (31 D) is a compound represented by the following formula (32D).

(32D)

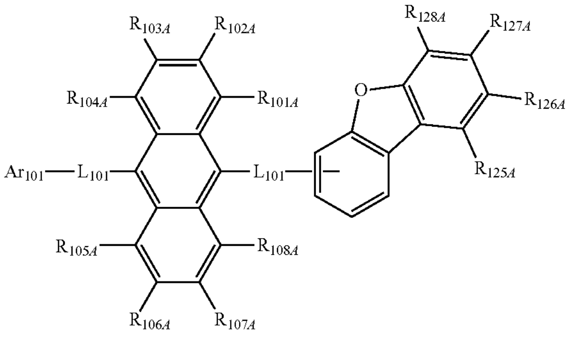

In the formula (32D), $R_{101A}$ to $R_{108A}$, $R_{125}$A to $R_{128}$A, $L_{101}$'s and $Ar_{101}$ are the same as defined in the formula (31D).

Here, at least one of, $R_{101A}$ to $R_{108A}$ which are hydrogen atoms, hydrogen atoms possessed by $R_{101A}$ to $R_{108A}$ which are the substituents R, $R_{125}$A to $R_{128A}$ which are hydrogen atoms, hydrogen atoms possessed by $R_{125}$A to $R_{128A}$ which are the substituents R, hydrogen atoms bonding to the carbon atoms of the dibenzofuran skeleton in the formula (32D), hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ is a deuterium atom.

In one embodiment, the compound represented by the formula (32D) is a compound represented by the following formula (32D-1) or (32D-2).

(32D-1)

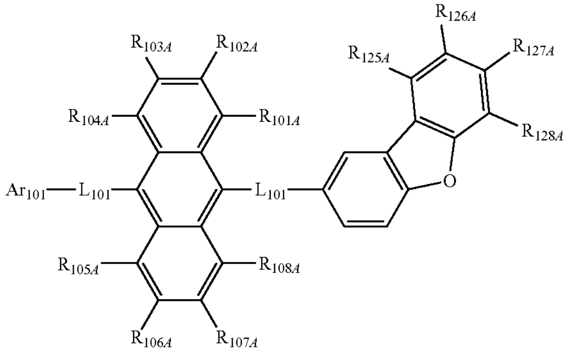

(32D-2)

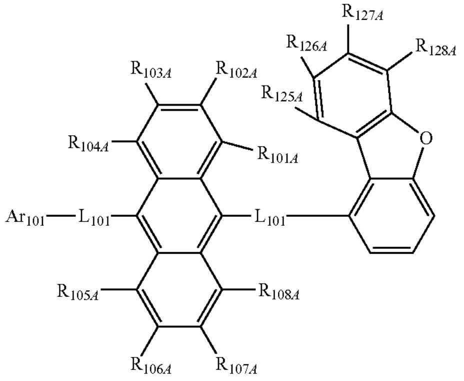

In the formulas (32D-1) and (32D-2), $R_{101A}$ to $R_{108A}$, $R_{125}$A to $R_{128}$A, $L_{101}$'s and $Ar_{101}$ are the same as defined in the formula (32D).

Here, at least one of, $R_{101A}$ to $R_{108A}$ which are hydrogen atoms, hydrogen atoms possessed by $R_{101A}$ to $R_{108A}$ which are the substituents R, $R_{125}$A to $R_{128A}$ which are hydrogen atoms, hydrogen atoms possessed by $R_{125}$A to $R_{128A}$ which are the substituents R, hydrogen atoms bonding to the carbon atoms of the dibenzofuran skeleton in the formulas (32D-1) and (32D-2), hydrogen atoms possessed by $L_{101}$, hydrogen atoms possessed by the substituent of $L_{101}$, hydrogen atoms possessed by $Ar_{101}$, and hydrogen atoms possessed by the substituent of $Ar_{101}$ is a deuterium atom.

In one embodiment, at least one of the hydrogen atoms possessed by the compound represented by the formula (40), (41), (42-1) to (42-3) or (43-1) to (43-3) is a deuterium atom.

In one embodiment, at least one of the hydrogen atoms ($R_{101A}$ to $R_{108A}$ which are hydrogen atoms) bonding to the carbon atoms constituting the anthracene skeletons in the compound represented by the formula (41) is a deuterium atom.

In one embodiment, the compound represented by the formula (40) is a compound represented by the following formula (40D).

(40D)

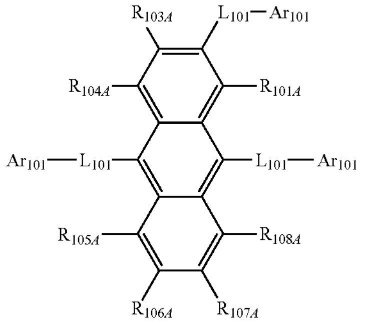

In the formula (40D), $L_{101}$'s and $Ar_{101}$'s are the same as defined in the formula (10).

One or more sets of the adjacent two or more of $R_{101A}$, and $R_{103A}$ to $R_{108A}$ do not form the substituted or unsubstituted, saturated or unsaturated ring.

$R_{101A}$, and $R_{103A}$ to $R_{108A}$ are independently
a hydrogen atom, or
a substituent R.

The substituent R is the same as defined in the formula (10).

Here, at least one of, $R_{101A}$, and $R_{103A}$ to $R_{108A}$ which are hydrogen atoms,
hydrogen atoms possessed by $R_{101A}$, and $R_{103A}$ to $R_{108A}$ which are the substituents R,
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$
is a deuterium atom.

In one embodiment, at least one of $R_{101A}$, and $R_{103A}$ to $R_{108A}$ in the formula (40D) is a deuterium atom.

In one embodiment, the compound represented by the formula (40D) is a compound represented by the following formula (41 D).

(41D)

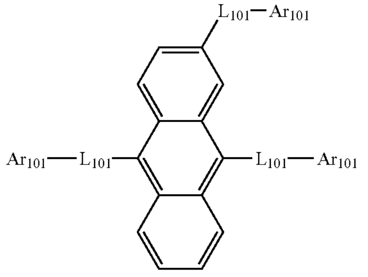

In the formula (41 D), $L_{101}$ s and $Ar_{101}$'s are the same as defined in the formula (40D).

Here, in the formula (41 D), at least one of,
hydrogen atoms bonding to the carbon atoms constituting the anthracene skeleton,
hydrogen atoms possessed by $L_{101}$,
hydrogen atoms possessed by the substituent of $L_{101}$,
hydrogen atoms possessed by $Ar_{101}$, and
hydrogen atoms possessed by the substituent of $Ar_{101}$
is a deuterium atom.

In one embodiment, the compound represented by the formula (40D) is a compound represented by any one of the following formulas (42D-1) to (42D-3).

(42D-1)

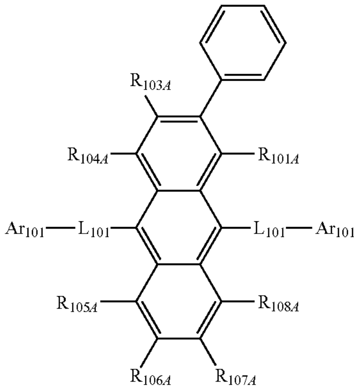

(42D-2)

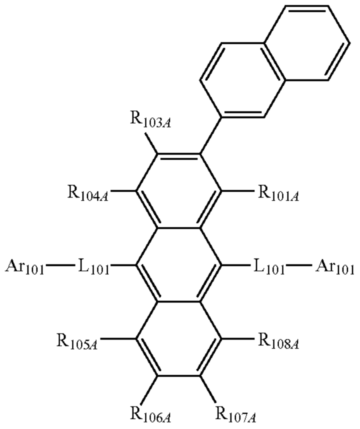

(42D-3)

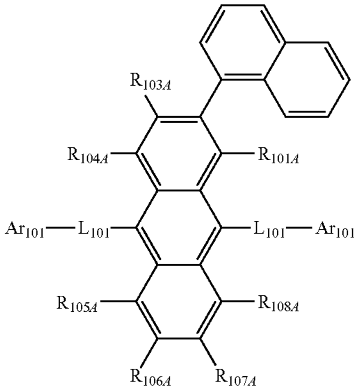

In the formula (42D-1) to (42D-3), $R_{101A}$ to $R_{108A}$, $L_{101}$'s and $Ar_{101}$'s are the same as defined in the formula (40D).

Here, in the formula (42D-1), at least one of,
$R_{101A}$, and $R_{103A}$ to $R_{108A}$ which are hydrogen atoms,
hydrogen atoms possessed by $R_{101A}$, and $R_{103A}$ to $R_{108A}$ which are the substituents R,
hydrogen atoms possessed by $L_{101}$,
hydrogen atoms possessed by the substituent of $L_{101}$,
hydrogen atoms possessed by $Ar_{101}$,
hydrogen atoms possessed by the substituent of $Ar_{101}$, and
hydrogen atoms bonding to the carbon atoms constituting the phenyl group in the formula (42D-1) is a deuterium atom.

At least one of, $R_{101A}$, and $R_{103A}$ to $R_{108A}$ which are hydrogen atoms in the formula (42D-2),
hydrogen atoms possessed by $R_{101A}$, and $R_{103A}$ to $R_{108A}$ which are the substituents R, hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, and hydrogen atoms bonding to the carbon atoms constituting the naphthyl group in the formula (42D-2) is a deuterium atom.

At least one of, $R_{101A}$, and $R_{103A}$ to $R_{108A}$ which are hydrogen atoms in the formula (42D-3), hydrogen atoms possessed by $R_{101A}$, and $R_{103A}$ to $R_{108A}$ which are the substituents R, hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, and hydrogen atoms bonding to the carbon atoms constituting the naphthyl group in the formula (42D-3)

is a deuterium atom.

In one embodiment, the compounds represented by the formulas (42D-1) to (42D-3) are a compound represented by any one of the following formulas (43D-1) to (43D-3).

(43D-1)

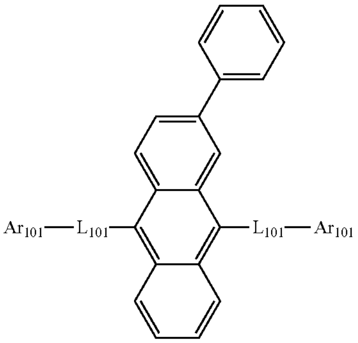

(43D-2)

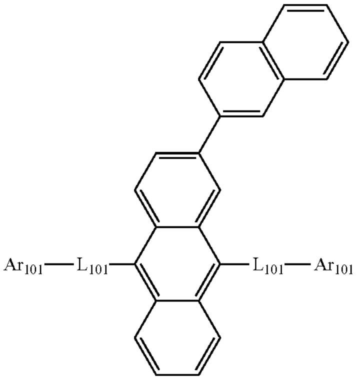

(43D-3)

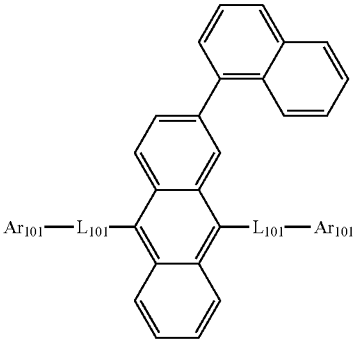

In the formula (43D-1) to (43D-3), $L_{101}$ s and $Ar_{101}$'s are the same as defined in the formula (40D).

Here, at least one of, hydrogen atoms bonding to the carbon atoms constituting the anthracene skeleton in the formula (43D-1), hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, and hydrogen atoms bonding to the carbon atoms constituting the phenyl group in the formula (43D-1) is a deuterium atom.

At least one of, hydrogen atoms bonding to the carbon atoms constituting the anthracene skeleton in the formula (43D-2), hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, and hydrogen atoms bonding to the carbon atoms constituting the naphthyl group in the formula (43D-2) is a deuterium atom.

At least one of, hydrogen atoms bonding to the carbon atoms constituting the anthracene skeleton in the formula (43D-3), hydrogen atoms possessed by $L_{101}$, hydrogen atoms possessed by the substituent of $L_{101}$, hydrogen atoms possessed by $Ar_{101}$, hydrogen atoms possessed by the substituent of $Ar_{101}$, and hydrogen atoms bonding to the carbon atoms constituting the naphthyl group in the formula (43D-3)

is a deuterium atom.

In one embodiment, in the compound represented by the formula (20), at least one of $Ar_{101}$'s is a monovalent group having a structure represented by the following formula (50).

(50)

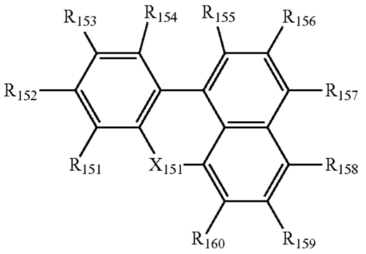

In the formula (50), $X_{151}$ is O, S or $C(R_{161})(R_{162})$.

One of R151 to R16o is a single bond bonding with $L_{101}$.

One or more sets of, the adjacent two or more of $R_{151}$ to $R_{154}$ and the adjacent two or more of $R_{155}$ to $R_{160}$, which are not single bonds bonding with $L_{101}$, form a substituted or unsubstituted, saturated or unsaturated ring by bonding with each other, or do not form the substituted or unsubstituted, saturated or unsaturated ring.

$R_{161}$ and $R_{162}$ form a substituted or unsubstituted, saturated or unsaturated ring by bonding with each other, or do not form the substituted or unsubstituted, saturated or unsaturated ring.

$R_{161}$ and $R_{162}$ which do not form the substituted or unsubstituted, saturated or unsaturated ring, and $R_{151}$ to $R_{160}$ which are not single bonds bonding with $L_{101}$ and which do not form the substituted or unsubstituted, saturated or unsaturated ring are independently hydrogen atoms or substituents R.

The substituent R is the same as defined in the formula (10).

$Ar_{101}$ which is not the monovalent group having the structure represented by the formula (50) is a substituted or unsubstituted aryl group having 6 to 50 ring carbon atoms, or a substituted or unsubstituted divalent heterocyclic group having 5 to 50 ring atoms.

The position of the single bond to $L_{101}$ in the formula (50) is not particularly limited.

In one embodiment, one of $R_{151}$ to $R_{154}$ or one of $R_{155}$ to $R_{160}$ in the formula (50) is a single bond bonding with $L_{101}$.

In one embodiment, $Ar_{101}$ is a monovalent group represented by the following formula (50-$R_{152}$), (50-$R_{153}$), (50-$R_{154}$), (50-$R_{157}$) or (50-$R_{158}$).

(50-$R_{152}$)

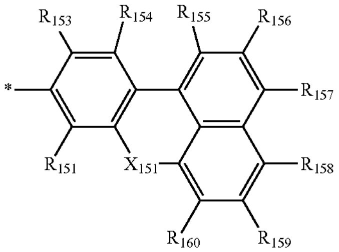

(50-$R_{153}$)

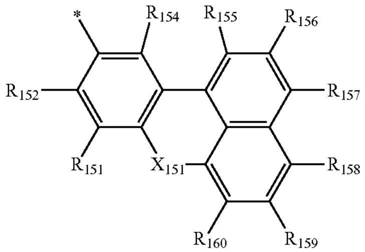

(50-$R_{154}$)

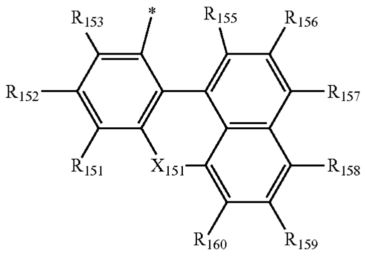

(50-$R_{157}$)

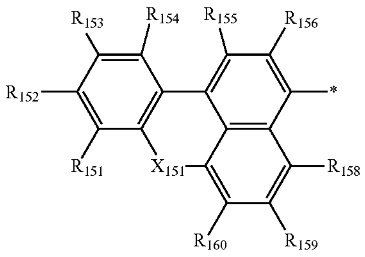

-continued (50-$R_{158}$)

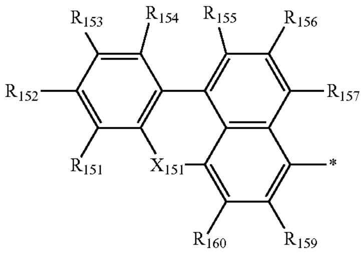

In the formulas (50-$R_{152}$), (50-$R_{153}$), (50-$R_{154}$), (50-$R_{157}$) and (50-$R_{158}$), $X_{151}$, and $R_{151}$ to $R_{160}$ are the same as defined in the formula (50).

* is bonded with $L_{101}$.

Specific examples of the compound represented by the formula (10) include the following compounds. The compound represented by the formula (10) is not limited to these specific examples. In the following specific examples, "D" represents a deuterium atom.

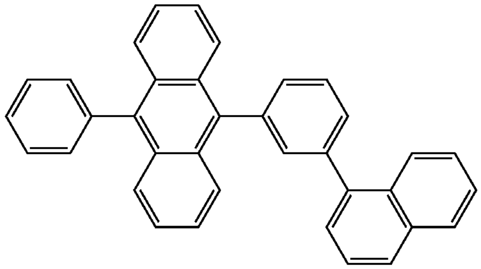

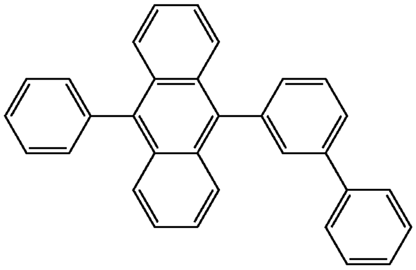

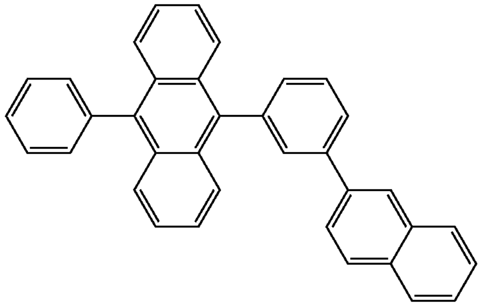

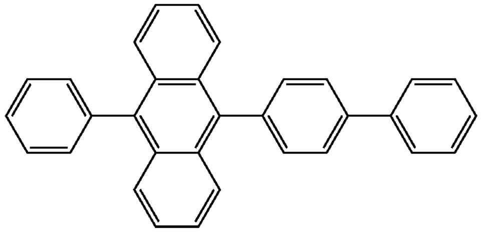

-continued
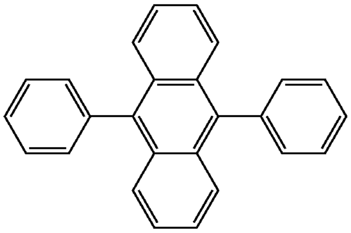
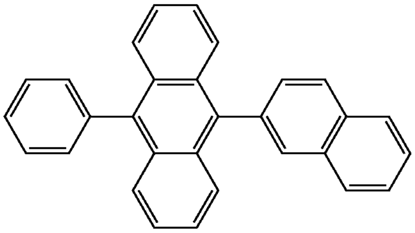
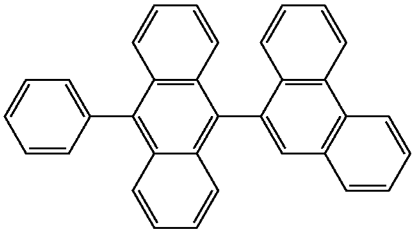
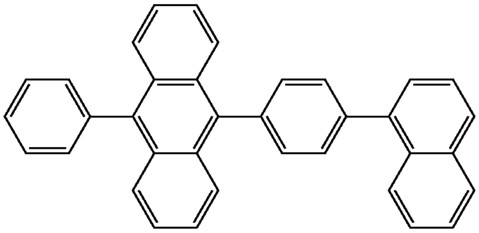
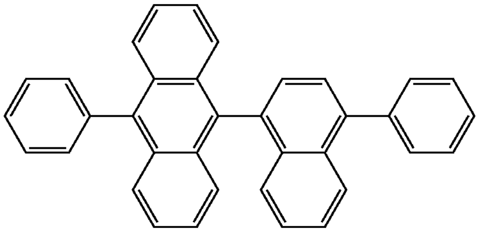
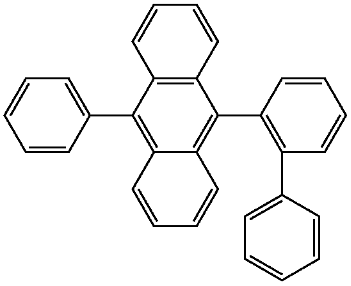
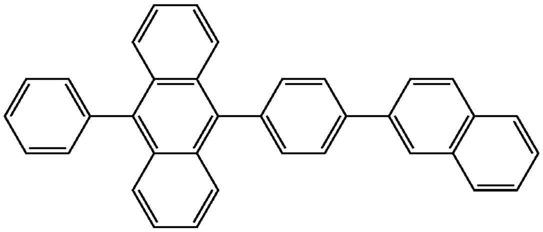
-continued
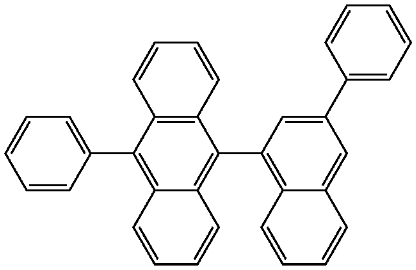
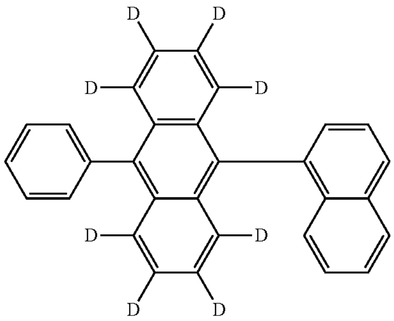
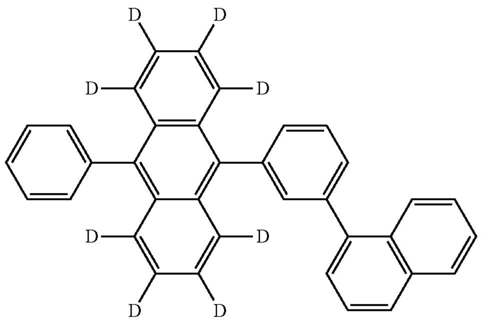
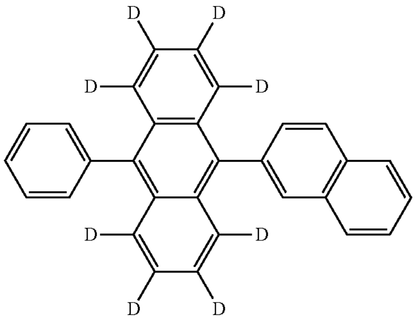
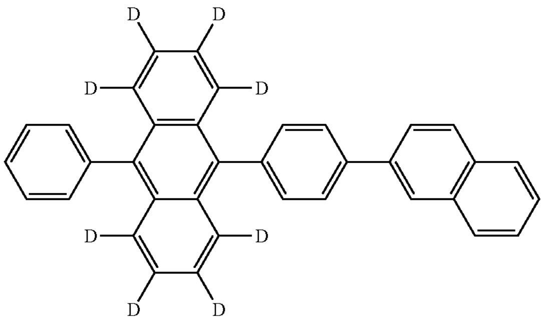

-continued
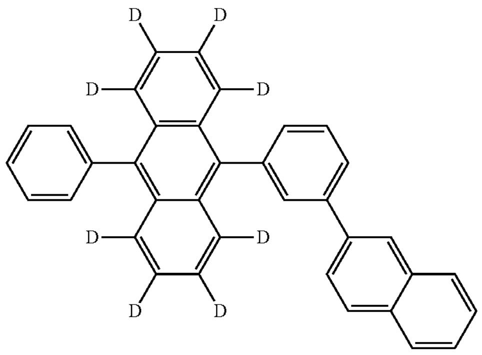
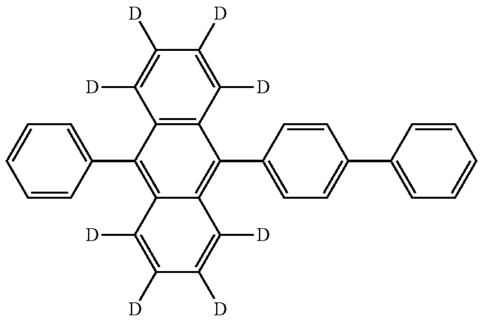
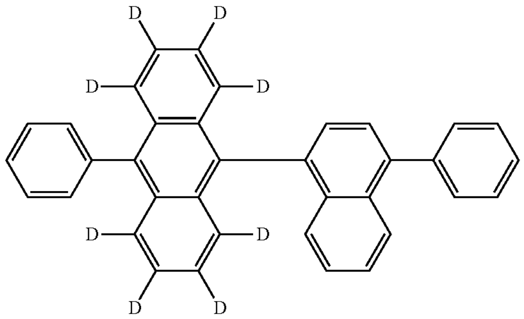
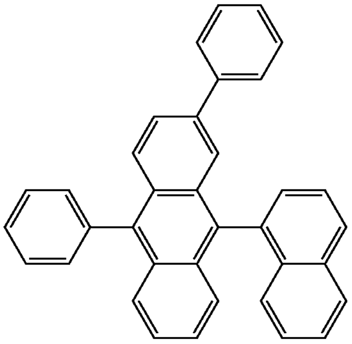
-continued
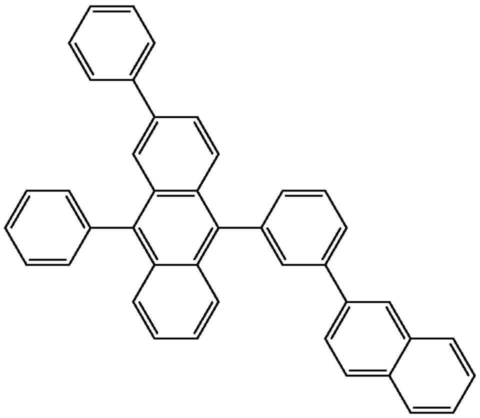
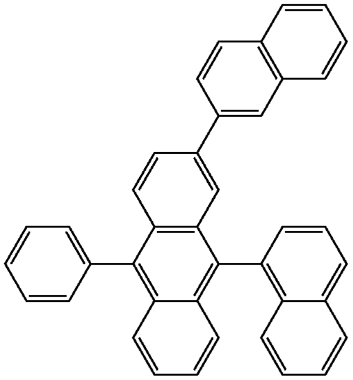
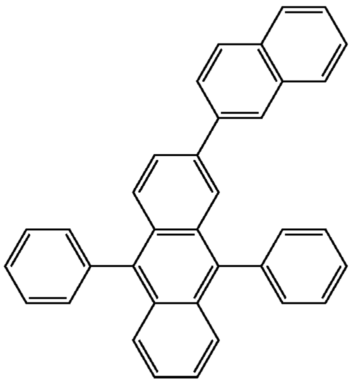
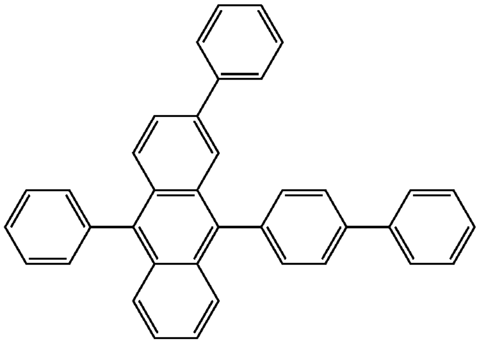

-continued
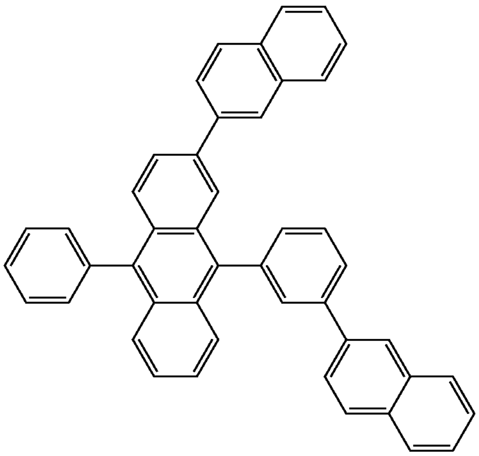
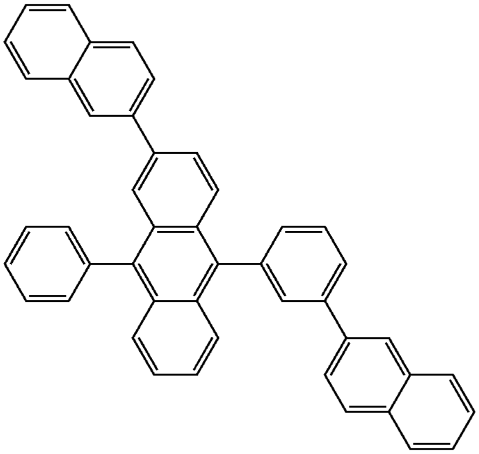
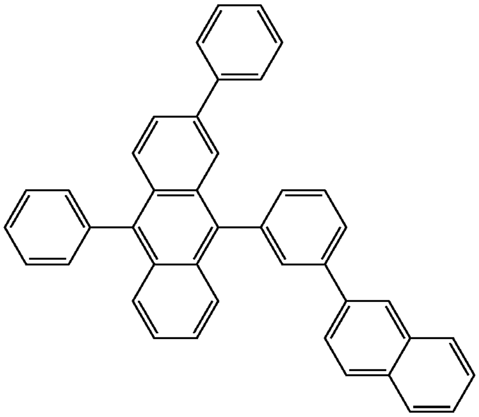
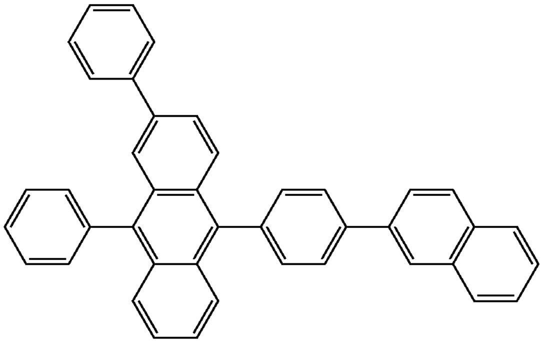
-continued
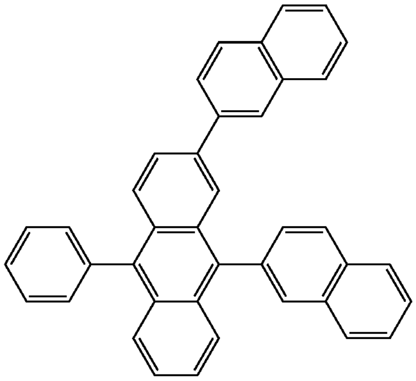
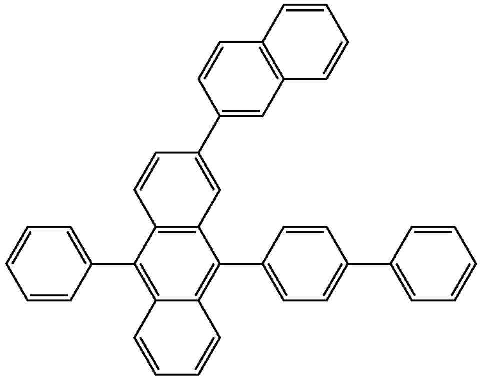
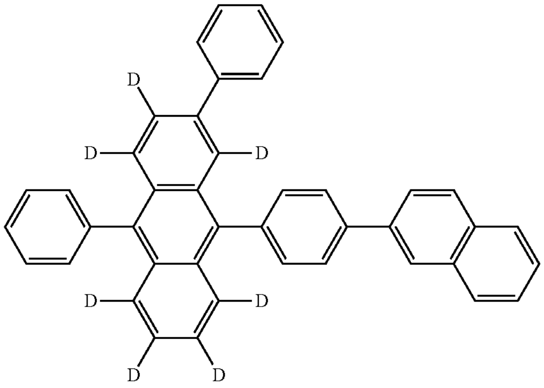
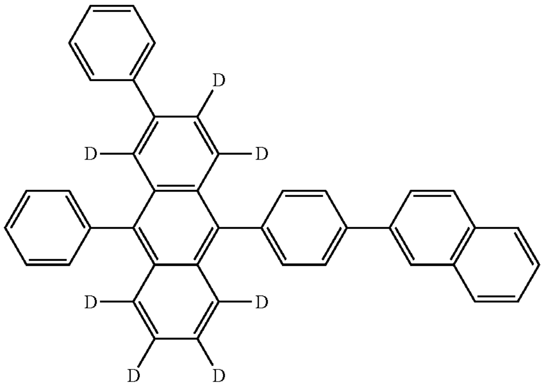

-continued
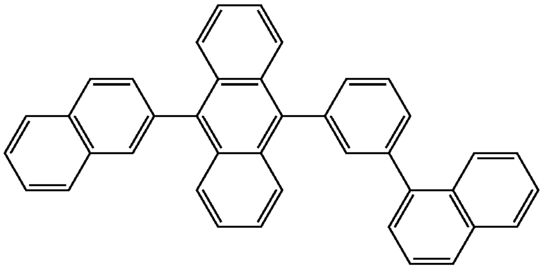
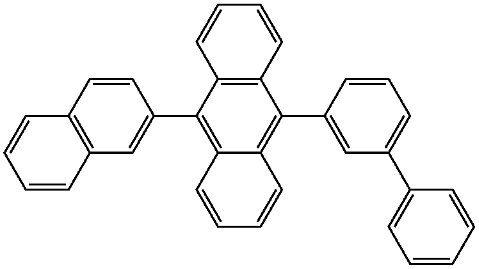
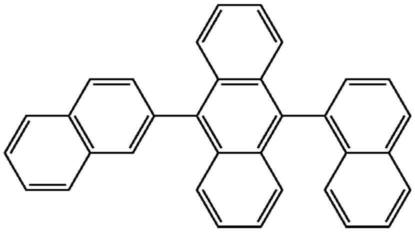
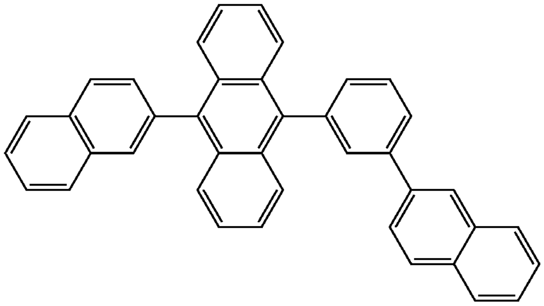
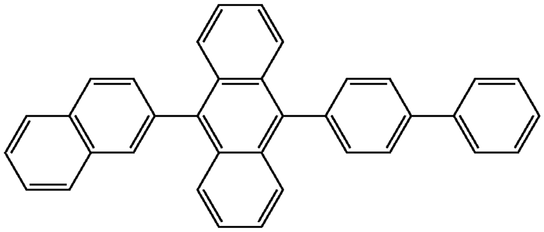
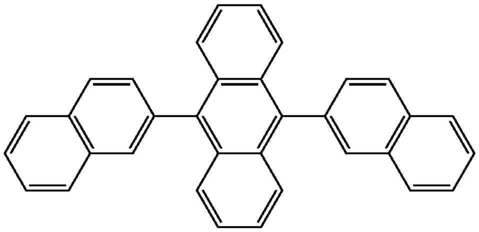
-continued
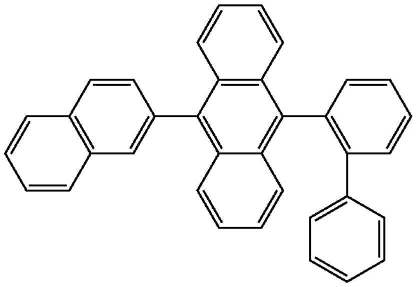
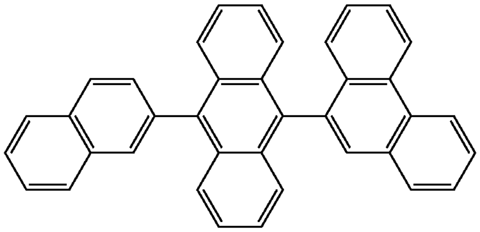
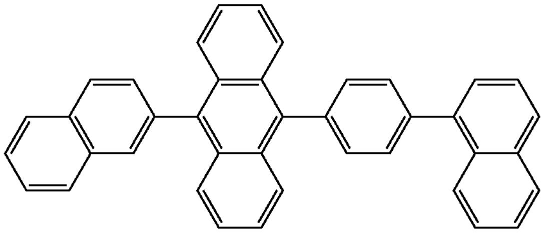
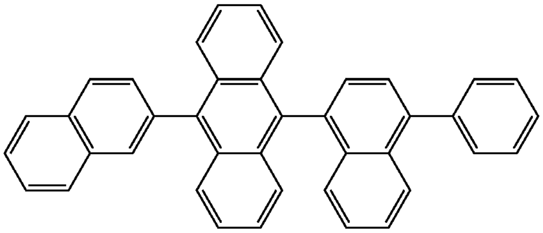
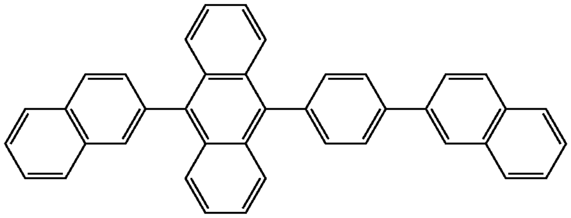
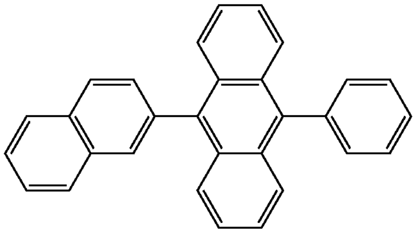
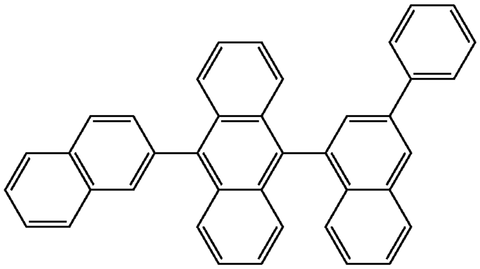

-continued
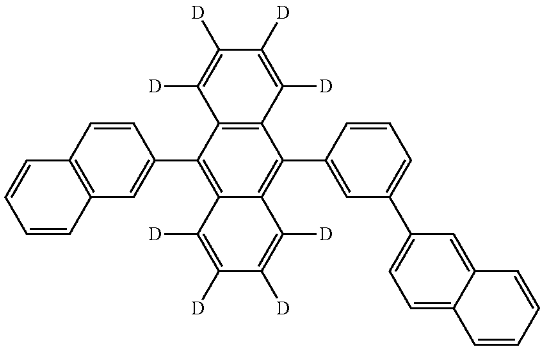
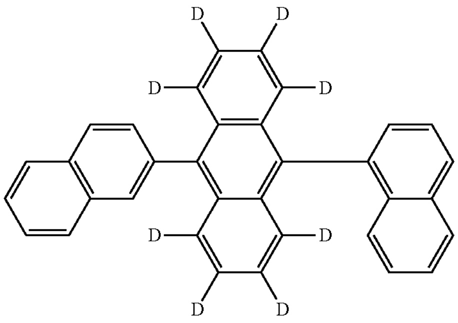
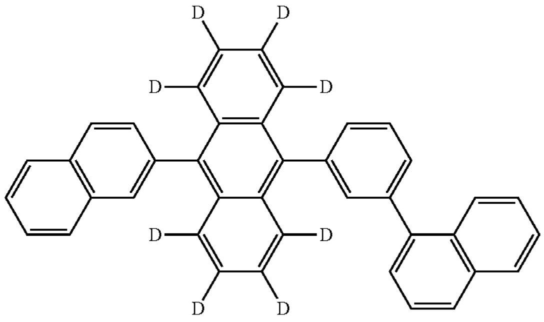
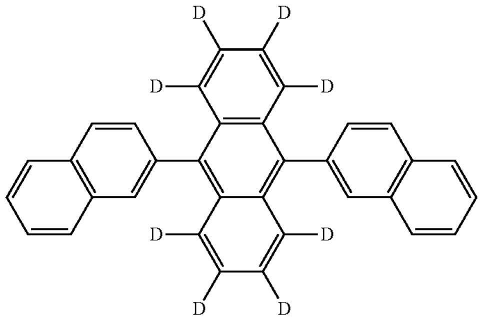
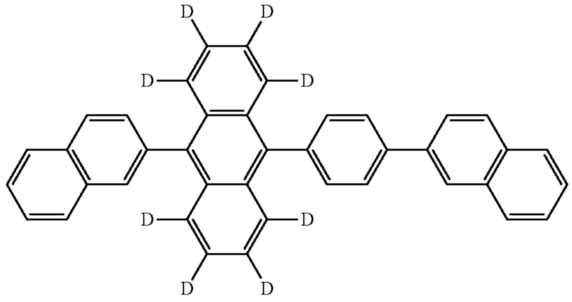
-continued
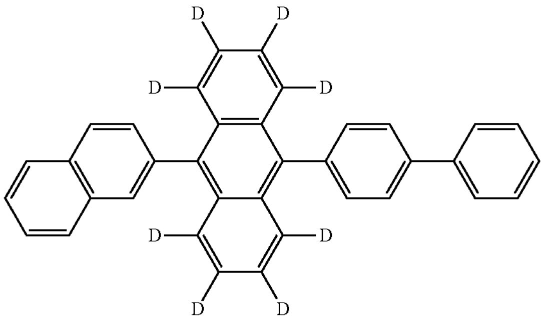
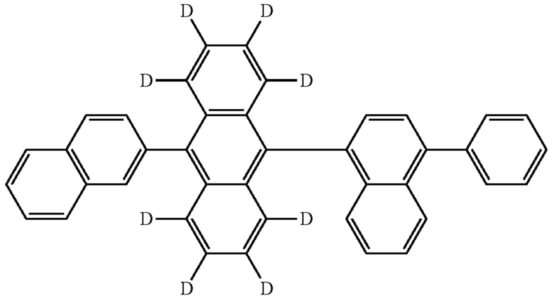
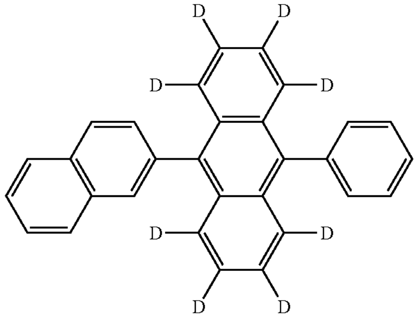
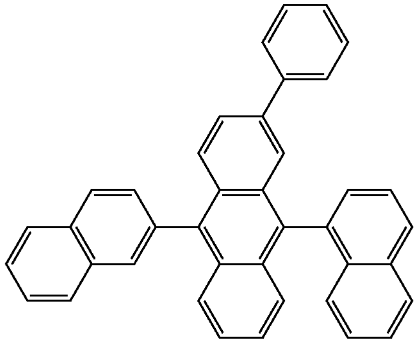
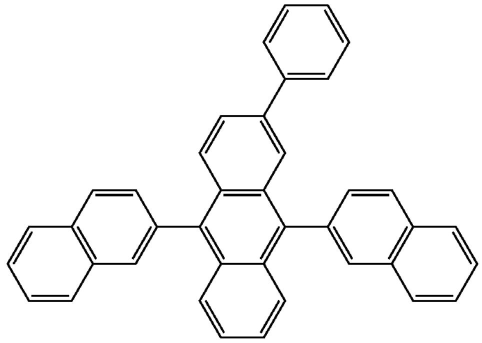

-continued
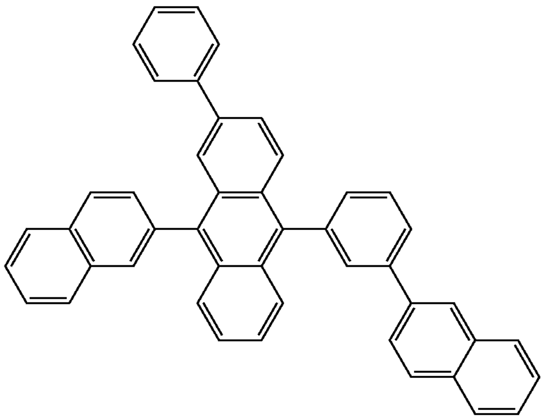
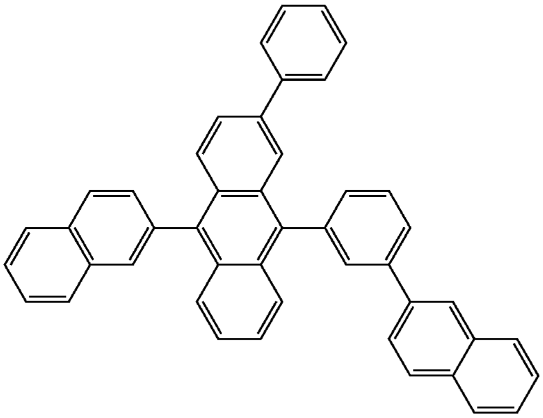
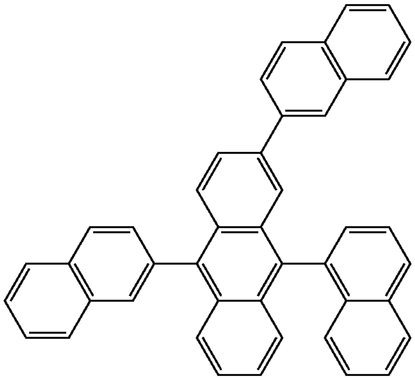
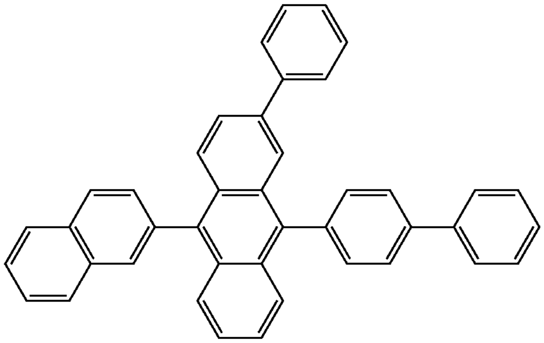
-continued
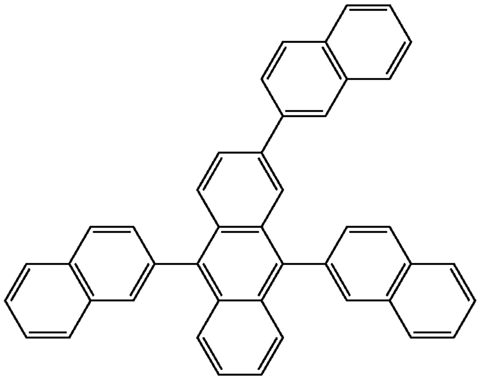
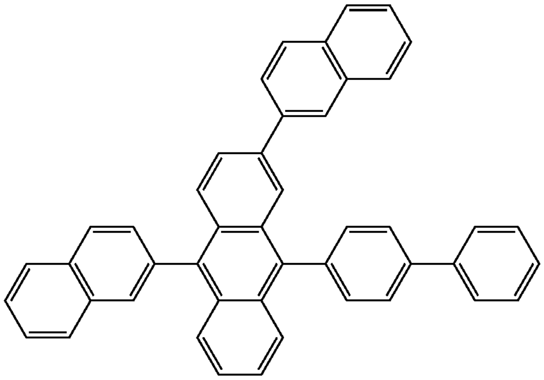
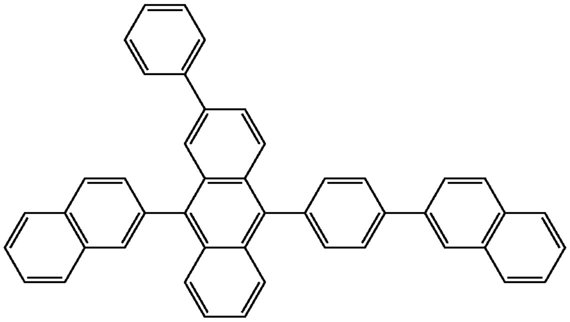
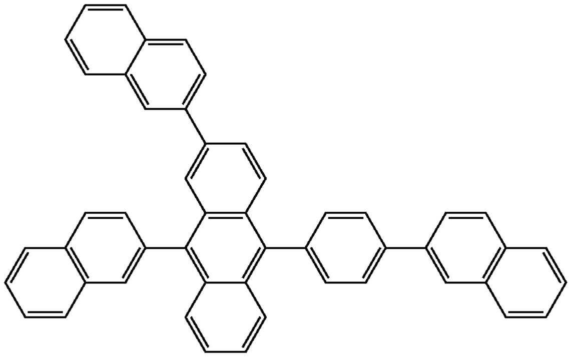

-continued
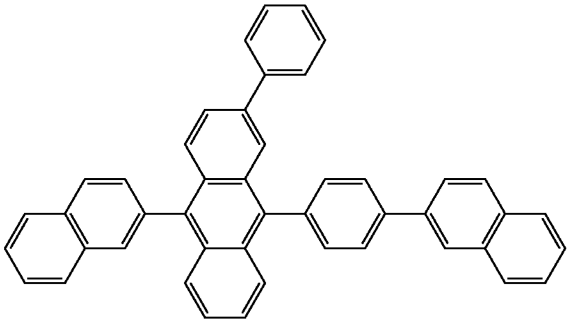
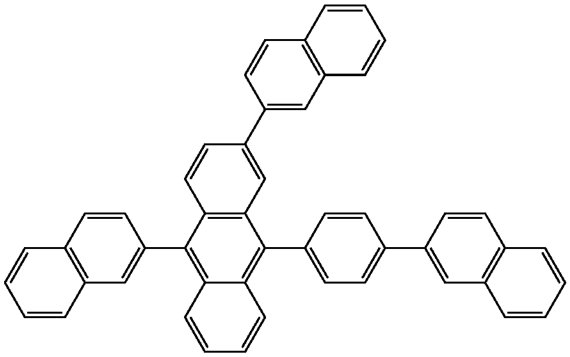
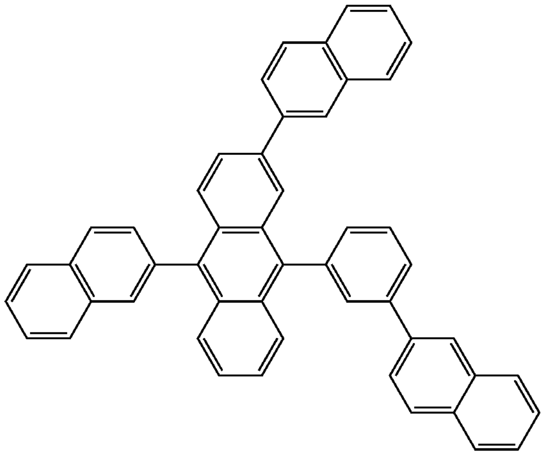
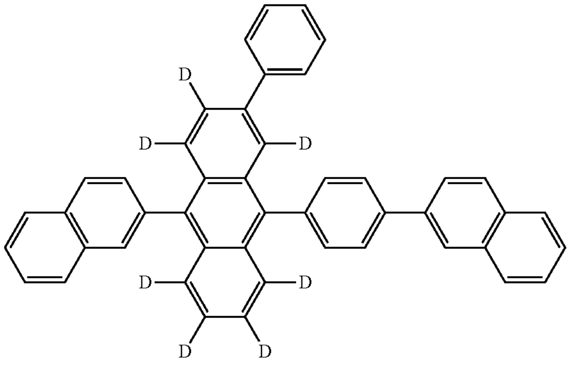
-continued
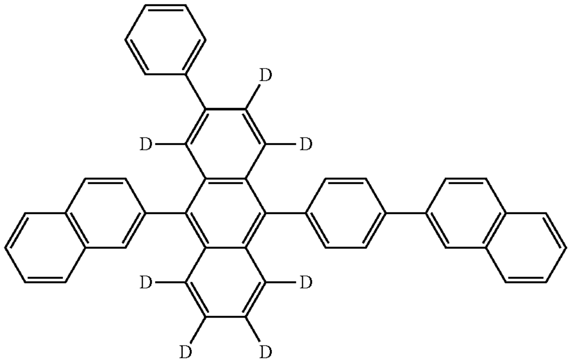
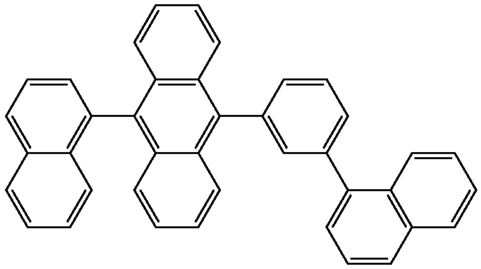
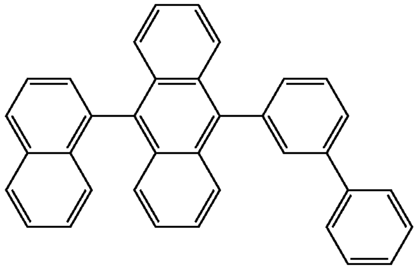
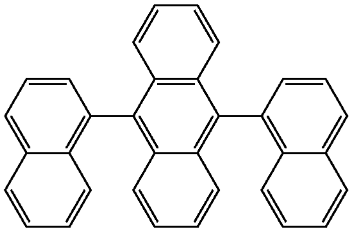
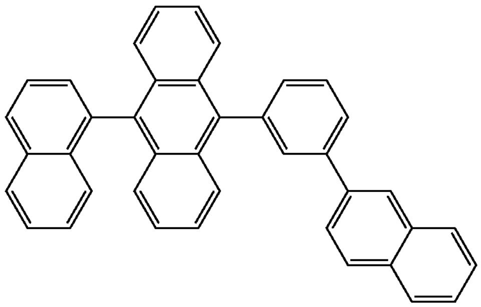
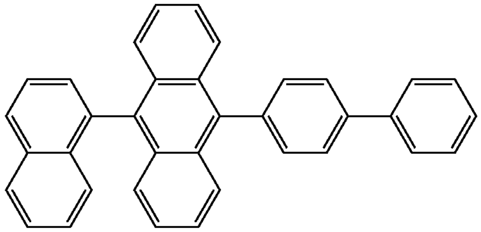

-continued
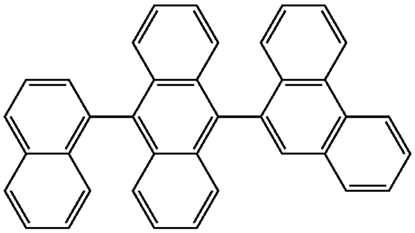
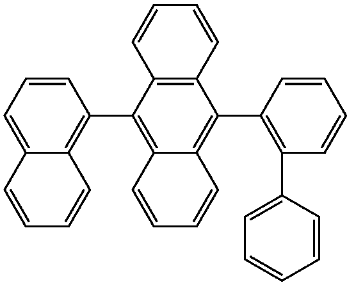
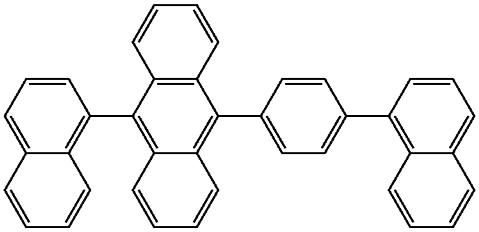
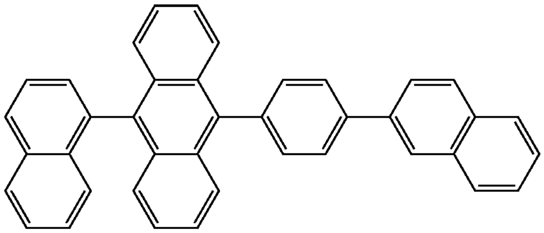
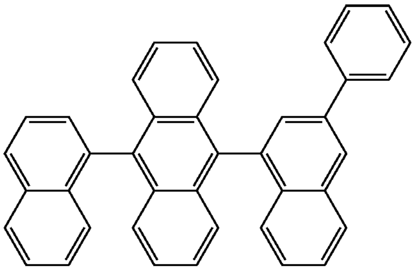
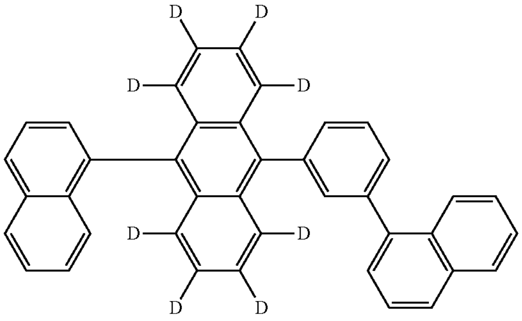
-continued
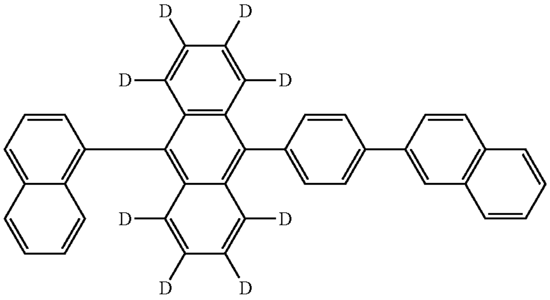
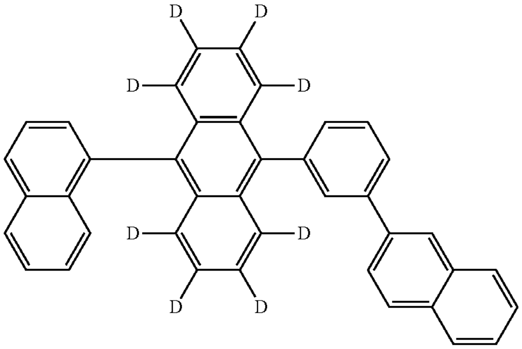
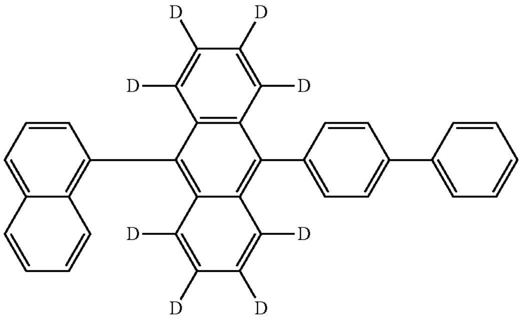
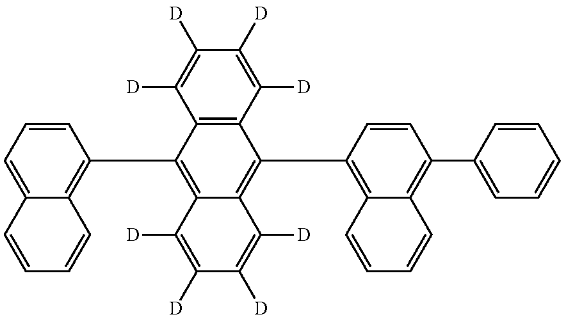
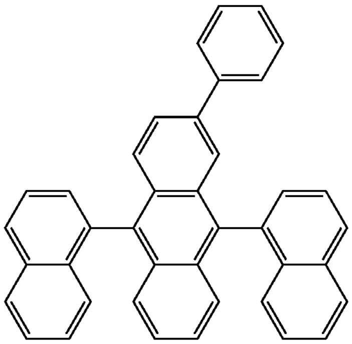

-continued
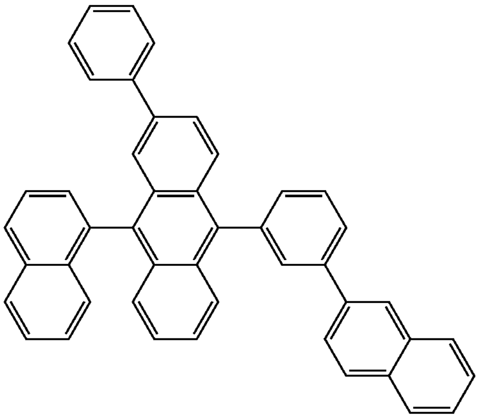
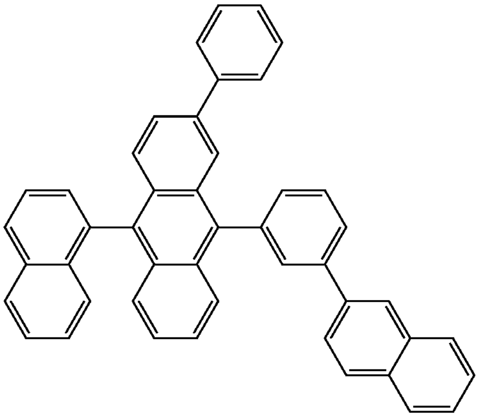
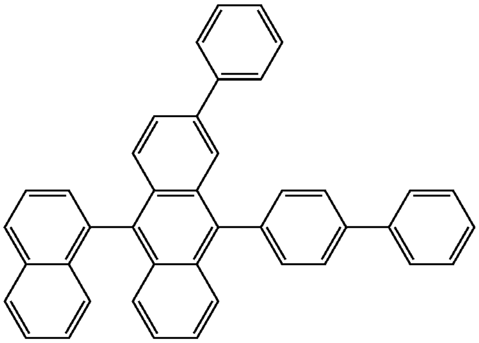
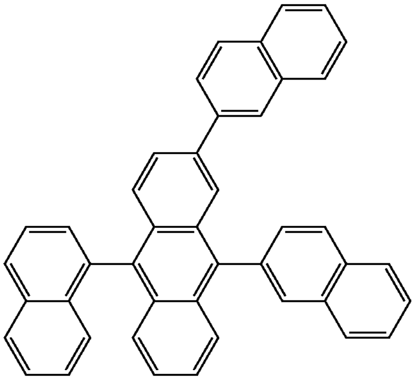
-continued
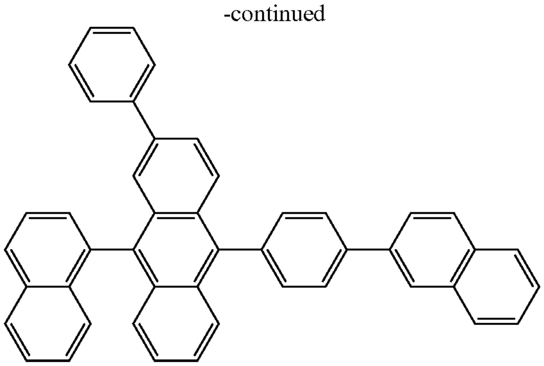
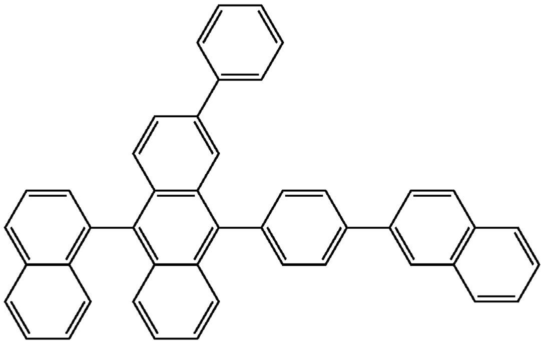
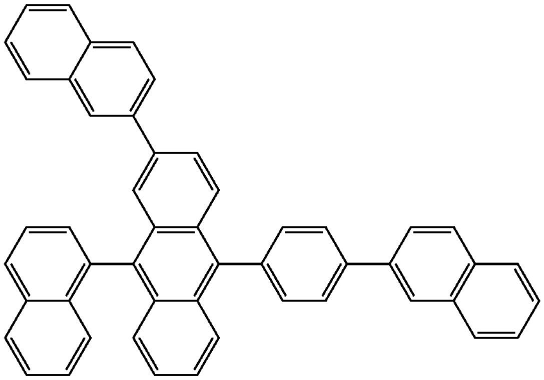
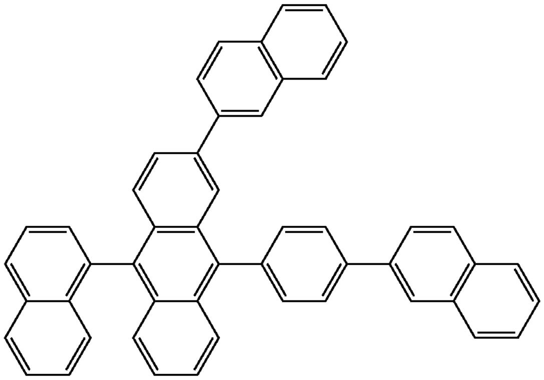

-continued
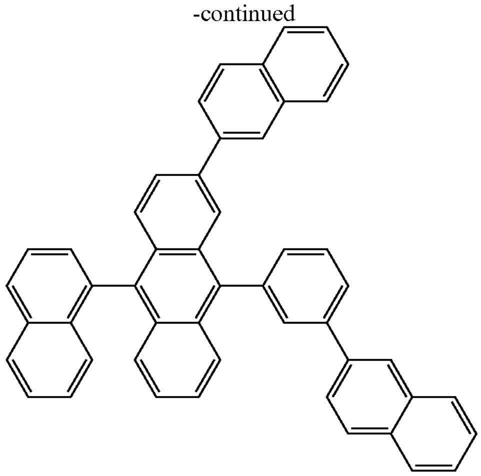
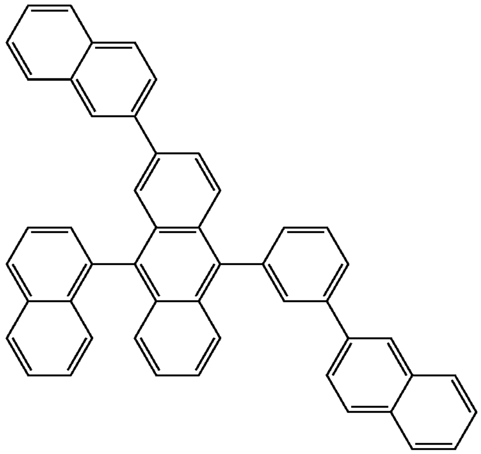
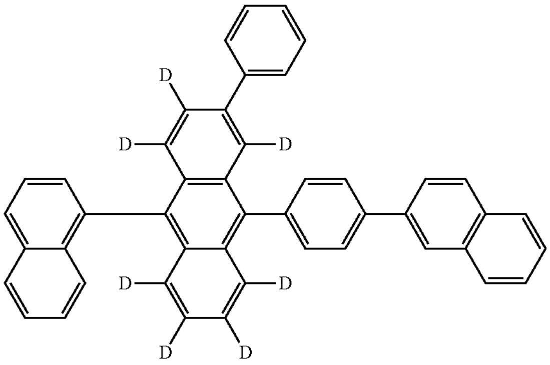
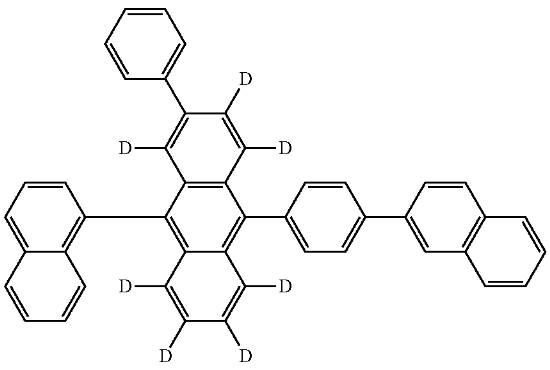
-continued
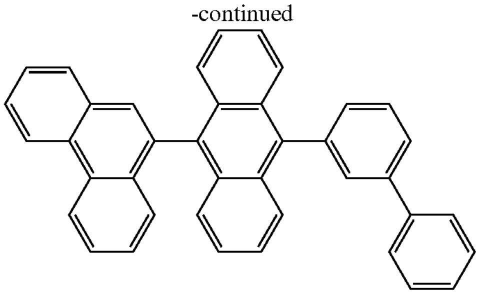
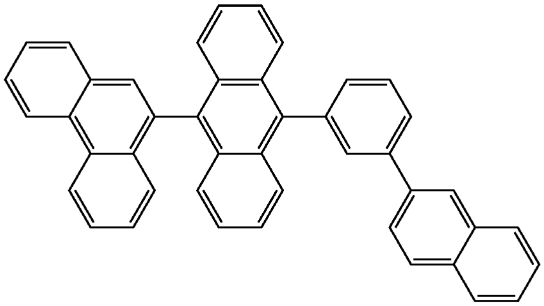
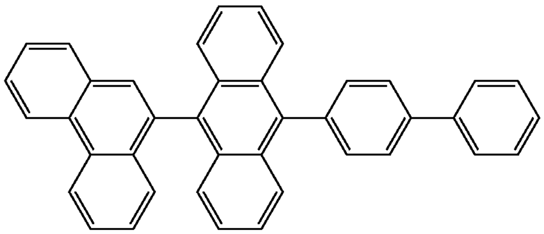
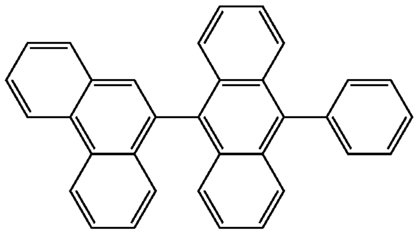
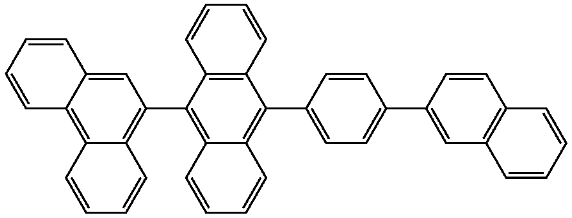
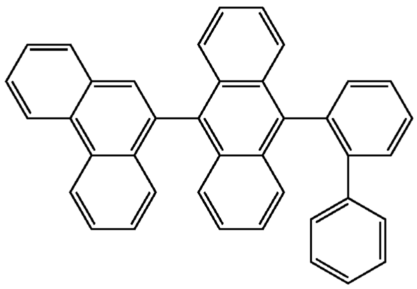

-continued
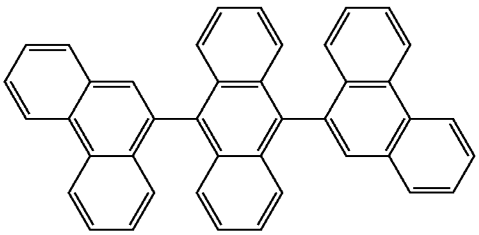
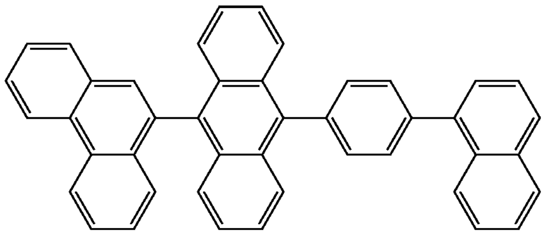
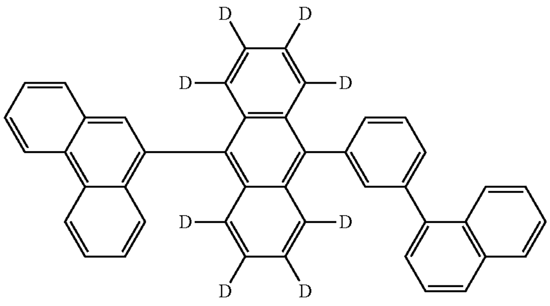
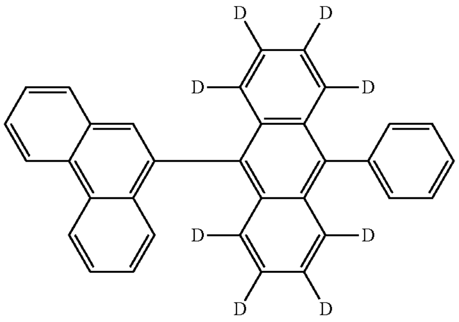
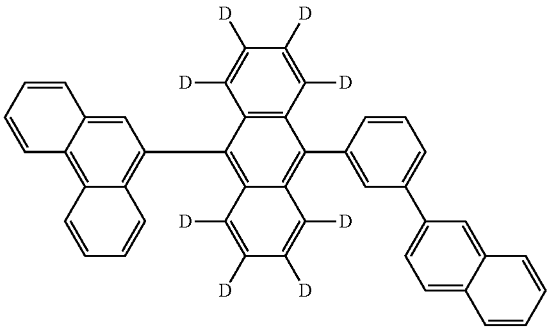
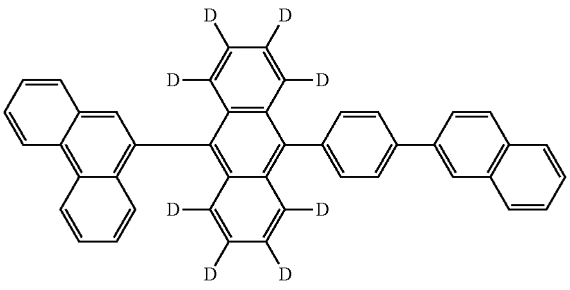
-continued
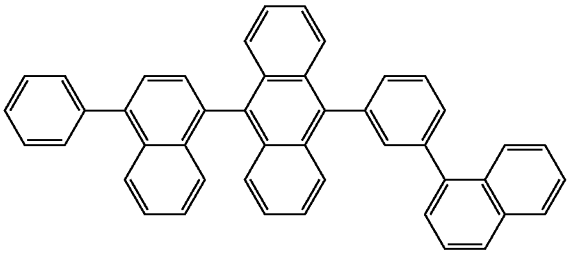
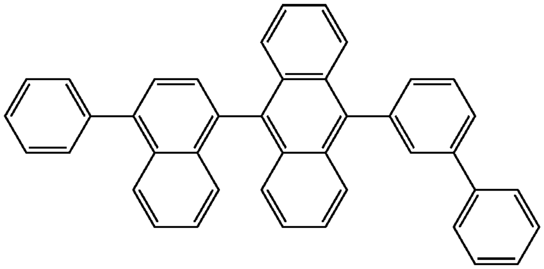
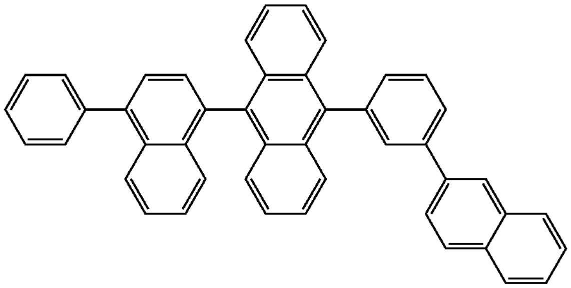
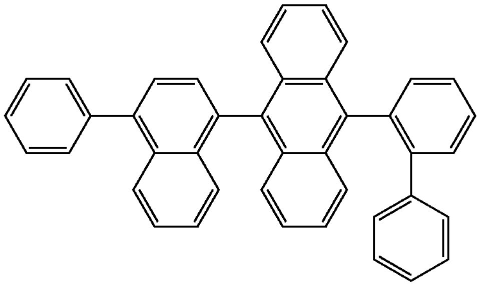
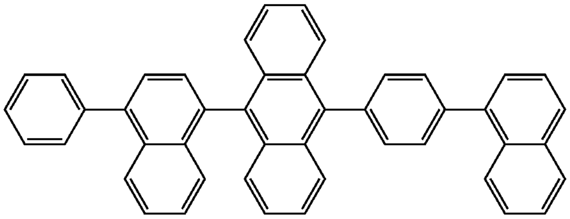
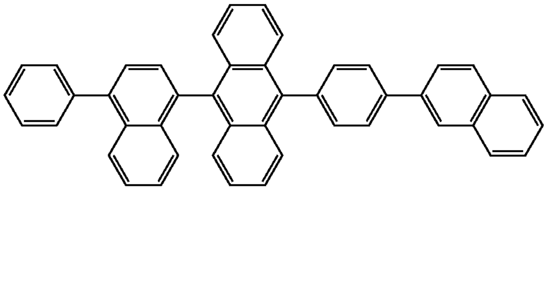

-continued
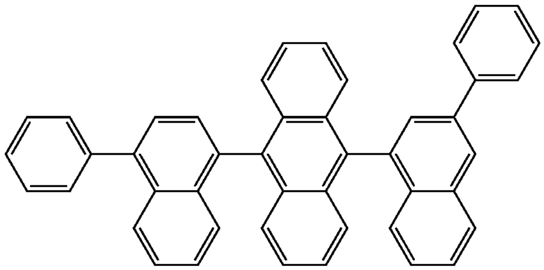
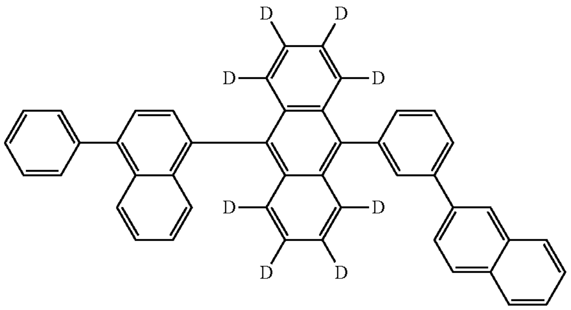
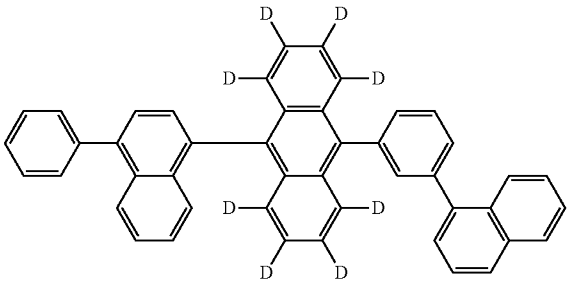
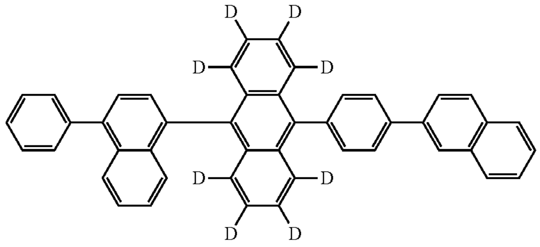
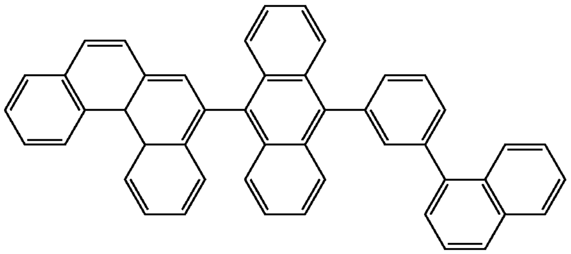
-continued
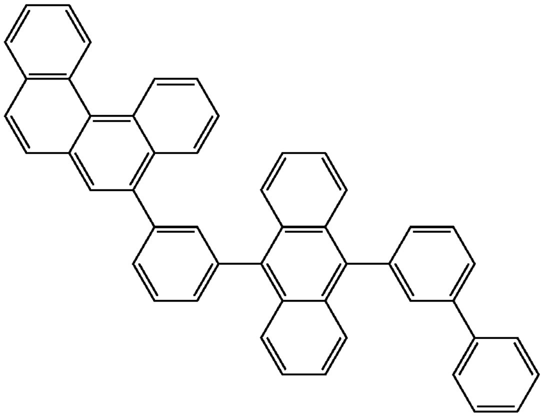
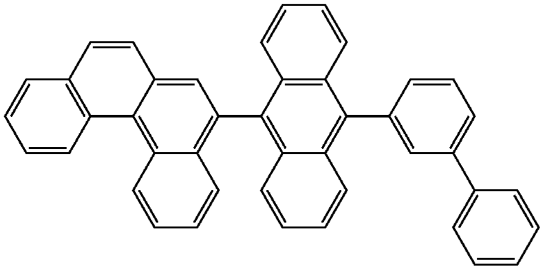
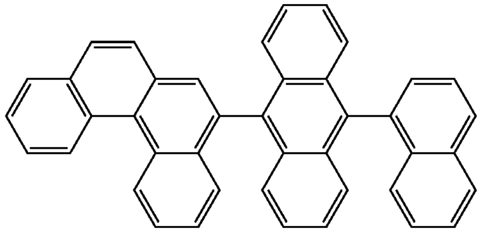
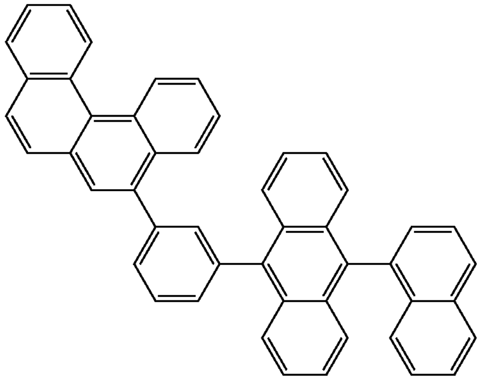
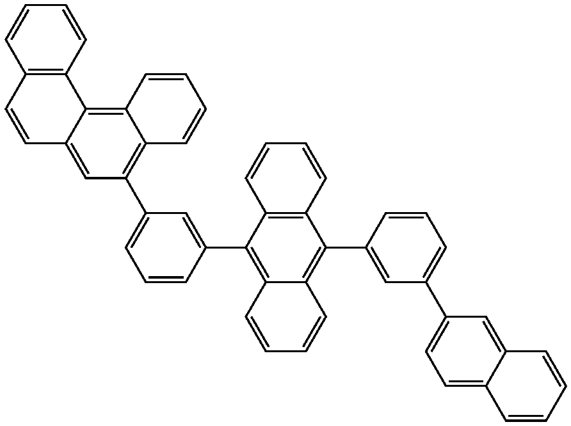

-continued
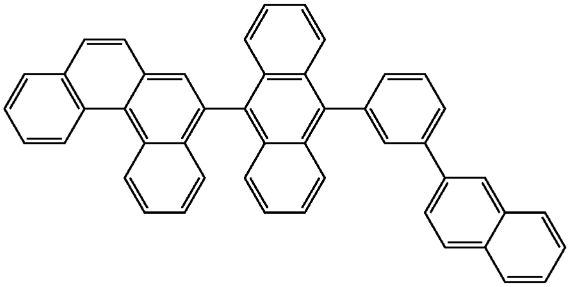
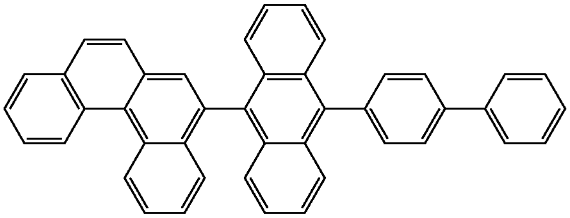
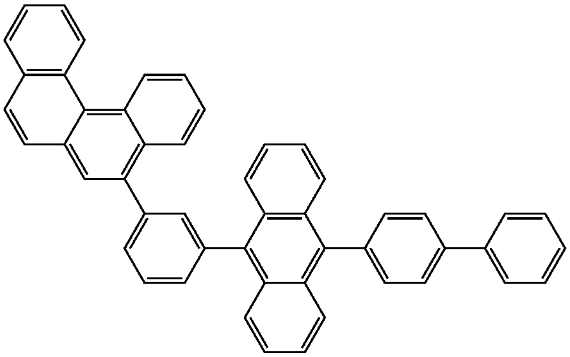
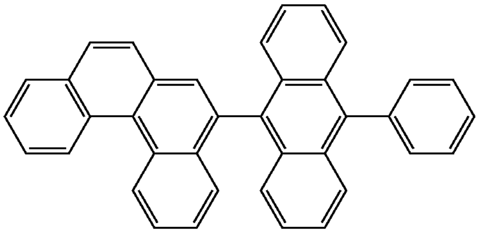
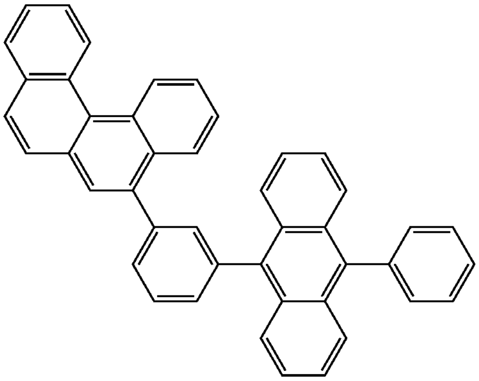
-continued
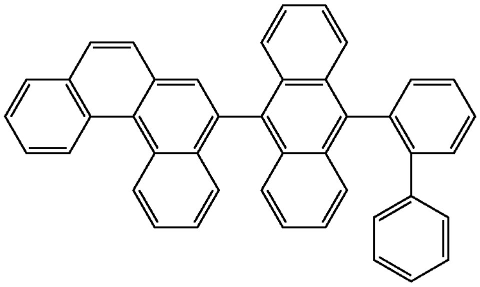
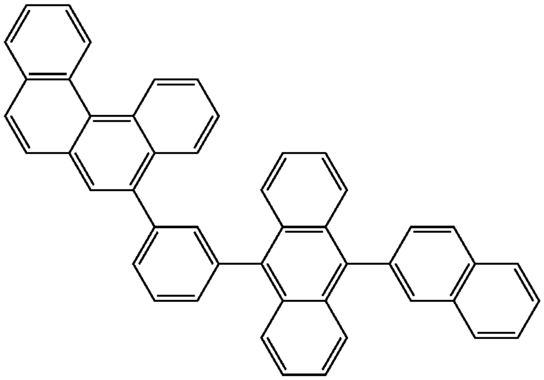
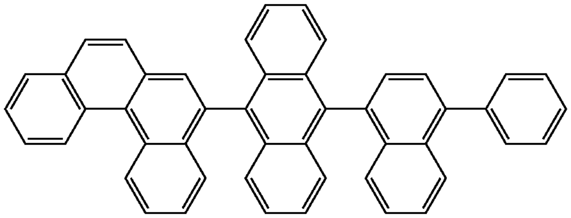
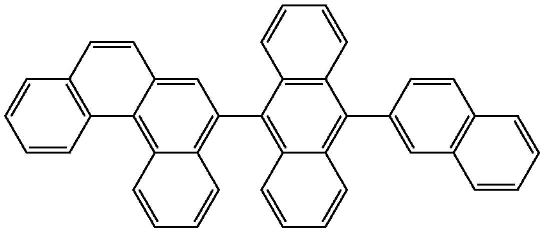
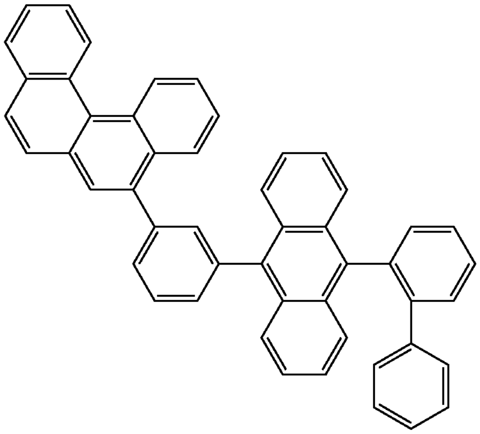

-continued
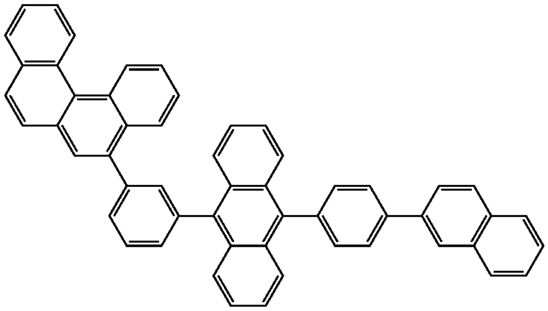
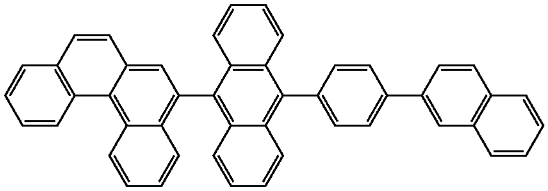
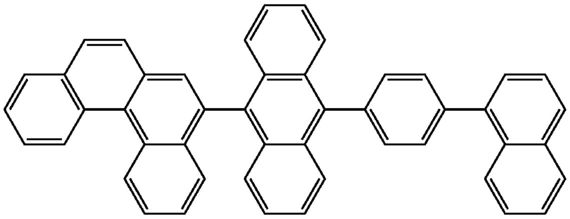
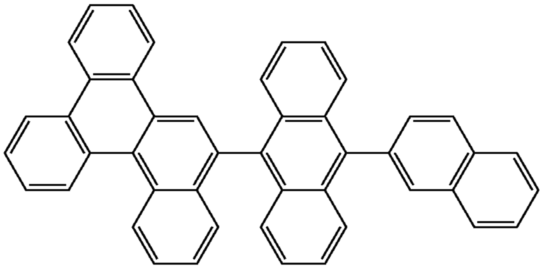
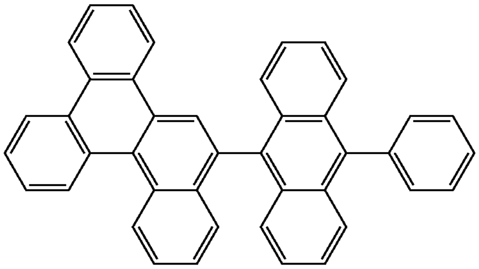
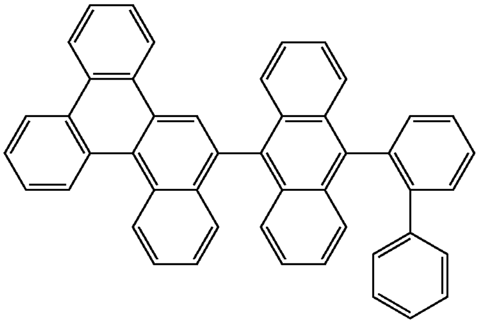
-continued
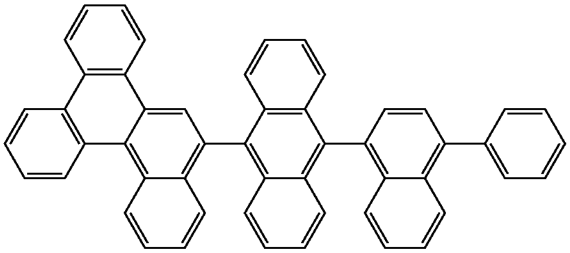
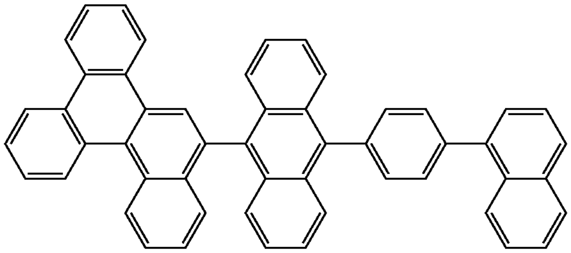
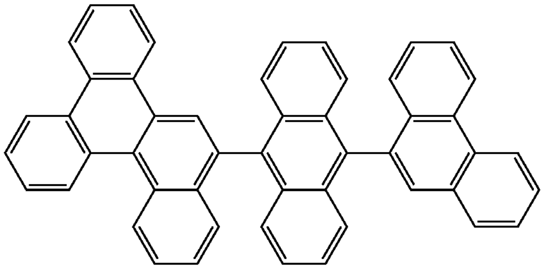
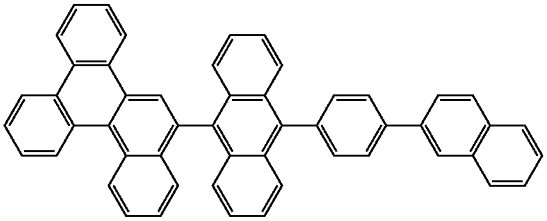
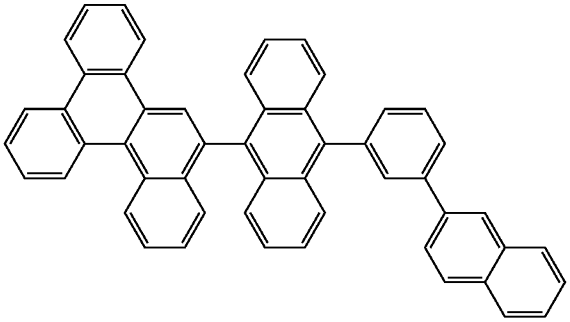
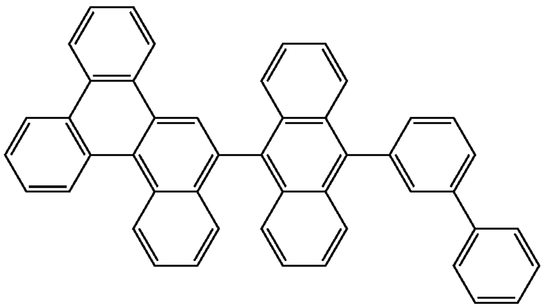

-continued
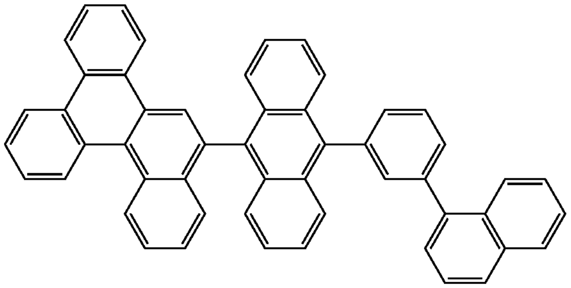
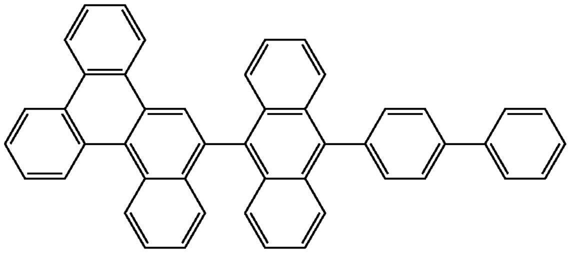
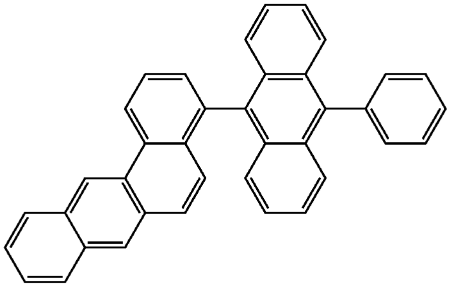
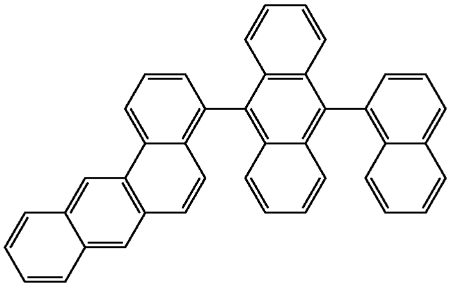
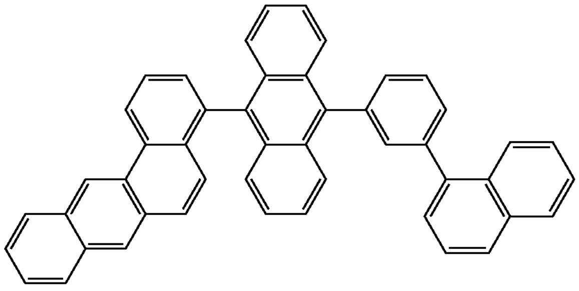
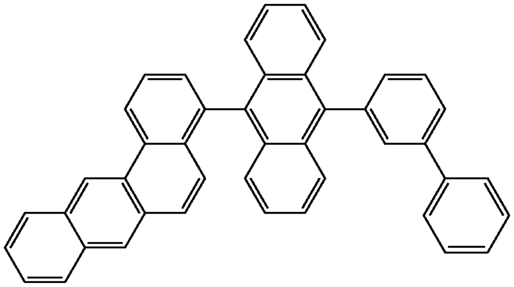
-continued
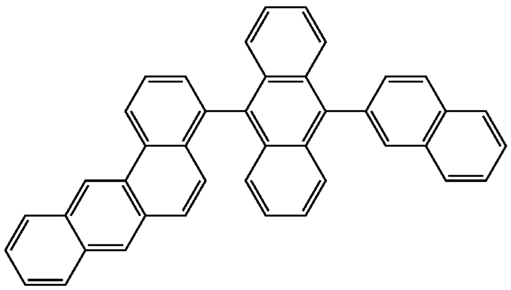
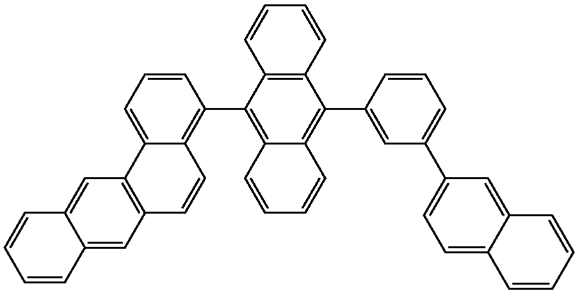
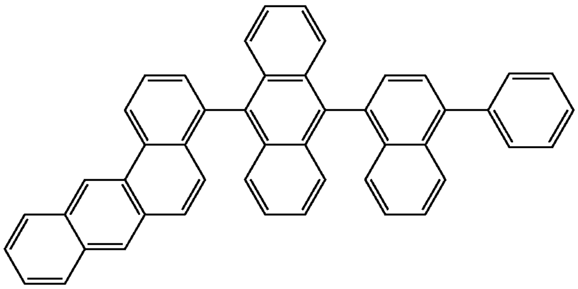
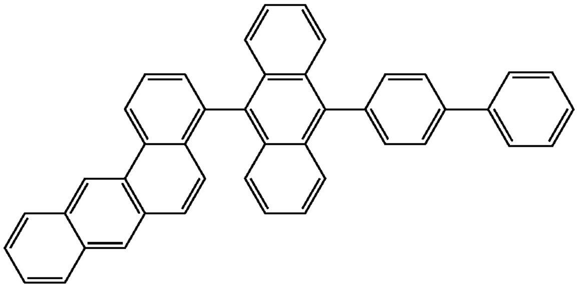
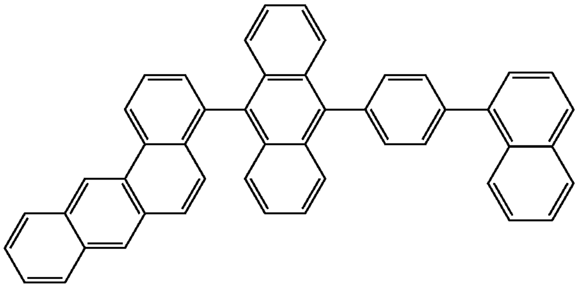
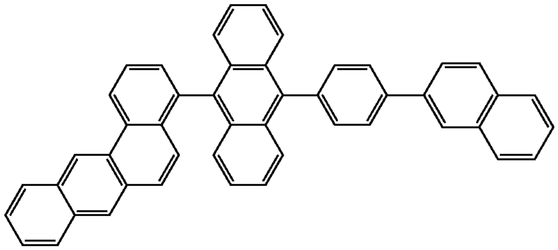

-continued
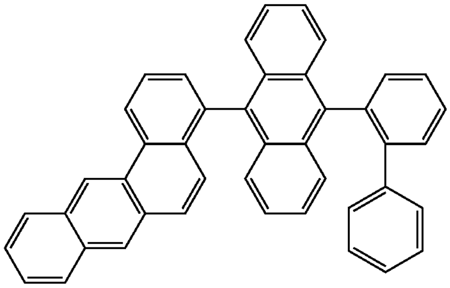
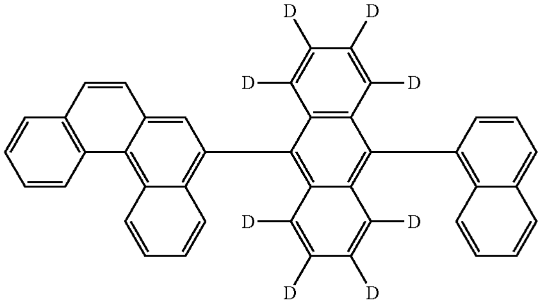
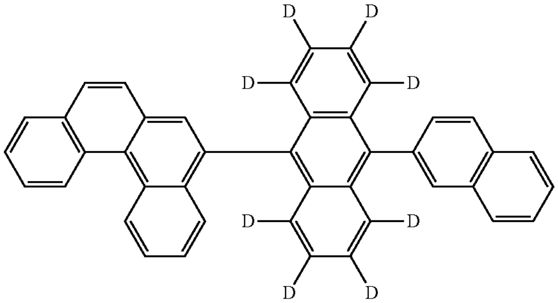
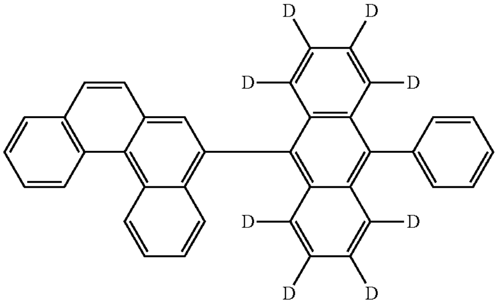
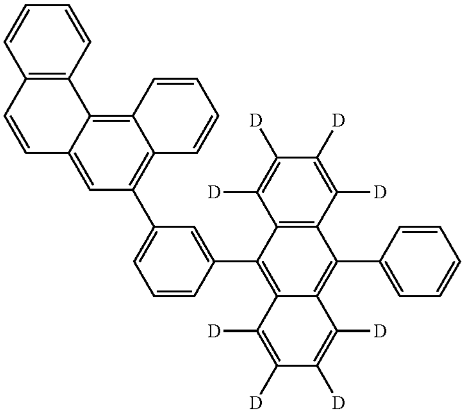
-continued
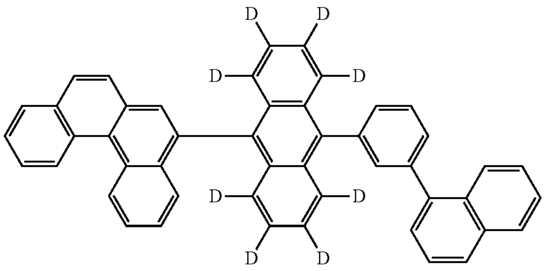
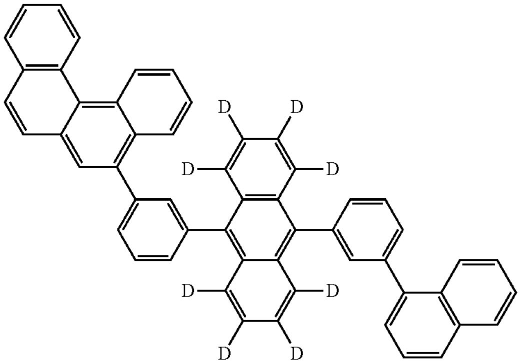
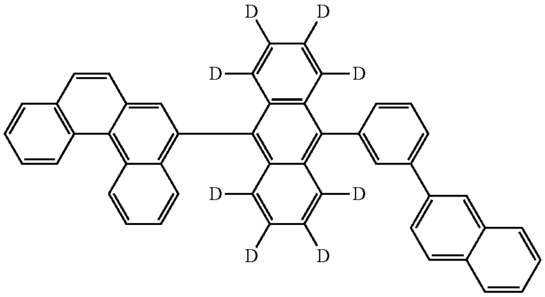
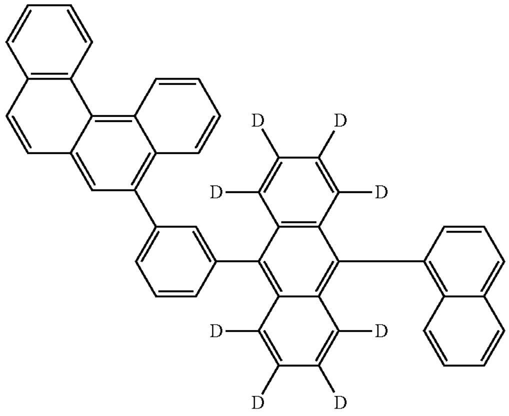
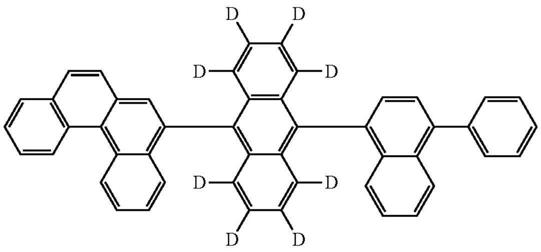

-continued
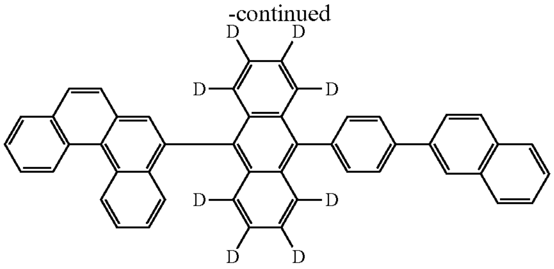
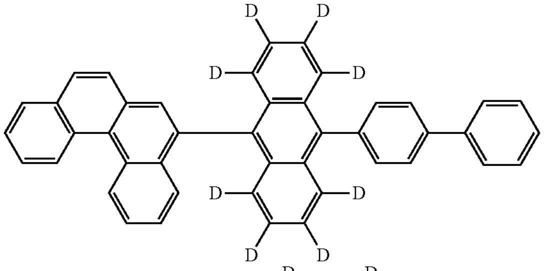
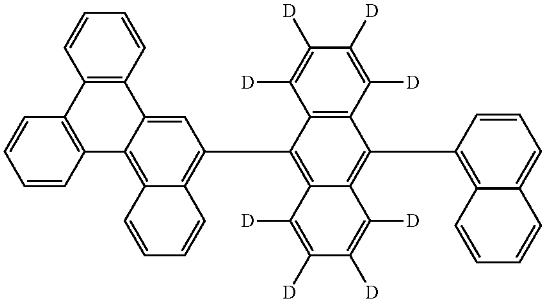
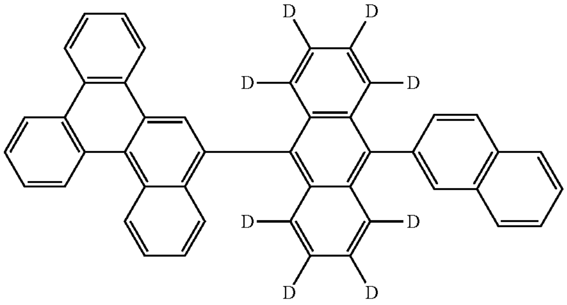
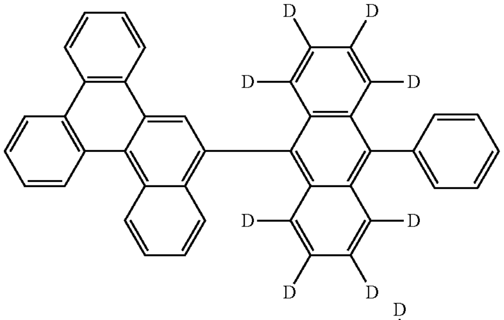
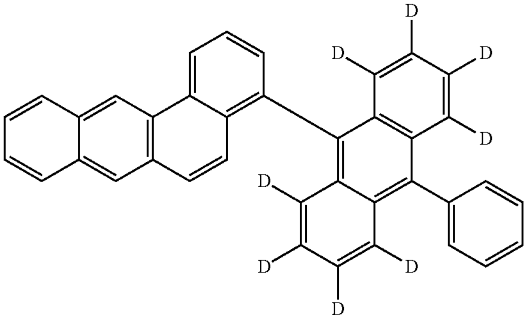
-continued
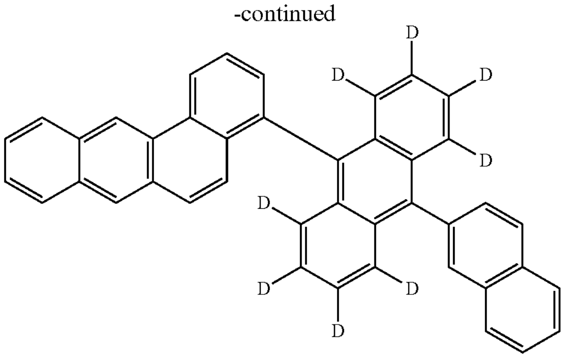
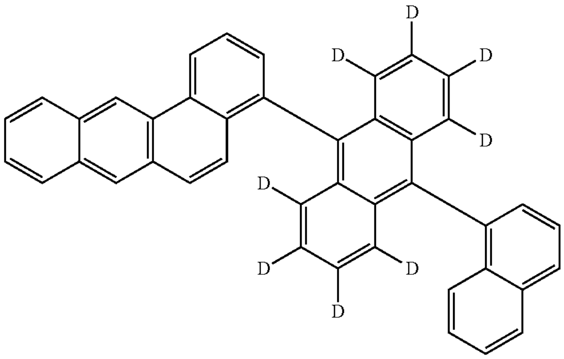
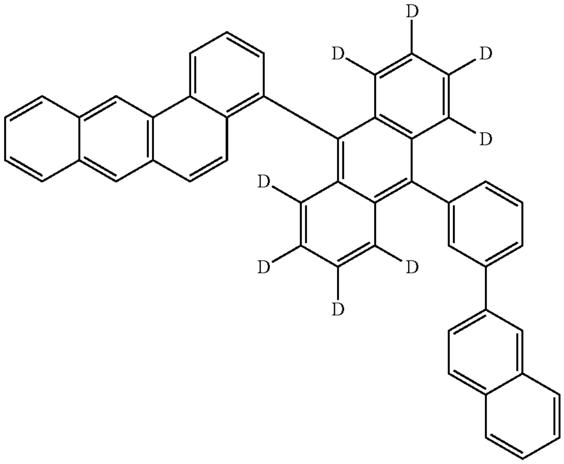
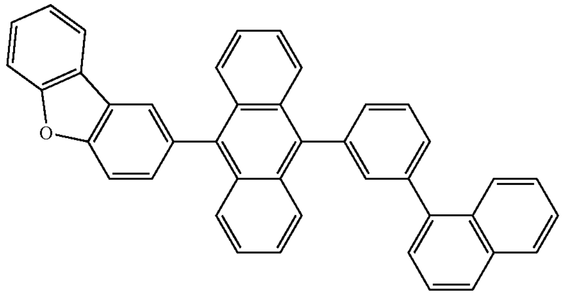

-continued
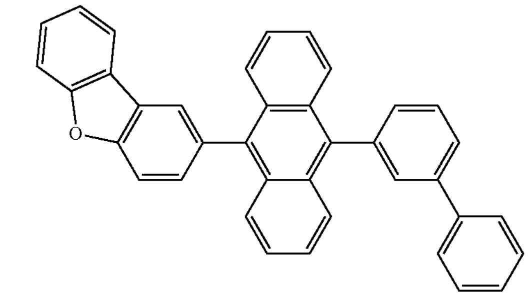
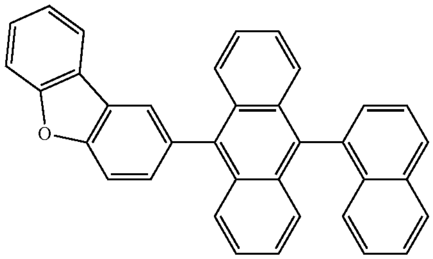
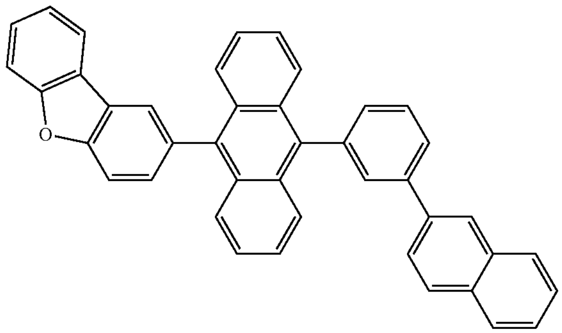
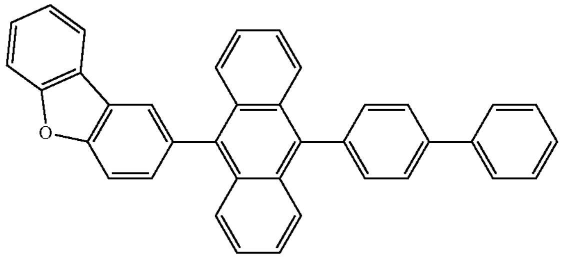
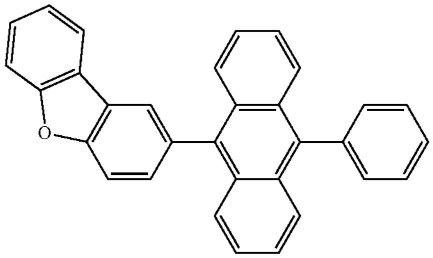
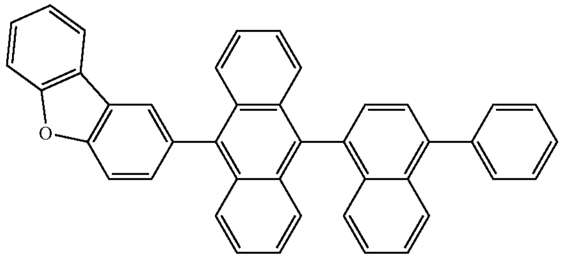
-continued
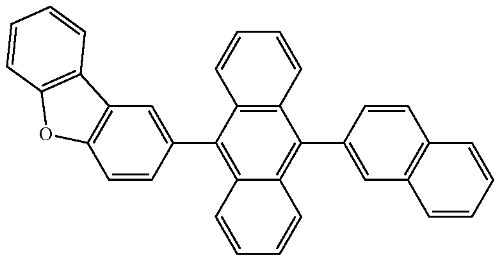
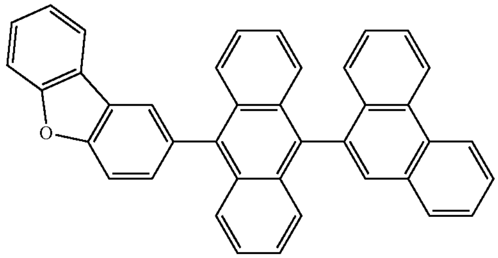
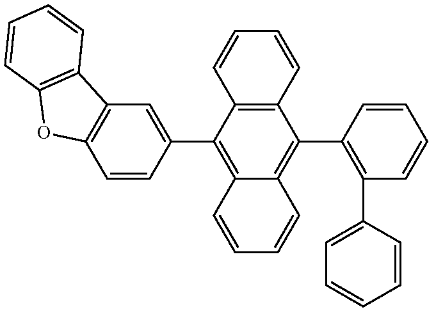
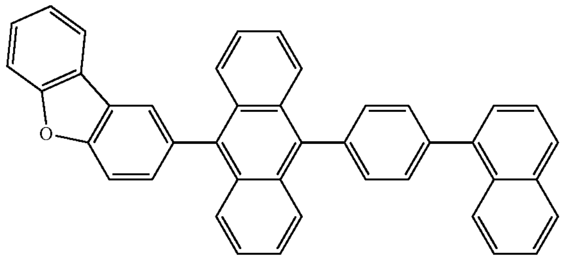
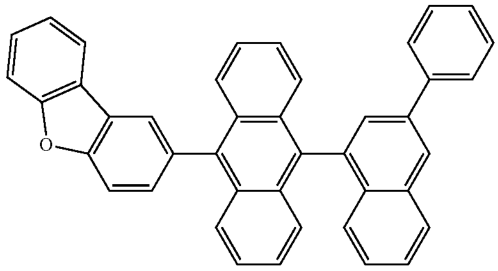
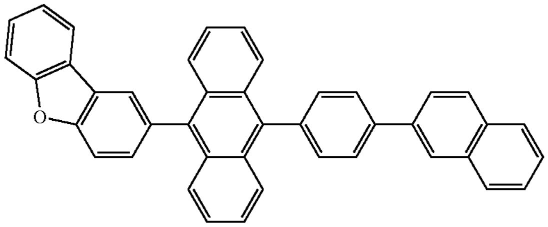

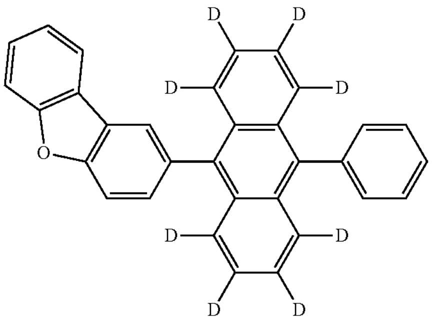
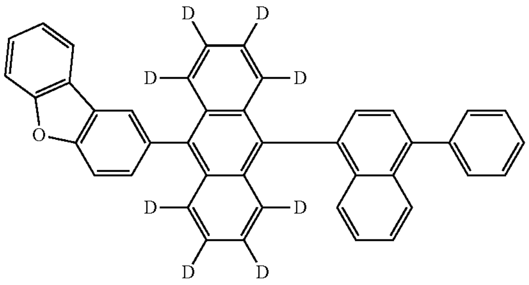
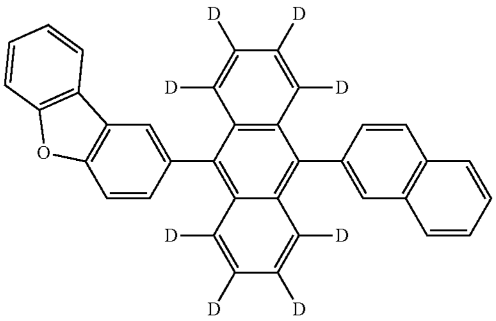
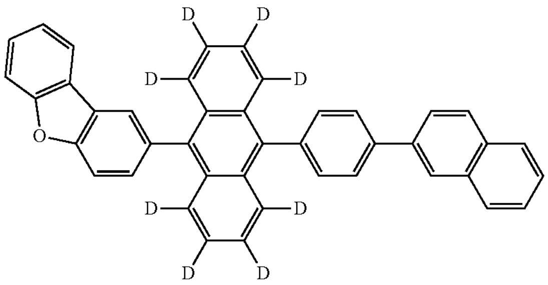
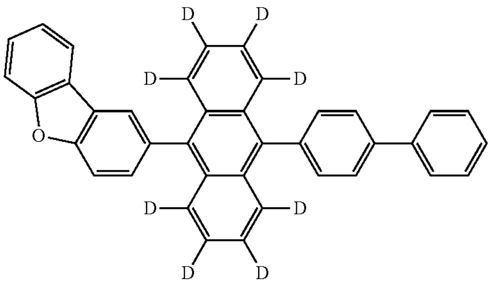
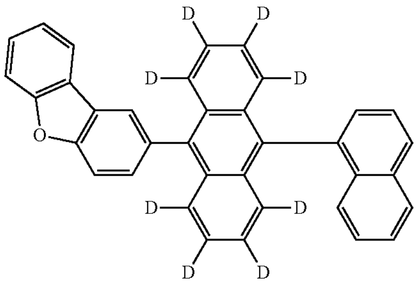
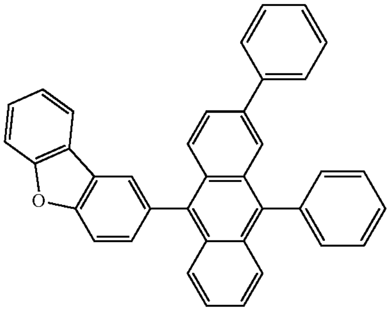
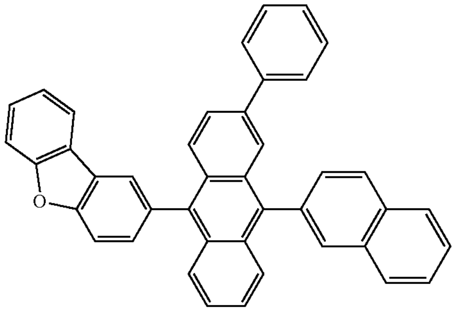
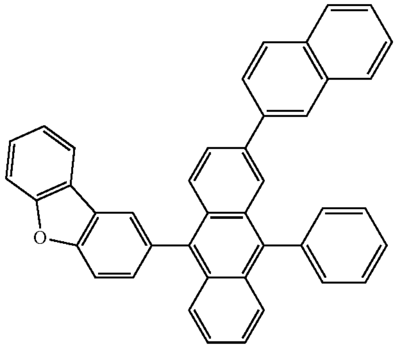
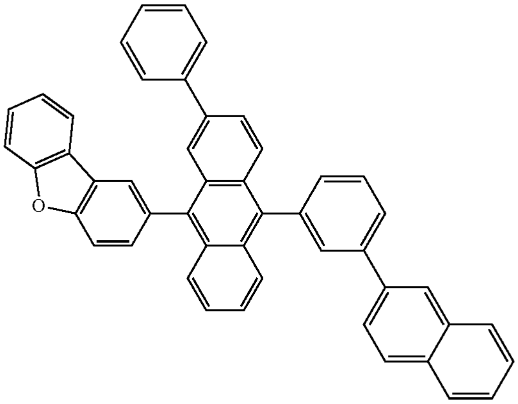

-continued
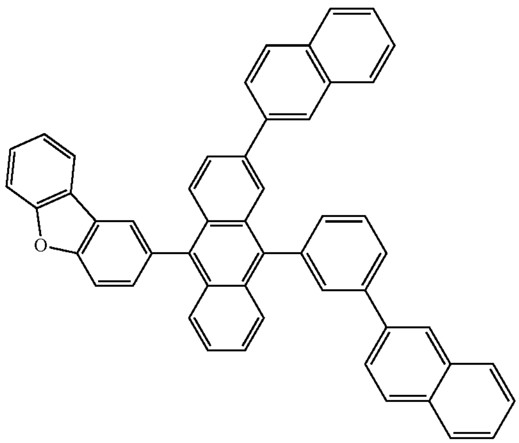
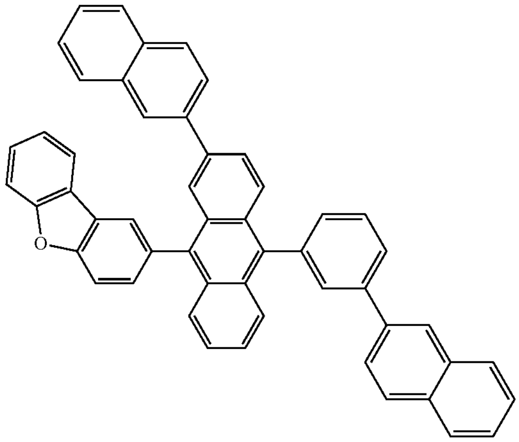
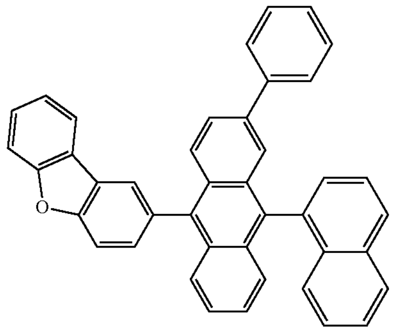
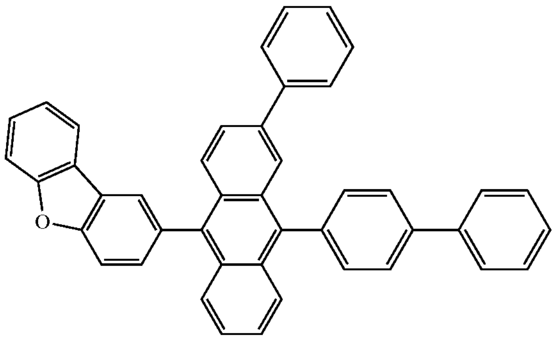
-continued
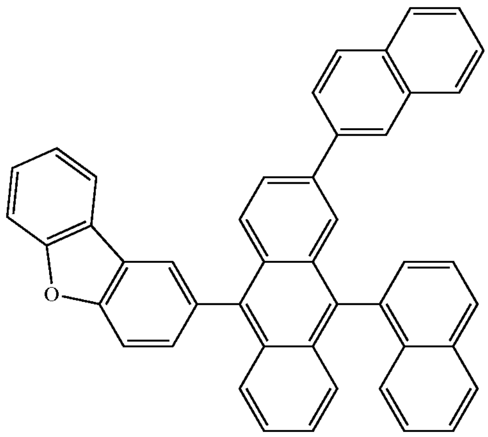
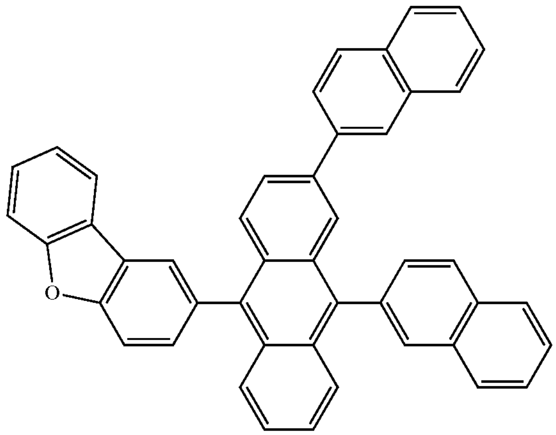
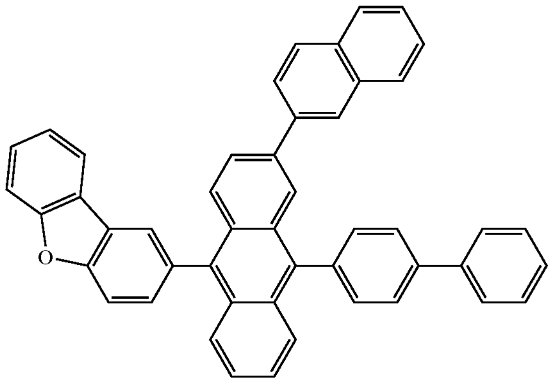
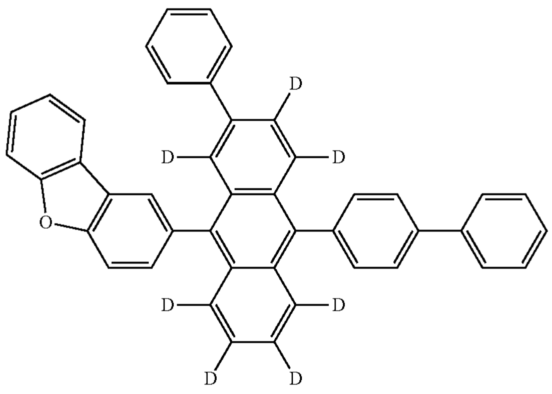

-continued
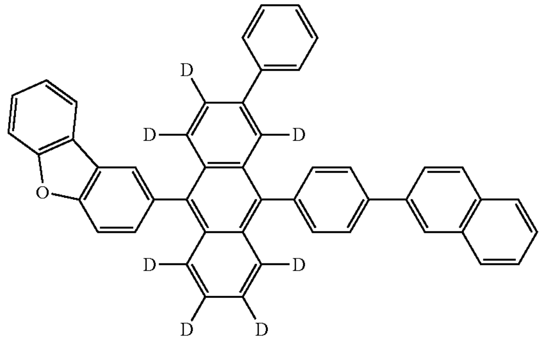
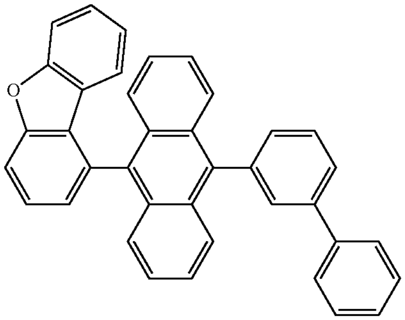
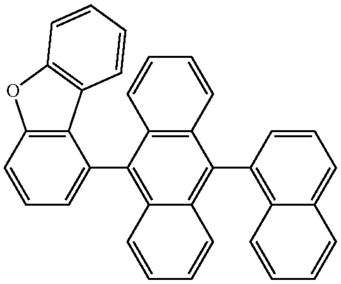
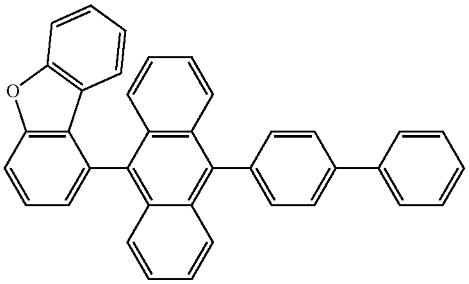
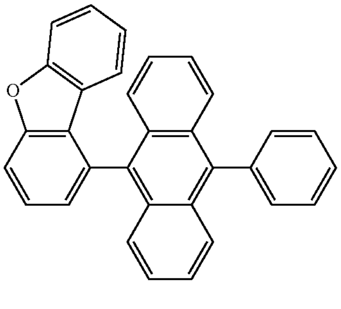
-continued
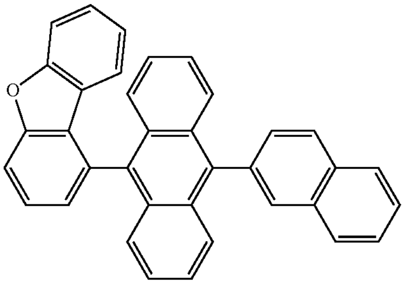
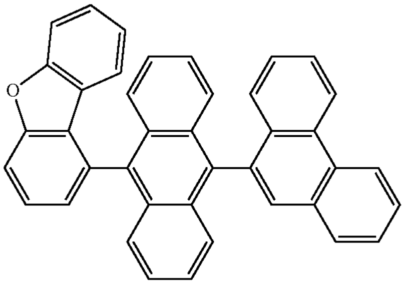
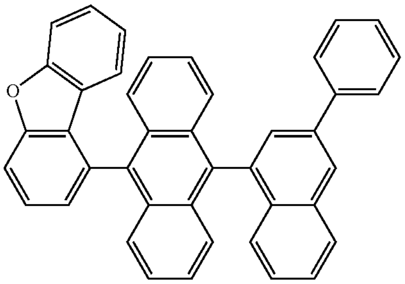
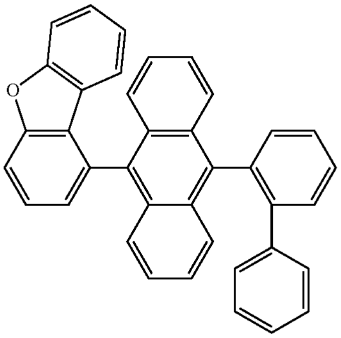
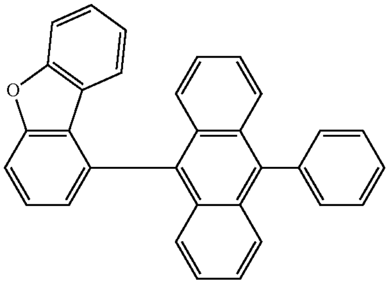

-continued
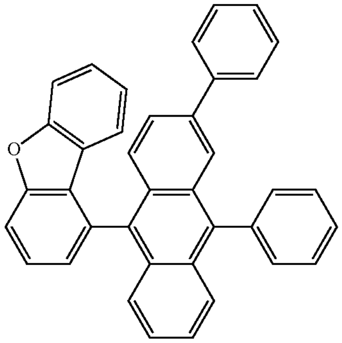
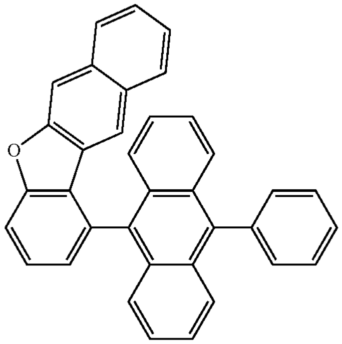
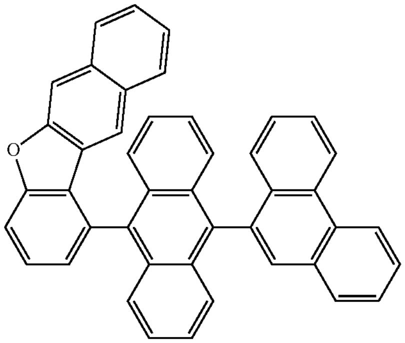
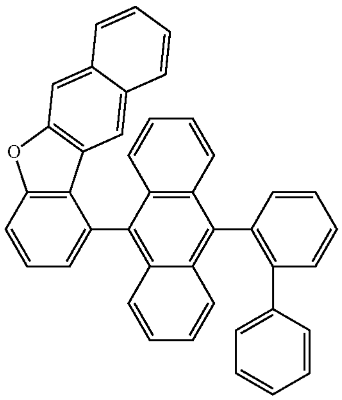
-continued
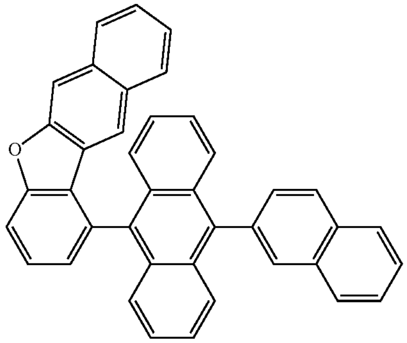
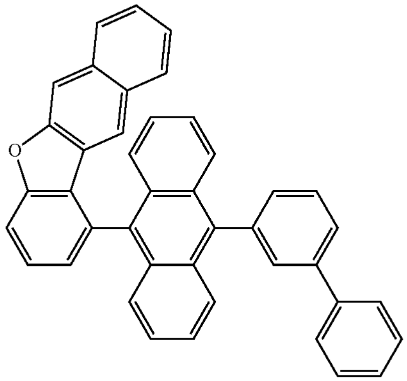
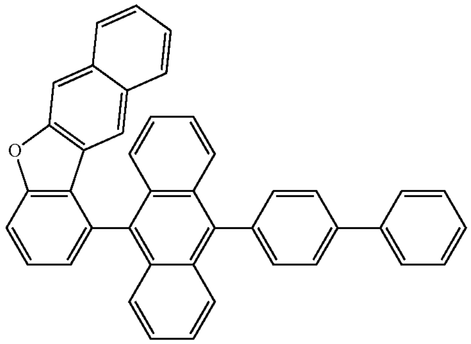
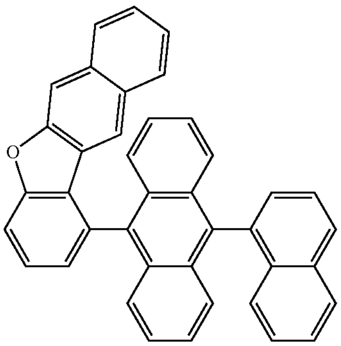

-continued
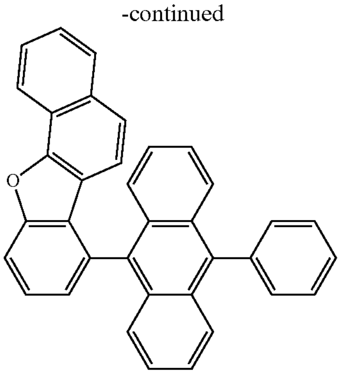
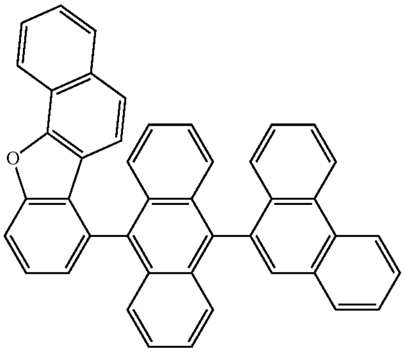
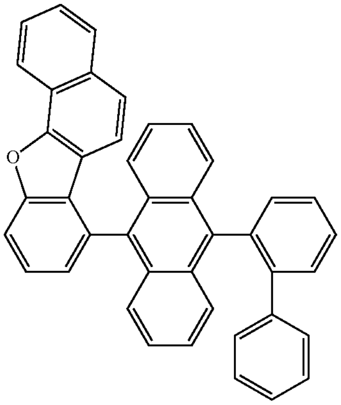
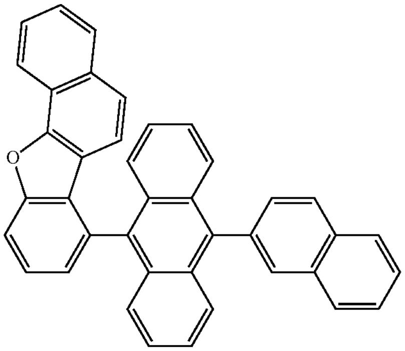
-continued
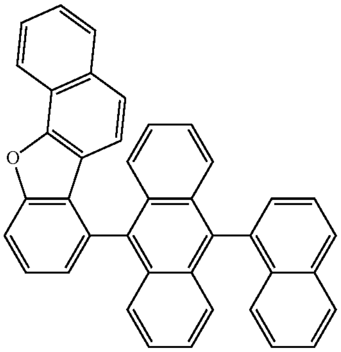
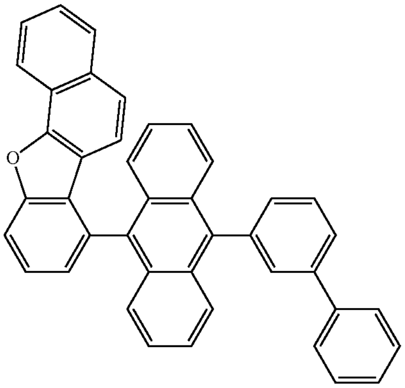
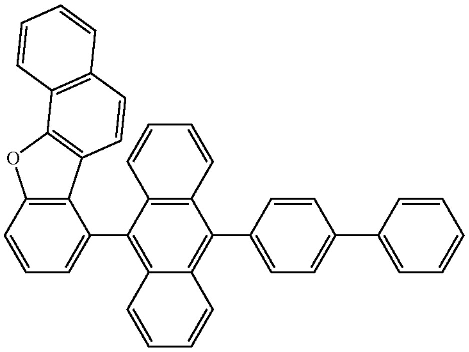
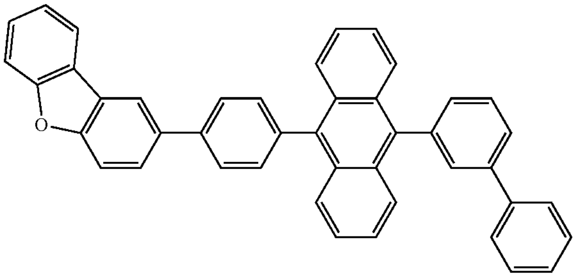
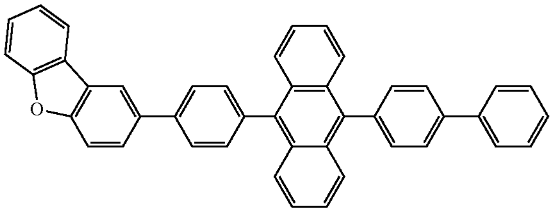

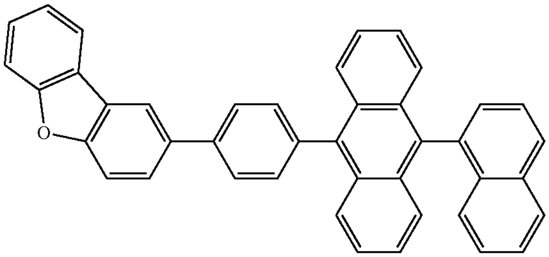
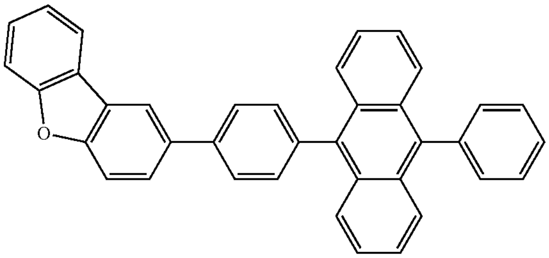
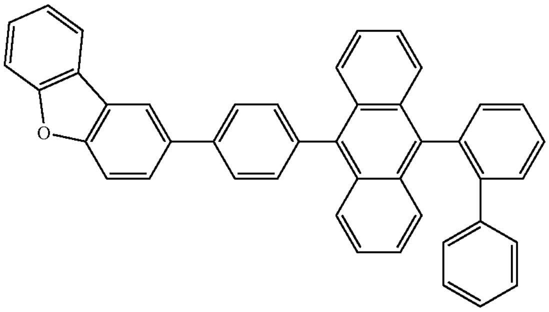
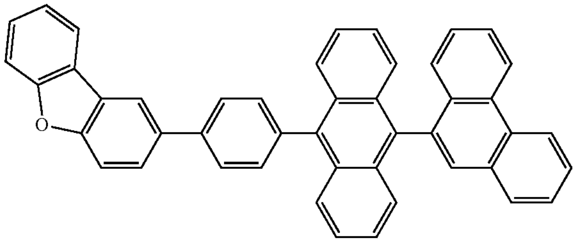
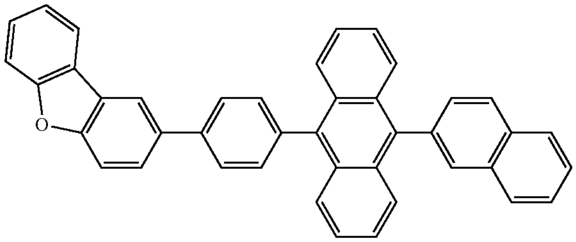
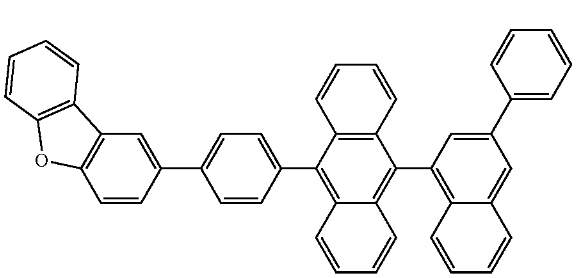
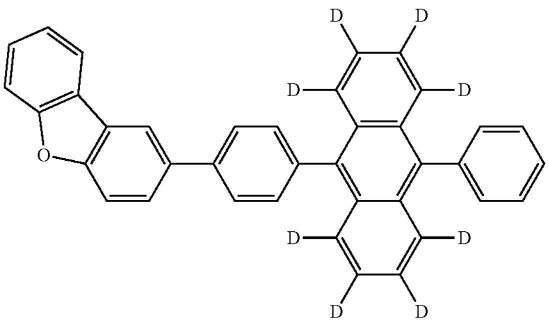
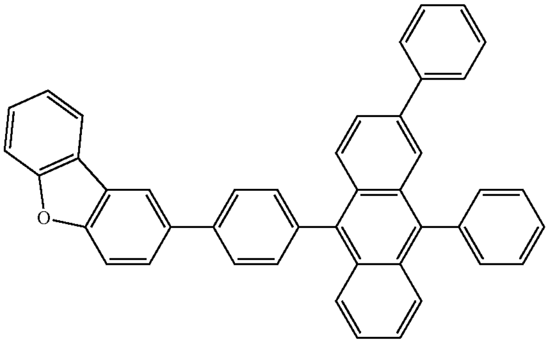
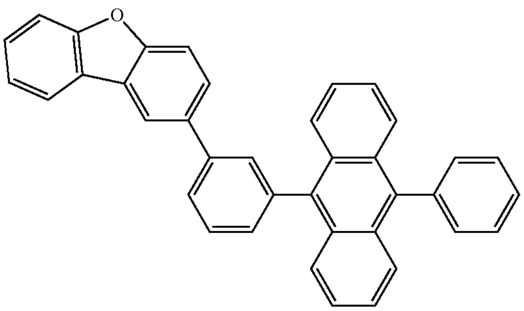
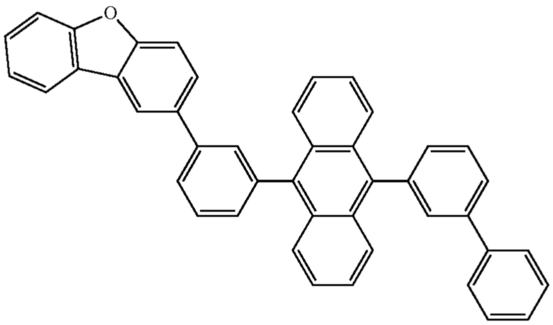
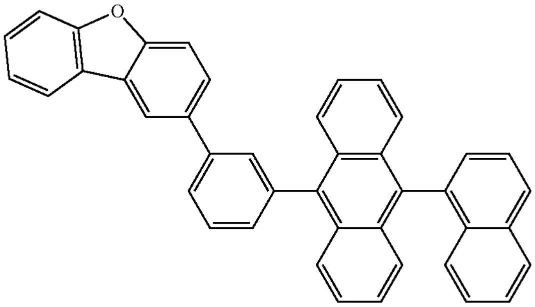

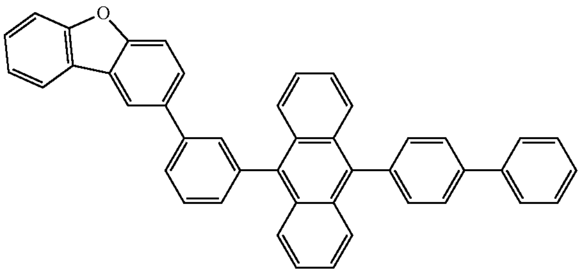
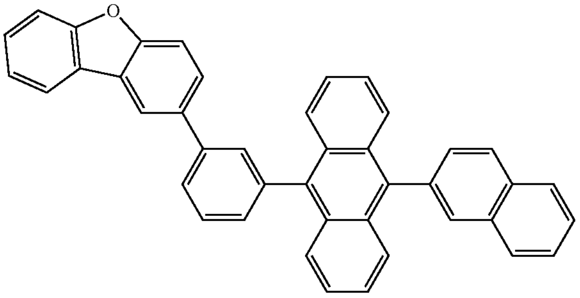
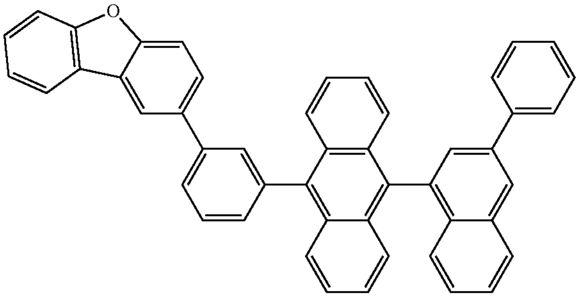
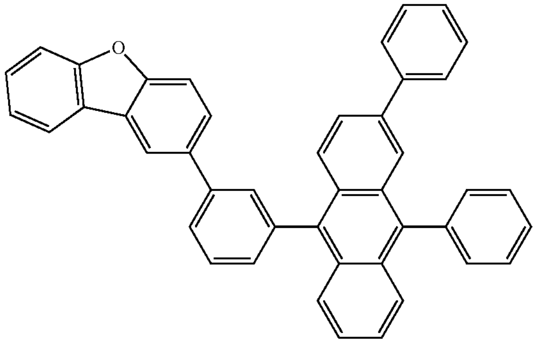
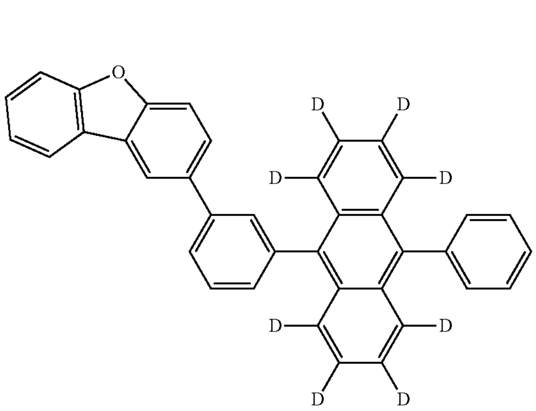
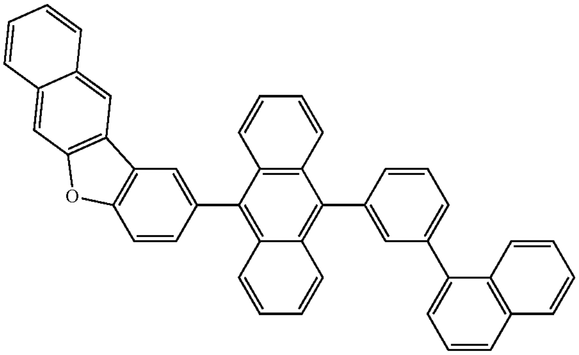
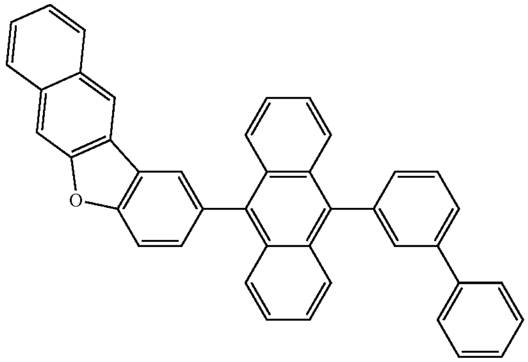
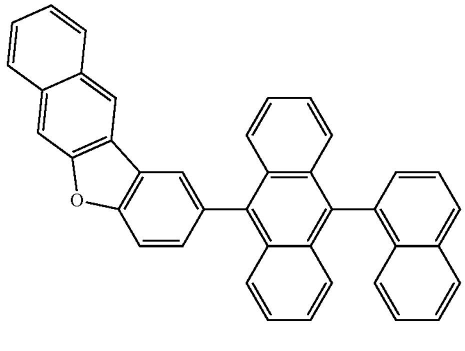
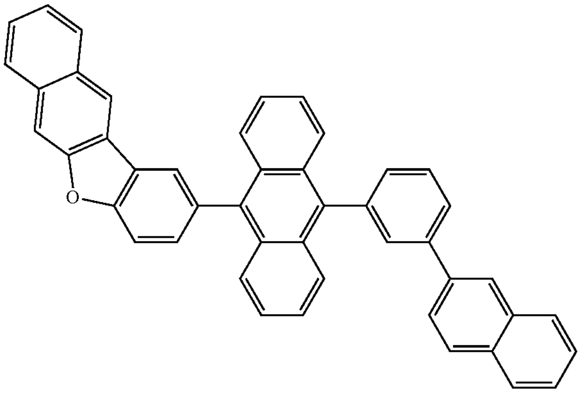

-continued
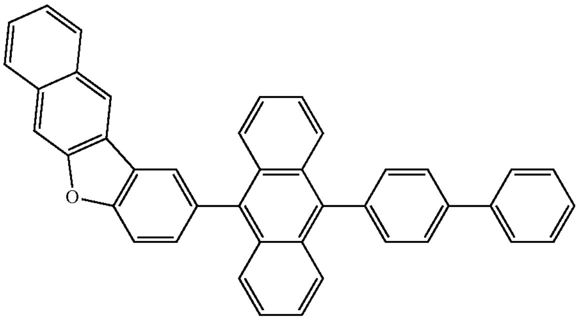
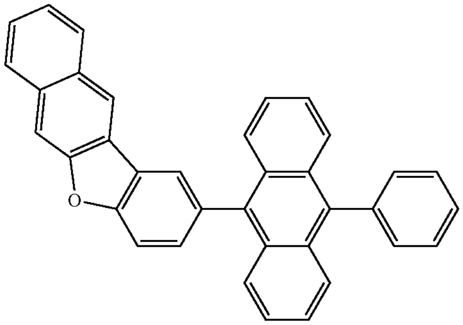
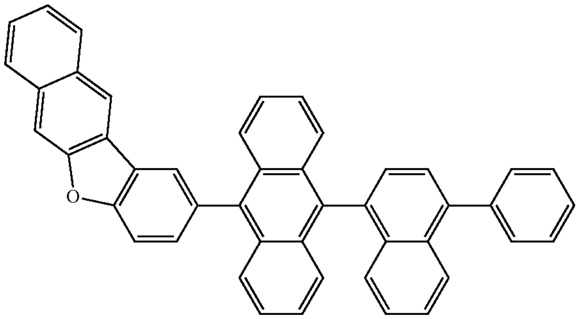
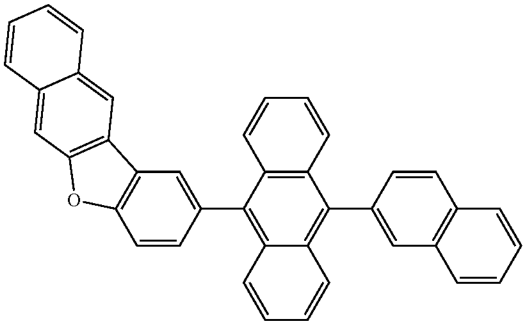
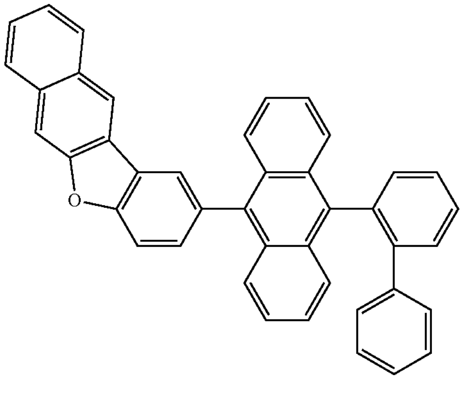
-continued
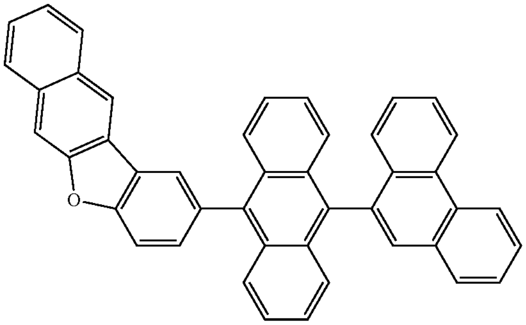
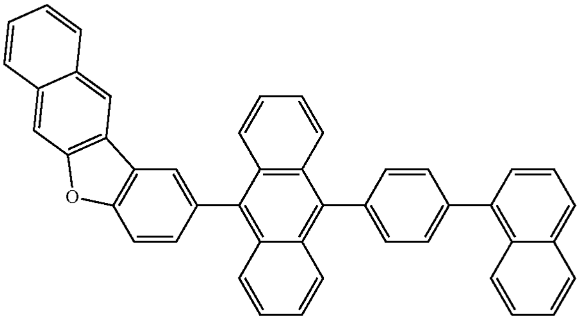
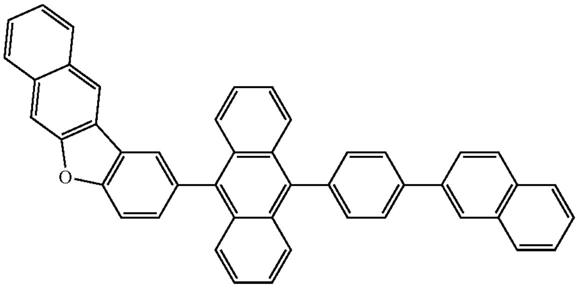
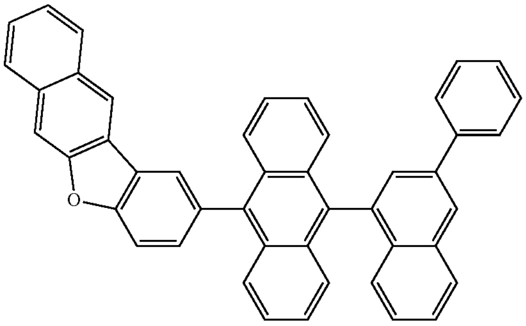
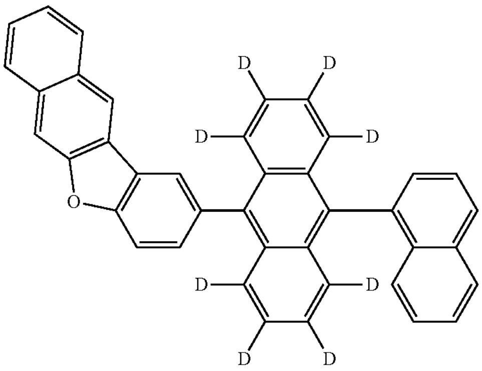

-continued
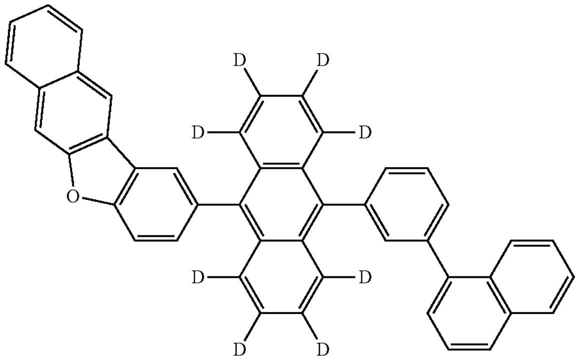
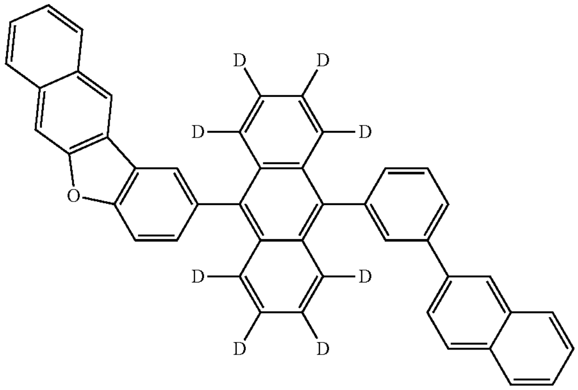
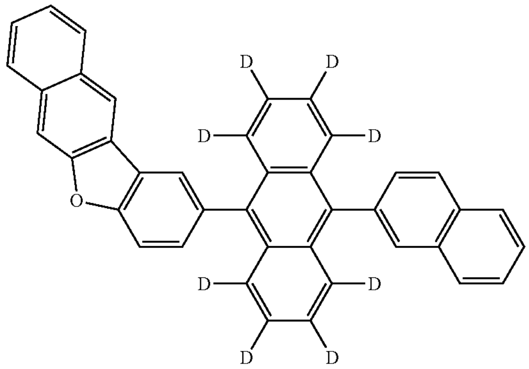
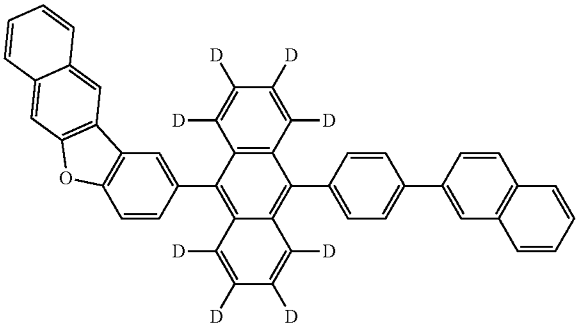
-continued
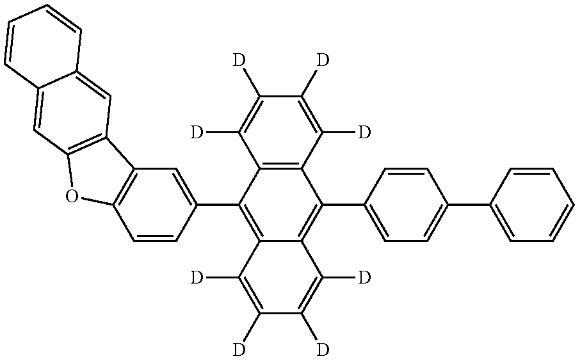
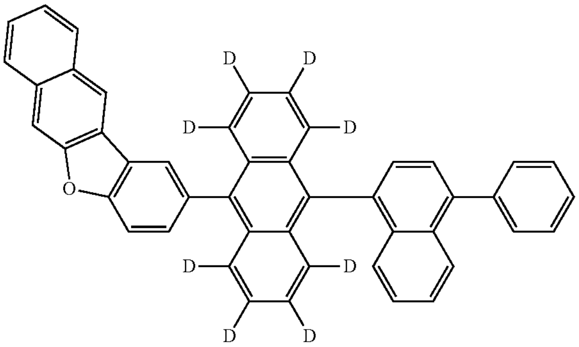
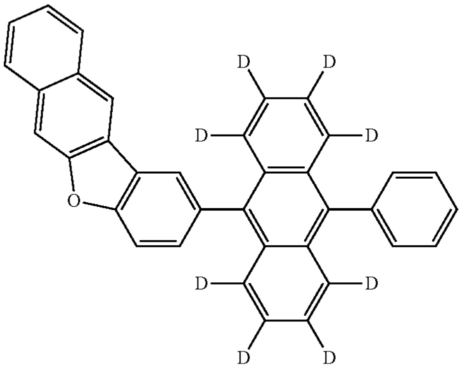
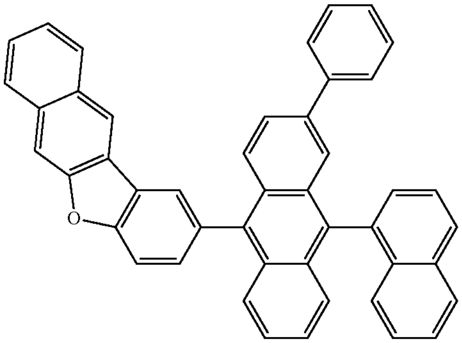

-continued
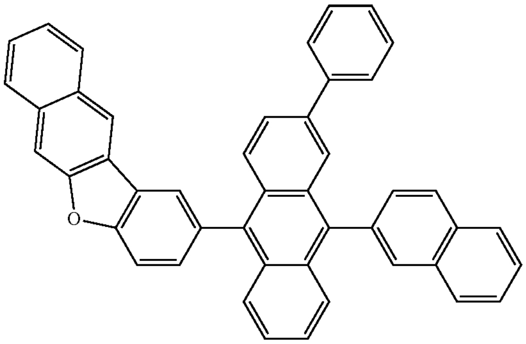
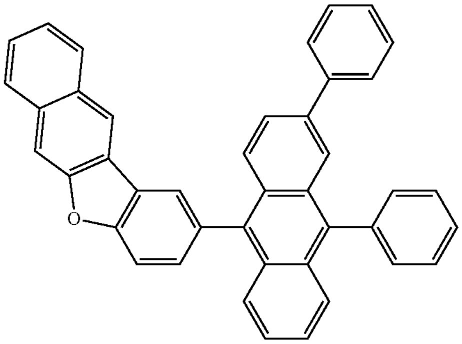
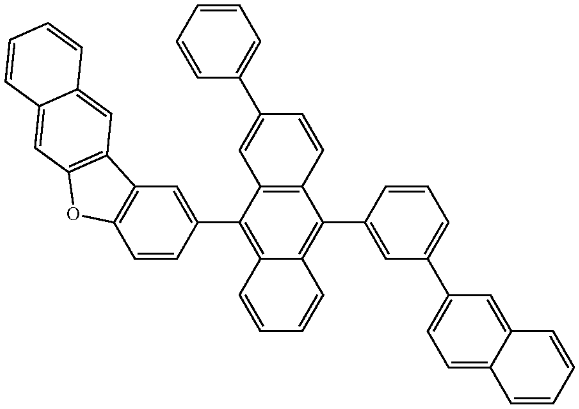
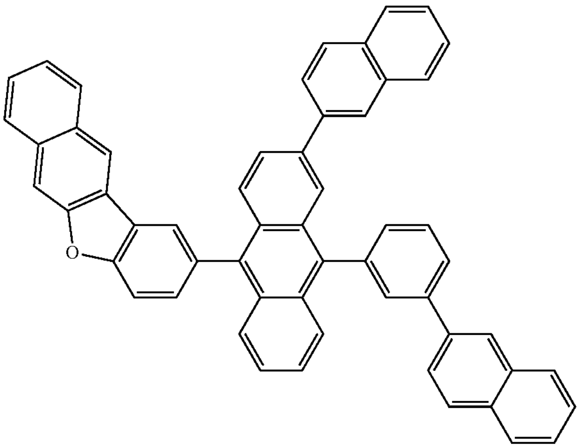
-continued
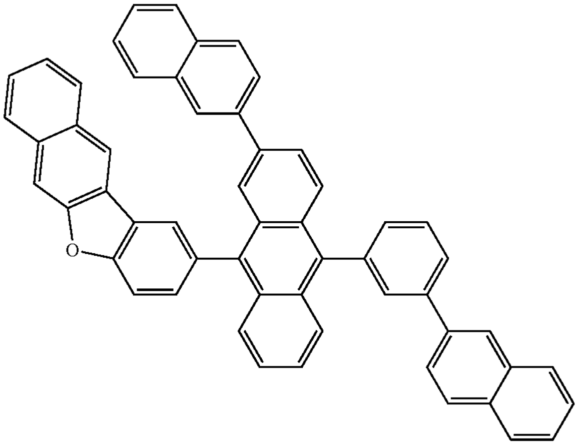
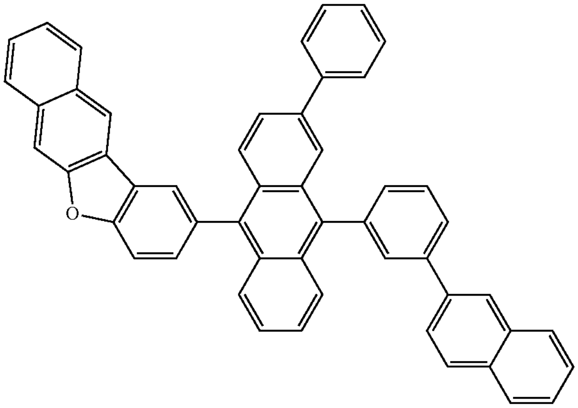
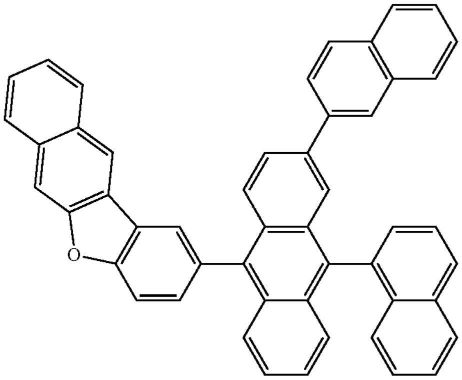
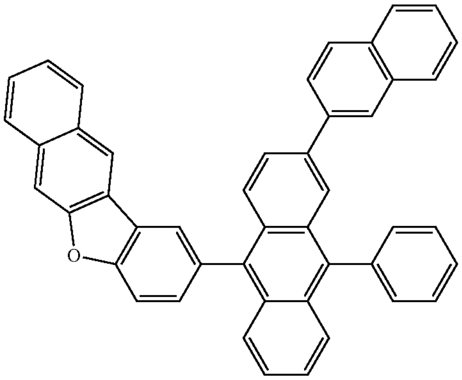

-continued
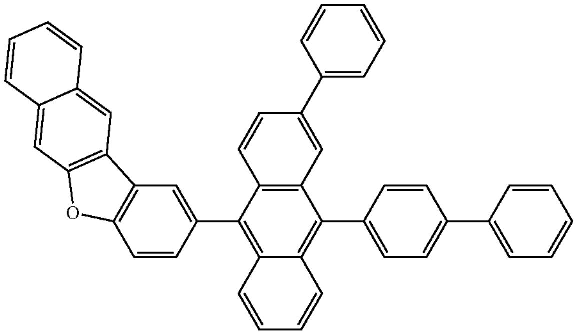
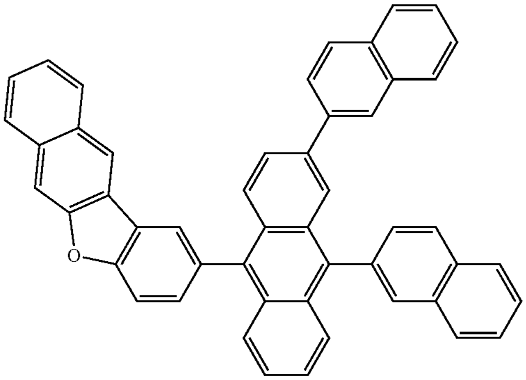
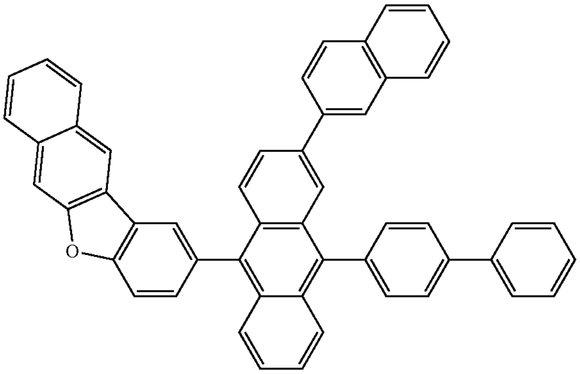
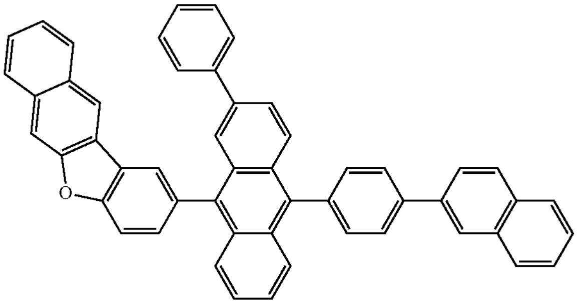
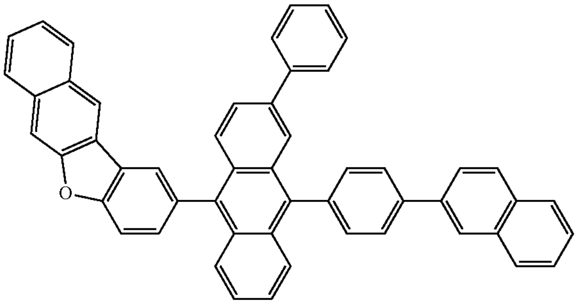
-continued
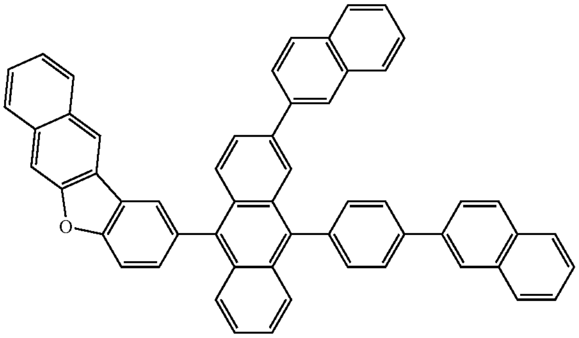
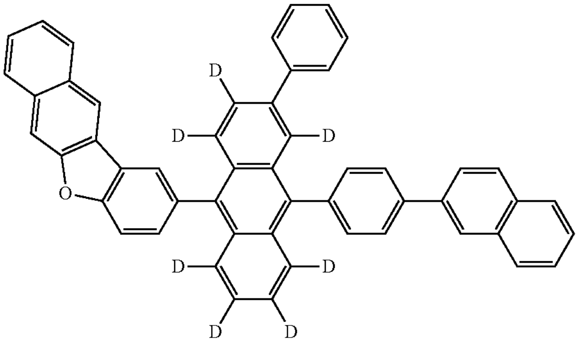
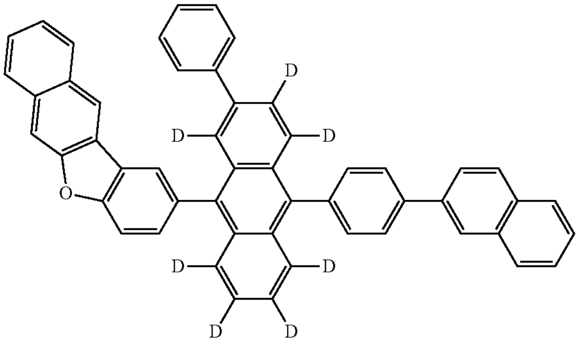
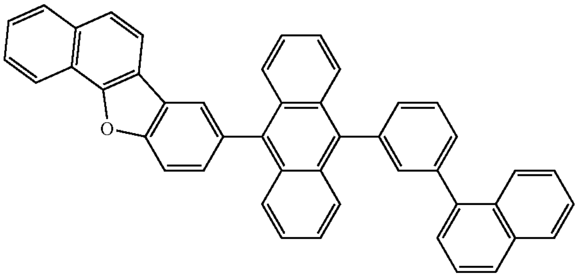
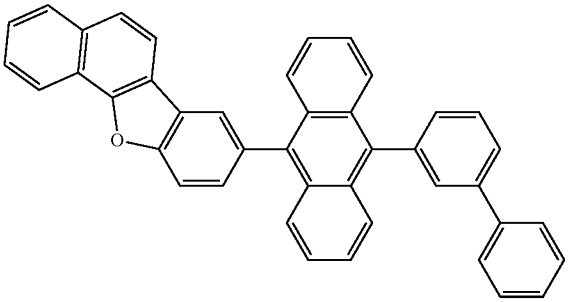

-continued
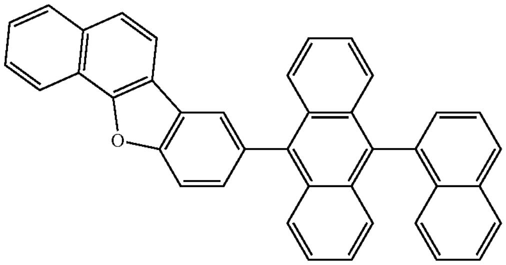
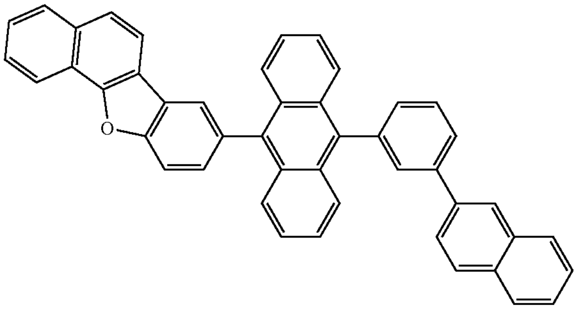
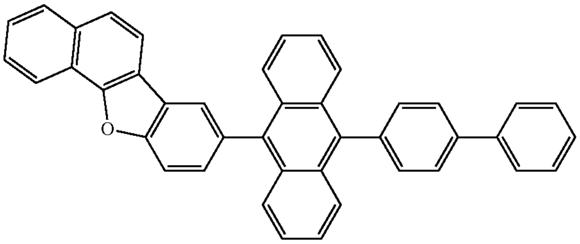
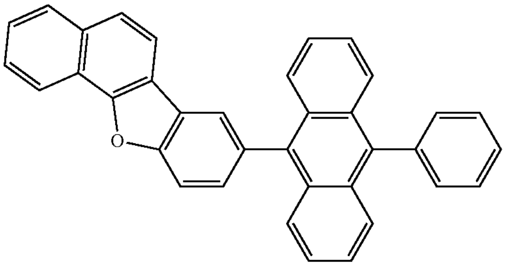
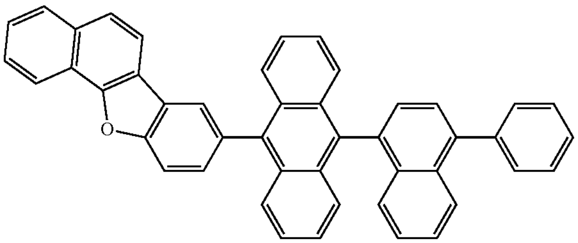
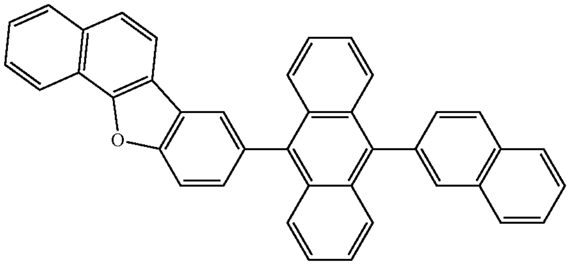
-continued
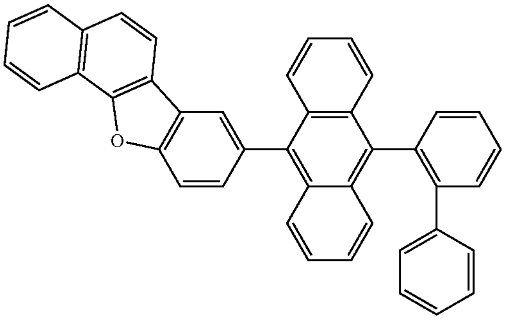
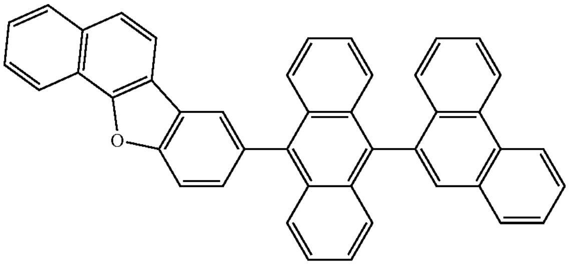
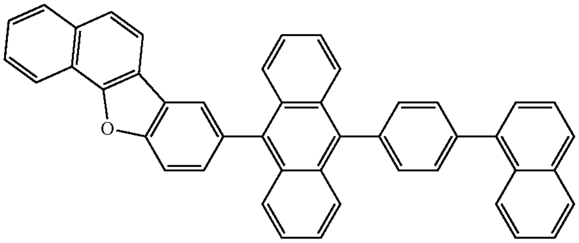
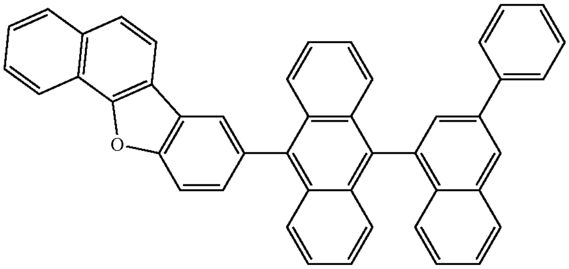
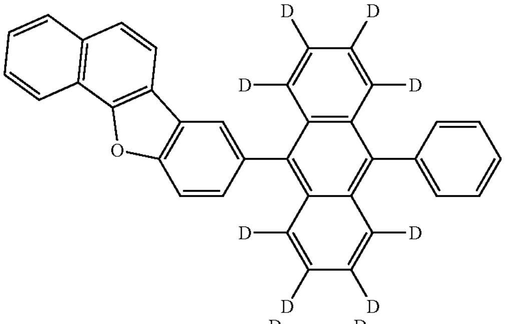
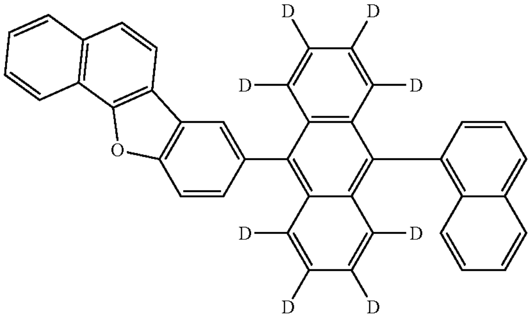

-continued
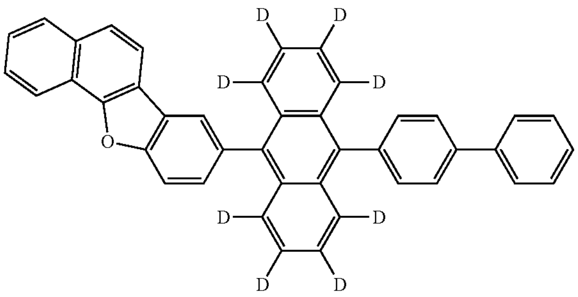
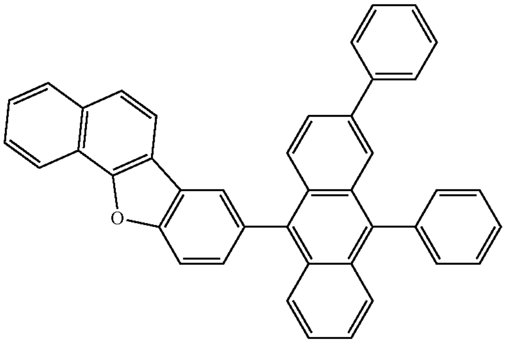
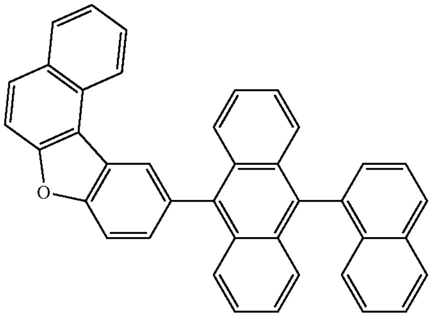
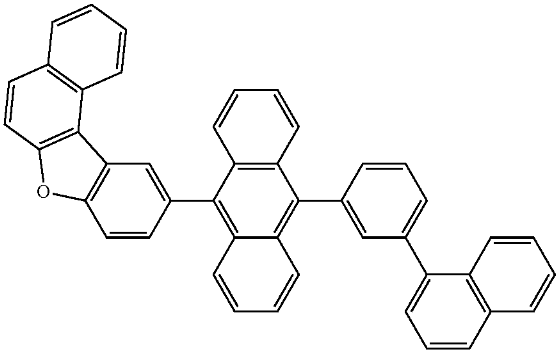
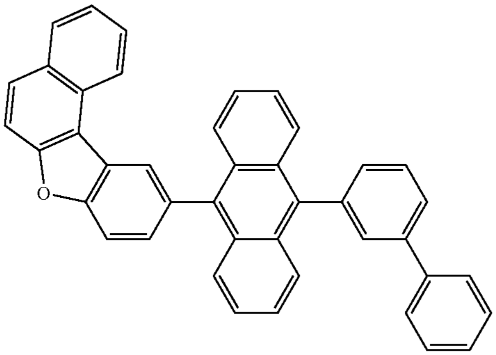
-continued
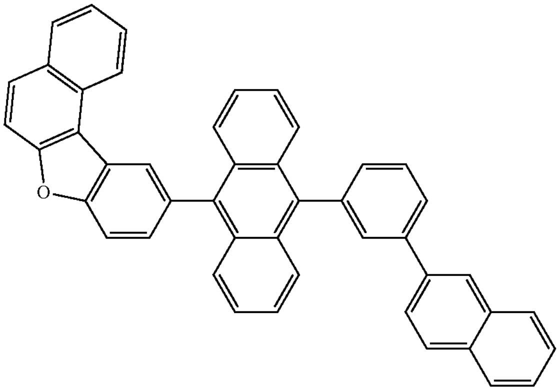
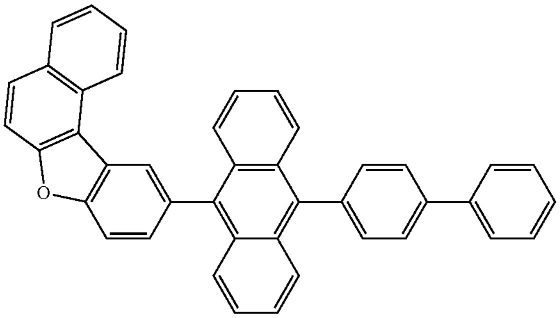
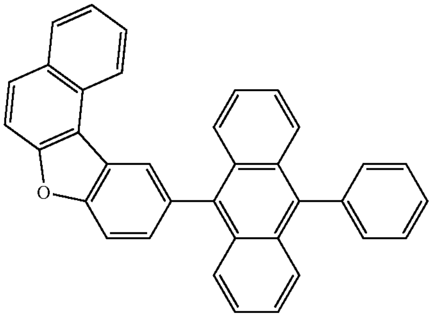
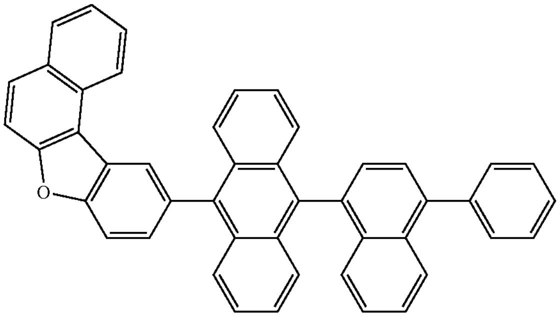
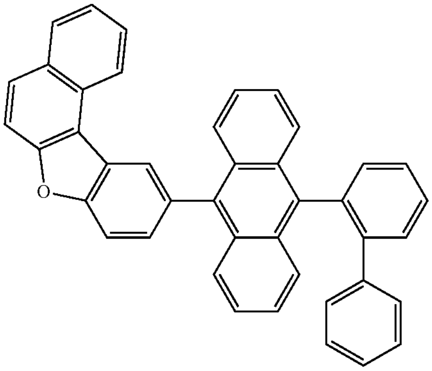

-continued
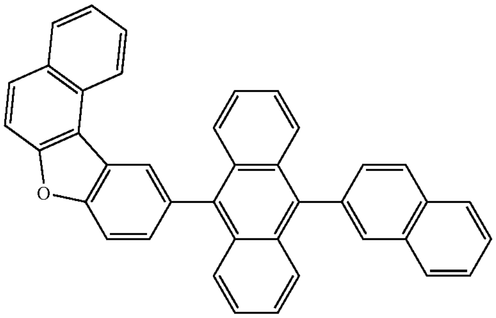
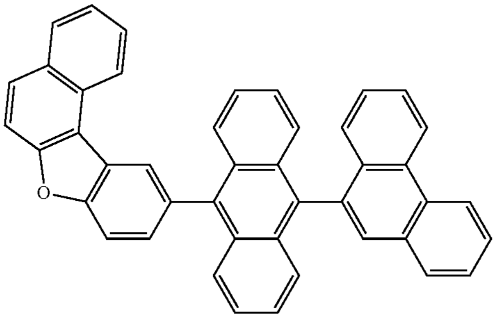
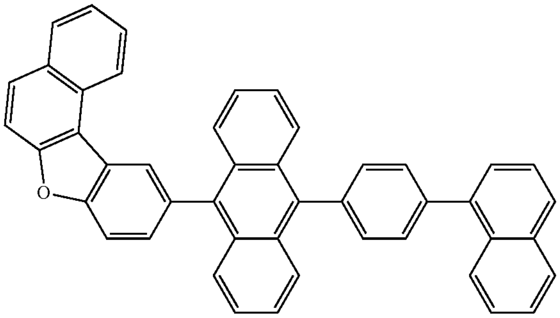
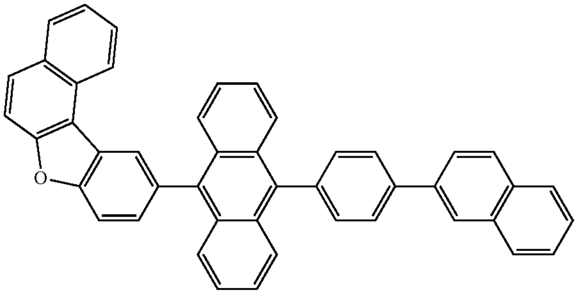
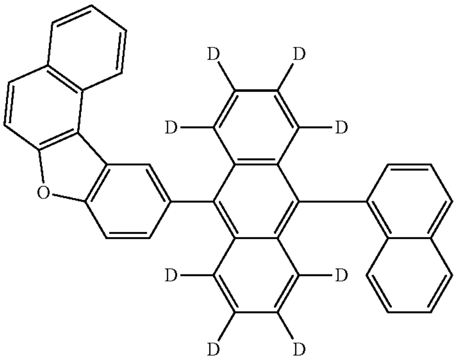
-continued
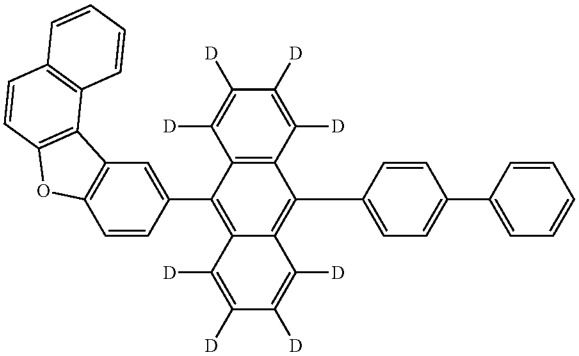
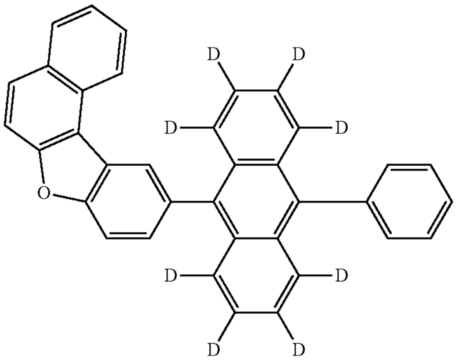
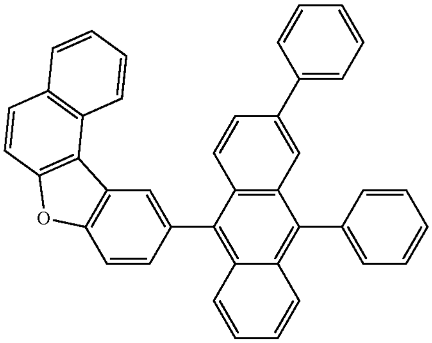
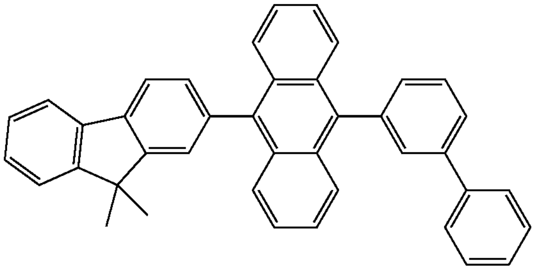
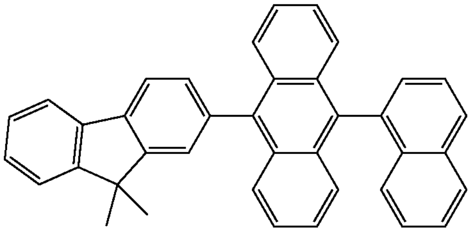

-continued
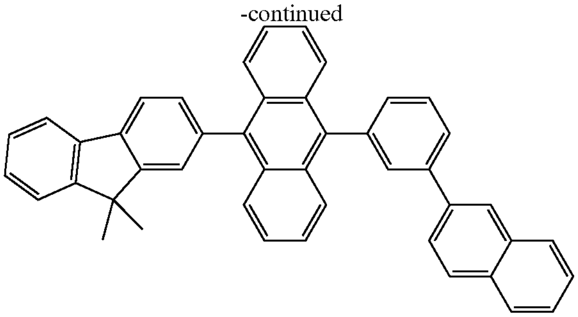
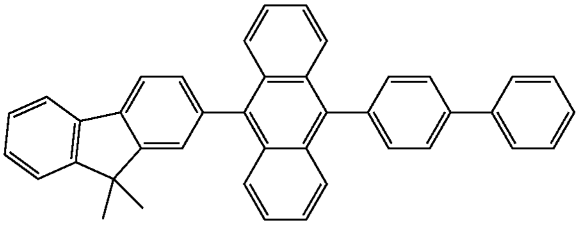
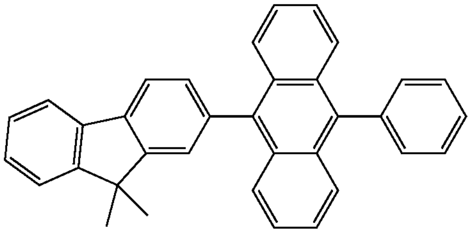
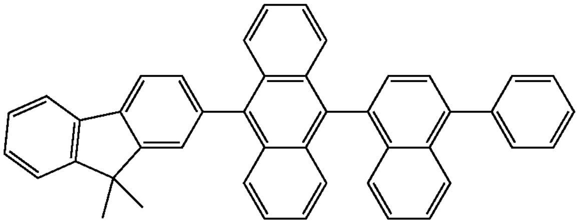
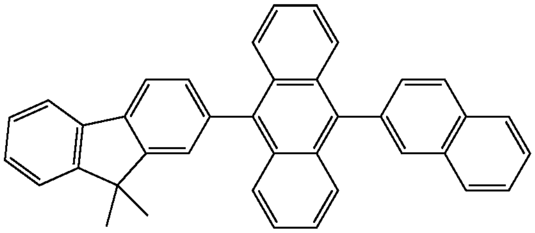
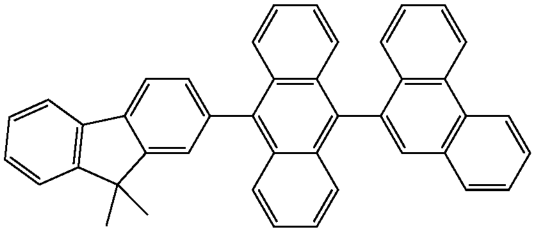
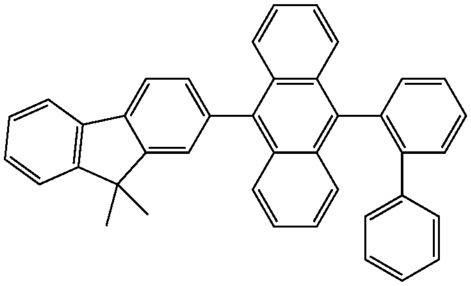
-continued
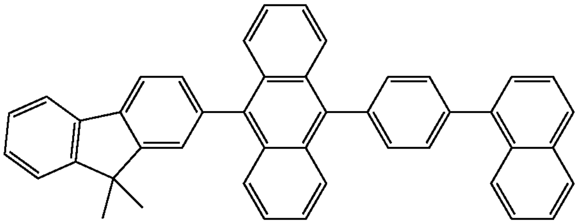
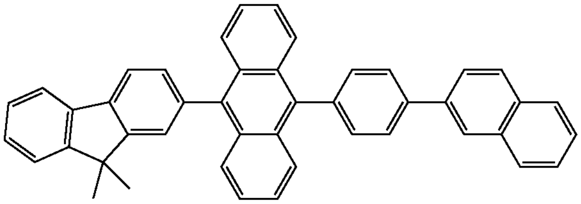
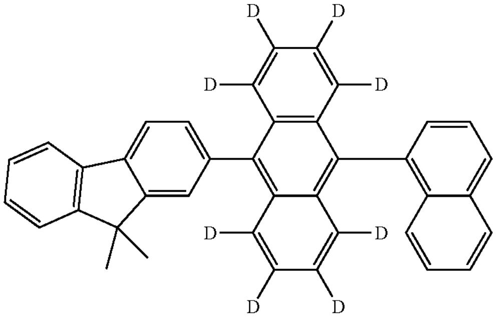
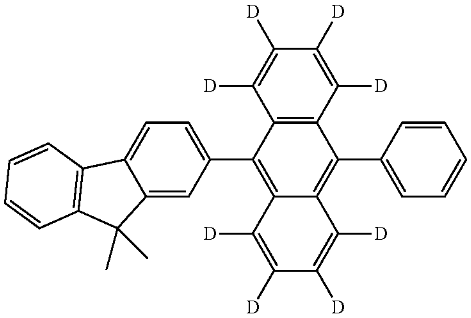
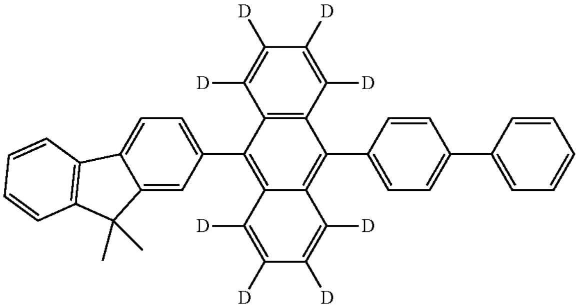
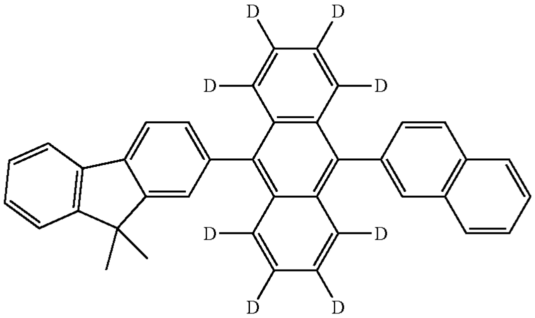

-continued
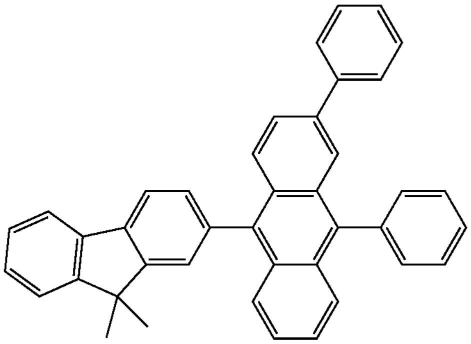
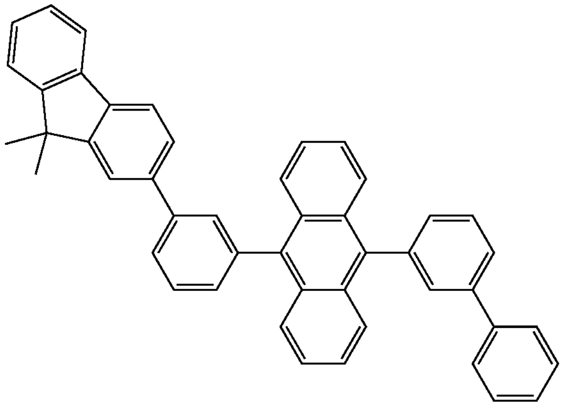
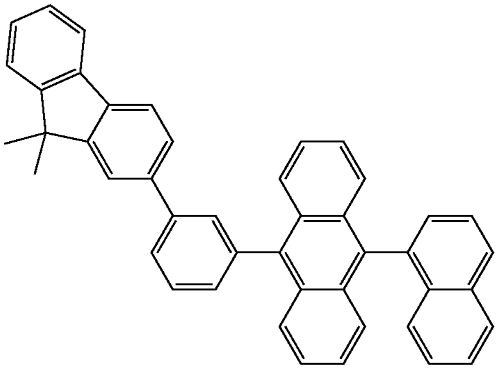
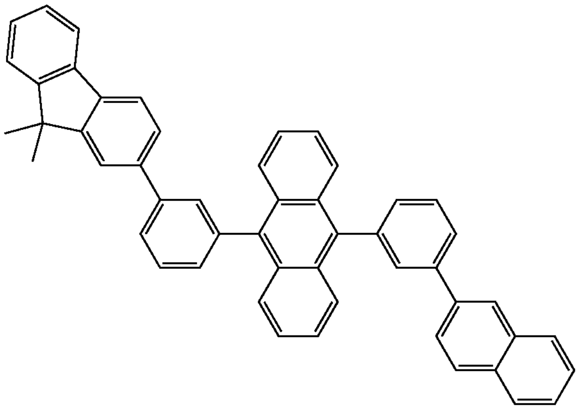
-continued
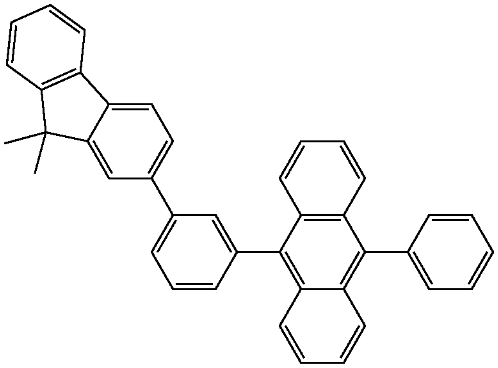
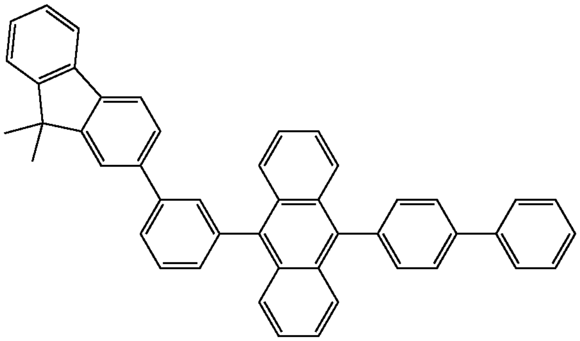
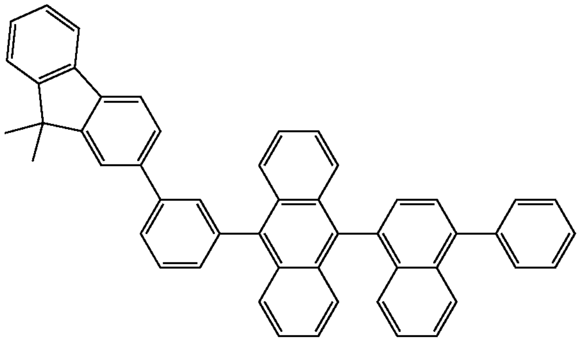
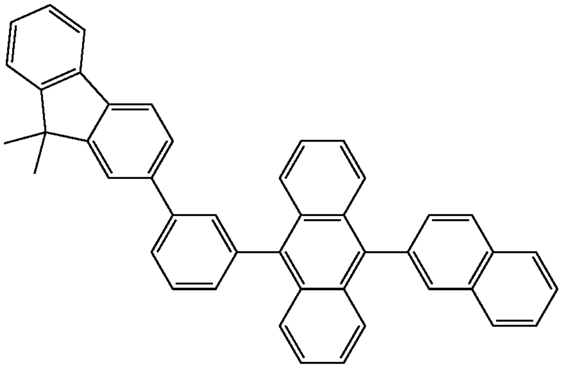

-continued
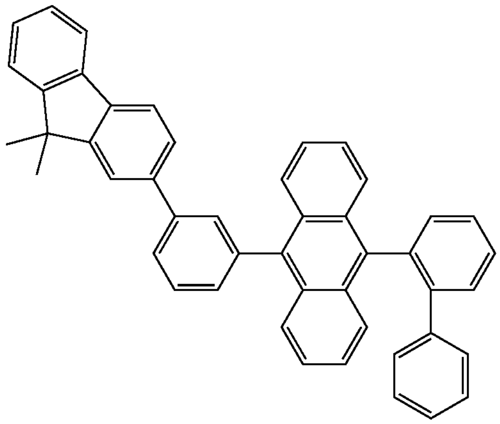
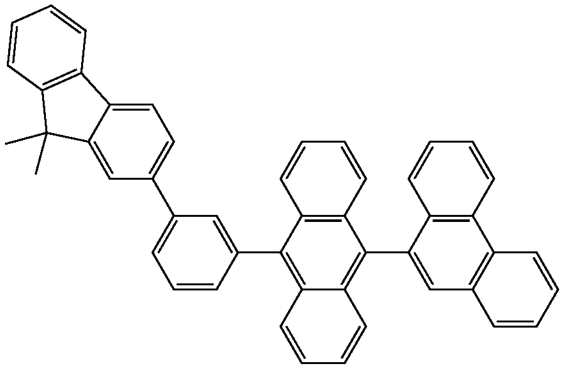
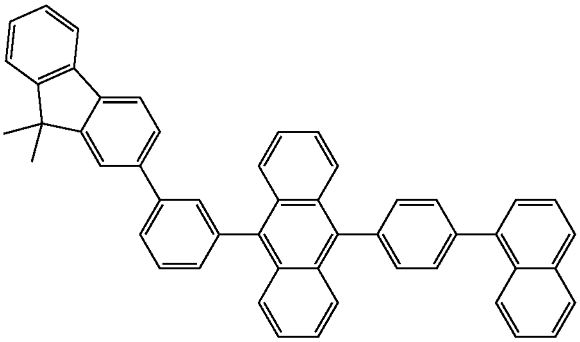
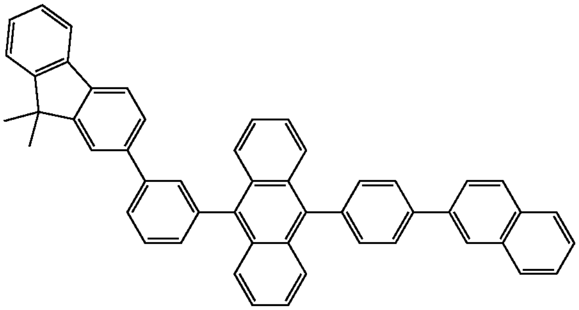
-continued
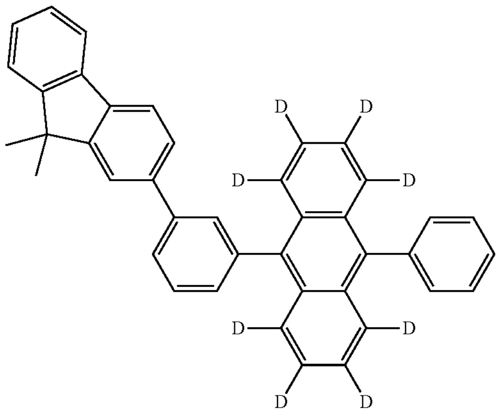
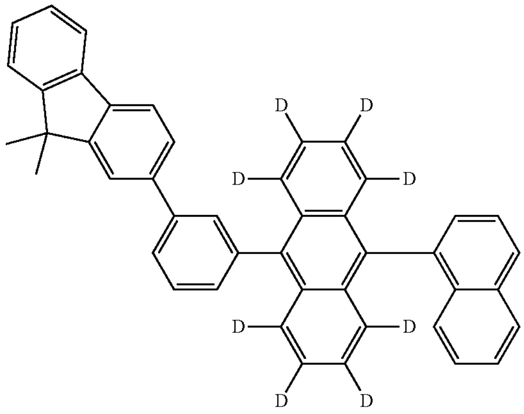
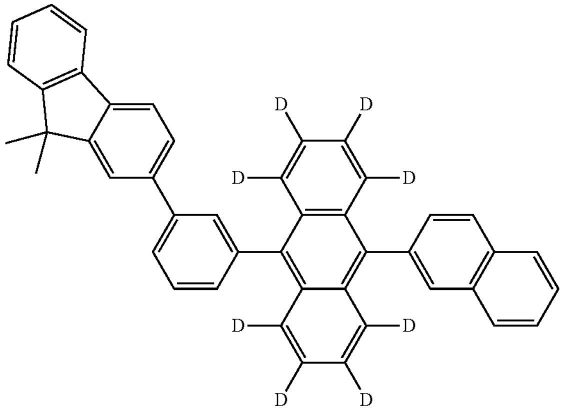
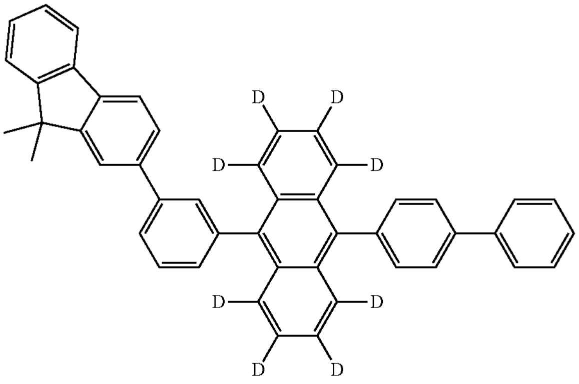

-continued
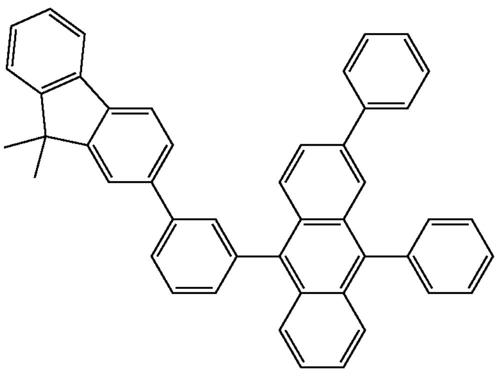
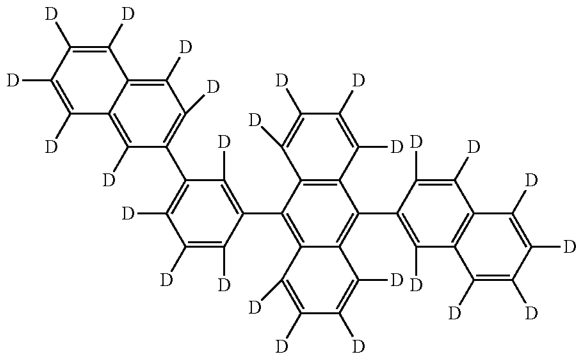
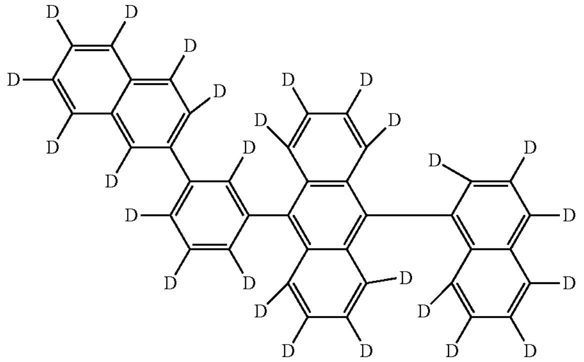
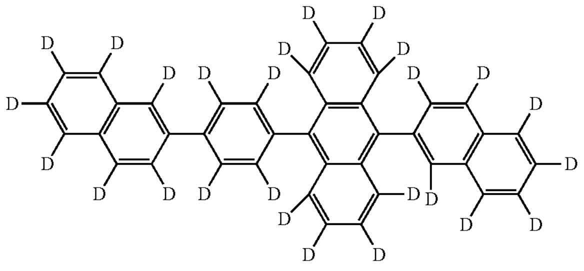
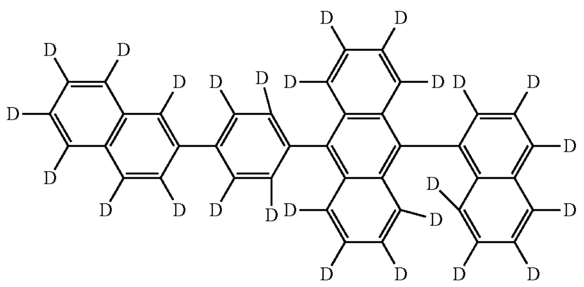
-continued
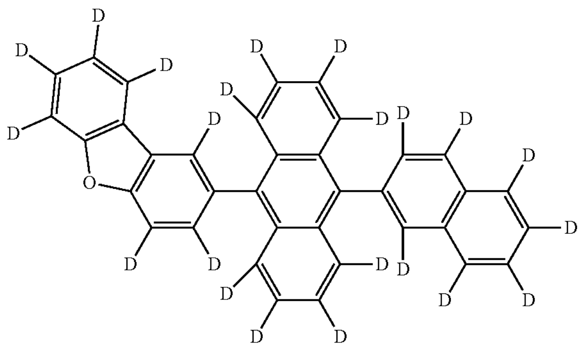
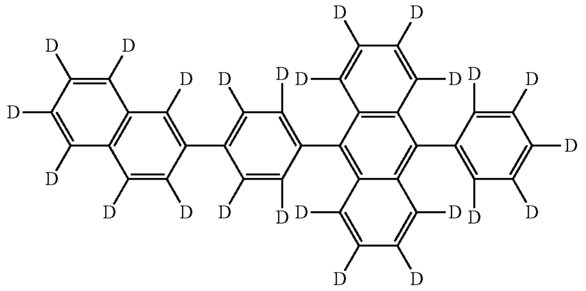
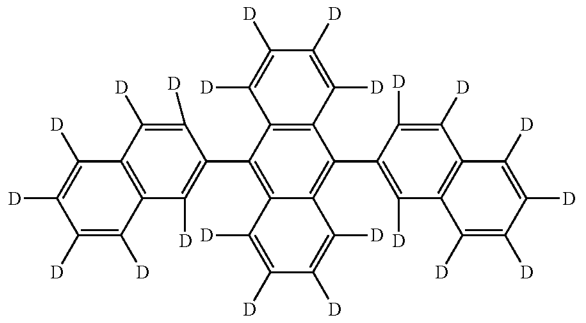
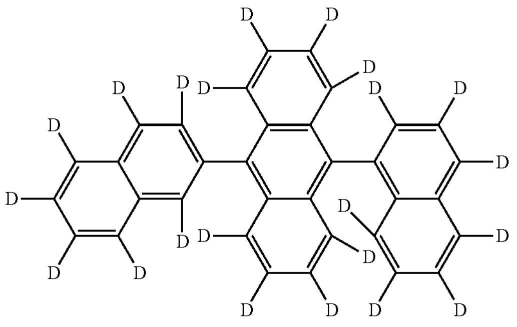
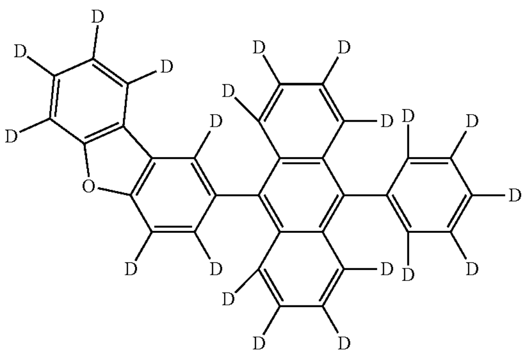

-continued

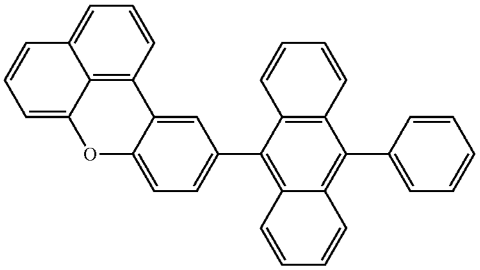

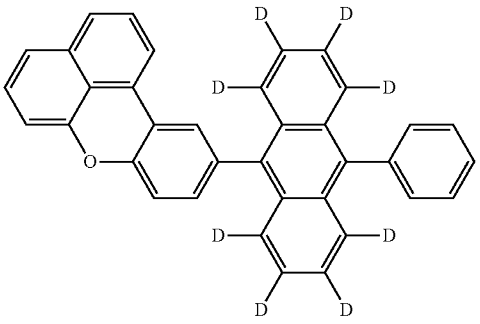

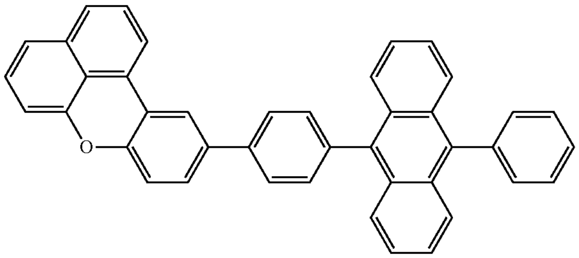

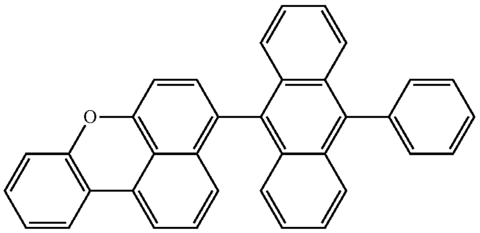

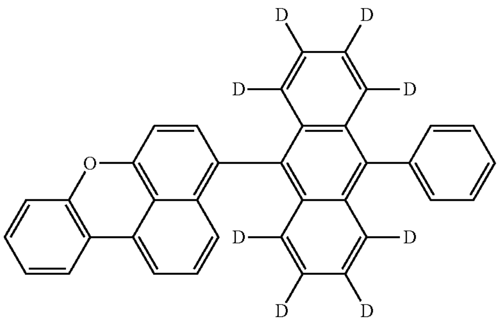

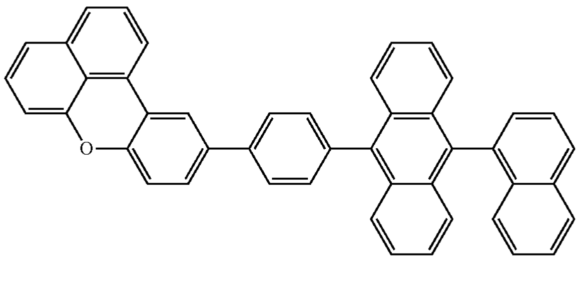

-continued

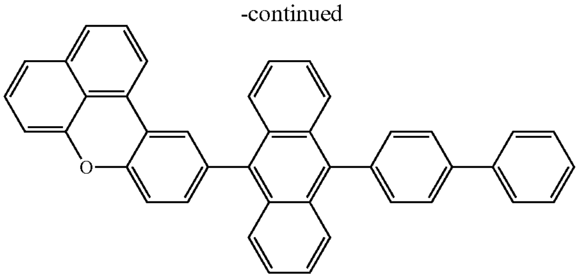

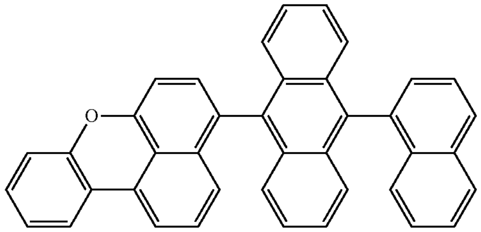

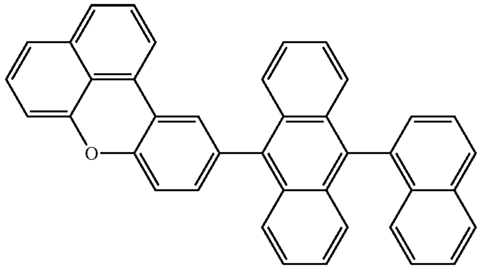 [SMILES: c1ccc2c(-c3c4ccccc4c(-c4ccc5c(c4)-c4cccc6cccc(c46)O5)c4ccccc34)cccc2c1]

Hereinafter, a layer configuration of the organic EL device according to an aspect of the present invention will be described.

The organic EL device according to an aspect of the present invention has an organic layer between a pair of electrodes composed of a cathode and an anode. The organic layer includes at least one layer containing an organic compound. Alternatively, the organic layer is formed by stacking a plurality of layers containing an organic compound. The organic layer may have a layer consisting only of one or more organic compounds. The organic layer may have a layer containing an organic compound and an inorganic compound together. The organic layer may have a layer consisting only of one or more inorganic compounds.

At least one of the layers included in the organic layer is an emitting layer. The organic layer may be formed, for example, as one layer being the emitting layer, or may include other layers which can be adopted in the layer configuration of an organic EL device. The layer that can be adopted in the layer configuration of the organic EL device is not particularly limited, and may include, for example, a hole-transporting region provided between the anode and the emitting layer (hole-transporting layer, hole-injecting layer, electron-blocking layer, exciton-blocking layer, or the like), the emitting layer, a space layer, an electron-transporting region provided between the cathode and the emitting layer (electron-transporting layer, electron-injecting layer, hole-blocking layer, or the like) and the like.

The organic EL device according to an aspect of the present invention may be, for example, a monochromatic emitting device of a fluorescent or phosphorescent type, or a white emitting device of a fluorescent/phosphorescent hybrid type. In addition, it may be a simple type including a single emitting unit or a tandem type including a plurality of emitting units.

The "emitting unit" refers to the smallest unit which includes organic layers, in which at least one of the organic layers is an emitting layer, and which emits light by recombination of injected holes and electrons.

The "emitting layer" described in the present specification is an organic layer having an emitting function. The emitting layer is, for example, a phosphorescent emitting layer, a fluorescent emitting layer, or the like, and may be a single layer or a plurality of layers.

The emitting unit may be a stacked type including a plurality of a phosphorescent emitting layer and a fluorescent emitting layer, and in this case, for example, may include a space layer each between the emitting layers for preventing excitons generated in the phosphorescent emitting layer from diffusing into the fluorescent emitting layer.

The simple type organic EL device includes, for example, a device configuration such as an anode/an emitting unit/a cathode.

Typical layer configurations of the emitting unit are shown below. The layers in parentheses are optional layers.

(a)(a hole-injecting layer/) a hole-transporting layer/a fluorescent emitting layer (/an electron-transporting layer/an electron-injecting layer)

(b)(a hole-injecting layer/) a hole-transporting layer/a phosphorescent emitting layer (/an electron-transporting layer/an electron-injecting layer)

(c)(a hole-injecting layer/) a hole-transporting layer/a first fluorescent emitting layer/a second fluorescent emitting layer (/an electron-transporting layer/an electron-injecting layer)

(d)(a hole-injecting layer/) a hole-transporting layer/a first phosphorescent emitting layer/a second phosphorescent emitting layer (/an electron-transporting layer/an electron-injecting layer)

(e)(a hole-injecting layer/) a hole-transporting layer/a phosphorescent emitting layer/a space layer/a fluorescent emitting layer (/an electron-transporting layer/an electron-injecting layer)

(f)(a hole-injecting layer/) a hole-transporting layer/a first phosphorescent emitting layer/a second phosphorescent emitting layer/a space layer/a fluorescent emitting layer (/an electron-transporting layer/an electron-injecting layer)

(g)(a hole-injecting layer/) a hole-transporting layer/a first phosphorescent emitting layer/a space layer/a second phosphorescent emitting layer/a space layer/a fluorescent emitting layer (/an electron-transporting layer/an electron-injecting layer)

(h)(a hole-injecting layer/) a hole-transporting layer/a phosphorescence emitting layer/a space layer/a first fluorescence emitting layer/a second fluorescence emitting layer (/an electron-transporting layer/an electron-injecting layer)

(i)(a hole-injecting layer/) a hole-transporting layer/an electron-blocking layer/a fluorescent emitting layer (/an electron-transporting layer/an electron-injecting layer)

(j)(a hole-injecting layer/) a hole-transporting layer/an electron-blocking layer/a phosphorescent emitting layer (/an electron-transporting layer/an electron-injecting layer)

(k)(a hole-injecting layer/) a hole-transporting layer/an exciton-blocking layer/a fluorescent emitting layer (/an electron-transporting layer/an electron-injecting layer)

(I)(a hole-injecting layer/) a hole-transporting layer/an exciton-blocking layer/a phosphorescent emitting layer (/an electron-transporting layer/an electron-injecting layer)

(m)(a hole-injecting layer/) a first hole-transporting layer/a second hole-transporting layer/a fluorescent emitting layer (/an electron-transporting layer/an electron-injecting layer)

(n)(a hole-injecting layer/) a first hole-transporting layer/a second hole-transporting layer/a fluorescent emitting layer (/a first electron-transporting layer/a second electron-transporting layer/an electron-injecting layer)

(o)(a hole-injecting layer/) a first hole-transporting layer/a second hole-transporting layer/a phosphorescent emitting layer (/an electron-transporting layer/an electron-injecting layer)

(p)(a hole-injecting layer/) a first hole-transporting layer/a second hole-transporting layer/a phosphorescent emitting layer (/a first electron-transporting layer/a second electron-transporting layer/an electron-injecting layer)

(q)(a hole-injecting layer/) a hole-transporting layer/a fluorescent emitting layer/hole-blocking layer (/an electron-transporting layer/an electron-injecting layer)

(r)(a hole-injecting layer/) a hole-transporting layer/a phosphorescent emitting layer/a hole-blocking layer (/an electron-transporting layer/an electron-injecting layer)

(s)(a hole-injecting layer/) a hole-transporting layer/a fluorescent emitting layer/an exciton-blocking layer (/an electron-transporting layer/an electron-injecting layer)

(t)(a hole-injecting layer/) a hole-transporting layer/a phosphorescent emitting layer/an exciton-blocking layer (/an electron-transporting layer/an electron-injecting layer)

Here, the layer configuration of the organic EL device according to an aspect of the present invention is not limited thereto. For example, when the organic EL device has a hole-injecting layer and a hole-transporting layer, it is preferable that a hole-injecting layer be provided between the hole-transporting layer and the anode. Further, when the organic EL device has an electron-injecting layer and an electron-transporting layer, it is preferable that an electron-injecting layer be provided between the electron-transporting layer and the cathode. Further, each of the hole-injecting layer, the hole-transporting layer, the electron-transporting layer, and the electron-injecting layer may be constituted of a single layer or of a plurality of layers.

The plurality of phosphorescent emitting layers, and the phosphorescent emitting layer and the fluorescent emitting layer may be emitting layers that emit mutually different colors. For example, the emitting unit (f) may be a hole-transporting layer/a first phosphorescent emitting layer (red light emission)/a second phosphorescent emitting layer (green light emission)/a space layer/a fluorescent emitting layer (blue light emission)/an electron-transporting layer.

An electron-blocking layer may be provided each between the emitting layer and the hole-transporting layer or the space layer. Further, a hole-blocking layer may be provided each between the emitting layer and the electron-transporting layer. When the electron-blocking layer or the hole-blocking layer is provided, it is possible to confine electrons or holes in the emitting layer, thereby improving the recombination probability of carriers in the emitting layer, and improving luminous efficiency.

As a representative device configuration of a tandem type organic EL device, for example, a device configuration such as an anode/a first emitting unit /an intermediate layer/a second emitting unit/a cathode can be given.

The first emitting unit and the second emitting unit are, for example, independently selected from the above-mentioned emitting units.

The intermediate layer is also generally referred to as an intermediate electrode, an intermediate conductive layer, a charge-generating layer, an electron-withdrawing layer, a connecting layer, a connector layer, or an intermediate insulating layer. The intermediate layer is a layer which supplies electrons to the first emitting unit and holes to the second emitting unit, and can be formed of known materials.

Hereinbelow, functions, materials, and the like of each layer constituting the organic EL device described in the present specification will be described.

(Substrate)

The substrate is used as a support of the organic EL device. The substrate preferably has a light transmittance of 50% or more in the visible light region within a wavelength of 400 to 700 nm, and a smooth substrate is preferable. Examples of the material of the substrate include soda-lime glass, aluminosilicate glass, quartz glass, plastic and the like. As the substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As an anode, for example, it is preferable to use a metal, an alloy, a conductive compound, a mixture thereof and the like, which have a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is possible to use gold, silver, platinum, nickel, tungsten, chromium, molybdenum, iron, cobalt, copper, palladium, titanium, nitrides of these metals (e.g., titanium nitride) and the like.

The anode is normally formed by depositing these materials on the substrate by a sputtering method. For example, indium oxide-zinc oxide can be formed by a sputtering method using a target in which 1 to 10% by mass zinc oxide is added to indium oxide. Further, indium oxide containing tungsten oxide or zinc oxide can be formed by a sputtering method using a target in which 0.5 to 5% by mass of tungsten oxide or 0.1 to 1% by mass of zinc oxide is added to indium oxide.

As the other methods for forming the anode, for example, a vacuum deposition method, a coating method, an inkjet method, a spin coating method or the like can be given. When, for example, silver paste or the like is used, it is possible to use the coating method, the inkjet method or the like.

The hole-injecting layer formed in contact with the anode is formed using a material that allows easy hole-injection regardless of the work function of the anode. Therefore, in the anode, it is possible to use a common electrode material, for example, a metal, an alloy, a conductive compound and a mixture thereof. Specifically, materials having a small work function such as alkaline metals such as lithium and cesium; magnesium; alkaline earth metals such as calcium and strontium; alloys containing these metals (for example, magnesium-silver and aluminum-lithium); rare earth metals such as europium and ytterbium; and an alloy containing a rare earth metal can also be used for the anode.

(Hole-Injecting Layer)

A hole-injecting layer is a layer containing a substance having high hole-injecting property, and has function of injecting holes from the anode to the organic layer. As the substance having high hole-injecting property, for example, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound, a polymer compound (oligomers, dendrimers, polymers, and the like), or the like can be given. Among these, an aromatic amine compound and an acceptor compound are preferable, and an acceptor compound is more preferable.

Specific examples of the aromatic amine compound include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

As the acceptor compound, for example, a heterocyclic derivative having an electron-withdrawing group, a quinone derivative having an electron-withdrawing group, an arylborane derivative, a heteroarylborane derivative, and the like are preferable, and specific examples thereof include hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane, and the like.

When the acceptor compound is used, it is preferable that the hole-injecting layer further include a matrix material. As the matrix material, a material known as the material for the organic EL device can be used. For example, an electron-donating (donor) compound is preferable.

(Hole-Transporting Layer)

A hole-transporting layer is a layer including a substance having high hole-transporting property, and has function of transporting holes from the anode to the organic layer.

As the substance having high hole-transporting property, a material having a hole mobility of $10^{-6}$ $cm^2/(V \cdot s)$ or more is preferable, and examples thereof include, for example, an aromatic amine compound, a carbazole derivative, an anthracene derivative, a polymer compound, and the like.

Specific examples of the aromatic amine compound include 4,4'-bis[N-(1-yl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4"4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and the like.

Specific examples of the carbazole derivative include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) and the like.

Specific examples of the anthracene derivative include 2-t-butyl-9,10-di(2-naphthyl)anthracene (abbreviation: t-BuDNA), 9,10-di(2-naphthyl)anthracene (abbreviation: DNA), 9,10-diphenylanthracene (abbreviation: DPAnth), and the like.

Specific examples of the polymer compound include poly(N-vinylcarbazole)(abbreviation: PVK), poly(4-vinyltriphenylamine)(abbreviation: PVTPA) and the like.

A substance other than the above-described substances may be used for the hole-transporting layer as long as the compound has higher hole-transporting property than electron-transporting property.

The hole-transporting layer may be a single layer, or may be a stacked layer of two or more layers. In this case, it is preferable that a layer which contains a substance having a larger energy gap among substances having higher hole-transporting property is arranged on a side nearer to the emitting layer.

(Emitting Layer)

An emitting layer is a layer containing a substance having high emitting property (dopant material). As the dopant material, various types of material can be used. For example, a fluorescent emitting compound (fluorescent dopant), a phosphorescent emitting compound (phosphorescent dopant) or the like can be used. The fluorescent emitting compound is a compound capable of emitting light from the singlet excited state, and the emitting layer containing the fluorescent emitting compound is referred to as a fluorescent emitting layer. Further, the phosphorescent emitting compound is a compound capable of emitting light from the triplet excited state, and the emitting layer containing the phosphorescent emitting compound is referred to as a phosphorescent emitting layer.

The emitting layer normally contains a dopant material and a host material which allows the dopant material to emit light efficiently. In some literatures, the dopant material is also referred to as a guest material, an emitter or an emitting material. In some literatures, the host material is also referred to as a matrix material.

A single emitting layer may include a plurality of dopant materials and a plurality of host materials. Further, a plurality of emitting layers may be present.

In the present specification, the host material combined with the fluorescent dopant is referred to as a "fluorescent host", and the host material combined with the phosphorescent dopant is referred to as the "phosphorescent host". The fluorescent host and the phosphorescent host are not distinguished only by the molecular structure. The phosphorescent host is a material for forming the phosphorescent emitting layer containing the phosphorescent dopant, but it does not mean that it cannot be used as a material for forming the fluorescent emitting layer. The same can be applied to the fluorescent host.

The amount of the dopant material in the emitting layer is not particularly limited, but from the viewpoint of adequate luminescence and concentration quenching, it is preferable, for example, to be 0.1 to 70% by mass, more preferably 0.1 to 30% by mass, still more preferably 1 to 30% by mass, still more preferably 1 to 20% by mass, and particularly preferably 1 to 10% by mass.

<Fluorescent Dopant>

As the fluorescent dopant, for example, a fused polycyclic aromatic derivative, a styrylamine derivative, a fused ring amine derivative, a boron-containing compound, a pyrrole derivative, an indole derivative, a carbazole derivative can be given. Among these, a fused ring amine derivative, a boron-containing compound, and a carbazole derivative are preferable.

As the fused ring amine derivative, for example, a diaminopyrene derivative, a diaminochrysene derivative, a diaminoanthracene derivative, a diaminofluorene derivative, a diaminofluorene derivative with which one or more benzofuro skeletons are fused, and the like can be given.

As the boron-containing compound, for example, a pyrromethene derivative, a triphenylborane derivative and the like can be given.

Examples of the blue fluorescent dopant include, for example, a pyrene derivative, a styrylamine derivative, a chrysene derivative, a fluoranthene derivative, a fluorene derivative, a diamine derivative, a triarylamine derivative, and the like. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like can be given.

As the green fluorescent dopant, for example, an aromatic amine derivative and the like can be given. Specifically, N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation :2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like can be given.

As the red fluorescent dopant, a tetracene derivative, a diamine derivative or the like can be given. Specifically, N,N,N',N'-tetrakis(4-methylphenyl)tetracen-5,11-diamine (abbreviation: p-mPhTD), 7,14-diphenyl-N,N,N',N'-tetrakis(4-methylphenyl)acenaphtho[1,2-a]fluoranthen-3,10-diamine (abbreviation: p-mPhAFD) and the like can be given.

<Phosphorescent Dopant>

As the phosphorescent dopant, for example, a phosphorescent emitting heavy metal complex and a phosphorescent emitting rare earth metal complex can be given.

As the heavy metal complex, for example, an iridium complex, an osmium complex, a platinum complex and the like can be given. As the heavy metal complex, an orthometalated complex of a metal selected from iridium, osmium and platinum is preferable.

As the rare earth metal complex, for example, a terbium complex, a europium complex and the like can be given. Specific examples thereof include tris(acetylacetonate)(monophenanthroline)terbium(III)(abbreviation: $Tb(acac)_3$(Phen)), tris(1,3-diphenyl-1,3-propanedionato)(monophenanthroline)europium(III)(abbreviation: $Eu(DBM)_3$(Phen)), tris[1-(2-thenoyl)-3,3,3-trifluoroacetonato](monophenanthroline)europium(III)(abbreviation: $Eu(TTA)_3$ (Phen)), and the like. These rare earth metal complexes are preferable as the phosphorescent dopant since rare earth metal ions emit light due to electronic transition between different multiplicity.

As the blue phosphorescent dopant, for example, an iridium complex, an osmium complex, a platinum complex, or the like can be given. Specific examples thereof include bis[2-(4',6'-difluorophenyl)pyridinato-N,C2]iridium(III)tetrakis(1-pyrazolyl)borate (abbreviation: Flr6), bis[2-(4',6'-difluorophenyl)pyridinato-N,C2]iridium(III)picolinate (abbreviation: Flrpic), bis[2-(3',5'-bistrifluoromethylphenyl) pyridinato-N,C2]iridium(III)picolinate (abbreviation: $Ir(CF3ppy)_2(pic)$), bis[2-(4',6'-difluorophenyl)pyridinato-N, C2]iridium(III) acetylacetonate (abbreviation: Flracac), and the like.

As the green phosphorescent dopant, for example, an iridium complex or the like can be given. Specific examples thereof include tris(2-phenylpyridinato-N,C2')iridium (Ill) (abbreviation: $Ir(ppy)_3$), bis(2-phenylpyridinato-N,C2') iridium (III) acetylacetonate (abbreviation: $Ir(ppy)_2(acac)$), bis(1,2-diphenyl-1H-benzimidazolato)iridium (III) acetylacetonate (abbreviation: $Ir(pbi)_2(acac)$), bis(benzo[h]quinolinato)iridium (III) acetylacetonate (abbreviation: $Ir(bzq)_2$ (acac)) and the like.

As the red phosphorescent dopant, for example, an iridium complex, a platinum complex, a terbium complex, a europium complex and the like can be given. Specific examples thereof include bis[2-(2'-benzo[4,5-α]thienyl) pyridinato-N,C3']iridium(III)acetylacetonate (abbreviation: $Ir(btp)_2(acac)$), bis(1-phenylisoquinolinato-N,C2')iridium (III)acetylacetonate (abbreviation: $Ir(piq)_2(acac)$), (acetylacetonate)bis[2,3-bis(4-fluorophenyl)quinoxalinato]iridium (III)(abbreviation: $Ir(Fdpq)_2(acac)$), 2,3,7,8,12 13,17,18-octaethyl-21H,23H-porphyrin platinum(II)(abbreviation: PtOEP) and the like.

<Host Material>

Examples of the host material include a metal complex such as an aluminum complex, a beryllium complex, and a zinc complex; a heterocyclic compound such as an indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, and a phenanthroline derivative; a fused aromatic compound such as a naphthalene derivative, a triphenylene derivative, a carbazole derivative, an anthracene derivative, a phenanthrene derivative, a pyrene derivative, a chrysene derivative, a naphthacene derivative, and a fluoranthene derivative; an aromatic amine compound such as a triarylamine derivative and a fused polycyclic aromatic amine derivative, and the like. A plurality of types of host materials can be used in combination.

Specific examples of the metal complex include tris(8-quinolinolato)aluminum (III) (abbreviation: Alq), tris(4-methyl-8-quinolinolato)aluminum (III)(abbreviation: Almq3), bis(10-hydroxybenzo [h] quinolino) beryllium (II) (abbreviation: BeBq2), bis(2-methyl-8-quinolinolato)(4-phenylphenolato) aluminum (III)(abbreviation: BAlq), bis (8-quinolinolato) zinc (II)(abbreviation: Znq), bis[2-(2-benzoxazolyl)phenolato]zinc (II)(abbreviated as ZnPBO), bis[2-(2-benzothiazolyl)phenolato]zinc (II)(abbreviated as ZnBTZ), and the like.

Specific examples of the heterocyclic compound include 2-(4-biphenylyl)-5-(4-tert-butylphenyl)-1,3,4-oxadiazole (abbreviation : PBD), 1,3-bis[5-(p-tert-butylphenyl)-1,3,4-oxadiazole-2-yl]benzene (abbreviation : OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole)(abbreviation: TPBI), bathophenanthroline (abbreviation: BPhen), bathocuproine (abbreviation: BCP), and the like.

Specific examples of the fused aromatic compound include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), 6,12-dimethoxy-5,11-diphenylchrysene, and the like.

Specific examples of the aromatic amine compound include N,N-diphenyl-9-[4-(10-phenyl-9-anthryl)phenyl]-9H-carbazole-3-amine (abbreviation: CzA1 PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 4,4'-bis[N-(1-naphthyl)-N-phenylamino]biphenyl (abbreviation: NPB or Δ-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi, 4,4'-bis[N-(spiro-9,9'-bifluoren-2-yl)-N-phenylamino]biphenyl (abbreviation: BSPB), and the like.

As the fluorescent host, a compound having higher singlet energy level as compared with a fluorescent dopant is preferable. For example, a heterocyclic compound, a fused aromatic compound and the like can be given. As the fused aromatic compound, an anthracene derivative, a pyrene derivative, a chrysene derivative, a naphthacene derivative and the like are preferable.

As the phosphorescent host, a compound having a higher triplet energy level as compared with a phosphorescent dopant is preferable. For example, a metal complex, a heterocyclic compound, a fused aromatic compound and the like can be given. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative and the like are preferable.

(Electron-Transporting Layer)

An electron-transporting layer is a layer which includes a substance having high electron-transporting property. As the substance having high electron-transporting property, a substance having an electron mobility of $10^{-6}$ $cm^2/Vs$ or more is preferable. For example, a compound represented by the formula (1), a metal complex, an aromatic heterocyclic compound, an aromatic hydrocarbon compound, a polymer compound and the like can be given.

As the metal complex, for example, an aluminum complex, a beryllium complex, a zinc complex and the like can be given. Specific examples thereof include tris(8-quinolinolato)aluminum (III)(abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato)

aluminum (Ill)(abbreviation: BAlq), bis(8-quinolinolato) zinc (II)(abbreviation: Znq), bis[2-(2-benzoxazolyl)phenolato]zinc (II)(abbreviated: ZnPBO), bis[2-(2-benzothiazolyl)phenolato]zinc (II)(abbreviated: ZnBTZ), and the like.

As the aromatic heterocyclic compound, for example, an imidazole derivative such as a benzimidazole derivative, an imidazopyridine derivative and a benzimidazophenanthridine derivative; an azine derivative such as a pyrimidine derivative and a triazine derivative; a compound having a nitrogen-containing six-membered ring structure such as a quinoline derivative, an isoquinoline derivative, and a phenanthroline derivative (also including one having a phosphine oxide-based substituent on the heterocyclic ring) and the like can be given. Specific examples thereof include 2-(4-biphenylyl)-5-(4-tert-butylphenyl)-1,3,4-oxadiazole (abbreviated: PBD), 1,3-bis[5-(ptert-butylphenyl)-1,3,4-oxadiazole-2-yl]benzene (abbreviated: OXD-7), 3-(4-tert-butylphenyl)-4-phenyl-5-(4-biphenylyl)-1,2,4-triazole (abbreviated: TAZ), 3-(4-tert-butylphenyl)-4-(4-ethylphenyl)-5-(4-biphenylyl)-1,2,4-triazole (abbreviation: p-EtTAZ), basophenanthroline (abbreviation: BPhen), bathocuproine (abbreviation: BCP), 4,4'-bis(5-methylbenzoxazol-2-yl) stilbene (abbreviation: BzOs), and the like.

As the aromatic hydrocarbon compound, for example, an anthracene derivative, a fluoranthene derivative and the like can be given.

Specific examples of the polymeric compound include poly[(9,9-dihexylfluoren-2,7-diyl)-co-(pyridine-3,5-diyl)] (abbreviation: PF-Py), poly[(9,9-dioctylfluoren-2,7-diyl)-co-(2,2'-bipyridin-6,6'-diyl)] (abbreviation: PF-BPy) and the like.

A substance other than the above-described substances may be used for the electron-transporting layer as long as the compound has higher electron-transporting property than hole-transporting property.

The electron-transporting layer may be a single layer, or may be a stacked layer of two or more layers. In this case, it is preferable that a layer which contains a substance having a larger energy gap among substances having higher electron-transporting property is arranged on a side nearer to the emitting layer.

The electron-transporting layer may contain, for example, a metal such as an alkali metal, magnesium, an alkaline earth metal, and an alloy containing two or more of these metals; a metal compound such as an alkali metal compound containing 8-quinolinolato lithium (abbreviation: Liq) or the like, and an alkaline earth metal compound. When the metal such as an alkali metal, magnesium, an alkaline earth metal, and an alloy containing two or more of these metals is contained in the electron-transporting layer, the amount thereof is not particularly limited, but is preferably 0.1 to 50% by mass, more preferably 0.1 to 20% by mass, and still more preferably 1 to 10% by mass.

When the metal compound such as an alkali metal compound and an alkaline earth metal compound is contained in the electron-transporting layer, the amount thereof compound is preferably 1 to 99% by mass, and more preferably 10 to 90% by mass. A layer arranged on the emitting layer side in the case where a plurality of electron-transporting layers is provided can be formed only of these metal compounds as mentioned above.

(Electron-Injecting Layer)

An electron-injecting layer is a layer containing a substance having high electron-injecting property, and has function of efficiently injecting electrons from the cathode to the emitting layer. As the substance having high electron-injecting property, for example, an alkali metal, magnesium, an alkaline earth metal, a compound thereof, and the like can be given. Specific examples thereof include lithium, cesium, calcium, lithium fluoride, cesium fluoride, calcium fluoride, lithium oxide, and the like. In addition, a material in which an alkali metal, magnesium, an alkaline earth metal, or a compound thereof is including in a substance having electron-transporting property, for example, a material in which magnesium is included in Alq can also be used.

Alternatively, a composite material including an organic compound and a donor compound may also be used in the electron-injecting layer. Such a composite material is excellent in the electron-injecting property and the electron-transporting property since the organic compound receives electrons from the donor compound.

The organic compound is preferably a substance excellent in transporting property of the received electrons, and for example, the metal complex, the aromatic heterocyclic compound and the like, which are a substance having high electron-transporting property as mentioned above, can be used.

The donor compound may be any of materials capable of donating electrons to the organic compound, and for example, an alkali metal, magnesium, an alkaline earth metal, a rare earth metal and the like can be given. Specific examples thereof include lithium, cesium, magnesium, calcium, erbium, ytterbium, and the like. Further, an alkali metal oxide and an alkaline earth metal oxide are preferable, and examples thereof include lithium oxide, calcium oxide, barium oxide, and the like. Lewis bases such as magnesium oxide can also be used. Alternatively, an organic compound such as tetrathiafulvalene (abbreviation: TTF) can also be used.

(Cathode)

As a cathode, it is preferable to use a metal, an alloy, a conductive compound, a mixture thereof and the like, which have a low work function (specifically, 3.8 eV or less). Specific examples of the material for the cathode include, for example, alkaline metals such as lithium and cesium; magnesium; alkaline earth metals such as calcium and strontium; alloys containing these metals (for example, magnesium-silver, and aluminum-lithium); rare earth metals such as europium and ytterbium; an alloy containing a rare earth metal, and the like.

The cathode is usually formed by a vacuum deposition method or a sputtering method. Further, when silver paste or the like is used, it is possible to use the coating method, the inkjet method or the like.

When the electron-injecting layer is provided, the cathode can be formed using various conductive materials such as aluminum, silver, ITO, graphene, indium oxide-tin oxide containing silicon or silicon oxide, regardless of the work function value. The film can be formed using these conductive materials and by using a sputtering method, an inkjet method, a spin coating method, or the like.

(Insulating Layer)

In the organic EL device, pixel defects based on leakage or a short circuit are easily generated since an electric field is applied to a thin film. In order to prevent this, a thin insulating layer may be inserted between a pair of electrodes.

Specific examples of substances used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. A mixture thereof may be used in the insulating layer, and a stacked body of a plurality of layers which include these substances can be also used for the insulating layer.

(Space Layer)

When, for example, the fluorescent emitting layer and the phosphorescent emitting layer are stacked, a space layer is provided between both of the layers in order to prevent excitons generated in the phosphorescent emitting layer from diffusing into the fluorescent emitting layer and in order to adjust the carrier balance. The space layer can be provided between a plurality of phosphorescent emitting layers and the like.

Since the space layer is provided between a plurality of emitting layers, the space layer is preferably formed of a substance having both electron-transporting property and hole-transporting property. Further, the triplet energy thereof is preferably 2.6 eV or more in terms of preventing diffusion of the triplet energy into adjacent phosphorescent emitting layers.

As the material used for the space layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided adjacent to the emitting layer.

The electron-blocking layer is a layer which has a function of preventing leakage of electrons from the emitting layer to the hole-transporting layer. The hole-blocking layer is a layer which has a function of preventing leakage of holes from the emitting layer to the electron-transporting layer. The exciton-blocking layer is a layer which has a function of preventing diffusion of excitons generated in the emitting layer into the adjacent layers to confine the excitons within the emitting layer.

(Capping Layer)

The organic EL device can be provided with a capping layer above the cathode in order to adjust the intensity of the extracted light by the optical interference effect.

As the capping layer, for example, a polymer compound, a metal oxide, a metal fluoride, a metal boride, silicon nitride, a silicon compound (silicon oxide, or the like) and the like can be used.

Further, an aromatic amine derivative, an anthracene derivative, a pyrene derivative, a fluorene derivative, or a dibenzofuran derivative can also be used for the capping layer.

A stacked body in which layers containing these substances are stacked can also be used as the capping layer.

(Intermediate Layer)

In tandem type organic EL device, an intermediate layer is provided.

(Method for Forming Layer)

The method for forming each layer of the organic EL device is not particularly limited, unless otherwise specified. As the method for forming it, a conventional method such as a dry film-forming method and a wet film-forming method can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, and an inkjet method.

(Film Thickness)

The film thickness of each layer of the organic EL device is not particularly limited, unless otherwise specified. When the film thickness is too thin, defects such as pinholes are likely to occur to make it difficult to obtain an enough luminance. On the other hand, when the film thickness is too thick, high driving voltage is required to be applied, thereby decreasing efficiency of it. In view of these above, normally, the film thickness is preferably 1 nm to 10 μm, and more preferably 1 nm to 0.2 μm.

[Electronic Apparatus]

An electronic apparatus according to an aspect of the present invention includes the above-described organic EL device according to an aspect of the present invention. Specific examples of the electronic apparatus include display components such as an organic EL panel module; display devices for a television, a cellular phone, a smart phone and a personal computer; and emitting devices such as a light and a vehicular lamp; and the like.

EXAMPLES

Next, the present invention will be described in more detail by referring to Examples and Comparative Examples, but the present invention is not limited to the description of these Examples.

<Compound>

Compounds represented by the formula (1) used in the fabrication of the organic EL devices of Examples 1-1 to 1-16 and Examples 2-1 to 2-5 are shown below.

ET-1

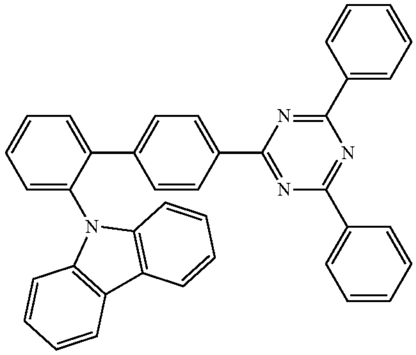

ET-2

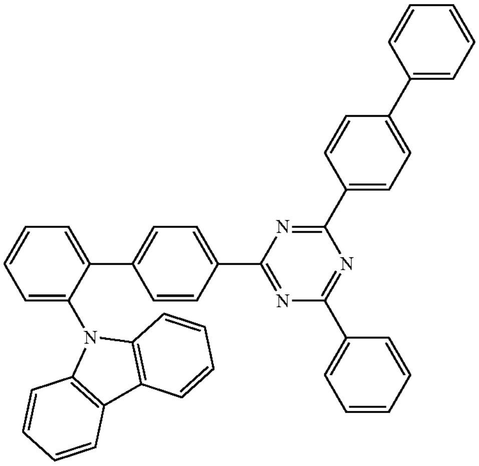

-continued
ET-3
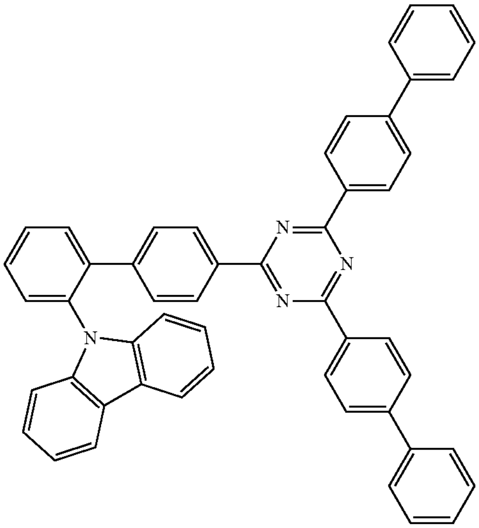
ET-5
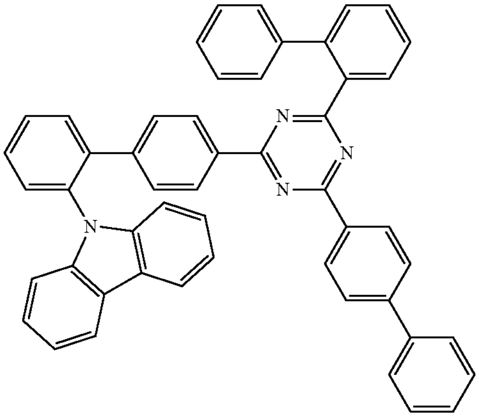
ET-6
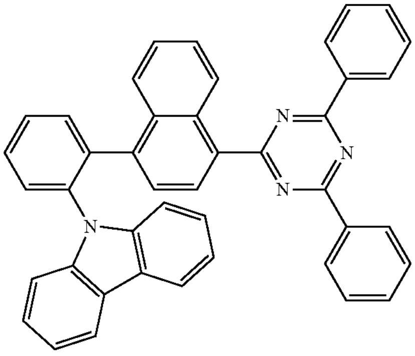
-continued
ET-7
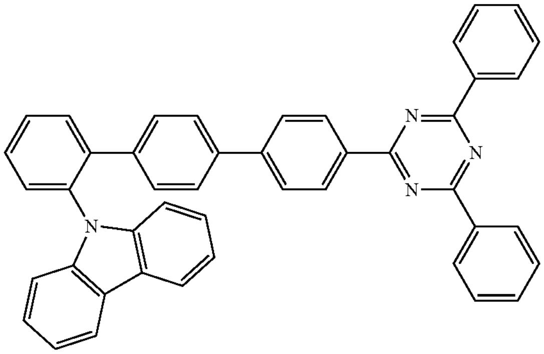
ET-8
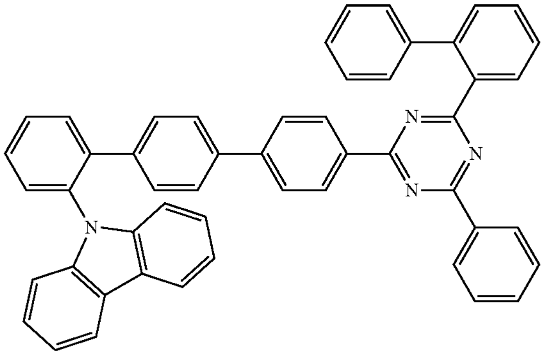
ET-9
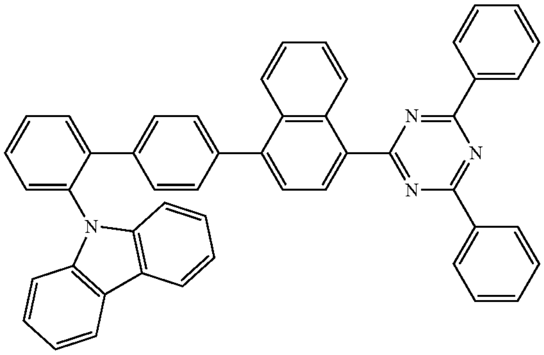
ET-10
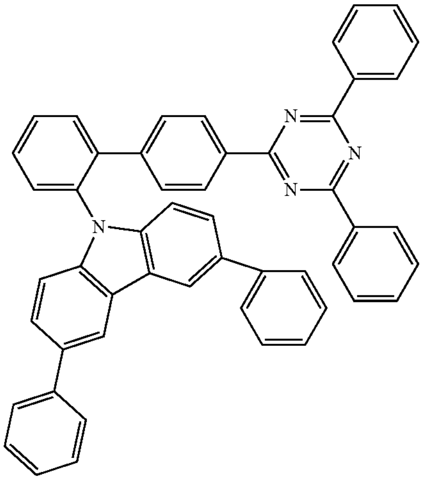

-continued
ET-11
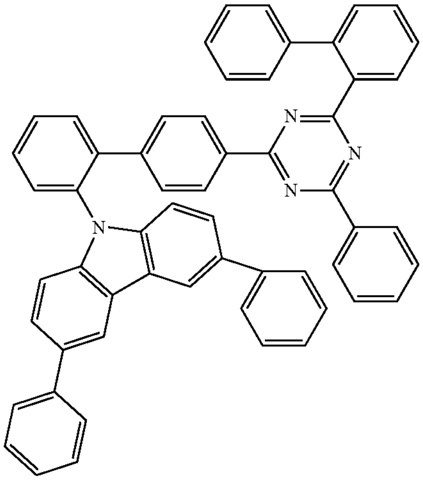
ET-12
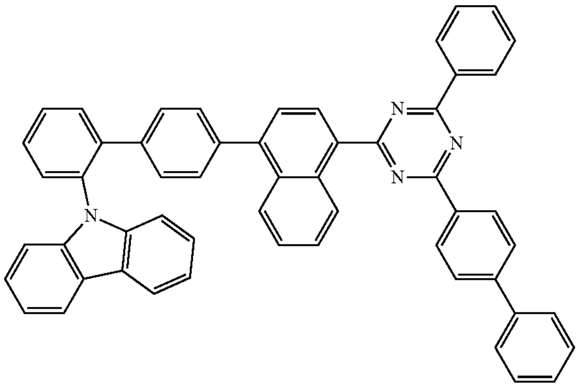
ET-13
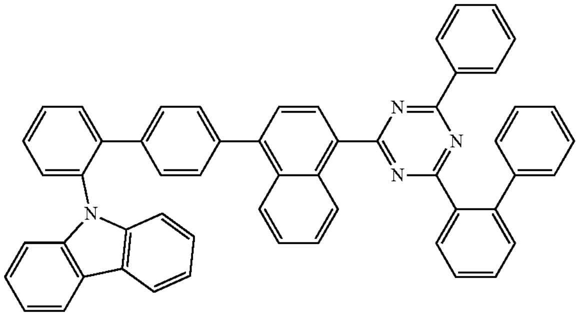
ET-14
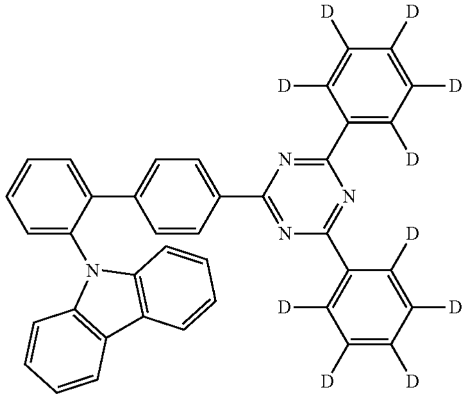
-continued
ET-15
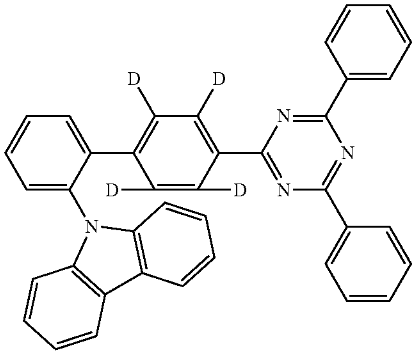
ET-16
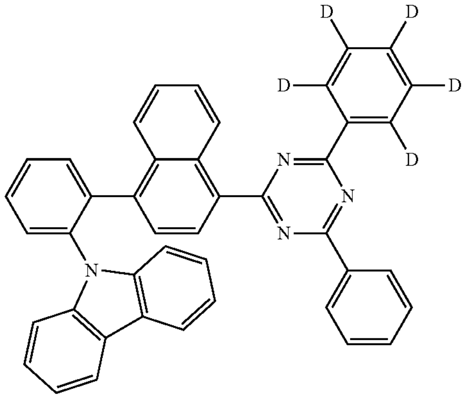
ET-17
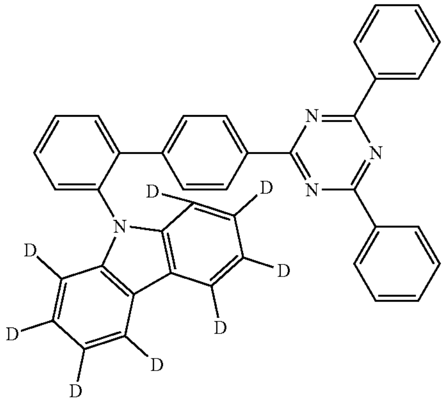
Ref. ET-1
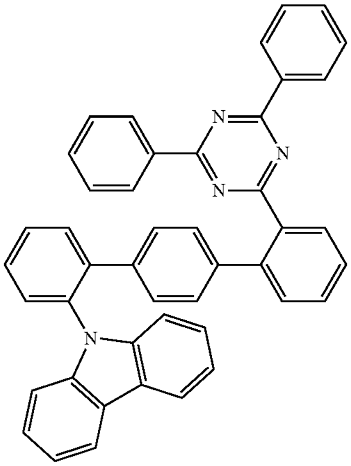

-continued
Ref. ET-2
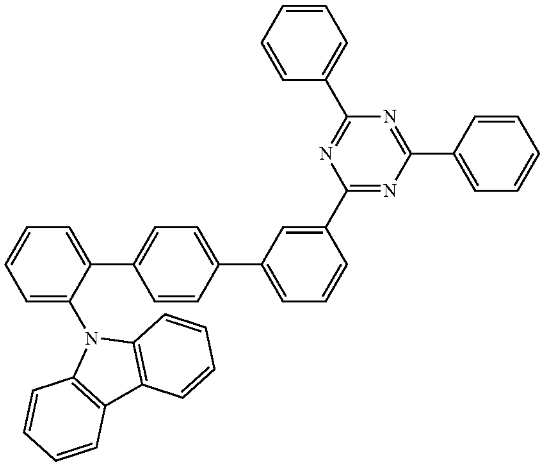
Compounds used for fabricating the organic EL devices of Comparative Examples 1 to 4 are shown below.
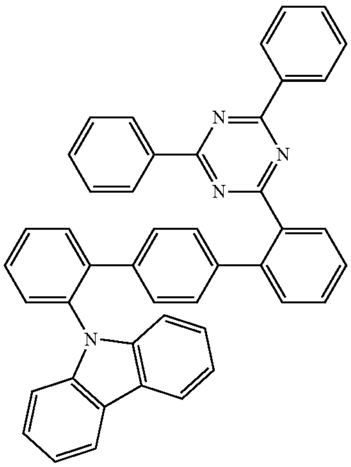
Ref. ET-1
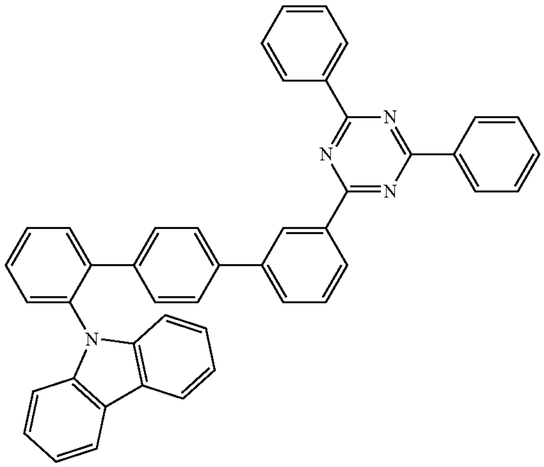
Ref. ET-2
Other compounds used in the fabrication of the organic EL devices of Examples 1-1 to 1-16, Examples 2-1 to 2-5 and Comparative Examples 1 to 4 are shown below.
HT-1
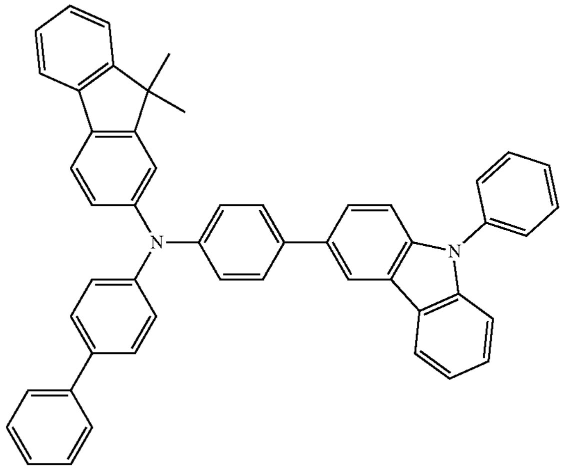
HI-1
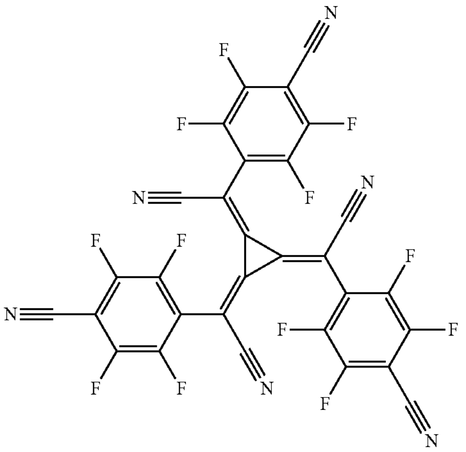
EBL-1
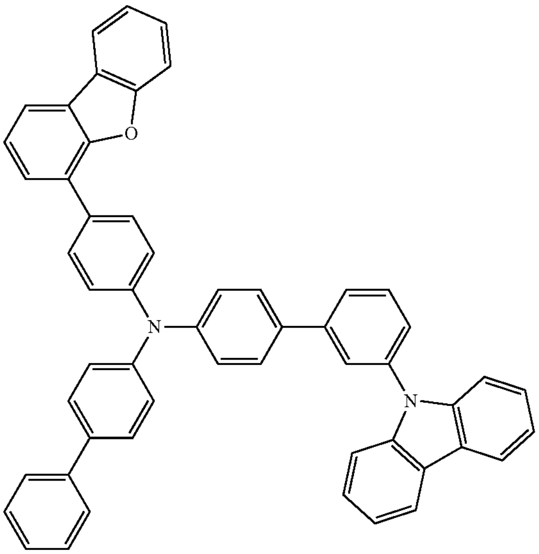

-continued

BH-1

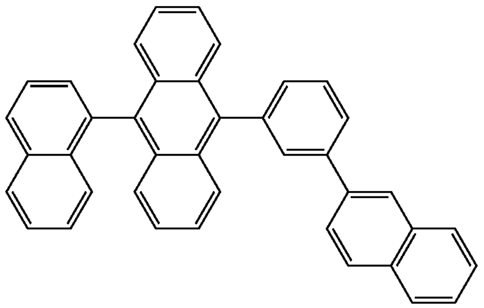

BD-1

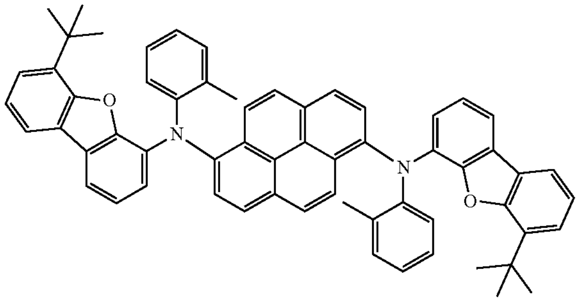

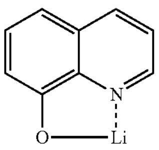

Liq b ET-1

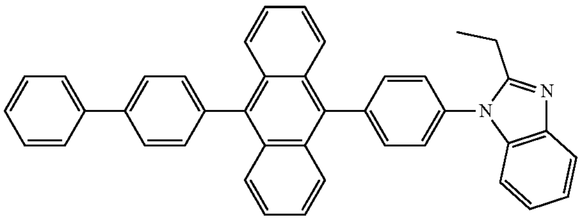

HBL-1

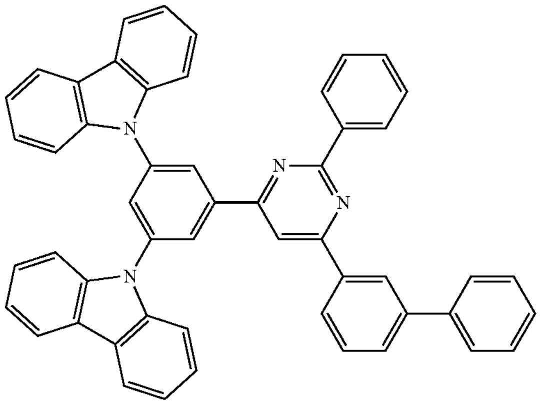

<Fabrication of Organic EL Device>

Organic EL devices were fabricated and evaluated as follows.

Example 1-1

A glass substrate with an ITO transparent electrode of 25 mm×75 mm×1.1 mm (anode) (manufactured by GEOMATEC Co., Ltd.) was ultrasonically cleaned in isopropyl alcohol for 5 minutes, and then UV ozone-cleaned for 30 minutes. The ITO has the film thickness of 130 nm.

The glass substrate with the transparent electrode after being cleaned was mounted onto a substrate holder in a vacuum vapor deposition apparatus. First, a compound HT-1 and a compound HT-1 were co-deposited on the surface on the side where the transparent electrode was formed so as to cover the transparent electrode to form a hole-injecting layer having the thickness of 10 nm. The weight ration of the compound HT-1 and the compound HT-1 was 97:3.

Subsequently, a compound HT-1 was deposited on the hole-injecting layer to form a hole-transporting layer having the thickness of 80 nm.

A compound EBL-1 was deposited on the hole-transporting layer to form an electron-blocking layer having the thickness of 10 nm.

Next, a compound BH-1 (host material) and a compound BD-1 (dopant material) were co-deposited on the electron-blocking layer to form an emitting layer having the thickness of 25 nm. The weight ration of the compound BH-1 and the compound BD-1 was 96:4.

Subsequently, a compound ET-7 was deposited on the emitting layer to form a first electron-transporting layer (hole-blocking layer) having the thickness of 10 nm.

A bET-1 was deposited on the first electron-transporting layer (hole-blocking layer) to form a second electron-transporting layer (electron-injecting layer) having the thickness of 15 nm.

LiF was deposited on the second electron-transporting layer (electron-injecting layer) to form an electron-injecting electrode having the thickness of 1 nm.

Finally, a metal Al was deposited on the electron-injecting electrode to form a metal cathode having the thickness of 50 nm.

The layer configuration of the organic EL device of Example 1-1 is shown below. The numerical values in parentheses are the film thickness (nm), and the ratios is the mass ratio.

ITO(130)/HT-1:HI-1=97:3(10)/HT-1(80)/EBL-1(10)/BH-1:BD-1=96:4(25)/ET-7(10)/bET-1(15)/LiF(1)/Al (50)

<Evaluation of Organic EL Device>

95% lifetime (LT95)

The obtained organic EL device was driven using DC constant current with the current density of 50 mA/cm$^2$, the time until the luminance was decreased to 95% of the initial luminance was measured, and the value was defined as 95% lifetime (LT95). The results are shown in Table 1.

Comparative Examples 1 and 2

An organic EL device was fabricated and evaluated in the same manner as in Example 1-1, except that a material of the first electron-transporting layer (hole-blocking layer) shown in Table 1 was used instead of the compound ET-7. The results are shown in Table 1.

TABLE 1

| | Material of first electron-transporting layer | LT95 (hr) |
|---|---|---|
| Example 1-1 | ET-7 | 185 |
| Comparative Example 1 | Ref. ET-1 | 90 |
| Comparative Example 2 | Ref. ET-2 | 98 |

As seen from the results shown in Table 1, it was found that the organic EL device of Example 1-1 in which the compound represented by the formula (1) is used as the material of the first electron-transporting layer (hole-blocking layer) exhibits long lifetime, as compared to the devices of Comparative Examples 1 and 2.

When the device of Example 1-1 and the devices of Comparative Examples 1 and 2 are compared, they are different from each other in consideration that each phenylene group directly bonded with an azine ring is bonding to each adjacent phenylene group each at the para (p)-position, the ortho (o)-position, and the meta (m)-position in the material compound of the first electron-transporting layer (hole-blocking layer) used in each device. It was found that the compound (1) has p-phenylene structure, thereby stabilizing the compound, and the device using the compound exhibits an effect of prolonging the lifetime thereof.

Examples 1-2 to 1-16

Organic EL devices were fabricated and evaluated in the same manner as in Example 1-1, except that a material of the first electron-transporting layer (hole-blocking layer) shown in Table 2 was used instead of the compound ET-7. The results are shown in Table 2.

TABLE 2

| | Material of first electron-transporting layer | LT95 (hr) |
|---|---|---|
| Example 1-2 | ET-1 | 121 |
| Example 1-3 | ET-2 | 180 |
| Example 1-4 | ET-3 | 210 |
| Example 1-5 | ET-5 | 116 |
| Example 1-6 | ET-6 | 135 |
| Example 1-7 | ET-8 | 123 |
| Example 1-8 | ET-9 | 202 |
| Example 1-9 | ET-10 | 185 |
| Example 1-10 | ET-11 | 132 |
| Example 1-11 | ET-12 | 220 |
| Example 1-12 | ET-13 | 175 |
| Example 1-13 | ET-14 | 122 |
| Example 1-14 | ET-15 | 121 |
| Example 1-15 | ET-16 | 136 |
| Example 1-16 | ET-17 | 120 |

As seen from the results shown in Tables 1 and 2, it was found that the organic EL devices of Examples 1-2 to 1-16 in which the compound represented by the formula (1) is used as the material of the first electron-transporting layer (hole-blocking layer) exhibit long lifetime, as compared to the devices of Comparative Examples 1 and 2.

<Fabrication of organic EL device>

Example 2-1

A glass substrate with an ITO transparent electrode of 25 mm×75 mm×1.1 mm (anode) (manufactured by GEOMATEC Co., Ltd.) was ultrasonically cleaned in isopropyl alcohol for 5 minutes, and then UV ozone-cleaned for 30 minutes. The ITO has the film thickness of 130 nm.

The glass substrate with the transparent electrode after being cleaned was mounted onto a substrate holder in a vacuum vapor deposition apparatus. First, a compound HT-1 and a compound HI-1 were co-deposited on the surface on the side where the transparent electrode was formed so as to cover the transparent electrode to form a hole-injecting layer having the thickness of 10 nm. The weight ration of the compound HT-1 and the compound HI-1 was 97:3.

Subsequently, a compound HT-1 was deposited on the hole-injecting layer to form a hole-transporting layer having the thickness of 80 nm.

A compound EBL-1 was deposited on the hole-transporting layer to form an electron-blocking layer having the thickness of 5 nm.

Next, a compound BH-1 (host material) and a compound BD-1 (dopant material) were co-deposited on the electron-blocking layer to form an emitting layer having the thickness of 25 nm. The weight ration of the compound BH-1 and the compound BD-1 was 96:4.

Subsequently, a compound HBL-1 was deposited on the emitting layer to form a first electron-transporting layer (hole-blocking layer) having the thickness of 5 nm.

A compound ET-7 and Liq were co-deposited on the first electron-transporting layer (hole-blocking layer) to form a second electron-transporting layer (electron-injecting layer) having the thickness of 20 nm. The weight ration of the compound ET-7 and Liq was 50:50.

Yb was deposited on the second electron-transporting layer (electron-injecting layer) to form an electron-injecting electrode having the thickness of 1 nm.

Finally, a metal Al was deposited on the electron-injecting electrode to form a metal cathode having the thickness of 80 nm.

The layer configuration of the organic EL device of Example 2-1 is shown below. The numerical values in parentheses are the film thickness (nm), and the ratios is the mass ratio.

ITO(130)/HT-1:HI-1=97:3(10)/HT-1(80)/EBL-1(5)/BH-1:BD-1=96:4(25)/HBL-1(5)/ET-7:Liq=50:50(20)/Yb(1)/Al (80)

<Evaluation of Organic EL Device>

95% lifetime (LT95)

The obtained organic EL device was driven using DC constant current with the current density of 50 mA/cm$^2$, the time until the luminance was decreased to 95% of the initial luminance was measured, and the value was defined as 95% lifetime (LT95). The results are shown in Table 3.

Comparative Examples 3 and 4

Organic EL devices were fabricated and evaluated in the same manner as in Example 2-1, except that a material of the second electron-transporting layer (electron-injecting layer) shown in Table 3 was used instead of the compound ET-7. The results are shown in Table 3.

TABLE 3

| | Material of second electron-transporting layer | LT95 (hr) |
|---|---|---|
| Example 2-1 | ET-7 | 141 |
| Comparative Example 3 | Ref. ET-1 | 118 |
| Comparative Example 4 | Ref. ET-2 | 120 |

As seen from the results shown in Table 3, it was found that the organic EL device of Example 2-1 in which the compound represented by the formula (1) is used as the material of the second electron-transporting layer (electron-injecting layer) exhibits long lifetime, as compared to the devices of Comparative Examples 3 and 4.

When the device of Example 2-1 and the devices of Comparative Examples 3 and 4 are compared, they are different from each other in consideration that each phenylene group directly bonded with an azine ring is bonding to each adjacent phenylene group each at the para (p)-position, the ortho (o)-position, and the meta (m)-position in the material compound of the second electron-transporting layer (electron-injecting layer) used in each device. It was found that the compound (1) has p-phenylene structure, thereby stabilizing the compound, and the device using the compound exhibits an effect of prolonging the lifetime thereof.

Examples 2-2 to 2-5

Organic EL devices were fabricated and evaluated in the same manner as in Example 2-1, except that a material of the second electron-transporting layer (electron-injecting layer) shown in Table 4 was used instead of the compound ET-7. The results are shown in Table 4.

TABLE 4

| | Material of second electron-transporting layer | LT95 (hr) |
|---|---|---|
| Example 2-2 | ET-2 | 138 |
| Example 2-3 | ET-3 | 160 |
| Example 2-4 | ET-9 | 146 |
| Example 2-5 | ET-12 | 150 |

As seen from the results shown in Tables 3 and 4, it was found that the organic EL devices of Examples 2-2 to 2-5 in which the compound represented by the formula (1) is used as the material of the second electron-transporting layer (electron-injecting layer) exhibit long lifetime, as compared to the devices of Comparative Examples 3 and 4.
<Synthesis of Compound>

(Synthesis Example 1) Synthesis of Compound ET-1

The compound ET-1 was synthesized through the synthetic route described below.

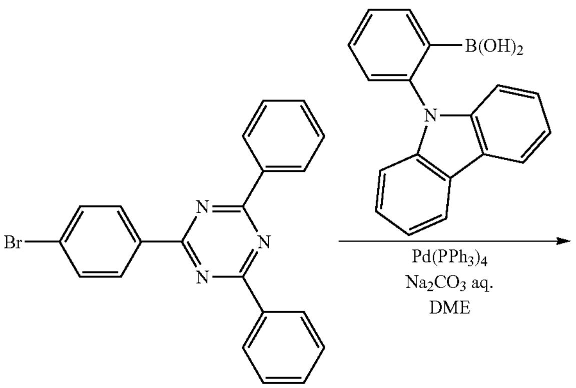

-continued

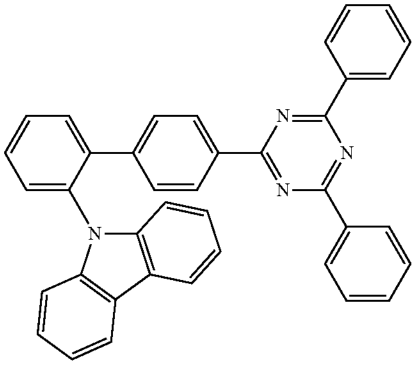

ET-1

2-(4-bromophenyl)-4,6-diphenyl-1,3,5-triazine (3.9 g) and 2-(9-carbazolyl)phenylboronic acid (2.9 g) were dissolved in dimethoxyethane (DME)(40 mL), and argon gas was passed through the solution for 5 minutes. Tetrakis (triphenylphosphine)palladium (Pd(PPh3)4)(300 mg) and aqueous solution of sodium carbonate (2 M, 12 mL) were added thereto, and they were heated at reflux for 5 hours with stirring under an argon atmosphere. The reaction solution was subjected to column chromatography, and the obtained solids were recrystallized using xylene to obtain ET-1 (3.9 g, 71% yield). The mass spectrum of the obtained compound was analyzed as m/z (ratio of mass to charge)=550.

(Synthesis Example 2) Synthesis of Compound ET-2

The compound ET-2 was synthesized through the synthetic route described below.

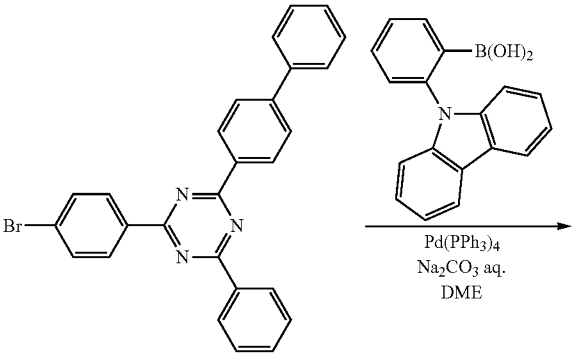

Int-1

-continued

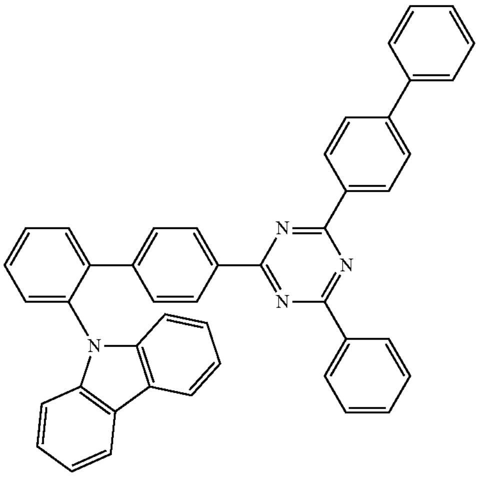

ET-2

ET-2 was obtained in the same manner as in Synthetic Example 1, except that Int-1 was used instead of 2-(4-bromophenyl)-4,6-diphenyl-1,3,5-triazine. The mass spectrum of the obtained compound was analyzed as m/z=626.

(Synthesis Example 3) Synthesis of compound ET-3

The compound ET-3 was synthesized through the synthetic route described below.

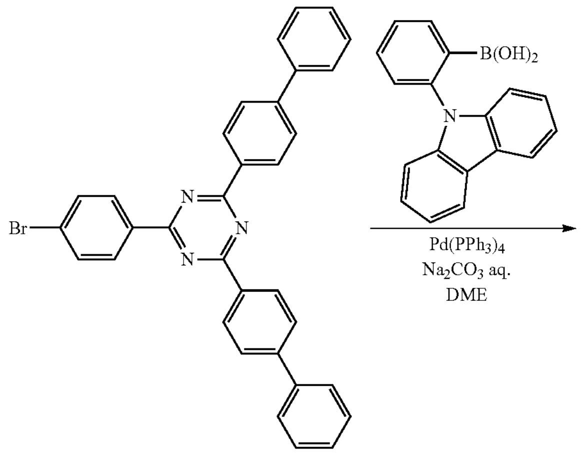

Int-2

-continued

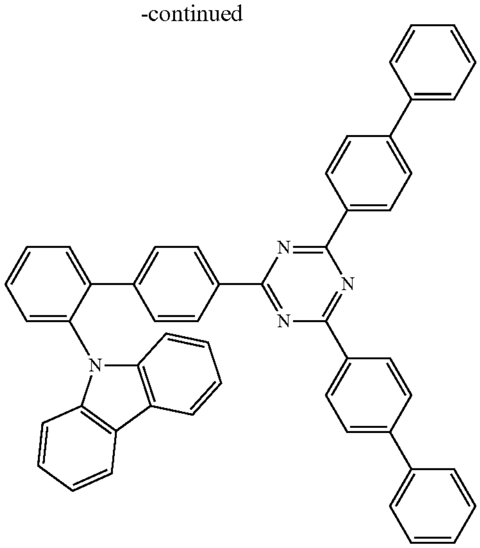

ET-3

ET-3 was obtained in the same manner as in Synthetic Example 1, except that Int-2 was used instead of 2-(4-bromophenyl)-4,6-diphenyl-1,3,5-triazine. The mass spectrum of the obtained compound was analyzed as m/z=702.

(Synthesis Example 4) Synthesis of Compound ET-4

The compound ET-4 was synthesized through the synthetic route described below.

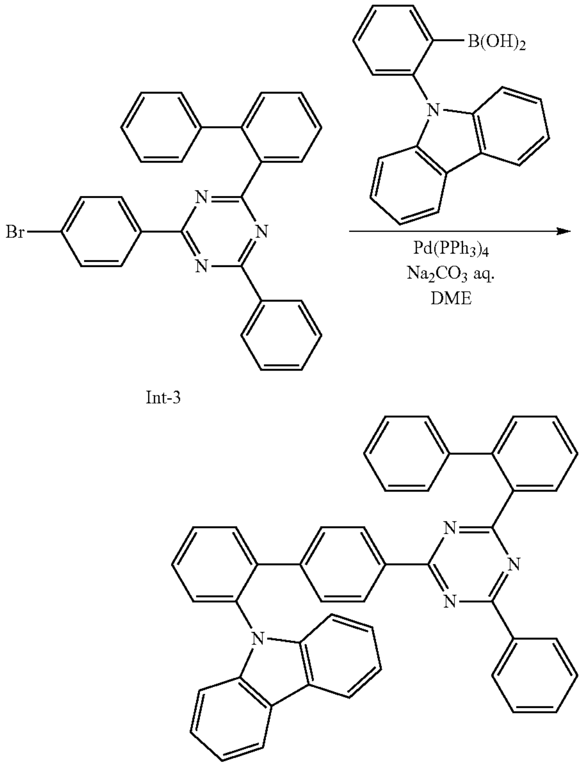

Int-3

ET-4

ET-4 was obtained in the same manner as in Synthetic Example 1, except that Int-3 was used instead of 2-(4-bromophenyl)-4,6-diphenyl-1,3,5-triazine. The mass spectrum of the obtained compound was analyzed as m/z=626.

(Synthesis Example 5) Synthesis of Compound ET-5

The compound ET-5 was synthesized through the synthetic route described below.

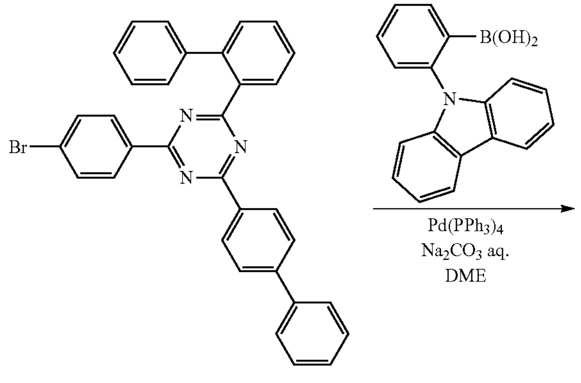

Int-4

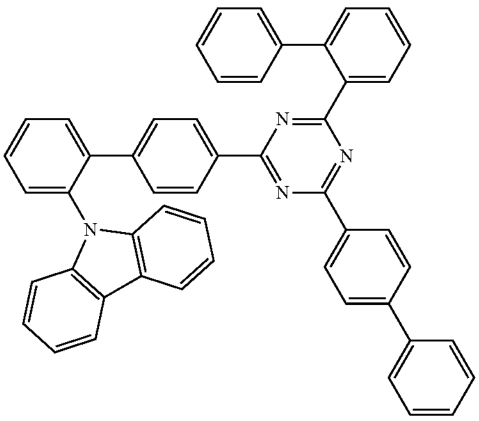

ET-5

ET-5 was obtained in the same manner as in Synthetic Example 1, except that Int-4 was used instead of 2-(4-bromophenyl)-4,6-diphenyl-1,3,5-triazine. The mass spectrum of the obtained compound was analyzed as m/z=702.

(Synthesis Example 6) Synthesis of Compound ET-6

The compound ET-6 was synthesized through the synthetic route described below.

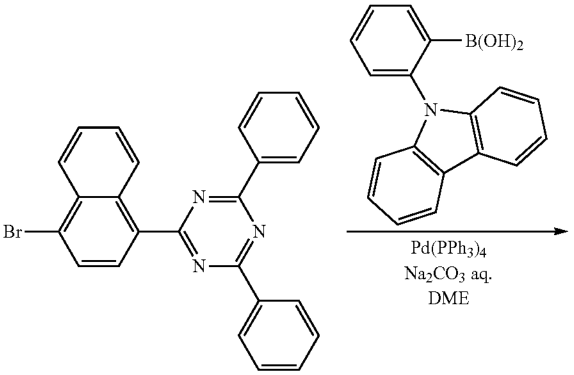

Int-5

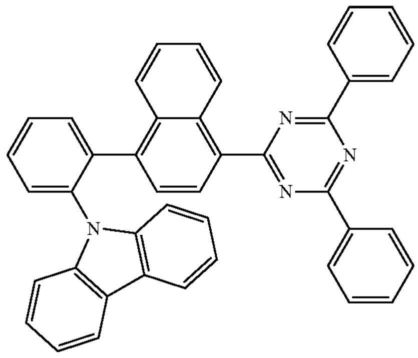

ET-6

ET-6 was obtained in the same manner as in Synthetic Example 1, except that Int-5 was used instead of 2-(4-bromophenyl)-4,6-diphenyl-1,3,5-triazine. The mass spectrum of the obtained compound was analyzed as m/z=600.

(Synthesis Example 7) Synthesis of Compound ET-7

The compound ET-7 was synthesized through the synthetic route described below.

(7-1) Synthesis of Int-7

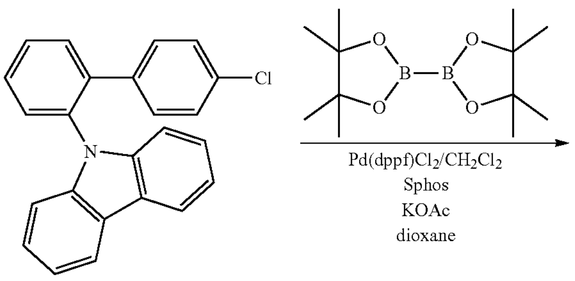

Int-6

-continued

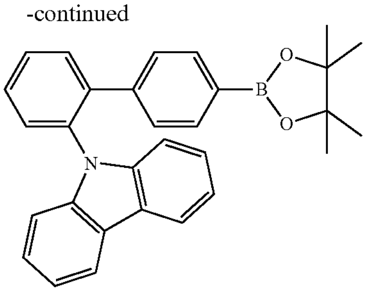

Int-7

Int-6 (25 g) and bispinacolborane (36 g) were added to dioxane (350 mL), and argon gas was passed through the solution for 5 minutes. [1,1'-bis(diphenylphosphino)ferrocene]palladium (II) dichloride-dichloromethane adduct (Pd $(dppf)Cl_2/CH_2Cl_2$)(1.1 g), 2-dichlorohexylphosphino-2',6'-dimethoxybiphenyl (Sphos)(2.3 g), and potassium acetate (21 g) were added thereto, and they were heated to 100° C. for 7 hours with stirring under an argon atmosphere. Solvents were removed from the reaction solution, and the obtained solids were subjected to silica gel column chromatography to obtain Int-7 (22 g, 70% yield).

(7-2) Synthesis of compound ET-7

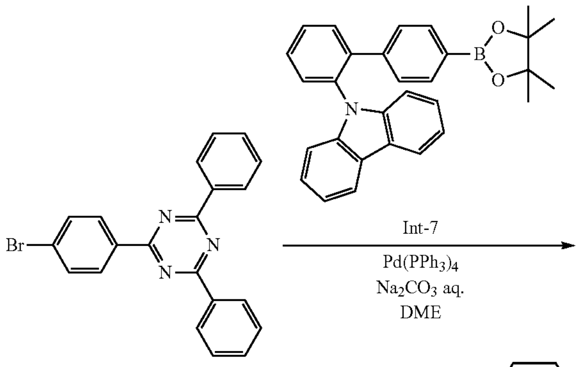

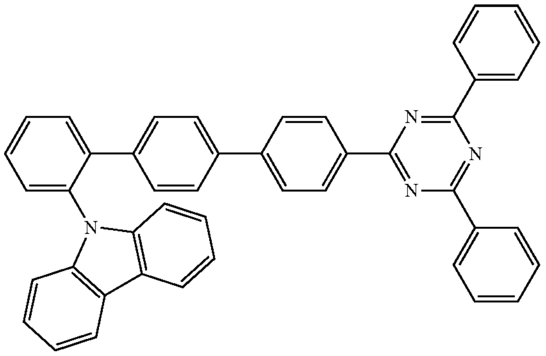

ET-7

ET-7 was obtained in the same manner as in Synthetic Example 1, except that Int-7 was used instead of 2-(9-carbazolyl)phenylboronic acid. The mass spectrum of the obtained compound was analyzed as m/z=626.

(Synthesis Example 8) Synthesis of Compound ET-8

The compound ET-8 was synthesized through the synthetic route described below.

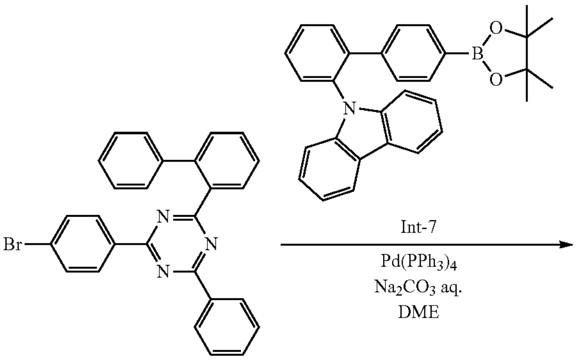

Int-3

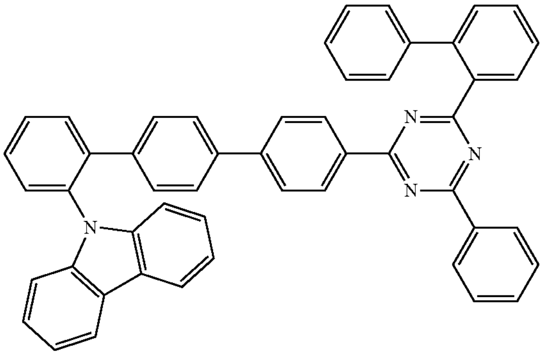

ET-8

ET-8 was obtained in the same manner as in (7-2) of Synthetic Example 7, except that Int-3 was used instead of 2-(4-bromophenyl)-4,6-diphenyl-1,3,5-triazine. The mass spectrum of the obtained compound was analyzed as m/z=702.

(Synthesis Example 9) Synthesis of Compound ET-9

The compound ET-9 was synthesized through the synthetic route described below.

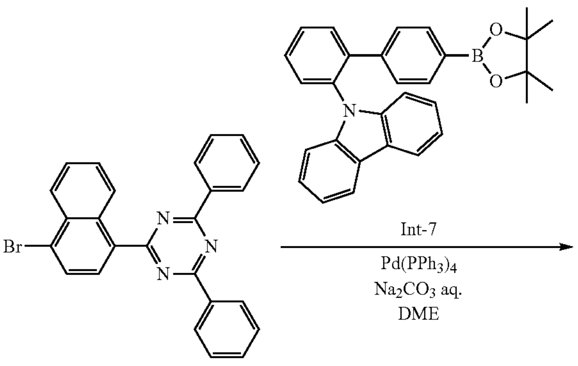

Int-5

-continued

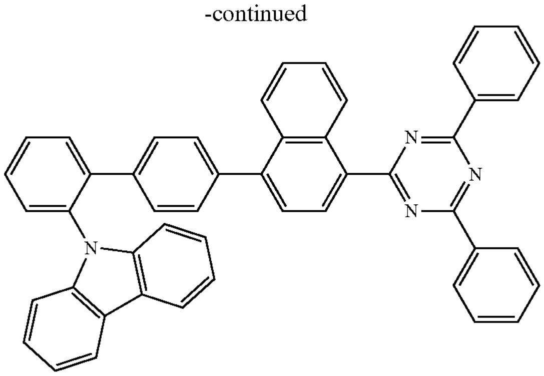

ET-9

ET-9 was obtained in the same manner as in (7-2) of Synthetic Example 7, except that Int-5 was used instead of 2-(4-bromophenyl)-4,6-diphenyl-1,3,5-triazine. The mass spectrum of the obtained compound was analyzed as m/z=676.

(Synthesis Example 10) Synthesis of Compound ET-10

The compound ET-10 was synthesized through the synthetic route described below.

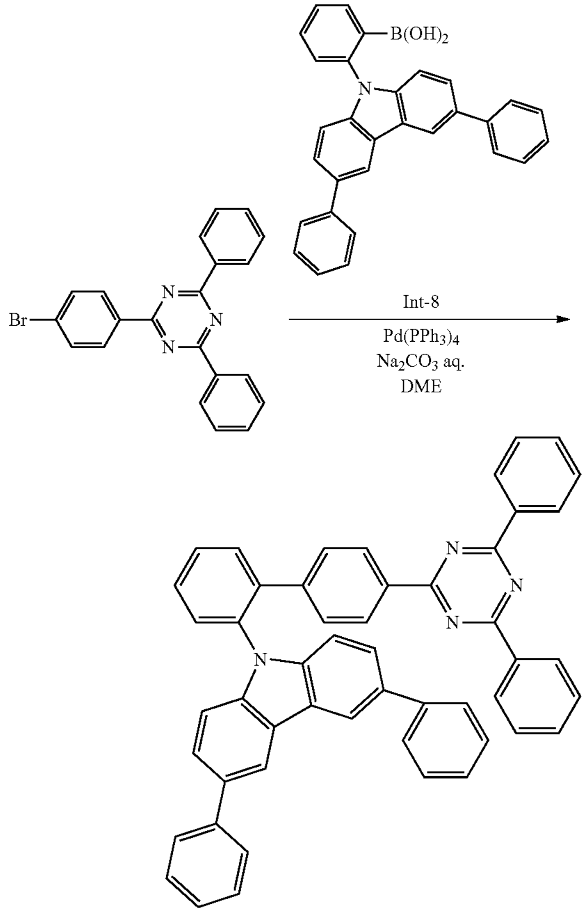

ET-10

ET-10 was obtained in the same manner as in Synthetic Example 1, except that Int-8 was used instead of 2-(9-carbazolyl)phenylboronic acid. The mass spectrum of the obtained compound was analyzed as m/z=702.

(Synthesis Example 11) Synthesis of Compound ET-11

The compound ET-11 was synthesized through the synthetic route described below.

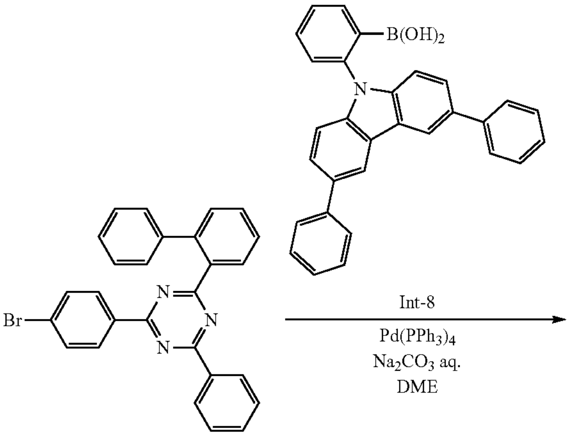

Int-3

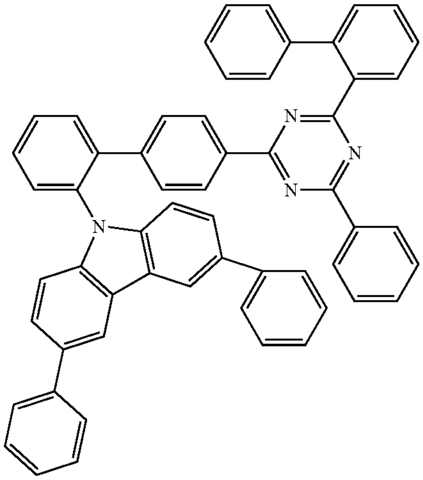

ET-11

ET-11 was obtained in the same manner as in Synthetic Example 4, except that Int-8 was used instead of 2-(9-carbazolyl)phenylboronic acid. The mass spectrum of the obtained compound was analyzed as m/z=778.

(Synthesis Example 12) Synthesis of Compound ET-12
The compound ET-12 was synthesized through the synthetic route described below.
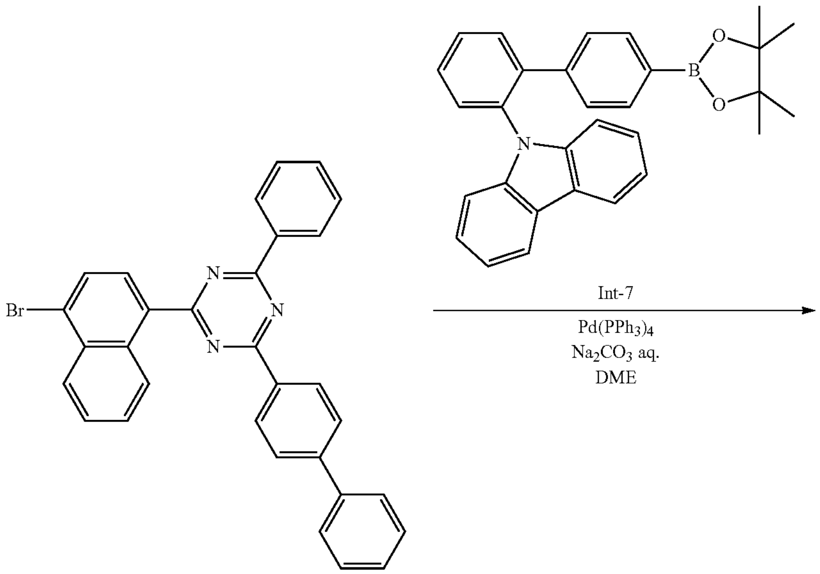
Int-9
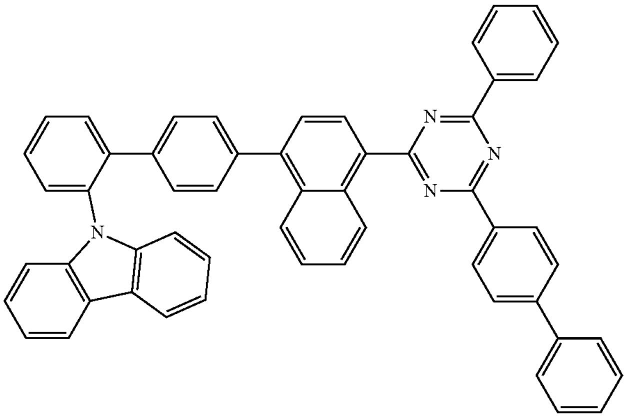
ET-12

ET-12 was obtained in the same manner as in Synthetic Example 9, except that Int-9 was used instead of Int-5. The mass spectrum of the obtained compound was analyzed as m/z=752.
(Synthesis Example 13) Synthesis of Compound ET-13
The compound ET-13 was synthesized through the synthetic route described below.
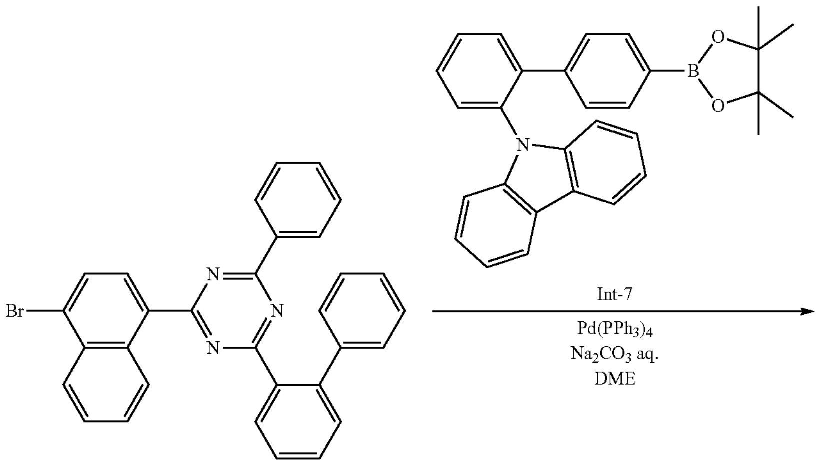
Int-10
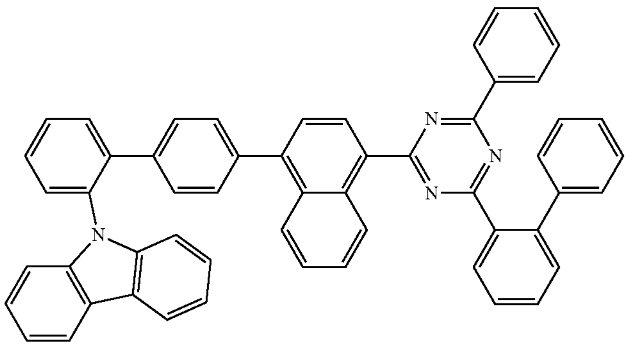
ET-13

ET-13 was obtained in the same manner as in Synthetic Example 9, except that Int-10 was used instead of Int-5. The mass spectrum of the obtained compound was analyzed as m/z=752.

(Synthesis Example 14) Synthesis of Compound ET-14

The compound ET-14 was synthesized through the synthetic route described below.

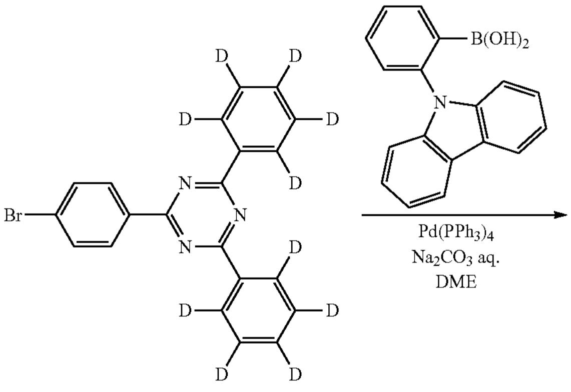

Int-11

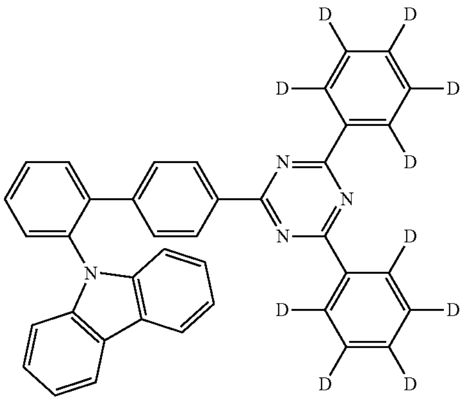

ET-14

ET-14 was obtained in the same manner as in Synthetic Example 1, except that Int-11 was used instead of 2-(4-bromophenyl)-4,6-diphenyl-1,3,5-triazine. The mass spectrum of the obtained compound was analyzed as m/z=560.

(Synthesis Example 15) Synthesis of Compound ET-15

The compound ET-15 was synthesized through the synthetic route described below.

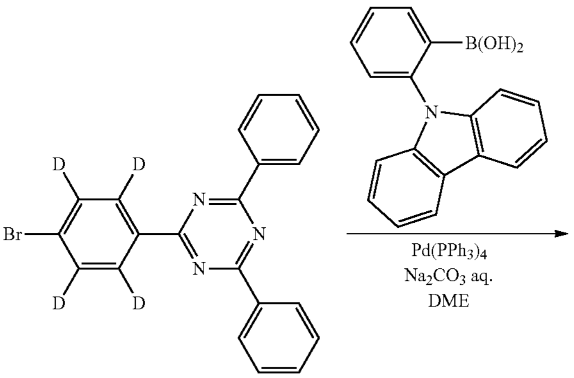

Int-12

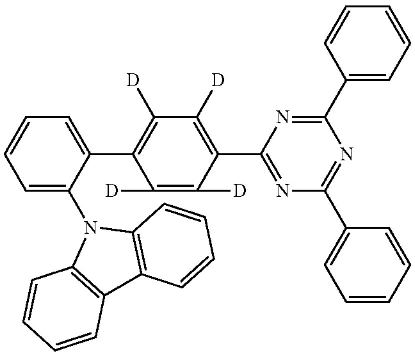

ET-15

ET-15 was obtained in the same manner as in Synthetic Example 1, except that Int-12 was used instead of 2-(4-bromophenyl)-4,6-diphenyl-1,3,5-triazine. The mass spectrum of the obtained compound was analyzed as m/z=554.

(Synthesis Example 16) Synthesis of Compound ET-16

The compound ET-16 was synthesized through the synthetic route described below.

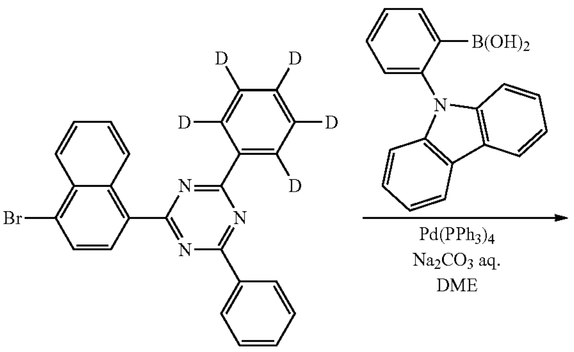

Int-13

-continued

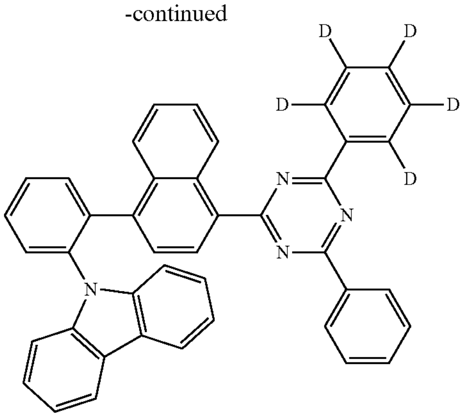

ET-16

ET-16 was obtained in the same manner as in Synthetic Example 6, except that Int-13 was used instead of Int-5. The mass spectrum of the obtained compound was analyzed as m/z=605.

(Synthesis Example 17) Synthesis of Compound ET-17

The compound ET-17 was synthesized through the synthetic route described below.

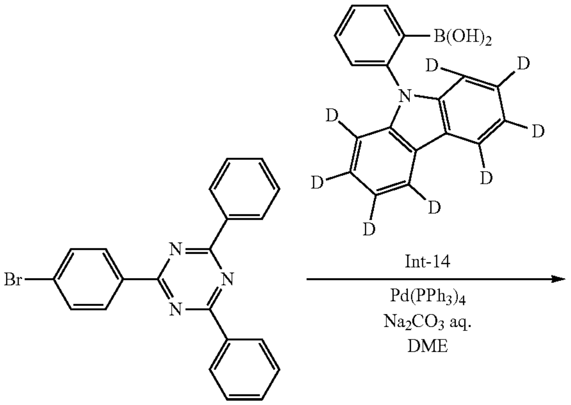

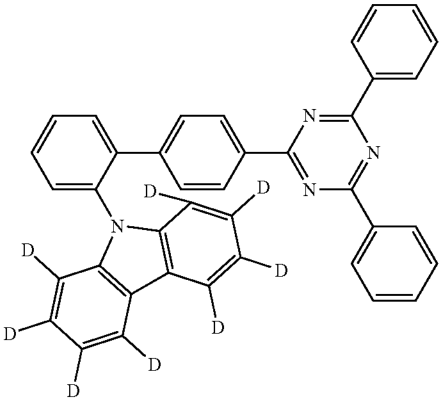

ET-17

ET-17 was obtained in the same manner as in Synthetic Example 1, except that Int-14 was used instead of 2-(9-carbazolyl)phenylboronic acid. The mass spectrum of the obtained compound was analyzed as m/z=558.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:

1. A compound represented by the following formula (1):

(1)

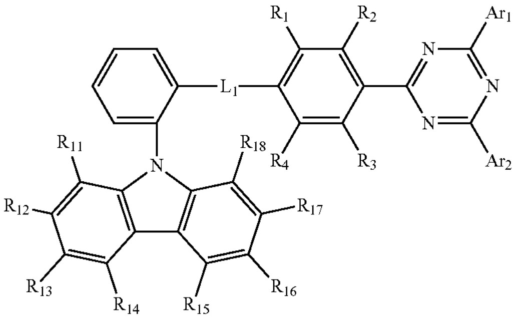

wherein in the formula (1), $Ar_1$ and $Ar_2$ are independently an unsubstituted aryl group having 6 to 50 ring carbon atoms;

$R_1$ and $R_2$ form an unsubstituted, saturated or unsaturated hydrocarbon ring having 6 to 50 ring carbon atoms by bonding with each other, or do not form the ring;

$R_3$ and $R_4$, and $R_1$ and $R_2$ which do not form the ring are independently a hydrogen atom, or a substituent $R_a$;

one or more sets of the adjacent two or more of $R_{11}$ to $R_{18}$ form an unsubstituted, saturated or unsaturated hydrocarbon ring having 6 to 50 ring carbon atoms, or an unsubstituted, saturated or unsaturated heterocyclic ring having 5 to 50 ring atoms, by bonding with each other, or do not form the rings;

$R_{11}$ to $R_{18}$ which do not form the rings are independently a hydrogen atom, or a substituent $R_a$;

$L_1$ is a divalent group represented by any one of the following formulas (a1) to (a9):

(a1)

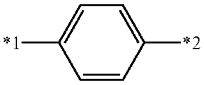

(a2)

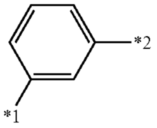

(a3)

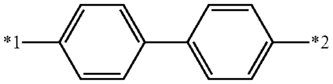

-continued (a4)

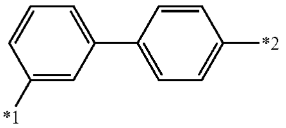

(a5)

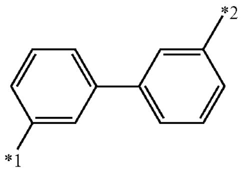

(a6)

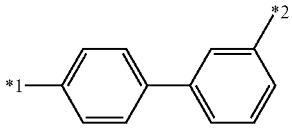

(a7)

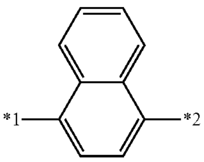

(a8)

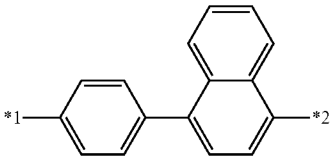

(a9)

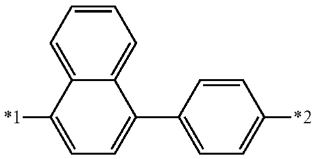

wherein in the formulas (a1) to (a9), *1 is bonded with a benzene ring on a carbazolyl group side, and *2 is bonded with a benzene ring on a triazine ring side, wherein the substituent $R_a$ is selected from the group consisting of:

a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O-($R_{904}$),

—S-($R_{905}$),

—N($R_{906}$)($R_{907}$), and a substituted or unsubstituted aryl group having 6 to 50 ring carbon atoms (wherein, $R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, or a substituted or unsubstituted aryl group having 6 to 50 ring carbon atoms; when two or more of each of $R_{901}$ to $R_{907}$ are present, the two or more of each of $R_{901}$ to $R_{907}$ may be the same as or different from each other).

2. The compound according to claim 1, wherein the compound represented by the formula (1) is a compound represented by any one of the following formulas (2-1) to (2-8):

(2-1)

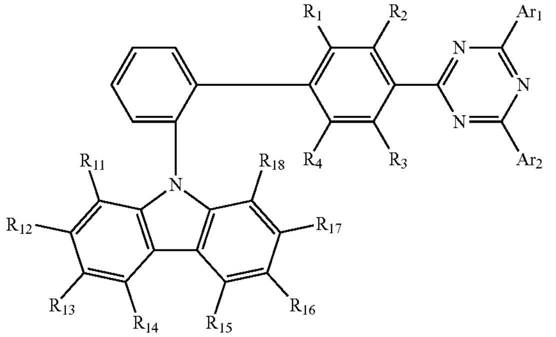

(2-2)

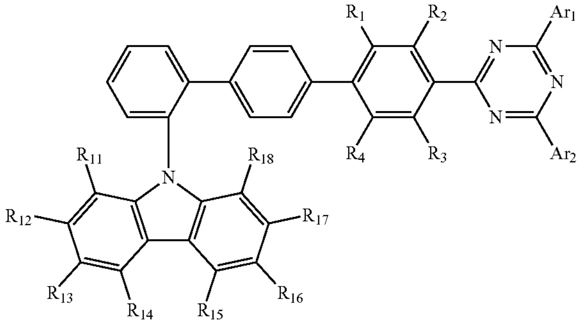

(2-3)

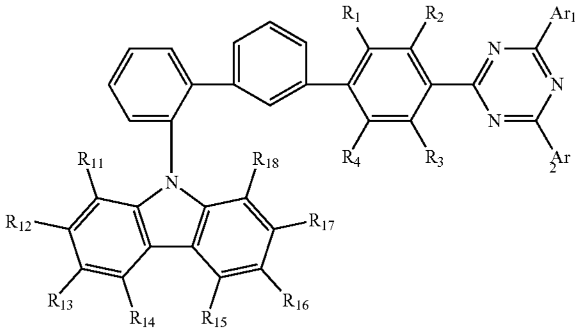

(2-4)

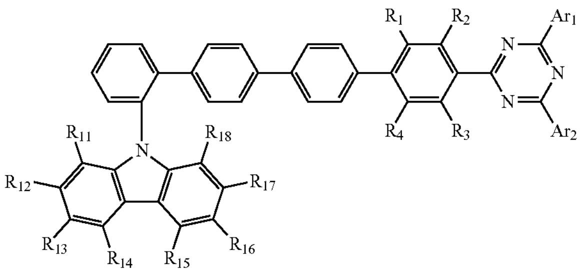

-continued (2-5)

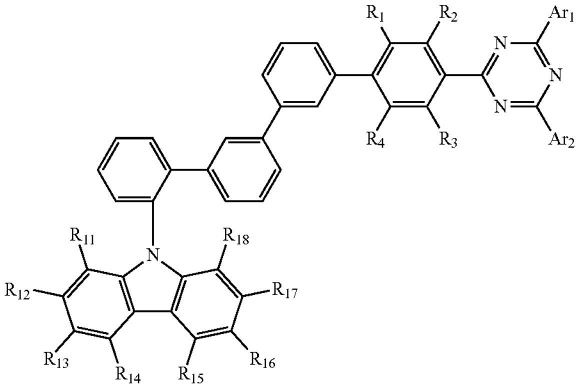

(2-6)

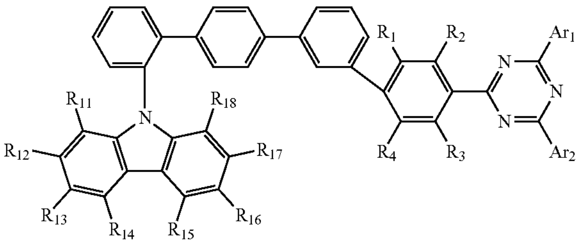

(2-7)

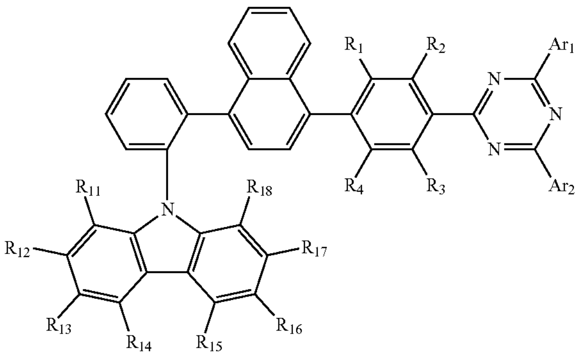

(2-8)

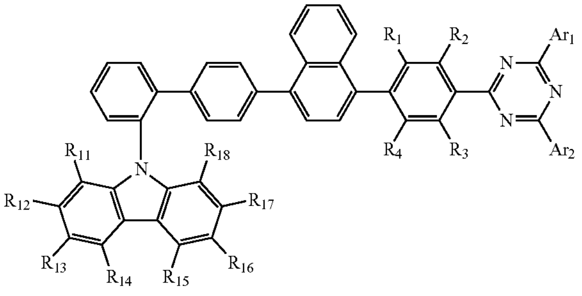

wherein in the formulas (2-1) to (2-8), $Ar_1$, $Ar_2$, $R_1$ to $R_4$, and $R_{11}$ to $R_{18}$ are the same as defined in the formula (1).

3. The compound according to claim 1, wherein $L_1$ in the formula (1) is a group represented by the formula (a1).

4. The compound according to claim 1, wherein $Ar_1$ and $Ar_2$ in the formula (1) are independently an unsubstituted phenyl group, an unsubstituted biphenyl group, an unsubstituted terphenyl group, an unsubstituted naphthyl group, or an unsubstituted phenanthryl group.

5. The compound according to claim 1, wherein $Ar_1$ and $Ar_2$ in the formula (1) are independently a group represented by any one of the following formulas (b1) to (b4):

(b1)

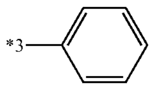

(b2)

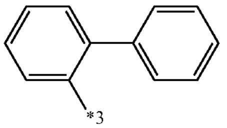

(b3)

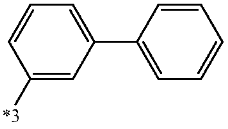

(b4)

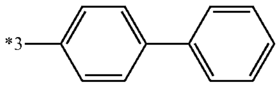

wherein in the formulas (b1) to (b4), *3 represents a binding site with a triazine ring.

6. The compound according to claim 1, wherein the compound represented by the formula (1) is a compound represented by any one of the following formulas (4-1) to (4-6):

(4-1)

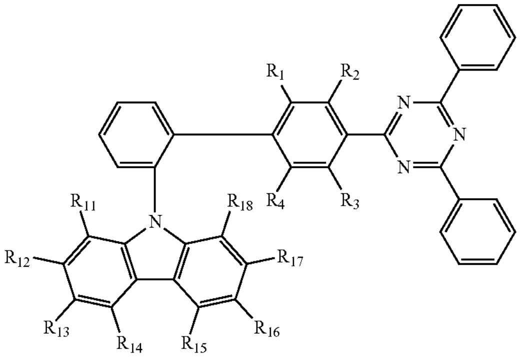

(4-2)

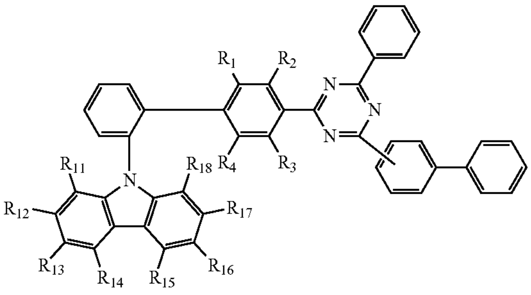

-continued (4-3)

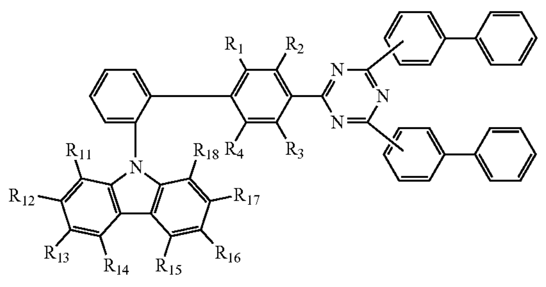

(4-4)

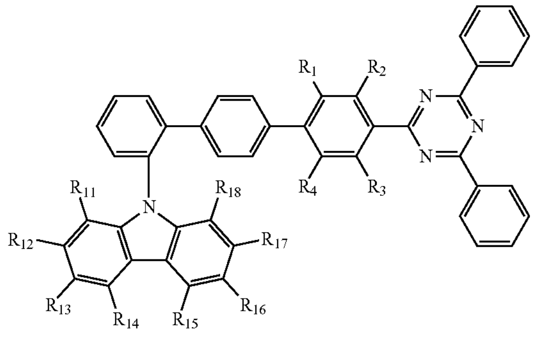

(4-5)

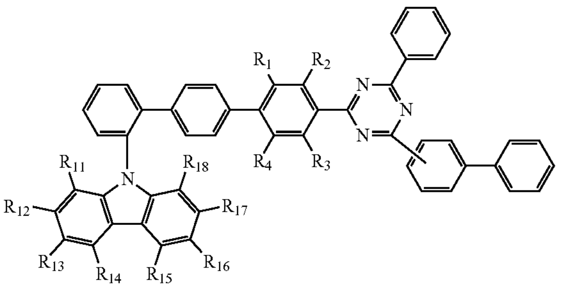

(4-6)

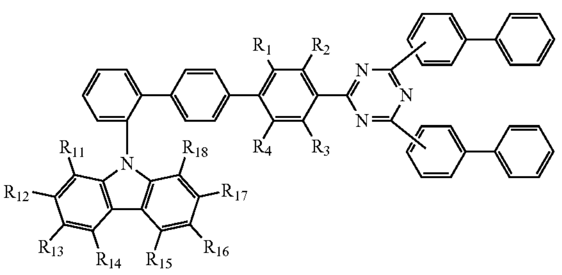

wherein in the formulas (4-1) to (4-6), $R_1$ to $R_4$, and $R_{11}$ to $R_{18}$ are the same as defined in the formula (1).

7. The compound according to claim 1, wherein $R_1$ and $R_2$ in the formula (1) are a hydrogen atom.

8. The compound according to claim 1, wherein the compound represented by the formula (1) is a compound represented by the following formula (5):

(5)

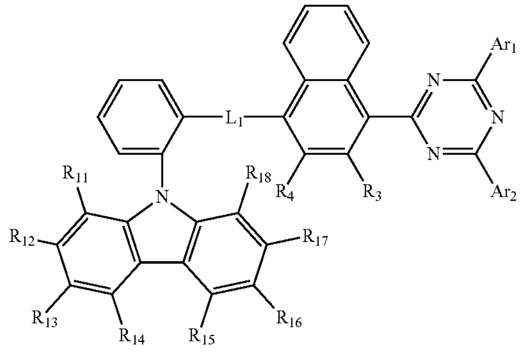

wherein in the formula (5), $L_1$, $Ar_1$, $Ar_2$, $R_3$, $R_4$, and $R_{11}$ to $R_{18}$ are the same as defined in the formula (1).

9. The compound according to claim 1, wherein $R_3$ and $R_4$ in the formula (1) are a hydrogen atom.

10. The compound according to claim 1, wherein $R_{11}$ to $R_{18}$ in the formula (1) are a hydrogen atom.

11. The compound according to claim 1, wherein the substituent $R_a$ is selected from the group consisting of a halogen atom, a cyano group, a nitro group, a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms.

12. The compound according to claim 1, wherein the compound represented by the formula (1) comprises at least one deuterium atom.

13. The compound according to claim 1, which is a material for an organic electroluminescence device.

14. An electron-transporting material for an organic electroluminescence device, comprising the compound according to claim 1.

15. An organic electroluminescence device comprising a cathode;

an anode; and one or two or more organic layers arranged between the cathode and the anode, wherein at least one layer of the organic layers comprises the compound according to claim 1.

16. An electronic apparatus comprising the organic electroluminescence device according to claim 15.

17. An organic electroluminescence device comprising an anode, an emitting layer, an electron-transporting region, and a cathode in this order, wherein the electron-transporting region comprises the compound according to claim 1.

18. The organic electroluminescence device according to claim 17, wherein the electron-transporting region comprises a first electron-transporting layer, and a second electron-transporting layer, the organic electroluminescence device comprises the emitting layer, the first electron-transporting layer, and the second electron-transporting layer in this order, and at least one layer of the first electron-transporting layer and the second electron-transporting layer comprises the compound.

19. The organic electroluminescence device according to claim 17, wherein a hole-transporting region is provided between the anode and the emitting layer.

* * * * *